US008415459B2

(12) United States Patent
LaVallie et al.

(10) Patent No.: US 8,415,459 B2
(45) Date of Patent: Apr. 9, 2013

(54) ANTIBODY TO GDF8 AND USES THEREOF

(75) Inventors: Edward Roland LaVallie, Harvard, MA (US); Lisa Anne Collins-Racie, Acton, MA (US); Christopher John Corcoran, Arlington, MA (US); Lioudmila Gennadievna Tchistiakova, Andover, MA (US); John Adam Nowak, Stratham, NH (US); Riyez Karim, North Andover, MA (US); Xiang-Yang Tan, Reading, MA (US); Kimberly Ann Marquette, Somerville, MA (US); Geertruida Machteld Veldman, Sudbury, MA (US)

(73) Assignee: Pfizer Inc., New York, NY (US)

( * ) Notice: Subject to any disclaimer, the term of this patent is extended or adjusted under 35 U.S.C. 154(b) by 816 days.

(21) Appl. No.: 12/262,712

(22) Filed: Oct. 31, 2008

(65) Prior Publication Data
US 2009/0148436 A1  Jun. 11, 2009

Related U.S. Application Data

(60) Provisional application No. 61/001,783, filed on Nov. 1, 2007.

(51) Int. Cl.
*C07K 16/00* (2006.01)
*C07K 16/18* (2006.01)
*C07K 16/22* (2006.01)

(52) U.S. Cl.
USPC ............... 530/387.1; 530/387.3; 530/387.9; 530/388.1; 530/388.15; 530/388.23; 530/389.1; 530/389.2

(58) Field of Classification Search .................. None
See application file for complete search history.

(56) References Cited

U.S. PATENT DOCUMENTS

| | | | |
|---|---|---|---|
| 4,708,871 A | 11/1987 | Geysen | |
| 4,816,567 A | 3/1989 | Cabilly et al. | |
| 5,565,332 A | 10/1996 | Hoogenboom et al. | |
| 5,624,821 A | 4/1997 | Winter et al. | |
| 5,648,260 A | 7/1997 | Winter et al. | |
| 5,951,974 A | 9/1999 | Gilbert et al. | |
| 6,012,454 A | 1/2000 | Hodson et al. | |
| 6,030,613 A | 2/2000 | Blumberg et al. | |
| 6,102,035 A | 8/2000 | Asking et al. | |
| 6,506,559 B1 | 1/2003 | Fire et al. | |
| 6,656,475 B1 | 12/2003 | Lee et al. | |
| 7,320,789 B2 * | 1/2008 | Dunham et al. | 424/130.1 |
| 7,888,486 B2 * | 2/2011 | Walsh et al. | 530/388.24 |
| 2003/0118592 A1 | 6/2003 | Ledbetter et al. | |
| 2003/0133939 A1 | 7/2003 | Ledbetter et al. | |
| 2003/0162714 A1 | 8/2003 | Hill et al. | |
| 2003/0180306 A1 | 9/2003 | Hill et al. | |
| 2004/0058445 A1 | 3/2004 | Ledbetter et al. | |
| 2004/0077053 A1 | 4/2004 | Lee et al. | |
| 2004/0142382 A1 | 7/2004 | Veldman et al. | |
| 2004/0223966 A1 | 11/2004 | Wolfman et al. | |
| 2005/0136049 A1 | 6/2005 | Ledbetter et al. | |
| 2005/0175614 A1 | 8/2005 | Ledbetter et al. | |
| 2005/0180970 A1 | 8/2005 | Ledbetter et al. | |
| 2005/0186216 A1 | 8/2005 | Ledbetter et al. | |
| 2005/0202012 A1 | 9/2005 | Ledbetter et al. | |
| 2005/0202023 A1 | 9/2005 | Ledbetter et al. | |
| 2005/0202028 A1 | 9/2005 | Ledbetter et al. | |
| 2005/0202534 A1 | 9/2005 | Ledbetter et al. | |
| 2005/0238646 A1 | 10/2005 | Ledbetter et al. | |
| 2006/0240487 A1 | 10/2006 | Nowak et al. | |
| 2006/0240488 A1 | 10/2006 | Nowak et al. | |
| 2007/0087000 A1 | 4/2007 | Walsh et al. | |

FOREIGN PATENT DOCUMENTS

| | | |
|---|---|---|
| WO | WO 92/01047 | 1/1992 |
| WO | WO 94/02602 | 2/1994 |
| WO | WO 96/33735 | 10/1996 |
| WO | WO 96/34015 | 10/1996 |
| WO | WO 96/34096 | 10/1996 |
| WO | WO 97/10847 | 3/1997 |
| WO | WO 00/43781 | 7/2000 |
| WO | WO 03/014161 A2 | 2/2003 |
| WO | WO 03/027248 A2 | 4/2003 |
| WO | WO 2005/094446 A2 | 10/2005 |
| WO | WO 2006/116269 A2 | 11/2006 |
| WO | WO 2007/024535 A2 | 3/2007 |
| WO | WO 2007/044411 A2 | 4/2007 |
| WO | WO 2007/047112 A2 | 4/2007 |
| WO | WO 2008/030706 A2 | 3/2008 |

OTHER PUBLICATIONS

Paul, Fundamental Immunology, 1993, pp. 292-295, under the heading Fv Structure and Diversity in Three Dimensions.*
Casset et al. (Biochem Biophys Res Comm. 2003; 307:198-205).*
MacCallum et al. (J Mol Biol. 1996; 262:732-745).*
Vajdos et al. (J Mol Biol. 2002; 320(2):415-428).*
Holm et al. (Mol Immunol. 2007; 44(6):1075-1084).*
Chen et al. (J Mol Biol. 1999; 293:865-881).*
International Preliminary Report on Patentability (IPRP) from PCT/US2008/012338 (WO 2009/056346): date of issuance of report is May 4, 2010.
Haffar, OK, et al., Topogenic Analysis of the Human Immunodeficiency Virus Type 1 Envelope Glycoprotein, p. 160, in Microsomal Membranes, J. Cell Biol., Nov. 1, 1988, 107:1677-87.
Wagner, KR, et al., A Phase I/II Trial of MYO-029 in Adult Subjects With Muscular Dystrophy, Ann. Neurol., May 2008, 63:561-71.
Kingsley, David M. et al., "The TGF-β superfamily: new members, new receptors, and new genetic tests of function in different organisms," 1994, *Genes & Development*, vol. 8, pp. 133-146.
Hoodless, P. A. and Wrana, J. L., "Mechanism and Function of Signaling by the TGFβ Superfamily," 1998, Current Topics in Microbiology and Immunology, vol. 228, pp. 235-272.

(Continued)

*Primary Examiner* — Elizabeth C Kemmerer

(57) ABSTRACT

The disclosure provides novel molecules related to growth and differentiation factor-8 (GDF8), in particular epitopes specific to GDF8 and other specific antagonists of GDF8 in particular anti-GDF8 antibodies or antigen binding protein or fragment thereof which may inhibit GDF8 activity and signal in vitro and/or in vivo. The disclosure also provides for an immunoassay used to detect and quantitate GDF8. The disclosure also provides methods for diagnosing, preventing, ameliorating, and treating GDF8-associated disorders, e.g., degenerative orders of muscle, bone, and insulin metabolism. Finally, the disclosure provides pharmaceuticals for the treatment of such disorders by using the antibodies, polypeptides, polynucleotides, and vectors of the invention.

20 Claims, 44 Drawing Sheets

OTHER PUBLICATIONS

Miyazono, Kohei et al., "Latent High Molecular Weight Complex of Transforming Growth Factor β1 Purification From Human Platelets and Structural Characterization," 1988, Journal of Biological Chemistry, vol. 263, pp. 6407-6415.

Wakefield, Lalage M. et al., "Latent Transforming Growth Factor-β from Human Platelets A High Molecular Weight Complex Containing Precursor Sequence," 1988, Journal of Biological Chemistry, vol. 263, pp. 7646-7654.

Brown, Peter D. et al., "Physicochemical Activation of Recombinant Latent Transforming Frowth Factor-beta's 1, 2, and 3," 1990, Growth Factors, vol. 3, pp. 35-43.

Thies, R. Scott et al., "GDF-8 Propeptide Binds to GDF-8 and Antagonizes Biological Activity by Inhibiting GDF-8 Receptor Binding," 2001, Growth Factors, vol. 18, pp. 251-259.

Gentry, Larry E. et al., "The Pro Domain of Pre-Pro-Transforming Growth Factor β1 When Independently Expressed Is a Functional Binding Protein for the Mature Growth Factor," 1990 *Biochemistry*, vol. 29, pp. 6851-6857.

Derynck, Rik et al., "Human transforming growth factor-β complementary DNA sequence and expression in normal and transformed cells," 1995, Nature, vol. 316, pp. 701-705.

Massague, Joan, "The Transforming Growth Factor-β Family," 1990, Annual Review of Cell Biology, vol. 6, pp. 597-641.

Gamer, Laura W. et al., "A Novel BMP Expressed in Developing Mouse Limb, Spinal Cord, and Tail Bud Is a Potent Mesoderm Inducer in *Xenopus* Embryos," 1999, Developmental Biology, vol. 208, pp. 222-232.

McPherron, Alexandra C. and Lee, Se-Jin, "Double muscling in cattle due to mutations in the myostatin gene," 1997, Proceedings of the National Academy of Science U.S.A. vol. 94, pp. 12457-12461.

Lee, Se-Jin and McPherron, Alexandra C., "Myostatin and the control of skeletal muscle mass," 1999, Current Opinion in Genetics & Development, vol. 9, pp. 604-607.

McCroskery, Seumas et al., "Myostatin negatively regulates satellite cell activation and self-renewal," 2003, Journal of Cell Biology, vol. 162, pp. 1135-1147.

Zimmers, Teresa A. et al., "Induction of Cachexia in Mice by Systemically Administered Myostatin," 2002, Science, vol. 296, pp. 1486-1488.

Gonzalez-Cadavid, Nestor F. et al., "Organization of the human myostatin gene and expression in healthy men and HIV-infected men with muscle wasting," 1998, Proceedings of the National Academy of Science U.S.A, vol. 95, pp. 14938-14943.

McPherron, Alexandra C. et al., "Regulation of skeletal muscle mass in mice by a new TGF-β superfamily member," 1997, Nature, vol. 387, pp. 83-90.

Hamrick, M. W. et al., Femoral Morphology and Cross-sectional Geometry of Adult Myostatin-deficient Mice, 2000, Bone, vol. 27, pp. 343-349.

Ashmore, C. R. et al., "Comparative Aspects of Muscle Fiber Types in Fetuses of the Normal and "Double-Muscled" Cattle," 1974, Growth, vol. 38, pp. 501-507.

Swatland, H. J. et al., "Fetal Development of the Double Muscled Condition in Cattle," 1974, Journal of Animal Science, vol. 38, pp. 752-757.

Kambadur, Ravi et al., "Mutations in myostatin (GDF8) in Double-Muscled Belgian Blue and Piedmontese Cattle," 1997, Genome Research, vol. 7, pp. 910-915.

Kim, H. S. et al., "Inhibition of Preadipocyte Differentiation by Myostatin Treatment in 3T3-L1 Cultures," 2000, Biochemical and Biophysical Research Communications, vol. 281, pp. 902-906.

Lee, Se-Jin and McPherron, Alexandra C., "Regulation of myostatin activity and muscle growth," 2001, Proceedings of the National Academy of Science USA, vol. 98, pp. 9306-9311.

Thomas, Mark et al., "Myostatin, a Negative Regulator of Muscle Growth, Functions by Inhibiting Myoblast Proliferation," 2000, Journal of Biological Chemistry, vol. 275, pp. 40235-40243.

McCroskery, Seumas et al., "Improved muscle healing through enhanced regeneration and reduced fibrosis in myostatin-null mice," 2005, Journal of Cell Science, vol. 118, pp. 3531-3541.

Whittemore, Lisa-Anne et al., "Inhibition of myostatin in adult mice increases skeletal muscle mass and strength," 2003, Biochemical and Biophysical Research Communications, vol. 300, pp. 965-971.

Bogdanovich, Sasha et al., "Functional improvement of dystrophic muscle by myostatin blockade," 2002, Nature, vol. 420, pp. 418-421.

Wagner, Kathryn R. et al., "Loss of Myostatin Attenuates Severity of Muscular Dystrophy in *mdx* Mice," 2002, Ann. Neurol., vol. 52, pp. 832-836.

Kohler, et al., "Continuous cultures of fused cells secreting antibody of predefined specificity," 1975, Nature, vol. 256, pp. 495-499.

Clackson, Tim et al., "Making antibody fragments using phage display libraries," 1991, Nature, vol. 352, pp. 624-628.

Marks, James D. et al., "By-passing Immunization Human Antibodies from V-gene Libraries displayed on Phage," 1991, Journal of Molecular Biology, vol. 222, pp. 581-597.

Antibodies: A Laboratory Manual, eds. Harlow et al., Cold Spring Harbor Laboratory, 1988.

Epitope Mapping Protocols in Methods in Molecular Biology, vol. 66 (Glenn E. Morris, Ed., 1996) Humana Press, Totowa, N. J.

Geysen, H. Mario et al., "Use of peptide synthesis to probe viral antigens for epitopes to a resolution of a single amino acid," 1984, Proceedings of the National Academy of Science USA, vol. 81, pp. 3998-4002.

Geysen, H, Mario et al., "*A Priori* Delineation of a Peptide Which Mimics a Discontinuous Antigenic Determinant," 1986, Molecular Immunology, vol. 23, pp. 709-715.

Bergmann, Cornelia et al., "An endogenously synthesized decamer peptide efficiently primes cytotoxic T cells specific for the HIV-1 envelope glycoprotein," 1993, European Journal of Immunology, vol. 23, pp. 2777-2781.

Bergmann, Cornelia C. et al., "Flanking residues Alter Antigenicity and Immunogenicity of Multi-Unit CTL Epitopes," 1996, Journal of Immunology, vol. 157, pp. 3242 3249.

Suhrbier, A., "Multi-epitope DNA vaccines," 1997, Immunology and Cell Biology, vol. 75, pp. 402 408.

Gardner et al. (1998) 12th World AIDS Conference, Geneva, Switzerland, Jun. 28 Jul. 3, 1998.

Karp, Peter D., "An ontology for biological function based on molecular interactions," 2000, *Bioinformatics Ontology*, vol. 16, pp. 269-285.

Verkman, A. S., "Drug discovery in academia," 2004, *AJP—Cell Physiol*,. vol. 286, pp. 465-474.

Voet and Voet, *Biochemistry*, 2nd ed., ed. N. Rose, Wiley and Sons, New York, 14 (1995).

Davis, Mindy I. et al., "Crystal structure of prostate-specific membrane antigen, a tumor marker and peptidase," 2005, *Proceedings of the National Academy of Science US*, vol. 102, pp. 5981-5986.

Halpin, David R. and Harbury, Pehr B., "DNA Dsisplay II. Genetic Manipulation of Combinatorial Chemistry Libraries for Small-Molecule Evolution," 2004, PLos Biology, vol. 2, pp. 1022-1030.

Alfarano, C. et al., "The Biomolecular Interaction Network Database and related tools 2005 update," 2005, Nuc. Acids Res. Database Issue, vol. 33, pp. D418-D424.

Sambrook, et al., Molecular Cloning: A Laboratory Manual: Second Edition, Cold Spring Harbor Laboratory Press, 1989.

DNA Cloning, vols. I and II (D. N Glover ed. 1985).

Oligonucleotide Synthesis (M. J. Gait ed., 1984).

Nucleic Acid Hybridization (B. D. Hames & S. J. Higgins eds. 1984).

Transcription and Translation (B. D. Hames & S. J. Higgins eds. 1984).

Animal Cell Culture (R. I. Freshney ed. 1986).

Immobilized Cells and Enzymes (IRL Press, 1986).

Gene Transfer Vectors for Mammalian Cells (J. H. Miller and M. P. Calos eds. 1987, Cold Spring Harbor Laboratory).

Immunochemical Methods in Cell and Molecular Biology (Academic Press, London), Scopes, (1987).

Handbook of Experimental Immunology, vols. I IV (D. M. Weir and C. C. Blackwell eds. (1986).

Altschul, Stephen F. et al., "Basic Local Alignment Search Tool," 1990, Journal of Molecular Biology, vol. 215, pp. 403-410.

Needleman, Saul B. and Wunsch, Christan D., "A General Method Applicable to the Search for Similarities in the Amino Acid Sequence of Two Proteins," 1970, Journal of Molecular Biology, vol. 48, pp. 444-453.

Meyers et al. ((1988) *Comput. Appl. Biosci.*, vol. 4, pp. 11-17.

Fundamental Immunology, 3rd ed. (1993), ed. Paul, Raven Press, New York, NY.

Immunoglobulin Genes, 2nd ed. (1995), eds. Jonio et al., Academic Press, San Diego, CA.

Sequences of Proteins of Immunological Interest, U.S. Department of Health and Human Services (1991), eds. Kabat et al.

Al-Lazikani, Bissan et al., "Standard Conformations for the Canonical Structures of Immunoglobulins," 1997, Journal of Molecular Biology, vol. 273, pp. 927-948.

Antibody Engineering, 2nd ed., ed. Borrebaeck, Oxford University Press, 1995.

Marks, James D. et al., "By-passing Immunization: Building High Affinity Human Antibodies by Chain Shuffling,"1992, Bio/Technology, vol. 10, pp. 779-783.

Stemmer, Willem P. C., "Rapid evolution of a protein in vitro by DNA shuffling," 1994, Nature, vol. 370, pp. 389-391.

Gram, Hermann et al., "In vitro selection and affinity maturation of antibodies from a naïve combinatorial immunoglobulin library," 1992, Proceedings of the National Academy of Science U.S.A., vol. 89, pp. 3576-3580.

Barbas, Carlos F. et al., "In vitro evolution of a neutralizing human antibody to human immunodeficiency virus type 1 to enhance affinity and broaden strain cross-reactivity," 1994, Proceedings of the National Academy of Science U.S.A., vol. 91, pp. 3809-3813.

Schier, Robert et al., "Isolation of Picomolar Affinity Anti-c-erbB-2 Single-chain Fv by Molecular Evolution of the Complementarity Determining Regions in the Center of the Antibody Binding Site," 1996, Journal of Molecular Biology, vol. 263, pp. 551-567.

Lund, John et al., Human FcγRI and FcγRII Interact with Distinct but Overlapping Sites on Human IgG[1], 1991, Journal of Immunology, vol. 147, pp. 2657-2662.

Morgan, A. et al., "The N-terminal end of the $C_H2$ domain of chimeric human IgG1 anti-HLA-DR is necessary for C1q, FcγRI and FcγRIII binding," 1995, Immunology, vol. 86, pp. 319-324.

Angal, S. et al., A Single Amino Acid Substitution Abolishes the Heterogeneity of Chimeric Mouse/Human (IgG4) Antibody, 1993, Molecular Immunology, vol. 30, pp. 105-108.

Sambrook et al., Molecular Cloning: A Laboratory Manual, Chs. 9 & 11, Cold Spring Harbor Laboratory Press, Cold Spring Harbor, NY (1989).

Ausubel et al., eds., Current Protocols in Molecular Biology, Sects. 2.10 & 6.3-6.4, John Wiley & Sons, Inc. (1995).

Galderisi, Umberto et al., "Antisense Oligonucleotides as Therapeutic Agents," 1999, Journal of Cellular Physiology, vol. 181, pp. 251-257.

Sioud, Mouldy, "Nucleic Acid Enzymes as a Novel Generation of Anti-gene Agents," 2001, Current Molecular Medicine, vol. 1, pp. 575-588.

Knauert, Melissa P. and Glazer, Peter M., "Triplex forming oligonucleotides: sequence-specific tools for gene targeting," 2001, Human Molecular Genetics, vol. 10, pp. 2243-2251.

Bass, Brenda L., "The short answer," 2001, Nature, vol. 411, pp. 428-429.

Dorn, Gabriele et al., "siRNA relieves chronic neuropathic pain," 2004, Nucleic Acids Research, vol. 32, pp. e49.

Elbashir, Sayda M. et al., "Functional anatomy of siRNAs for mediating efficient RNAi in *Drosophila melanogaster* embryo lysate," 2001, EMBO Journal, vol. 20, pp. 6877-6888.

Reynolds, Angela et al., "Rational siRNA design for RNA interference," 2004, Nature Biotechnology, vol. 22, pp. 326-330.

Yu, Jenn-Yah et al., RNA interference by expression of short-interfering RNAs and hairpin RNAs in mammalian cells, 2002, Proceedings of the National Academy of Science USA, vol. 99, pp. 6047-6052.

Elbashir, Sayda M. et al., "Duplexes of 21-nucleotide RNAs mediate RNA interference in cultured mammalian cells," 2001, Nature, vol. 411, pp. 494-498.

Sui, Guangchao et al., A DNA vector-based RNAi technology to suppress gene expression in mammalian cells, 2002, Proceedings of the National Academy of Science USA, vol. 99, pp. 5515-5520.

Paddison, Patrick J. et al., "Stable suppression of gene expression by RNAi in mammalian cells," 2002, Proceedings of the National Academy of Science USA, vol. 99, pp. 1443-1448.

Arts et al. (2003)., vol. 13, pp. 2325-2332.

Heasman, Janet, "Morpholino Oligos: Making Sense of Antisense?" 2002, Developmental Biology, vol. 243, pp. 209-214.

Micklefield, Jason, "Backbone Modification of Nucleic Acids: Synthesis, Structure and Therapeutic Applications," 2001, Current Medicinal Chemistry, vol. 8, pp. 1157-1179.

Current Protocols in Molecular Biology, 2nd ed., Ausubel et al. eds., John Wiley & Sons, 1992.

Rebbapragada, A. et al., "Myostatin Signals through a Transforming Growth Factor β-Like Signaling Pathway to Block Adipogenesis," 2003, Molecular and Cellular Biology, vol. 23, pp. 7230-7242.

McPherron, Alexandra C. and Lee, Se-Jin, "Suppression of body fat accumulation in myostatin-deficient mice," 2002, Journal of Clinical Investigation, vol. 109, pp. 595-601.

Antibodies: A Laboratory Manual, Cold Spring Harbor Laboratory, eds. Harlow et al., 1988.

Gardlik, Roman et al., "Vectors and delivery systems in gene therapy," 2005, Medical Science Monitor, vol. 11, pp. RA110-RA121.

Pedley, R. B. et al., "The potential for enhanced tumour localization by poly(ethylene glycol) modification of anti-CEA antibody," 1994, British Journal of Cancer, vol. 70, pp. 1126-1130.

Molina, F. et al., "Improved Performances of Spot Multiple Peptide Synthesis," 1996, Peptide Research, vol. 9, pp. 151-155.

Frank, Ronald, "Spot-Synthesis: An Easy Technique for the Positionally Addressable, Parallel Chemical Synthesis on a Membrane Support," 1992, Tetrahedron, vol. 48, pp. 9217-9232.

Bhasin, Shalender et al., "Older Men Are as Responsive as Young Men to the Anabolic Effects of Graded doses of Testosterone on the Skeletal Muscle," 2005, Journal of Clinical Endocrinology & Metabolism, vol. 90, pp. 678-688.

Bhasin, Shalender et al., "Testosterone dose-response relationships in healthy young men," 2001, American Journal of Physiology Endocrinology and Metabolism, vol. 281, E1172-E1181.

Storer, Thomas W. et al., "Testosterone Dose-Dependently Increases Maximal Voluntary Strength and Leg Power, but Does Not Affect Fatigability or Specific Tension," 2003, Journal of Clinical Endocrinology Metabolism, vol. 88, pp. 1478-1485.

Sinha-Hikim, Indrani et al., "The Use of a Sensitive Equilibrium Dialysis Method for the Measurement of Free Testosterone Levels in Healthy, Cycling Women and in Human Immunodeficiency Virus-Infected Women," 1998, Journal of Clinical Endocrinology and Metabolism, vol. 83, pp. 1312-1318.

PCT/US2008/012338 International Search Report mailed Mar. 3, 2009.

* cited by examiner

Kinetic Rate constants for the interaction between RK-22 Antibody and GDF-8

| | Antibody | Lot # | Activity (%) | ka1 (1/Ms) | kd1(1/s) | KA1 (1/M) | Kd (M) | Kd (nM) | Rmax | Chi2 |
|---|---|---|---|---|---|---|---|---|---|---|
| | | | | | Langmuir Model (global analysis) | | | | | |
| 71 RU (2.6.03) | RK 22 | PK1901 | 82.54 | 1.47E+05 | 5.72E-04 | 2.58E+08 | 3.88E-09 | 3.88 | 44.00 | 7.47 |
| 45 RU (4.30.03) | RK 22 | PK1901 | 82.54 | 4.61E+04 | 6.33E-04 | 7.28E+07 | 1.37E-08 | 13.70 | 84.00 | 2.12 |
| 42.4 RU (6.14.03) | RK 22 | PK1901 | 82.54 | 1.56E+05 | 4.82E-04 | 3.24E+08 | 3.09E-09 | 3.00 | 39.4 | 3.67 |
| Average of three independent experiments | | | | 1.16E+05 | 5.62E-04 | 2.18E+08 | 6.89E-09 | 7 | | |
| | | | | | Bivalent Model (global analysis) | | | | | |
| | Antibody | Lot # | Activity (%) | ka1 (1/Ms) | kd1(1/s) | KA1 (1/M) | Kd (M) | KD (nM) | Rmax | Chi2 |
| 71 RU (2.6.03) | RK 22 | PK1901 | 82.54 | 8.36E+04 | 7.80E-04 | 1.07E+08 | 9.33E-09 | 9.33 | 53.00 | 0.84 |
| 45 RU (4.30.03) | RK 22 | PK1901 | 82.54 | 2.31E+04 | 6.30E-04 | 3.67E+07 | 2.73E-08 | 27.00 | 84.00 | 1.29 |
| 42.4 RU (6.14.03) | RK 22 | PK1901 | 82.54 | 7.81E+04 | 7.14E-04 | 1.09E+08 | 9.14E-09 | 9.00 | 49.2 | 0.299 |
| Average of three independent experiments | | | | 6.16E+04 | 7.08E-04 | 8.44E+07 | 1.52E-08 | 15 | | |

FIG.2

*Percent Identity to mRK22:* *DP-7=71.43*
*DP-5=65.306*

```
DP-5_germl_VH    QVQLVQSGAE VKKPGASVKV SCKVSGYTLT ELSMHWVRQA PGKGLEWMGG
DP-7_germl_VH    QVQLVQSGAE VKKPGASVKV SCKASGYTFT SYYMHWVRQA PGQGLEWMGI
RK22_VH          QVQLQQSGAE LARPGASVKL SCKASGYTFT SYWMQWVKQR PGQGLEWIGA DP-5_germl_VH    FDPEDGETIY AQKFQGRVTM TEDTSTDTAY MELSSLRSED TAVYYCAT~~
DP-7_germl_VH    INPSGGSTSY AQKFQGRVTM TRDTSTSTVY MELSSLRSED TAVYYCAR~~
RK22_VH          IYPGDGDTRY TQKFKGKATL TADKSSSTAY MQLSSLASED SAVYYCARMG DP-5_germl_VH    ~~~~~~~~~~ ~~~~~~~~~~ ~~~V~~~~~~
DP-7_germl_VH    ~~~~~~~~~~ ~~~~~~~~~~ ~~~V~~~~~~
RK22_VH          GYDRYYFDYW GQGTTLTVSS
```

Amino acids in the framework regions that are different in mouse and human clones are highlighted in bold highlighted in bold.

CDR regions are underlined.

20 a.a substitutions in the framework regions of humanized RK 22 VH based on DP-5 FW.

19 a.a substitutions in the framework regions in humanized RK 22 VH based on DP-7 FW.

19 a.a. substitutions in the framework regions.

20 a.a substitutions to DP-5 FW.

FIG. 7

Percent Identity to mouse RK 22 VL: 78.218

```
DPK 24       DIVMTQSPDSLAVSLGERATINCKSSQSVLYSSNNKNYLAWYQQKP
             ||||||||||||:||.|.:.|..||||||:|..|.|.|||||||||
Mouse RK22   DIVMTQSPSSLAMSVGQKVTMSCKSSQSLLNSANQKNYLAWYQQKP DPK 24       GQPPKLLIYWASTRESGVPDRFSGSGSGTDFTLTISSLQAEDVAVY
             ||.|||||:|.||||||||||||.||||||||||||||.|||.||.
Mouse RK22   GQSPKLLVYFASTRESGVPDRFIGSGSGTDFTLTISSVQAEDLADY DPK 24       YCQQYYSTP...G...V.I.
             :||:|.||..:.|...|.|.
Mouse RK22   FCQQHYNTPLTFGAGTKLELK
```

Amino acids in the framework regions that are different in the mouse and human clones are highlighted in bold CDR regions are underlined.

17 a.a substitutions in the framework regions of humanized RK 22 VL based on DPK-24 acceptor FW.

FIG.8

Serum myostatin levels assayed in the presence of myostatin binding proteins under low pH.

Acidic Assay Conditions

| | No addition | MyO-029* | | | ActRIIB-Fc* | | |
|---|---|---|---|---|---|---|---|
| | x | 300 | 30 | 3 | 300 | 30 | 3 |

Myostatin (ng/ml): approximately 6 ng/ml across all conditions

*Final concentration (μg/ml)

FIG.29C

Regression plots showing correlation of the change in myostatin levels from baseline to Day 56 and changes in testosterone concentrations and lean body mass in young and older men

ANTIBODY TO GDF8 AND USES THEREOF

FIELD OF THE INVENTION

The technical field of the invention relates to the epitope(s) specific to growth and differentiation factor-8 (GDF8) and antagonists thereto (e.g., peptide mimetics, anti-GDF8 antibodies (e.g., mouse, human and humanized antibodies, fragments thereof, etc.), recombinant polynucleotides, inhibitory polynucleotides, etc.) that may be used to inhibit GDF8 activity in vitro and/or in vivo. The field further relates to immunoassay methods for the detection of GF8 in biological samples as well as methods of treating, ameliorating, preventing, diagnosing, prognosing, and/or monitoring GDF8-associated disorders (e.g., muscle disorders, neuromuscular disorders, bone-degenerative disorders, metabolic or induced bone disorders, adipose disorders, glucose metabolism disorders or insulin-related disorders), particularly in women of childbearing potential.

BACKGROUND OF THE INVENTION

Growth and differentiation factor-8 (GDF8), also known as myostatin, is a secreted protein and member of the transforming growth factor-beta (TGF-β) superfamily of structurally related growth factors. Members of this superfamily possess growth-regulatory and morphogenetic properties (Kingsley et al. (1994) *Genes Dev.* 8:133-46; Hoodless et al. (1998) *Curr. Topics Microbiol. Immunol.* 228:235-72). Human GDF8 is synthesized as a 375 amino acid precursor protein that forms a homodimer complex. During processing, the amino-terminal propeptide, known as the "latency-associated peptide" (LAP), is cleaved and may remain noncovalently bound to the homodimer, forming an inactive complex designated the "small latent complex" (Miyazono et al. (1988) *J. Biol. Chem.* 263:6407-15; Wakefield et al. (1988) *J. Biol. Chem.* 263:7646-54; Brown et al. (1999) *Growth Factors* 3:35-43; Thies et al. (2001) *Growth Factors* 18:251-59; Gentry et al. (1990) *Biochemistry* 29: 6851-57; Derynck et al. (1995) *Nature* 316:701-05; Massague (1990) *Ann. Rev. Cell Biol.* 12:597-641). Proteins such as follistatin and follistatin-related proteins including GASP-1 (Gamer et. al. (1999) *Dev Biol.* 208:222-232, US Patent Pub No. 2003-0180306-A1; US Patent Pub No. 2003-0162714-A1) and bind mature GDF8 homodimers and inhibit GDF8 biological activity.

An alignment of the deduced GDF8 amino acid sequence from various species demonstrates that GDF8 is highly conserved (McPherron et al. (1997) *Proc. Natl. Acad. Sci. U.S.A.* 94:12457-61). The sequences of human, mouse, rat, porcine, and chicken GDF8 are 100% identical in the C-terminal region, while baboon, bovine, and ovine GDF8 differ by a mere 3 amino acids at the C-terminus. The high degree of GDF8 conservation across species suggests that GDF8 has an essential physiological function.

GDF8 has been shown to play a major role in the regulation of muscle development and homeostasis by inhibiting both proliferation and differentiation of myoblasts and satellite cells (Lee and McPherron (1999) *Curr. Opin. Genet. Dev.* 9:604-7; McCroskery et al. (2003) *J. Cell. Biol.* 162:1135-47). It is expressed early in developing skeletal muscle, and continues to be expressed in adult skeletal muscle, preferentially in fast twitch types. GDF8 has also been implicated in the production of muscle-specific enzymes (e.g., creatine kinase) and myoblast proliferation (WO 00/43781).

Overexpression of GDF8 in adult mice results in significant muscle loss (Zimmers et al. (2002) *Science* 296:1486-88). Similarly, various studies indicate that increased GDF8 expression is associated with HIV-induced muscle wasting (Gonzalez-Cadavid et al. (1998) *Proc. Natl. Acad. Sci. U.S.A.* 95:14938-43). In contrast, GDF8 knockout transgenic mice are characterized by a marked hypertrophy and hyperplasia of the skeletal muscle and altered cortical bone structure (McPherron et al. (1997) *Nature* 387:83-90; Hamrick et al. (2000) *Bone* 27:343-49). Also, natural mutations that render the GDF8 gene inactive have been shown to cause both hypertrophy and hyperplasia in both animals and humans (Lee and McPherron (1997), supra). For example, increases in skeletal muscle mass are evident in natural GDF8 mutations in cattle (Ashmore et al. (1974) *Growth* 38:501-07; Swatland et al. (1994) *J. Anim. Sci.* 38:752-57; McPherron et al., supra; Kambadur et al. (1997) *Genome Res.* 7:910-15).

A number of human and animal muscle and bone disorders are associated with functionally impaired muscle tissue, and thus, may also be associated with GDF8. For example, GDF8 may be involved in the pathogenesis of amyotrophic lateral sclerosis ("ALS"), muscular dystrophy ("MD"; including Duchenne's muscular dystrophy, fascioscapular muscular dystrophy, and facioscapulohumeral muscular dystrophy), muscle atrophy, carpal tunnel syndrome, organ atrophy, frailty, congestive obstructive pulmonary disease (COPD), sarcopenia, cachexia, and muscle wasting syndromes caused by other diseases and conditions.

GDF8 is also believed to participate in numerous other physiological processes and related disorders, including glucose homeostasis during type 2 diabetes development, impaired glucose tolerance, metabolic syndromes (i.e., syndromes (e.g., syndrome X) involving the simultaneous occurrence of a group of health conditions (which may include insulin resistance, abdominal obesity, dyslipidemia, hypertension, chronic inflammation, a prothrombotic state, etc.) that places a person at high risk for type 2 diabetes and/or heart disease), insulin resistance (e.g., resistance induced by trauma such as burns or nitrogen imbalance), and adipose tissue disorders (e.g., obesity, dyslipidemia, nonalcoholic fatty liver disease, etc.) (Kim et al. (2000) *Biochem. Biophys. Res. Comm.* 281:902-06). Currently, few reliable or effective therapies exist to treat these disorders. The pathology of these processes indicates GDF8 as a potential target in the treatment of these related disorders.

In addition to neuromuscular disorders in humans, there are also growth factor-related conditions associated with a loss of bone, such as osteoporosis and osteoarthritis, which predominantly affect the elderly and/or postmenopausal women. Such metabolic bone diseases and disorders include low bone mass due to chronic glucocorticoid therapy, premature gonadal failure, androgen suppression, vitamin D deficiency, secondary hyperparathyroidism, nutritional deficiencies, and anorexia nervosa. Although many current therapies for these conditions function by inhibiting bone resorption, a therapy that promotes bone formation would be a useful alternative treatment. Because GDF8 plays a role in bone development as well as muscular development, GDF8 is also an excellent pharmacological target for the treatment of bone-degenerative disorders.

Like other members of the transforming growth factor-β (TGF-β) family, GDF8 is synthesized as a 376 amino acid precursor protein containing a signal sequence, a N-terminal propeptide domain, and a C-terminal domain considered as the active molecule. GDF8 is secreted in a latent form by binding to it's propeptide (latency-associated peptide, LAP); proteolytic processing between the propeptide domain and the C-terminal domain produces an N-terminal propeptide and the mature form of GDF8. Both unprocessed and mature GDF8 form disulfide-linked dimers, and the processed GDF8 dimer represents the only active form of the protein. In serum, as well as in skeletal muscle, GDF8 can be found bound to several proteins that are able to modulate its activation, secretion or receptor binding.

GDF8 exerts its effects through a transmembrane serine/threonine kinase heterotetramer receptor family, activation of which enhances receptor transphosphorylation, leading to the stimulation of serine/threonin kinase activity. It has been shown that the GDF8 pathway involves an active GDF8 dimer binding to the high affinity receptor, ActIIRB, which then recruits and activates the transphosphorylation of the low affinity receptor, ALK4/ALK5. It has also been shown that the proteins Smad 2 and Smad 3 are subsequently activated and form complexes with Smad 4 and are then translocated to the nucleus, which then activate target gene transcription. Lee and McPherron (*Proc Natl Acad Sci USA* 2001, 98 :9306-9311) have demonstrated that the ActRIIB receptor was able to mediate the influence of GDF8 in vivo, as expression of a dominant negative form of ActIIRB in mice that mimics GDF8 gene knockout.

It has been shown that under the influence of GDF8, C2C12 myoblasts accumulate in the G0/G1 and G2 phases of the cell-cycle, consequently decreasing the number of S-phase cells. Also, GDF8 induces failure of myoblast differentiation, associated with a strong decrease in the expression of differentiation markers. GDF8 expression also decreases the apoptotic rate of cells under both proliferation and differentiation conditions (Thomas et al., *J. Biol Chem* 2000, 275:40235-40243).

Inhibition of myostatin (GDF8) expression leads to both muscle hypertrophy and hyperplasia (Lee and McPherron, supra; McPherron et al., supra). Myostatin negatively regulates muscle regeneration after injury, and lack of myostatin in GDF8 null mice results in accelerated muscle regeneration (McCroskery et al., (2005) *J. Cell. Sci.* 118:3531-41). Human anti-GDF8 antibodies (U.S. Published Application No. 2004/0142382) have been shown to bind GDF8 and inhibit GDF8 activity in vitro and in vivo, including GDF8 activity associated with negative regulation of skeletal muscle mass and bone density. For example, myostatin-neutralizing antibodies increase body weight, skeletal muscle mass, and muscle size and strength in the skeletal muscle of wild type mice (Whittemore et al. (2003) *Biochem. Biophys. Res. Commun.* 300: 965-71) and the mdx mouse, a model for muscular dystrophy (Bogdanovich et al. (2002) *Nature* 420:418-21; Wagner et al. (2002) *Ann. Neurol.* 52:832-36). Furthermore, myostatin antibodies in these mice decrease the damage to the diaphragm, a muscle that is also targeted during ALS pathogenesis. It has been hypothesized that the action of growth factors, such as HGF, on muscle may be due to inhibition of myostatin expression (McCroskery et al. (2005), supra), thereby helping to shift the balance between regeneration and degeneration in a positive direction. However, these prior art antibodies were not specific for GDF8, i.e., these antibodies have high affinity for other members of the TGF-β superfamily, such as BMP11.

To date, all known inhibitors of GDF8 activity (e.g., propeptide, soluble ActRIIB receptor, anti-GDF8 antibodies, etc.) also neutralize the biological activities of other factors (e.g., BMP11, activin, etc.) that have important biological functions. For example, activin and BMP11 play important roles during embryogenesis. Activin βA is identified as a critical gonadal growth factor, and BMP11 is responsible for homeotic transformation of the axial skeleton. Homozygous BMP11 knockout mice are perinatal lethal; mice with one wild type copy of the BMP11 gene are viable but have skeletal defects. Since activin and BMP11 play important roles during embryogenesis, an antagonist that inhibits GDF8 and other factors, e.g., BMP11 poses theoretical safety risks that could present either as toxicity in treated patients or as reproductive toxicity in, e.g., women of childbearing potential. Thus, there is a need for compounds and methods of treatment that contribute to an overall increase in muscle mass and/or strength and/or bone density, particularly in humans, but do not interfere with, e.g., BMP11. In other words, there is a need for specific inhibition of GDF8 activity in treatments of GDF8-associated disorders for which it is desirable to increase muscle mass, size, strength, etc., particularly in women with childbearing potential.

As methods of using GDF-8 modulating agents are developed, there is a need to develop methods to monitor and to optimize the administration of such agents to an individual. In particular, the ability to measure GDF-8 protein levels in biological fluids has important implications for ongoing clinical trials. For example, circulating GDF-8 levels might be diagnostic for pathological conditions that could benefit from anti-GDF-8 therapy, or might predict which individuals are more likely to respond to anti-GDF-8 therapy. In addition, changes in GDF-8 levels in peripheral blood during anti-GDF-8 treatment may be an early indicator of later measurable response in muscle mass and/or function.

In order to accomplish such optimization goals, methods to detect or monitor GDF-8 protein levels in biological fluids, such as serum and plasma are needed. It is desirable to monitor GDF-8 levels prior to, during, and post treatment with a GDF-8 modulating agent in order to identify appropriate individuals for such treatment, monitor responses to the treatment, and follow post-treatment progress, for example. In particular, methods allowing the detection and/or quantitation of endogenous GDF-8 levels in response to administration of GDF-8 modulating agents, including GDF-8 inhibitors and anti-GDF-8 antibodies are needed.

It is accordingly a primary object of the present invention to provide compounds and methods that specifically inhibit GDF8 activity as well as immunological assays to detect and quantitate GDF-8 levels in biological samples, such as, for example, in serum and plasma.

SUMMARY OF THE INVENTION

The invention is based on the discovery of antibodies or antigen binding proteins that specifically bind to Growth and Differentiation Factor 8 (GDF8) that specifically antagonize at least one GDF8 activity (e.g., GDF8 binding to its receptor or other GDF8-mediated signaling events). The present invention is also based on the identification of the epitopes on GDF8 recognized by these specific anti-GDF8 antibodies or antigen binding proteins, since the antibodies of the invention are specific to GDF8 and do not bind specifically to, for example, BMP11.

In addition to providing epitope(s) specific to GDF8, the invention also provides antagonists specific for GDF8 (also referred to herein as "specific GDF8 antagonists," "GDF8 antagonist," and the like), e.g., antagonists that specifically antagonize (e.g., inhibit, reduce, and/or neutralize) at least one GDF8 activity (e.g., GDF8-mediated signaling events (e.g., GDF8 binding to its receptor (e.g., its ALK4/ALK5 receptor)), and do not significantly antagonize BMP11 activity. The present invention also provides methods for detecting and quantifying GDF-8 in biological samples. In certain embodiments, the methods comprise immunoassays, and the sample is serum and/or plasma. The invention further provides kits for use in the methods of the invention. The invention also provides methods of using the disclosed specific GDF8 antagonists in methods of treating (which includes ameliorating, preventing, diagnosing, prognosing) or monitoring GDF8-associated disorders, e.g., muscle disorders, neuromuscular disorders, bone-degenerative disorders, metabolic or induced bone disorders, adipose disorders, glucose metabolism disorders, insulin-related disorders, etc.

Thus, in one aspect, the invention provides antagonists to GDF8 wherein the antagonists comprises at least one of a peptide mimetic of a GDF8 binding domain; an isolated nucleic acid that encodes an amino acid for a peptide mimetic of a GDF8 binding domain; an inhibitory polynucleotide specific to GDF8; and an anti-GDF8 antibody or antigen binding protein that specifically binds to GDF8 and does not specifically bind to BMP11.

In one embodiment, the invention provides the antagonist described herein wherein the antagonist is a peptide mimetic of a GDF8 binding domain and is selected from the group consists essentially of an amino acid sequence selected from the group consisting of the amino acid sequence of SEQ ID NO:4; the amino acid sequence of SEQ ID NO:6; the amino acid sequence of SEQ ID NO:8; the amino acid sequence of SEQ ID NO:10; and the amino acid sequence of SEQ ID NO:12. In some embodiments, the invention provides an antagonist that is a peptide mimetic as described herein and is cyclized. In some embodiments, the invention provides an antagonist that is a peptide mimetic as described herein and is cyclized by means of a disulfide bond. In any one or more embodiments the invention provides an antagonist that is a peptide mimetic as described herein that has at least one D-amino acid. In some embodiments the invention provides an antagonist that is a peptide mimetic that may be used as an immunogen.

In another embodiment the invention provides an antagonist described herein wherein the antagonist is an anti-GDF8 antibody, antigen binding protein or fragment thereof that specifically binds to GDF8 but does not specifically bind to BMP11, wherein the antibody or antigen binding protein is selected from the group consisting of: polyclonal antibody; a monoclonal antibody; a monospecific antibody; polyspecific antibody; humanized antibody; a tetrameric antibody; a tetravalent antibody; a multispecific antibody; a single chain antibody; a domain-specific antibody; a single domain antibody; a domain-deleted antibody; a fusion protein; an ScFc fusion protein; a single-chain antibody; chimeric antibody; synthetic antibody; recombinant antibody; hybrid antibody; mutated antibody; CDR-grafted antibodies; an antibody fragment which may include an Fab; an F(ab')2; an Fab' fragment; an Fv fragment; a single-chain Fv (ScFv) fragment; an Fd fragment; a dAb fragment; an antigen binding protein which may include diabodies; a CDR3 peptide; a constrained FR3-CDR3-FR4 peptide; a nanobody; a bivalent nanobody; small modular immunopharmaceuticals (SMIPs); a shark variable IgNAR domain; and a minibody. In some embodiments the antagonist of the invention is a monoclonal antibody. In some embodiments, the antagonist of the invention is a humanized antibody.

In some embodiments the invention provides an antagonist that is an antibody, antigen binding protein or fragment thereof that is specific for GDF8 that is comprised of at least one complementarity determining regions (CDR) comprising an amino acid sequence selected from the group consisting of: the amino acid sequence of SEQ ID NO:19, the amino acid sequence of SEQ ID NO:20, the amino acid sequence of SEQ ID NO:21, the amino acid sequence of SEQ ID NO:22, the amino acid sequence of SEQ ID NO:23, the amino acid sequence of SEQ ID NO:24, the amino acid sequence of SEQ ID NO:25, the amino acid sequence of SEQ ID NO:26, the amino acid sequence of SEQ ID NO:27, the amino acid sequence of SEQ ID NO:28, the amino acid sequence of SEQ ID NO:29, the amino acid sequence of SEQ ID NO:30.

In some embodiments the antagonist of the invention is an anti-GDF8 antibody, antigen binding protein or fragment thereof that comprises a heavy chain which comprises a first, second and third CDR, wherein the first CDR comprise an amino acid selected from the amino acid sequence of SEQ ID NO:19; and the amino acid sequence of SEQ ID NO:25, the second CDR comprises an amino acid selected from sequence of SEQ ID NO:20; and the amino acid sequence of SEQ ID NO:26 and the third CDR comprises an amino acid selected from the amino acid sequence of SEQ ID NO:21; and the amino acid sequence of SEQ ID NO:27. In some embodiments the antibody or antigen binding protein of the invention comprises a heavy chain which comprises an amino acid sequence selected from the group consisting of: the amino acid sequence of SEQ ID NO:14 and the amino acid sequence of SEQ ID NO:17.

In some embodiments, the antagonist of the invention is an anti-GDF8 antibody or antigen binding protein that comprises a light chain which comprises a first, second and third CDR, wherein the first CDR comprises an amino acid selected from the amino acid sequence of SEQ ID NO:22; and the amino acid sequence of SEQ ID NO:28, the second CDR comprises an amino acid selected from the amino acid sequence of SEQ ID NO:23; and the amino acid sequence of SEQ ID NO:29, the third CDR comprising an amino acid selected from the amino acid sequence SEQ ID NO:24; and the amino acid sequence of SEQ ID NO:30. In some embodiments the antagonist of the invention is an anti-GDF8 antibody or antigen binding protein which comprises a light chain comprising an amino acid sequence selected from the group consisting of: the amino acid sequence of SEQ ID NO:16; and the amino acid sequence of SEQ ID NO:18.

In some embodiments the antagonist of the invention is an anti-GDF8 antibody or antigen binding protein that comprises a light chain comprising the amino acid sequence of SEQ ID NO:16, and further comprises a heavy chain comprising the amino acid sequence of SEQ ID NO:14. In some embodiments the antagonist of the invention is an anti-GDF8 antibody or antigen binding protein that comprises a light chain comprising the amino acid sequence of SEQ ID NO:18, and further comprises a heavy chain comprising the amino acid sequence of SEQ ID NO:17. In some embodiments, the invention provides a polynucleotide that encodes any one or more of the amino acids comprising the GDF8 antagonist of the invention, as described herein.

In some embodiments the antagonist of the invention is an inhibitory polynucleotide that specifically binds to GDF8 and is selected from the group consisting of: an siRNA molecule and an antisense molecule. In some embodiments the invention provides any one or more of the polynucleotides described herein that encode the antagonists of the invention. In some embodiments the invention provides a polynucleotide that encodes an amino acid sequence selected from the group consisting of the amino acid sequence of SEQ ID NO:4; the amino acid sequence of SEQ ID NO:6; the amino acid sequence of SEQ ID NO:8; the amino acid sequence of SEQ ID NO:10; and the amino acid sequence of SEQ ID NO:12. In another embodiment the invention provides a polynucleotide wherein the isolated polynucleotide consists essentially of a nucleic acid sequence selected from the group consisting of: the nucleic acid sequence of SEQ ID NO:3, the nucleic acid sequence of SEQ ID NO:5, the nucleic acid sequence of SEQ ID NO:7, the nucleic acid sequence of SEQ ID NO:9, the nucleic acid sequence of SEQ ID NO:11, and the nucleic acid sequences of fragments thereof.

In some embodiments the invention provides a host cell comprising any one or more polynucleotides of the invention, wherein the polynucleotide is operably linked to a regulatory sequence. In another embodiment the invention provides a vector comprising any of the polynucleotides of the invention. In another embodiment the invention provides a host cell comprising a vector comprising any one or more of the polynucleotides of the invention.

In some embodiments the invention provides a method for producing a GDF8 antagonist from a cultured a host cell as described herein comprising any one or more of the polynucleotides of the invention and isolating the GDF8 antagonist expressed by the host cell. In yet another embodiment the invention provides an isolated GDF8 antagonist produced by the method for producing a GDF8 antagonist as described herein.

In another aspect of the invention, the invention provides an assay to detect the presence of GDF8 in a sample from a subject which comprises the following steps: combining (i) the sample with (ii) a capture reagent that specifically binds GDF8 and (iii) a detection reagent that specifically binds GDF8 and detecting whether or not specific binding occurs between the capture reagent and GDF8 wherein detection of specific binding indicates the presence of GDF8 in the sample.

In one embodiment of the invention the GDF8 in the sample is dissociated from the GDF8 binding proteins and anti-GDF8 present in the sample. In one embodiment, the assay of the invention further comprises combining the sample with an acidic buffer prior to the combination of the sample with the capture reagent, as described herein. In another embodiment the acidic buffer of the assay of the invention has a pH between about pH 1.0 and pH 6.0. In another embodiment the pH of the acidic buffer is about pH2.5.

In one embodiment, the invention provides any one or more of the assays described herein wherein the sample is selected from the group consisting of serum, whole blood, plasma, biopsy sample, tissue sample, cell suspension, saliva, oral fluid, cerebrospinal fluid, amniotic fluid, milk, colostrums, mammary gland secretion, lymph, urine, sweat, lacrimal fluid, gastric fluid, synovial fluid and mucus. In another embodiment, the invention provides that the sample is chosen from whole blood, serum or plasma.

In one embodiment, the invention provides any one or more of the assays described herein wherein the detecting step comprises at least one of a sandwich assay and a competitive binding assay. In some embodiments the detecting step comprises a sandwich assay In some embodiments, the detecting step comprises at least one of: detecting a change in refractive index at a solid optical surface in contact with the sample; detecting a change in luminescence; measuring a change in color; detecting a change in radioactivity; measuring using biolayer interferometry; measuring using cantilever-detection; measuring using label-free intrinsic Imaging; and measuring using acoustic-detection. In some embodiments, the detection step of the invention measures a change in color. In some embodiments, the detecting step comprises an assay selected from the group consisting of: an enzyme-linked immunosorbent assay (ELISA); an electro-chemiluminescent assay (ECL); radioimmunoassay (RIA); solid-phase radioimmunoassay (SPRIA); immunoblotting; immunoprecipitation; Fluorescent Activated Cell Sorting (FACS). In another embodiment the detecting step comprises and ELISA.

In one embodiment the presence of GDF8 is detected by the specific binding of a compound to the detection reagent that specifically binds GDF8 wherein the compound further comprises a detectable label. In another embodiment the detectable label comprises at least one label selected from the group consisting of an enzyme label; a luminescent label, a protein label; a vitamin label; a chromophoric label; a radioisotopic label and an electron dense molecule label. In another embodiment the detectable label is a protein label and further comprises biotin.

In one embodiment, the assay of the invention provides a capture reagent that is selected from the group consisting of an anti-GDF8 antibody, antigen binding protein or fragment thereof; a GDF8 binding protein; and a GDF8 binding domain. In another embodiment, the assay of the invention provides that the capture reagent is an anti-GDF8 antibody, antigen binding protein or fragment thereof and is selected from the group of consisting of RK35, RK22, MYO-028, MYO-029 and JA16. In some embodiments the capture reagent is RK35. In some embodiments the capture reagent is RK22.

In one embodiment of the assay of the invention provides the detection reagent is selected from the group consisting of: an anti-GDF8 antibody, antigen binding protein or fragment thereof; a GDF8 binding protein and a GDF8 binding domain. In one embodiment the detection reagent is an anti-GDF8 antibody, antigen binding protein or fragment thereof and is selected from the group consisting of: RK22 and RK35. In another embodiment, the assay of the invention provides the detection reagent is RK35. In another embodiment, the assay of the invention provides the detection reagent is RK22.

In one embodiment the invention provides an assay wherein the capture reagent is RK22 and the detection reagent is RK35. In another embodiment, the invention provides an assay wherein the capture reagent is RK35 and the detection reagent is RK22.

In another aspect of the invention, the invention provides an assay to quantitate the presence of GDF8 in a sample from a subject which comprises the following steps: combining (i) the sample with (ii) a capture reagent that specifically binds GDF8 and (iii) a detection reagent that specifically binds GDF8 detecting whether or not specific binding occurs between the capture reagent and GDF8 and quantitate the level of GDF8 in the sample, wherein detection of specific binding indicates the presence of GDF8 in the sample and can be quantitated. In one embodiment of the invention provides the GDF8 in the sample is dissociated from the GDF8 binding proteins and anti-GDF8 present in the sample. In one embodiment, the assay of the invention further comprises combining the sample with an acidic buffer prior to the combination of the sample with the capture reagent, as described herein. In another embodiment the acidic buffer of the assay of the invention has a pH between about pH 1.0 and pH 6.0. In another embodiment the pH of the acidic buffer is about pH2.5.

In another aspect of the invention, the invention provides a pharmaceutical composition for treating (which includes ameliorating, and/or preventing) a GDF8-associated disorder in a subject comprising a pharmaceutically acceptable carrier and at least one GDF8 antagonist is selected from the group consisting of a peptide mimetic of a GDF8 binding domain; an isolated nucleic acid that encodes an amino acid for a peptide mimetic of a GDF8 binding domain; an inhibitory polynucleotide specific to GDF8 and an anti-GDF8 antibody, antigen binding protein or fragment thereof that specifically binds to GDF8 and does not specifically bind to BMP11.

In one embodiment the pharmaceutical composition of the invention comprises a peptide mimetic of a binding domain specific for GDF8 consisting essentially of an amino acid sequence selected from the group consisting of the amino acid sequence of SEQ ID NO:4; the amino acid sequence of SEQ ID NO:6; the amino acid sequence of SEQ ID NO:8; the amino acid sequence of SEQ ID NO:10; and the amino acid sequence of SEQ ID NO:12.

In one embodiment the pharmaceutical composition of the invention comprises a isolated nucleic acid that encodes for an amino acid specific to GDF8 consists essentially of a nucleic acid sequence selected from the group consisting of the nucleic acid sequence of SEQ ID NO:3; the nucleic acid sequence of SEQ ID NO:5; the nucleic acid sequence of SEQ ID NO:7; the nucleic acid sequence of SEQ ID NO:9; the nucleic acid sequence of SEQ ID NO:11 and the nucleic acid sequences of fragments thereof.

In one embodiment the pharmaceutical composition of the invention comprises an anti-GDF8 antibody, antigen binding protein or fragment thereof that specifically binds with GDF8 and does not specifically bind BMP11 which comprises a light chain comprising the amino acid sequence of SEQ ID NO: 16, and wherein the antibody further comprises a heavy chain comprising the amino acid sequence of SEQ ID NO: 14. In another embodiment, the pharmaceutical composition of the invention provides an anti-GDF8 antibody, antigen binding protein or fragment thereof that specifically binds with GDF8 and does not specifically bind BMP11 comprises a light chain comprising the amino acid sequence of SEQ ID NO: 18, and wherein the antibody, antigen binding protein or fragment thereof further comprises a heavy chain comprising the amino acid sequence of SEQ ID NO: 17.

In one embodiment the pharmaceutical composition of the invention comprises an anti-GDF8 antibody or antigen binding protein that specifically binds with GDF8 and does not bind BMP11 and comprises at least one complementarity determining region (CDR) comprising an amino acid sequence selected from the group consisting of the amino acid sequence of SEQ ID NO: 19, the amino acid sequence of SEQ ID NO: 20, the amino acid sequence of SEQ ID NO:21, the amino acid sequence of SEQ ID NO:22, the amino acid sequence of SEQ ID NO:23, the amino acid sequence of SEQ ID NO:24, the amino acid sequence of SEQ ID NO:25, the amino acid sequence of SEQ ID NO:26, the amino acid sequence of SEQ ID NO:27, the amino acid sequence of SEQ ID NO:28, the amino acid sequence of SEQ ID NO:29, the amino acid sequence of SEQ ID NO:30.

In one embodiment the pharmaceutical composition of the invention is used to treat a GDF8 associated disorder selected from the group consisting of a muscle disorder, neuromuscular disorder, bone-degenerative disorder, metabolic or induced bone disorder, adipose disorder, glucose metabolism disorder, and insulin-related disorder in a mammalian patient. In another embodiment, the pharmaceutical composition of the invention wherein the GDF8 associated disorder is selected from the group consisting of muscular dystrophy, ALS, muscle atrophy, organ atrophy, carpal tunnel syndrome, frailty, congestive obstructive pulmonary disease, sarcopenia, cachexia, muscle wasting syndromes, obesity, type-2 diabetes, impaired glucose tolerance, metabolic syndromes, insulin resistance, nutritional disorders, premature gonadal failure, androgen suppression, secondary hyperparathyroidism, osteoporosis, osteopenia, osteoarthritis, low bone mass, vitamin D deficiency, and anorexia nervosa.

Another aspect of the invention provides a method of treating (which includes ameliorating and/or preventing) a GDF8-associated disorder in a mammalian patient comprising administering to the patient a therapeutically effective amount of an antagonist specific for GDF8 that has little to no toxicity. In another embodiment the method of the invention provides that the antagonist of the invention is selected from the group consisting of a peptide mimetic of a GDF8 binding domain; an isolated nucleic acid that encodes an amino acid for a peptide mimetic of a GDF8 binding domain; an inhibitory polynucleotide specific to GDF8 and an anti-GDF8 antibody, antigen binding protein or fragment thereof that specifically binds to GDF8 and does not specifically bind to BMP11.

In one embodiment the invention provides that the antagonist of the invention is a peptide mimetic of a GDF8 binding domain and the GDF8 binding domain consists essentially of an amino acid sequence selected from the group consisting of the amino acid sequence of SEQ ID NO:4; the amino acid sequence of SEQ ID NO:6; the amino acid sequence of SEQ ID NO:8; the amino acid sequence of SEQ ID NO:10; and the amino acid sequence of SEQ ID NO:12.

In one embodiment the method of treatment of the invention provides a method of treatment wherein the antagonist of the invention is a isolated nucleic acid that encodes for an amino acid specific to GDF8 consists essentially of a nucleic acid sequence selected from the group consisting of the nucleic acid sequence of SEQ ID NO:3, the nucleic acid sequence of SEQ ID NO:5, the nucleic acid sequence of SEQ ID NO:7, the nucleic acid sequence of SEQ ID NO:9, the nucleic acid sequence of SEQ ID NO:11, and the nucleic acid sequences of fragments thereof.

In one embodiment of the invention provides a method of treatment wherein the antagonist of the invention is an anti-GDF8 antibody, antigen binding protein or fragment thereof that specifically binds with GDF8 and does not specifically bind to BMP11 and comprises a light chain comprising the amino acid sequence of SEQ ID NO:16, and further comprises a heavy chain comprising the amino acid sequence of SEQ ID NO:14. In some embodiments the method of treatment of the invention provides that the antagonist of the invention is an anti-GDF8 antibody, antigen binding protein or fragment thereof that specifically binds with GDF8 and does not specifically bind to BMP11 which comprises a light chain comprising the amino acid sequence of SEQ ID NO:18, and wherein the antibody, antigen binding protein or fragment thereof further comprises a heavy chain comprising the amino acid sequence of SEQ ID NO:17. In some embodiments the method of treatment of the invention provides that the antagonist of the invention is an anti-GDF8 antibody, antigen binding protein or fragment thereof that specifically binds with GDF8 and does not specifically bind to BMP11 that comprises at least one complementarity determining region (CDR) comprising an amino acid sequence selected from the group consisting of: the amino acid sequence of SEQ ID NO:19, the amino acid sequence of SEQ ID NO:20, the amino acid sequence of SEQ ID NO:21, the amino acid sequence of SEQ ID NO:22, the amino acid sequence of SEQ ID NO:23, the amino acid sequence of SEQ ID NO:24, the amino acid sequence of SEQ ID NO:25, the amino acid sequence of SEQ ID NO:26, the amino acid sequence of SEQ ID NO:27, the amino acid sequence of SEQ ID NO:28, the amino acid sequence of SEQ ID NO:29, the amino acid sequence of SEQ ID NO:30.

In one embodiment of the invention the method of treatment of the invention provides that the GDF8-associated disorder is selected from the group consisting of a muscle disorder, neuromuscular disorder, bone-degenerative disorder, metabolic or induced bone disorder, adipose disorder, glucose metabolism disorder, and insulin-related disorder in a subject. In some embodiments of the invention the method of treatment of the invention provides that the GDF8-associated disorder is selected from the group consisting of muscular dystrophy, ALS, muscle atrophy, organ atrophy, carpal tunnel syndrome, frailty, congestive obstructive pulmonary disease, sarcopenia, cachexia, muscle wasting syndromes, obesity, type-2 diabetes, impaired glucose tolerance, metabolic syndromes, insulin resistance, nutritional disorders, premature gonadal failure, androgen suppression, secondary hyperparathyroidism, osteoporosis, osteopenia, osteoarthritis, low bone mass, vitamin D deficiency, and anorexia nervosa.

Another aspect of the invention provides a method of diagnosing, prognosing or detecting whether a subject is afflicted with a GDF8-associated disorder comprising the steps of: obtaining a first sample from the subject; combining a first sample with the antagonist of the invention; detecting the presence of GDF8 in the first sample; quantitating the level of GDF8 in the first sample; obtaining a second sample from a subject not afflicted with the GDF8-associated disorder; combining the second sample with the antagonist; detecting the level of GDF8 in the second sample; quantitating the level of GDF8 in the second sample and comparing the levels of GDF8 in the first and second samples, wherein an increase, decrease, or similarity in the level of GDF8 in the second sample compared to the first sample indicates whether the GDF8-associated disorder has changed in severity.

Another aspect of the invention provides a method of monitoring the severity of a GDF8-associated disorder comprising the steps of: (i) obtaining a first sample from the subject; (ii) combining a first sample with the antagonist as in any one of claims 1-16; (iii) detecting the presence of GDF8 in the first sample; (iv) quantitating the level of GDF8 in the first sample; (v) obtaining a second sample from a subject not afflicted with the GDF8-associated disorder; (vi) combining the second sample with the antagonist; (vii) detecting the level of GDF8 in the second sample; (viii) quantitating the level of GDF9 in the second sample and (ix) comparing the levels of GDF8 in the first and second samples, wherein an increase, decrease, or similarity in the level of GDF8 in the first sample compared to the second sample indicates whether the GDF8-associated disorder has changed in severity.

Another aspect of the invention provides a method of prognosing the likelihood that a subject will develop a GDF8-associated disorder comprising the steps of: (i) obtaining a first sample from the subject; (ii) combining a first sample with the antagonist as in any one of claims 1-16; (iii) detecting the presence of GDF8 in the first sample; (iv) quantitating the level of GDF8 in the first sample; (v) obtaining a second sample from a subject not afflicted with the GDF8-associated disorder; (vi) combining the second sample with the antagonist; (vii) detecting the level of GDF8 in the second sample; (viii) quantitating the level of GDF9 in the second sample and (ix) comparing the levels of GDF8 in the first and second samples, wherein an increase, decrease, or similarity in the level of GDF8 in the second sample compared to the first sample indicates the likelihood that the subject will develop a GDF8-associated disorder.

Another aspect of the invention provides a method of prognosing the likelihood that a subject will develop a GDF8-associated disorder comprising the steps of: (i) obtaining a first sample from the subject; (ii) combining a first sample with the antagonist as in any one of claims 1-16; (iii) detecting the presence of GDF8 in the first sample; (iv) quantitating the level of GDF8 in the first sample; (v) obtaining a second sample from a subject not afflicted with the GDF8-associated disorder; (vi) combining the second sample with the antagonist; (vii) detecting the level of GDF8 in the second sample; (viii) quantitating the level of GDF9 in the second sample and (ix) comparing the levels of GDF8 in the first and second samples, wherein an increase, decrease, or similarity in the level of GDF8 in first sample compared to the second sample indicates the likelihood that the subject will develop a GDF8-associated disorder.

Another aspect of the invention provides a use of a pharmaceutical composition in the preparation of a medicament for treating (which includes ameliorating, and/or preventing) a GDF8-associated disorder in a mammalian patient wherein the pharmaceutical composition comprises a pharmaceutically acceptable carrier and at least one GDF8 antagonist is selected from the group consisting of a peptide mimetic of a GDF8 binding domain; an isolated nucleic acid that encodes an amino acid for a peptide mimetic of a GDF8 binding domain; an inhibitory polynucleotide specific to GDF8 and an anti-GDF8 antibody, antigen binding protein or fragment thereof that specifically binds to GDF8 and does not specifically bind to BMP11.

Another aspect of the invention provides a kit for detecting the presence of GDF8 in a sample from a subject, the kit comprising a capture reagent that specifically binds GDF8 and a detection reagent that specifically binds GDF8 wherein detection of specific binding of GDF8 to the capture and detection reagents indicate the presence of GDF8 in the sample. In some embodiments the kit of the invention further comprises an acidic buffer.

Another aspect of the invention provides a kit for the quantitation of GDF8 in a sample from a subject, the kit comprising a capture reagent that specifically binds GDF8 and a detection reagent that specifically binds GDF8 wherein detection of specific binding of GDF8 to the capture and detection reagents allow quantitation of GDF8 in the sample. In some embodiments the kit of the invention further comprises an acidic buffer.

In another aspect the invention provides an antibody as described herein wherein the antibody is an anti-GDF8 antibody, antigen binding protein or fragment thereof that specifically binds to GDF8 but does not specifically bind to BMP11, wherein the antibody or antigen binding protein is selected from the group consisting of: polyclonal antibody; a monoclonal antibody; a monospecific antibody; polyspecific antibody; humanized antibody; a tetrameric antibody; a tetravalent antibody; a multispecific antibody; a single chain antibody; a domain-specific antibody; a single domain antibody; a domain-deleted antibody; a fusion protein; an ScFc fusion protein; a single-chain antibody; chimeric antibody; synthetic antibody; recombinant antibody; hybrid antibody; mutated antibody; CDR-grafted.antibodies; an antibody fragment which may include an Fab; an F(ab')2; an Fab' fragment; an Fv fragment; a single-chain Fv (ScFv) fragment; an Fd fragment; a dAb fragment; an antigen binding protein which may include diabodies; a CDR3 peptide; a constrained FR3-CDR3-FR4 peptide; a nanobody; a bivalent nanobody; small modular immunopharmaceuticals (SMIPs); a shark variable IgNAR domain; and a minibody. In some embodiments the antagonist of the invention is a monoclonal antibody. In some embodiments, the antagonist of the invention is a humanized antibody. In some embodiments the antibody is an anti-GDF8 antibody. In some embodiments the antibody of the invention is an anti-GDF8 antibody or antigen binding protein that comprises a light chain comprising the amino acid sequence of SEQ ID NO:16, and further comprises a heavy chain comprising the amino acid sequence of SEQ ID NO:14. In some embodiments the antibody of the invention is an anti-GDF8 antibody or antigen binding protein that comprises a light chain comprising the amino acid sequence of SEQ ID NO:18, and further comprises a heavy chain comprising the amino acid sequence of SEQ ID NO:17.

BRIEF DESCRIPTION THE SEQUENCES

DNA and amino acid sequences are set forth in the Seq. Listing and are enumerated in Table 1.

TABLE 1

| SEQ ID NO | DESCRIPTION |
| --- | --- |
| 1 | A.A. seq. mature human GDF8 |
| 2 | A.A. seq. human GDF8 precursor |
| 3 | DNA seq. peptide mimetic(GE1) |
| 4 | A.A. seq. peptide mimetic (GE1) |
| 5 | DNA seq. peptide mimetic (GE2) |
| 6 | A.A. seq. peptide mimetic (GE2) |
| 7 | DNA seq. peptide mimetic (GE3) |
| 8 | A.A. seq. peptide mimetic (GE3) |
| 9 | DNA seq. peptide mimetic (GE4) |
| 10 | A.A. seq. peptide mimetic (GE4) |
| 11 | DNA seq. peptide mimetic (GE5) |
| 12 | A.A. seq. peptide mimetic (GE5) |
| 13 | DNA seq. RK22 VH mouse |
| 14 | A.A. seq. RK22 VH mouse |
| 15 | DNA seq. RK22 VL mouse |
| 16 | A.A. seq. RK22 VL mouse |
| 17 | A.A. seq. RK22 VH humanized |
| 18 | A.A. seq. RK22 VL humanized |
| 19 | A.A. seq. CDR H1 (Kabat) |
| 20 | A.A. seq. CDR H2 (Kabat) |
| 21 | A.A. seq. CDR H3 (Kabat) |
| 22 | A.A. seq. CDR L1 (Kabat) |
| 23 | A.A. seq. CDR L2 (Kabat) |
| 24 | A.A. seq. CDR L3 (Kabat) |
| 25 | A.A. seq. CDR H1 (AbM) |
| 26 | A.A. seq. CDR H2 (AbM) |
| 27 | A.A. seq. CDR H3 (AbM) |
| 28 | A.A. seq. CDR L1 (AbM) |
| 29 | A.A. seq. CDR L2 (AbM) |
| 30 | A.A. seq. CDR L3 (AbM) |
| 31 | DNA seq. RK35 VH |
| 32 | DNA seq. RK35 VL |
| 33 | DNA seq. MYO-029 VH |
| 34 | DNA seq. MYO-029 VL |
| 35 | DNA seq. ActRIIB |
| 36 | A.A. seq. ActRIIB |
| 37 | A.A. seq. human DP-5 germline |
| 38 | A.A. seq. human DP-7 germline |
| 39 | A.A. seq. human DPK 24 germline |

BRIEF DESCRIPTION OF THE DRAWINGS

FIG. 2 shows the kinetic rate constants for the interaction between RK22 antibody and GDF8 as determined by BIAcore 2000 system Sensor Chip SA.

FIG. 7 shows the alignment of the RK22 variable heavy chain domain (RK22_VH) with the human germline framework sequences of DP-7 (DP-7_germl_VH) and DP-5 (DP-5_germl_VH); the amino acids of the murine RK22 variable heavy chain domain that are changed in the humanized RK22 variable heavy chain domain are designated with an asterisk and the CDRs of RK22 are boxed and underlined.

FIG. 8 shows the alignment of the RK22 variable light chain domain with the human germline framework sequence of DPK 24 VL; the amino acids of the murine RK22 variable light chain domain that are changed in the humanized RK22 variable light chain domain are designated with an asterisk and the CDRs of RK22 are boxed and underlined.

FIG. 13A shows that there is approximately 30% inhibition of signal when RK22 is used as the capture antibody. FIG. 13B shows that inhibition is nearly 100% (from 5 to 20 pg/ml of MYO-029) when RK35 is used as the capture antibody. Also shown is the reduction in background signal (serum) by the use of 2IR (also known as "IIR"). Total signal is shown in both graphs and has not been converted to percent inhibition.

FIG. 13B shows the results from a spike-recovery assay where sera, but no MYO-029, was added. The results show a linear increase in signal with the addition of GDF-8.

In FIG. 24A, GDF-8 dimer diluted in THST buffer +/−10 μg/ml of MYO-029 was diluted five-fold into either assay buffer at neutral pH (THST), 200 mM sodium acetate pH 5.0 (NaOAc), 200 mM phosphate-citrate buffer pH 3 or 7 (PO4Cit), or 200 mM glycine-HCl pH 2.5 (Gly). Samples were then diluted 1:1 into ELISA wells (coated with RK35 antibody) containing either THST buffer or non-buffered Tris. Dilution of GDF-8 with solutions of different pH and buffering capacities and the subsequent dilution into THST or non-buffered Tris allowed measurement of the efficiency of the analyte capture step at a pH range from approximately 3 to 8. Under assay conditions approaching neutral pH, MYO-029 reduced GDF-8 detection (THST/THST). GDF-8 acidified with glycine-HCl and subsequently diluted into THST buffer maintained a sufficiently low pH to prevent MYO-029 binding and allowed full detection of GDF-8 in the presence or absence of MYO-029 (Gly/THST). However, dilution of glycine-acidified GDF-8 into non-buffered Tris resulted in analyte capture conditions at pH greater than 7 and reduced detection of GDF-8 in the presence of MYO-029 (Gly/Non-buffered Tris). FIG. 24B shows a schematic of the ELISA assay at pH3 (left panel) and pH7 (right panel).

FIGS. 29B and 29C. Myostatin levels in cynomolgous monkey serum measured in the myostatin ELISA under non-dissociative (pH 8.0, panel B) or dissociative (pH 2.5, panel C) conditions following addition of increasing concentrations of anti-myostatin antibody MYO-029 or soluble myostatin receptor ActRIIB-Fc. Bars represent mean+/−SD of replicate samples (n=3). Dashed line indicates the LLQ.

FIG. 31. Changes in myostatin levels in young men in response to administration of graded doses of testosterone (bar diagram showing mean+/−SEM levels at baseline, and days 56 and 140.

FIG. 32. Regression plots showing correlation of the change in myostatin levels from baseline to day 56 and changes in total and free testosterone concentrations and lean body mass in young and older men.

DETAILED DESCRIPTION OF THE INVENTION

Definitions

Figure 1A:
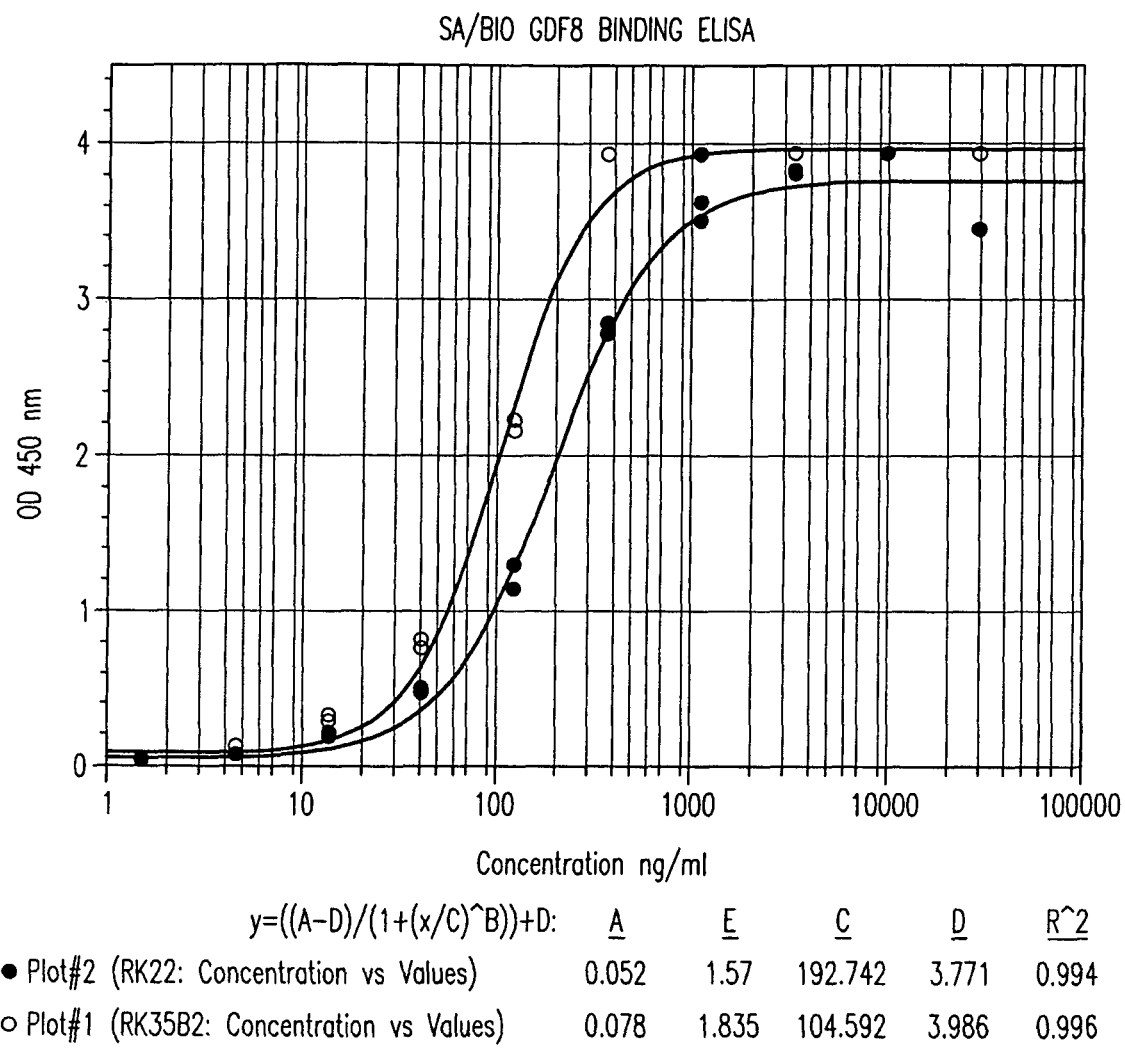
FIGS. 1A and 1B demonstrates the binding (O.D. 450 nm; y-axis) of various concentrations (ng/ml; x-axis) of supernatant from RK22 and RK35 (a control antibody that binds with both GDF8 and BMP11) expressing hybridomas to GDF8 or BMP11.

As used in the specification and the appended claims, the singular forms "a," "an" and "the" include reference to the plural unless the context clearly dictates otherwise.

The term "antibody," as used herein, refers to an immunoglobulin or a fragment thereof, and includes, but is not limited to: a polyclonal antibody, a monoclonal antibody, a monospecific antibody, polyspecific antibody, humanized antibody, a tetrameric antibody, a tetravalent antibody, a multispecific antibody, a single chain antibody, a domain-specific antibody, a single domain antibody, a domain-deleted antibody, a fusion protein, an ScFc fusion protein, a single-chain antibody, chimeric antibody, synthetic antibody, recombinant antibody, hybrid antibody, mutated antibody, CDR-grafted antibodies and antibody fragments which includes: Fab, F(ab')2, an Fab' fragment, an Fv fragment, a single-chain Fv (ScFv) fragment, an Fd fragment, and a dAb fragment or any chemically or genetically manipulated counterparts, of the foregoing that retains antigen binding function.

The invention also provides antigen binding proteins, which are different from antibodies as described herein, which include diabodies, a CDR3 peptide, a constrained FR3-CDR3-FR4 peptide, a nanobody (US patent application 2008/0107601), a bivalent nanobody, small modular immunopharmaceuticals (SMIPs), a shark variable IgNAR domain (WO 03/014161), a minibody and any fragment or chemically or genetically manipulated counterparts that retain antigen-binding function. Typically, such fragments would comprise an antigen-binding domain. As will be recognized by those of skill in the art, any of such molecules, e.g., a "humanized" antibody or antigen binding protein, may be engineered (for example "germlined") to decrease its immunogenicity, increase its affinity, alter its specificity, or for other purposes.

Antibodies of the invention can be made, for example, via traditional hybridoma techniques (Kohler et al., Nature 256: 495-499 (1975)), recombinant DNA methods (U.S. Pat. No. 4,816,567), or phage display techniques using antibody libraries (Clackson et al., Nature 352:624-628 (1991); Marks et al., J. Mol. Biol. 222:581-597 (1991)). For various other antibody production techniques, see Antibodies: A Laboratory Manual, eds. Harlow et al., Cold Spring Harbor Laboratory, 1988. The term "antigen" refers to a compound, composition, or immunogenic substance that can stimulate the production of antibodies or a T-cell response, or both, in an animal, including compositions that are injected or absorbed into an animal. The immune response may be generated to the whole molecule, or to a portion of the molecule (e.g., an epitope or hapten). The term may be used to refer to an individual macromolecule or to a homogeneous or heterogeneous population of antigenic macromolecules. An antigen reacts with the products of specific humoral and/or cellular immunity. The term "antigen" broadly encompasses moieties including proteins, polypeptides, antigenic protein fragments, nucleic acids, oligosaccharides, polysaccharides, organic or inorganic chemicals or compositions, and the like. The term "antigen" includes all related antigenic epitopes. Epitopes of a given antigen can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1986) Molec. Immunol. 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Furthermore, for purposes of the present invention, an "antigen" can also include includes modifications, such as deletions, additions and substitutions (generally conservative in nature, but they may be non-conservative), to the native sequence, so long as the protein maintains the ability to elicit an immunological response. These modifications may be deliberate, as through site-directed mutagenesis, or through particular synthetic procedures, or through a genetic engineering approach, or may be accidental, such as through mutations of hosts, which produce the antigens. Furthermore, the antigen can be derived or obtained from any virus, bacterium, parasite, protozoan, or fungus, and can be a whole organism. Similarly, an oligonucleotide or polynucleotide, which expresses an antigen, such as in nucleic acid immunization applications, is also included in the definition. Synthetic antigens are also included, for example, polyepitopes, flanking epitopes, and other recombinant or synthetically derived antigens (Bergmann et al. (1993) Eur. J. Immunol. 23:2777 2781; Bergmann et al. (1996) J. Immunol. 157:3242 3249; Suhrbier, A. (1997) Immunol. and Cell Biol. 75:402 408; Gardner et al. (1998) 12th World AIDS Conference, Geneva, Switzerland, Jun. 28 Jul. 3, 1998).

The term "antigen-binding domain," "active fragments of an antibody", or antigen binding protein or the like refers to the part of an antibody or antigen binding protein molecule that comprises the area specifically binding to or complementary to a part or all of an antigen. Where an antigen is large, an antibody may only bind to a particular part of the antigen. The "epitope," "active fragments of an epitope," or "antigenic determinant" or the like is a portion of an antigen molecule that is responsible for specific interactions with the antigen-binding domain of an antibody. An antigen-binding domain may be provided by one or more antibody variable domains (e.g., a so-called Fd antibody fragment consisting of a VH domain). An antigen-binding domain may comprise an antibody light chain variable domain (VL) and an antibody heavy chain variable domain (VH) (U.S. Pat. No. 5,565,332).

A "sample" is biological material collected from cells, tissues, organs, or organisms, for example, to detect an analyte. Exemplary biological samples include serum, blood, plasma, biopsy sample, tissue sample, cell suspension, saliva, oral fluid, cerebrospinal fluid, amniotic fluid, milk, colostrum, mammary gland secretion, lymph, urine, sweat, lacrimal fluid, gastric fluid, synovial fluid, mucus, and other clinical specimens and samples.

The term "capture reagent" refers to a reagent, for example an antibody or antigen binding protein, capable of binding a target molecule or analyte to be detected in a biological sample. Typically, the capture reagent is immobilized, for example on an assay surface, for example, a solid substrate or reaction vessel. A "GDF-8 capture reagent" specifically binds to GDF-8.

A "detection reagent" is a reagent, for example an antibody or antigen binding protein, that is used in the immunoassays of the present invention to specifically bind to a target protein, for example, GDF-8. A detection reagent may optionally comprise a detectable label. A detection reagent typically recognizes and binds the target protein at a binding site or epitope distinct from that of the capture reagent. The detection reagent may be coupled to a detectable label. A "GDF-8 detection reagent" specifically binds to GDF-8.

The term "complimentary determining region" or "CDR" refers to the hypervariable regions of an antibody or antigen binding protein molecule, consisting of three loops from the heavy chain and three from the light chain that together form the antigen binding domain.

The term "detecting" is used in the broadest sense to include both qualitative and quantitative measurements of a target analyte, herein measurements of a specific target molecule such as GDF-8 or BMP-11. The assay methods described herein can be used to identify the presence of GDF-8 or BMP-11 in a biological sample, or may be used to quantify an amount of GDF-8 or BMP-11 in a sample.

A "detection agent" or "detection reagent" may be used in the methods of the present invention to detect the signal generated from a detection antibody or antigen binding protein that comprises an indirect label. A detection agent or reagent is a protein or small molecule that allows detection of a GDF-8 modulating agent or a complex. In a preferred embodiment, the detection agent specifically binds to a GDF-8 modulating agent. A detection agent may optionally comprise a detectable label. A detection agent may also be itself detected by a substance comprising a detectable label. A GDF-8 modulating agents detected by the methods provided herein, may also be used in the methods to detect other GDF-8 modulating agents, for example.

A "disorder associated with GDF8 activity", "disorder associated with GDF8", "GDF8-associated disorder," or the like refers to a disorder that may be caused, in full or in part, by dysregulation of GDF8, (e.g., abnormally increased or decreased expression and/or activity of GDF8) and/or a disorder that may be treated, ameliorated, prevented, prognosed, and/or monitored by regulating and/or monitoring GDF8 protein and/or activity. GDF8 associated disorders include muscle disorders, neuromuscular disorders, bone-degenerative disorders, metabolic or induced bone disorders, adipose disorders, glucose metabolism disorders, or insulin-related disorders.

The term "effective dose" "therapeutically effective dose" or "effective amount" refers to a dosage or level that is sufficient to ameliorate clinical symptoms of, or achieve a desired biological outcome (e.g. increasing muscle mass, muscle strength and/or bone density) in individuals, including individuals having a GDF-8 associated disorder. Such amount would be sufficient to reduce the activity of GDF-8 associated with negative regulation of skeletal muscle mass and bone density, for example. Therapeutic outcomes and clinical symptoms may include increase in muscle mass, improved cardiovascular indicators or improved glucose metabolism regulation. A GDF-8 inhibitor can increase muscle mass, muscle strength, modulate the levels of muscle specific enzymes and/or stimulate myoblast proliferation for example. In a preferred embodiment, a GDF-8 inhibitor reduces clinical manifestations of a GDF-8 associated disorder. A GDF-8 modulating agent can modulate preadipocyte differentiation to adipocytes, decrease fat accumulation, decrease serum triglyceride levels, decrease serum cholesterol levels, modulate glucose metabolism, modulate bone density and reduce hyperglycemia. A GDF-8 inhibitor may also be administered to an individual in order to increase muscle mass, to increase or accelerate growth, including muscle growth. A therapeutically effective amount of a GDF-8 inhibitor refers to an amount which is effective, upon single or multiple dose administration to an individual at treating, preventing, curing, delaying, reducing the severity of, or ameliorating at least one symptom of a disorder or recurring disorder, or prolonging the survival of the subject beyond that expected in the absence of such treatment.

An individual with a GDF-8 associated disorder, an individual at risk for developing a GDF-8 associated disorder, an individual undergoing therapy with a GDF-8 modulating agent, and an individual who is a candidate for administration of a GDF-8 modulating agent, may be a candidate for the methods herein provided. The methods of the invention may detect or prevent a deleterious immune response, and/or assess efficacy, biological stability or suitability of use of a GDF-8 modulating agent.

An individual having, or at risk for developing a GDF-8 associated disorder such as a muscle-related disorder or a neuromuscular disorder is a candidate for the methods provided herein. Inhibition of a GDF-8 activity increases muscle tissue individuals, including those suffering from muscle-related disorders. A number of disorders are associated with functionally impaired muscle or nerve tissue, for example but not limited to muscular dystrophies, amyotrophic lateral sclerosis (ALS), sarcopenia, cachexia, muscle wasting, muscle atrophy, or frailty. Muscular dystrophies include, for example, pseudohypertrophic, facioscapulohumeral, and limb-girdle dystrophies. Exemplary muscular dystrophies include Duchennes' muscular dystrophy (Leyden-Mobius), Becker muscular dystrophy, Emery Dreifuss muscular dystrophy, limb-girdle muscular dystrophy, rigid spine syndrome, Ullrich syndrome, Fukuyama muscular dystrophy, Walker Warberg syndrome, muscle_eye_brain disease, facioscapulo-humeral muscular dystrophy (Landouzy-Dejerine), congenital muscular dystrophy, myotonic dystrophy (Steinart's Disease), and other myotonias and Gower's disease.

A GDF-8 associated muscle disorder also includes a disorder chosen from muscle degeneration associated with cardiovascular disease, or secondary to another disease or condition such as organ atrophy, organ failure, cancer, Acquired Immune Deficiency Syndrome (AIDS), bed rest, immobilization, prolonged lack of use, or other disease or condition are also included in the term.

An individual having or at risk for developing adipose tissue disorders, e.g. obesity, cardiovascular disorders (when associated with muscle loss or muscle wasting) and disorders of insulin metabolism may be a candidate. Similarly, individuals having or at risk for developing, a disorder associated with a loss of bone, including osteoporosis, especially in the elderly and/or postmenopausal women, glucocorticoid-induced osteoporosis, osteopenia, osteoarthritis, and osteoporosis-related fractures are candidates for the treatment methods provided herein. Other GDF-8 associated conditions include metabolic bone disease and disorders characterized by low bone mass such as those due to chronic glucocorticoid therapy, premature gonadal failure, androgen suppression, vitamin D deficiency, secondary hyperparathyroidism, nutritional deficiencies, and anorexia nervosa.

Examples of cardiovascular disorders include coronary artery disease (atherosclerosis), angina (including acute and unstable angina), heart attack, stroke (including ischemic stroke), hypertension associated cardiovascular diseases, heart failure, congestive heart failure, coronary artery disease, hypertension, hyperlipidemia, peripheral arterial disease, and peripheral vascular disease. Examples of disorders of insulin metabolism include conditions associated with aberrant glucose homeostasis, type 2 diabetes, prediabetes, impaired glucose tolerance, dyslipidemia, metabolic syndrome (e.g. syndrome X), and insulin resistance induced by trauma such as burns or nitrogen imbalance.

The term "GDF-8" refers to a specific growth and differentiation factor-8, and may also be called "myostatin." The term refers to the full-length unprocessed precursor form of GDF-8 as well as the mature and propeptide forms resulting from post-translational cleavage. Unless otherwise specified as "inactive," a "GDF-8 protein" retains one or more GDF-8 biological activities. The term also refers to any fragments and variants of GDF-8 that maintain at least one biological activity associated with mature GDF-8, as discussed herein, including sequences that have been modified. The amino acid sequence of mature human GDF-8 is provided in SEQ ID NO: 1 The present invention relates to GDF-8 from all vertebrate species, including, but not limited to, human, bovine, chicken, mouse, rat, porcine, ovine, turkey, baboon, and fish (for sequence information, see, e.g., McPherron et al., Proc. Nat. Acad. Sci. U.S.A. 94:12457-12461 (1997)).

The term "GDF-8 activity" refers to one or more physiologically growth-regulatory or morphogenetic activities associated with active GDF-8 protein. For example, active GDF-8 is a negative regulator of skeletal muscle mass. Active GDF-8 can also modulate the production of muscle-specific enzymes (e.g., creatine kinase), stimulate myoblast proliferation, and modulate preadipocyte differentiation to adipocytes. "GDF-8 activity" includes "GDF-8 binding activity." For example, mature GDF-8 specifically binds to the propeptide region of GDF-8, to ActRIIB, to a GDF-8 receptor, to activin, to follistatin, to follistatin-domain-containing proteins, to GASP-1, and to other proteins. A GDF-8 inhibitor, such as an antibody or antigen binding protein or portion thereof, may reduce one or more of these binding activities. The biological activities of GDF-8 are well known to those of skill in the art, see, for example, U.S. Patent Application No. 2004/0223966 at examples 5-6 and 8-12.

A "GDF-8 associated disorder" is a disorder or condition in which a subject would benefit from the administration of a GDF-8 modulator, such as a GDF-8 inhibitor. A GDF-8 associated disorder includes a medical disorder such as a muscle-related or neuromuscular disorder or condition, for example, muscular dystrophy, amyotrophic lateral sclerosis (ALS), sarcopenia, cachexia, muscle wasting, muscle atrophy, or muscle degeneration, including wasting, atrophy, or frailty. Muscular dystrophies include, for example, pseudohypertrophic, facioscapulohumera, and limb-girdle muscular dystrophies. Exemplary muscular dystrophies include Duchenne's muscular dystrophy (Leyden-Möbius), Becker muscular dystrophy, Emery Dreifuss muscular dystrophy, limb girdle muscular dystrophy, rigid spine syndrome, Ullrich syndrome, Fukuyama muscular dystrophy, Walker Warburg syndrome, muscle eye brain disease, facioscapulohumeral muscular dystrophy (Landouzy-Dejerine), congenital muscular dystrophy, myotonic dystrophy (Steinert's disease), and othermyotonias, and Gowers disease.

Muscle degeneration associated with cardiovascular disease, or secondary to another disease or condition such as organ atrophy, organ failure, cancer, Acquired Immune Deficiency Syndrome (AIDS), bed rest, immobilization, prolonged lack of use, or other disease or condition is also included in the term.

GDF-8 associated disorders also include adipose tissue disorders (e.g., obesity), cardiovascular diseases or disorders (when associated with muscle loss or muscle wasting), and disorders of insulin metabolism. GDF-8 associated disorders also include disorders associated with a loss of bone, including osteoporosis, especially in the elderly and/or postmenopausal women, glucocorticoid-induced osteoporosis, osteopenia, osteoarthritis, and osteoporosis-related fractures. Other conditions include metabolic bone diseases and disorders characterized by low bone mass, such as those due to chronic glucocorticoid therapy, premature gonadal failure, androgen suppression, vitamin D deficiency, secondary hyperparathyroidism, nutritional deficiencies, and anorexia nervosa.

Examples of cardiovascular disorders include coronary artery disease (atherosclerosis), angina (including acute angina and unstable angina), heart attack, stroke (including ischemic stroke), hypertension associated cardiovascular diseases, heart failure, congestive heart failure, coronary artery disease, hypertension, hyperlipidemia, peripheral arterial disease, and peripheral vascular disease. Examples of disorders of insulin metabolism include conditions associated with aberrant glucose homeostasis, type 2 diabetes, prediabetes, impaired glucose tolerance, dyslipidemia, metabolic syndrome (e.g., syndome X), and insulin resistance induced by trauma such as burns or nitrogen imbalance.

The terms "GDF-8 latent complex" refers to the complex of proteins formed between the mature GDF-8 homodimer and the GDF-8 propeptide. It is believed that the two GDF-8 propeptides associate with the two molecules of mature GDF-8 in the homodimer to form an inactive tetrameric complex. The latent complex may include other GDF inhibitors in place of or in addition to one or more of the GDF-8 propeptides.

The term "mature GDF-8" refers to the protein that is cleaved from the carboxy-terminal domain of the GDF-8 precursor protein. The mature GDF-8 may be present as a monomer, homodimer, or in a GDF-8 latent complex. Depending on conditions, mature GDF-8 may establish equilibrium between any or all of these different forms. In its biologically active form, the mature GDF-8 is also referred to as "active GDF-8." Biologically active GDF-8 is not in a GDF-8 latent complex. The term also refers to any fragments and variants of GDF-8 that maintain at least one biological activity associated with mature GDF-8, as discussed herein, including sequences that have been modified.

The term "GDF-8 propeptide" refers to the polypeptide that is cleaved from the amino-terminal domain of the GDF-8 precursor protein. The GDF-8 propeptide is capable of binding to the propeptide binding domain on the mature GDF-8. The GDF-8 propeptide forms a complex with the mature GDF-8 homodimer. It is believed that two GDF-8 propeptides associate with two molecules of mature GDF-8 in the homodimer to form an inactive tetrameric complex, called a "latent complex." The latent complex may include other GDF inhibitors in place of or in addition to one or more of the GDF-8 propeptides.

The term "GDF-8 modulating agent" includes any agent capable of modulating activity, expression, processing, or secretion of GDF-8, or a pharmaceutically acceptable derivative thereof. GDF-8 modulating agents will increase or decrease one or more GDF-8 activities. A GDF-8 modulator, including a "GDF-8 inhibitor," may be used to treat adipocyte disorders, glucose metabolism-related disorders, or bone disorders, for example. Biological derivatives of a GDF-8 modulating agent are encompassed by the term. In certain embodiments, a GDF-8 modulating agent or inhibitor will affect binding of GDF-8 to one or more of its physiological binding partners, including, but not limited to a receptor (e.g. ActRIIB), a follistatin-domain containing protein (e.g. follistatin, FLRG, GASP-1, GASP-2), or a GDF-8 protein such as the GDF-8 propeptide and mutants and derivatives thereof. GDF-8 modulating agents include, for example, antibodies that specifically bind to GDF-8 (including MYO-029, MYO-028, MYO-022, JA-16, and fragments and derivatives thereof), antibodies that specifically bind to a GDF-8 receptor (see, e.g., U.S. Pat. No. 6,656,475, U.S. Patent Pub. No. 2004/0077053-A1), modified soluble receptors (including receptor fusion proteins, such as an ActRIIB-Fc fusion protein), other proteins that specifically bind to GDF-8 or BMP-11 (such as the GDF-8 or BMP-11 propeptide, mutants and derivatives of the GDF-8 propeptide, follistatin, follistatin-domain containing proteins, and Fc fusions of these proteins), proteins binding to the GDF-8 receptor and Fc fusions of these proteins, and mimetics are included. Non-proteinaceous inhibitors (such as nucleic acids) are also encompassed by the term GDF-8 inhibitor. GDF-8 inhibitors include proteins, antibodies, peptides, peptidomimetics, ribozymes, antisense oligonucleotides, double-stranded RNA (including siRNA or microRNA) and other small molecules, which specifically inhibit GDF-8.

The term "individual" refers to any vertebrate animal, including a mammal, bird, reptile, amphibian, or fish. The term "mammal" includes any animal classified as such, male or female, including humans, non-human primates, monkeys, dogs, horses, cats, sheep, pigs, goats, cattle, etc. Examples of non-mammalian animals include chicken, turkey, duck, goose, fish (such as salmon, catfish, bass, zebrafish, and trout), and frogs. An individual may be chosen from humans, or domesticated, feedstock, livestock, zoo, sports, racing, or pet animals, for example.

The terms "inhibit" and "inhibitory" refer to a reduction is one or more activities of GDF-8 by a GDF-8 inhibitor, relative to the activity of GDF-8 in the absence of the same inhibitor. The reduction in activity is preferably at least about 20%, 30%, 40%, 50%, 60%, 70%, 80%, 90% or higher. In certain embodiments, the activity of GDF-8 when affected by one or more of the presently disclosed inhibitors, is reduced at least 50%, preferable at least about 60%, 62%, 64%, 66%, 68%, 70%, 72%, 74%, 76%, 78%, 80%, 82%, 84%, 86%, 88%, 90%, 92%, 94%, 96%, 98% or 99%, and even more preferable at least 95% to 100%. The terms "neutralize" and "neutralizing" refer to a reduction one or more GDF-8 activities by at least 80%, 85%, 90% or 95%. Inhibition of GDF-8 activity can be measured for example, in the pGL3(CAGA)12 reporter gene assays as described in Thies et al. Growth Factors 18:251-259 (2001) or in ActRIIB receptor assays as illustrated in the Examples below.

The term "isolated" refers to a molecule that is substantially separated from its natural environment. For instance, an isolated protein is one that is substantially separated from the cell or tissue source from which it is derived.

A label may also be an enzyme, for example an enzyme that converts a substrate, such as a peroxidase (e.g., horseradish peroxidase), alkaline phosphatase, glucose oxidase, and β-galactosidase. Peroxidase, when incubated with soluble substrates (e.g., 3,3',5,5' tetramethylbenzidine (TMB), o-phenylenediamine (OPD), 2,2'-azino-di[3-ethyl-benzthiazoline] sulfonate (ABTS), luminol, polyphenols, acridine esters, and luciferin), results in a chromogenic or luminescent change in the substrate that can be detected spectroscopically. Typically, after a fixed incubation period with the substrate, the reaction is quenched (e.g., by acidification), and the result is quantified by measuring optical density (absorbance) or luminescence. Absorbance results can be compared with the OD values in the linear range for chomogenic reactions, and luminescent immunoassays are measured in relative light units (RLU).

A label may also be biotin, a hapten, or an epitope tag (e.g., histidine, HA (hemagglutinin peptide), maltose binding protein, AviTag®, or glutathione-S-transferase), which can be detected by the addition of a labeled detection agent that interacts with the label associated with the GDF 8 modulating agent or detection agent. A biotin-labeled ("biotinylated") detection agent may be detected through its interaction with an avidin-enzyme conjugate, e.g., avidin-horseradish peroxidase, after sequential incubation with the avidin-enzyme conjugate and a suitable chromogenic or luminescent substrate. Europium is also a label.

The term "peptide mimetic", as used herein, refers to a peptide that biologically mimics active determinants on hormones, cytokines, enzyme substrates, viruses or other biomolecules, and may antagonize, stimulate, or otherwise modulate the physiological activity of a natural ligand. Peptide mimetic are preferably defined as compounds which have a secondary structure like a peptide and optionally further structural characteristics; their mode of action is largely similar or identical to the mode of action of the native peptide however their activity (e.g. as an antagonist or an inhibitor) can be modified as compared with the native peptide especially receptors or enzymes. Moreover, they can imitate the effect of the native peptide (agonist). Throughout this specification the term "peptide mimetic" refers to a molecule which because of its structural properties is capable of mimicking the biological functions of either functional GDF8 or non-functional GDF8. In the present invention, a fragment of GDF8 that comprises a binding/dimerization domain of GDF8 is proposed to function as a dominant negative to GDF8. A peptide mimetic, per se, of a binding/dimerization domain of GDF8 could be present in multimolar excess and can "outcompete" wild type GDF8 and form heterodimers with the wild type molecules thereby acting as a dominant negative of the biological function of GDF8. In this sense, GDF8 function would be disrupted thus relieving the inhibition of muscle growth. One example of an in vivo biological assay of such growth promoting GDF8 mimetic activity is the enhancement of skeletal muscle mass in normal mice or other test animal by administration of an effective amount of at lest one growth promoting mimetic of the present invention.

The term "purified" refers to a molecule that is substantially free of other material that associates with the molecule in its natural environment. For instance, a purified protein is substantially free of the cellular material or other proteins from the cell or tissue from which it is derived. The term refers to preparations where the isolated protein is sufficiently pure to be administered as a therapeutic composition, or at least 70% to 80% (w/w) pure, more preferably, at least 80%-90% (w/w) pure, even more preferably, 90-95% pure; and, most preferably, at least 95%, 96%, 97%, 98%, 99%, or 100% (w/w) pure.

The term "siRNA", as used herein, refers to small interfering RNA molecules that can be used to silence the expression of target genes. The siRNA can be dsRNA having 19-25 nucleotides. siRNAs can be produced endogenously by degradation of longer dsRNA molecules by an RNase III-related nuclease called Dicer. siRNAs can also be introduced into a cell exogenously, or by transcription of an expression construct. Once formed, the siRNAs assemble with protein components into endoribonucleases-containing complexes known as RNA-induced silencing complexes (RISCs). An ATP-generated unwinding of the siRNA activates the RISCs, which in turn target the complementary mRNA transcript by Watson-Crick base-pairing, thereby cleaving and destroying the mRNA. Cleavage of the mRNA takes place near the middle of the region bound by the siRNA strand. This sequence specific mRNA degradation results in gene silencing.

At least two ways can be employed to achieve siRNA-mediated gene silencing. First, siRNAs can be synthesized in vitro and introduced into cells to transiently suppress gene expression. siRNAs are duplexes of short mixed oligonucleotides which can include, for example, 19 RNAs nucleotides with symmetric dinucleotide 3' overhangs. Using synthetic 21 bp siRNA duplexes (e.g., 19 RNA bases followed by a UU or dTdT 3' overhang), sequence specific gene silencing can be achieved in mammalian cells. These siRNAs can specifically suppress targeted gene translation in mammalian cells without activation of DNA-dependent protein kinase (PKR) by longer double-stranded RNAs (dsRNA), which may result in non-specific repression of translation of many proteins.

Second, siRNAs can be expressed in vivo from vectors. This approach can be used to stably express siRNAs in cells or transgenic animals. siRNA expression vectors are engineered to drive siRNA transcription from polymerase III (pol III) transcription units. Pol III transcription units are suitable for hairpin siRNA expression because they deploy a short AT rich transcription termination site that leads to the addition of 2 bp overhangs (e.g., UU) to hairpin siRNAs—a feature that is helpful for siRNA function. The Pol III expression vectors can also be used to create transgenic mice that express siRNA.

siRNAs can be also be expressed in a tissue-specific manner. Under this approach, long dsRNAs are first expressed from a promoter (such as CMV (pol II)) in the nuclei of selected cell lines or transgenic mice. The long dsRNAs are processed into siRNAs in the nuclei (e.g., by Dicer). The siRNAs exit from the nuclei and mediate gene-specific silencing. A similar approach can be used in conjunction with tissue-specific (pol II) promoters to create tissue-specific knockdown mice.

The term "small molecule" refers to compounds that are not macromolecules. See, e.g., Karp, (2000) *Bioinformatics Ontology* 16:269-85; Verkman, (2004) *AJP-Cell Physiol.* 286:465-74. Thus, small molecules are often considered those compounds that are less than one thousand daltons (e.g., Voet and Voet, *Biochemistry*, 2nd ed., ed. N. Rose, Wiley and Sons, New York, 14 (1995). For example, Davis et al. ((2005) *Proc. Natl. Acad. Sci. USA* 102:5981-86), use the phrase small molecule to indicate folates, methotrexate, and neuropeptides, while Halpin and Harbury ((2004) *PLos Biology* 2:1022-30), use the phrase to indicate small molecule gene products, i.e., DNAs, RNAs and peptides. Examples of natural small molecules include cholesterols, neurotransmitters, and siRNAs; synthesized small molecules include various chemicals listed in numerous commercially available small molecule databases, e.g., FCD (Fine Chemicals Database), SMID (Small Molecule Interaction Database), ChEBI (Chemical Entities of Biological Interest), and CSD (Cambridge Structural Database) (see, e.g., Alfarano et al. (2005) *Nuc. Acids Res. Database Issue* 33:D416-24).

The terms "specific binding," "specifically binds," and the like, mean that two or more molecules form a complex that is measurable under physiologic or assay conditions and is selective. An antibody or antigen binding protein or other inhibitor is said to "specifically bind" to a protein if, under appropriately selected conditions, such binding is not substantially inhibited, while at the same time non-specific binding is inhibited. Specific binding is characterized by a high affinity and is selective for the compound or protein. Nonspecific binding usually has a low affinity. Binding in IgG antibodies for example is generally characterized by an affinity of at least about $10^{-7}$ M or higher, such as at least about $10^{-8}$ M or higher, or at least about $10^{-9}$ M or higher, or at least about $10^{-10}$ or higher, or at least about $10^{-11}$ M or higher, or at least about $10^{-12}$ M or higher. The term is also applicable where, e.g., an antigen-binding domain is specific for a particular epitope that is not carried by numerous antigens, in which case the antibody or antigen binding protein carrying the antigen-binding domain will generally not bind other antigens.

Certain methods require high affinity for specific binding, whereas other methods, such as a surface plasmon resonance assay, may detect less stable complexes and lower affinity interactions. If necessary, non-specific binding can be reduced without substantially affecting specific binding by varying the binding conditions. Such conditions are known in the art, and a skilled artisan using routine techniques can select appropriate conditions. The conditions are usually defined in terms of concentration of the binding partners, ionic strength of the solution, temperature, time allowed for binding, concentration of non-related molecules (e.g., serum albumin, milk casein), etc. Exemplary binding conditions are set forth in the Examples below.

The term "specific GDF8 antagonist" or "specific GDF8 inhibitor" includes any agent capable of inhibiting, reducing and/or neutralizing activity, expression, processing, or secretion of GDF8 but does not significantly inhibit, reduce and/or neutralize the activity, expression, processing, or secretion of other proteins, e.g., of the TGF-β superfamily, e.g., BMP11. Such inhibitors include macromolecules and small molecules, e.g., proteins, antibodies, peptides, peptidomimetics, siRNA, ribozymes, anti-sense oligonucleotides, double-stranded RNA, and other small molecules, that specifically inhibit GDF8 activity. Such inhibitors are said to specifically "antagonize", (e.g., "inhibit," "decrease," "reduce" or "neutralize") the biological activity of GDF8. A GDF-8 inhibitor will inhibit or neutralize or reduce at least one biological acitivy of GDF-8, such as a physiological, growth-regulatory, or morphogenic activity associated with active GDF-8 protein. For example, GDF-8 is a negative regulator of skeletal muscle growth. A GDF-8 inhibitor can increase muscle mass, increase muscle strength, modulate the levels of muscle specific enzymes, stimulate myoblast proliferation, modulate preadipocyte differentiation to adipocytes, decrease fat accumulation, decrease serumtriglyceride levels, decrease serum cholesterol levels, modulate glucose metabolism and/or reduce hyperglycemia.

The term "treatment" is used interchangeably herein with the term "therapeutic method" and refers to both therapeutic treatment and prophylactic/preventative measures. The term treatment is also defined as being able to ameliorate, treat or prevent a disorder. Those in need of treatment may include individuals already having a particular medical disorder as well as those who may ultimately acquire the disorder (i.e., those needing preventive measures).

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, et al., Molecular Cloning; A Laboratory Manual, Second Edition (1989); DNA Cloning, Volumes I And II (D. N Glover ed. 1985); Oligonucleotide Synthesis (M. J. Gait ed., 1984); Nucleic Acid Hybridization (B. D. Hames & S. J. Higgins eds. 1984); Transcription And Translation (B. D. Hames & S. J. Higgins eds. 1984); Animal Cell Culture (R. I. Freshney ed. 1986); Immobilized Cells And Enzymes (IRL Press, 1986); B. Perbal, A Practical Guide To Molecular Cloning (1984); the series, Methods In Enzymology (Academic Press, Inc.); Gene Transfer Vectors For Mammalian Cells (J. H. Miller and M. P. Calos eds. 1987, Cold Spring Harbor Laboratory), Methods in Enzymology Vol. 154 and Vol. 155 (Wu and Grossman, and Wu, eds., respectively), Mayer and Walker, eds. (1987), Immunochemical Methods In Cell And Molecular Biology (Academic Press, London), Scopes, (1987), Protein Purification: Principles And Practice, Second Edition (Springer-Verlag, N.Y.), and Handbook Of Experimental Immunology, Volumes I IV (D. M. Weir and C. C. Blackwell eds. (1986).

Epitopes Specific to GDF8 and Antagonists Thereto

Epitope mapping using specific GDF8 antibodies and overlapping 13 amino acid peptides of human GDF8 revealed candidate epitopes specific to GDF8 that may be targeted for the specific antagonism of GDF8 (Example 4.2). Based on this approach, five independent epitope(s) specific to GDF8 were identified. The present invention provides these epitopes (including peptide mimetics thereof), polynucleotides encoding the epitopes, inhibitory polynucleotides thereto, and antibodies related thereto as specific antagonists to GDF8 activity.

Epitopes Specific to GDF8 and Peptide Mimetics Thereof

The present invention provides novel isolated and purified polypeptides homologous to epitopes, which may be biologically characterized as being specific to GDF8, and thus, are referred to herein as epitope(s) specific to GDF8. It is part of the invention that peptide mimetics of these GDF8 specific epitopes may be used as GDF8 antagonists, i.e., to antagonize GDF8 activity, e.g., GDF8 binding to its receptor.

For example, the invention provides purified and isolated polynucleotides encoding five binding domains specific to GDF8 (which may include ALK4/ALK4 receptor binding sites of GDF8), and which may also function as GDF8 receptor antagonists/peptide mimetics, herein designated "GE1," "GE2," "GE3," "GE4," and "GE5." Nucleic acid according to the present invention may comprise DNA or RNA and may be wholly or partially synthetic. Reference to a nucleotide sequence as set out herein encompass DNA molecules with the specified sequences or genomic equivalents (e.g., complementary sequences), as well as RNA molecules with the specified sequences where T is substituted with U, unless context requires otherwise. Preferred DNA sequences of the invention include genomic and cDNA sequences and chemically synthesized DNA sequences.

Nucleotide sequences of cDNAs encoding human GE1, GE2, GE3, GE4, and GE5, designated human cDNA, are set forth as SEQ ID NOs:3, 5, 7, 9, and 11, respectively. Polynucleotides of the present invention also include polynucleotides that hybridize under stringent conditions to polynucleotides having and/or consisting essentially of the nucleotide sequences set forth as SEQ ID NOs: 3, 5, 7, 9, and 11, or complements thereof, and/or encode polypeptides that retain substantial biological activity of GE1, GE2, GE3, GE4, or GE5, respectively. Polynucleotides of the present invention also include continuous portions of the nucleotide sequences set forth as SEQ ID NOs: 3, 5, 7, 9, and 11 comprising at least 12 consecutive nucleotides.

The amino acid sequences of human GE1, GE2, GE3, GE4, GE5, and mimetic polypeptides thereto are set forth as SEQ ID NOs: 4, 6, 8, 10 and 12, respectively. Polypeptides of the present invention also include polypeptides with an amino acid sequence having and/or consisting essentially of continuous portions of any of the sequences set forth as SEQ ID NOs: 4, 6, 8, 10 and 12, comprising at least 4 consecutive amino acids. Polypeptides of the invention also include any of the sequences set forth as SEQ ID NOs: 4, 6, 8, 10 and 12, including continuous portions thereof, wherein one or more of the L-amino acids are replaced with their corresponding D-amino acids. Polypeptides of the present invention also include active fragments of SEQ ID NOs: 4, 6, 8, 10 and 12, i.e., any continuous portion of any of the sequences set forth as SEQ ID NOs: 4, 6, 8, 10 and 12 that retains substantial biological activity of full-length human GE1, GE2, GE3, GE4, or GE5, i.e., any fragment of SEQ ID NOs: 4, 6, 8, 10 and 12 that is an binding domain specific for GDF8 and/or to which a mimetic peptide thereto may be a specific antagonist to GDF8 activity. Additionally, a polypeptide of the invention may be acetylated and/or amide blocked using well-known methods. Polynucleotides of the present invention also include, in addition to those polynucleotides described above, polynucleotides that encode any of the amino acid sequences set forth as SEQ ID NOs: 4, 6, 8, 10 and 12 and continuous portions thereof, and that differ from the polynucleotides of human origin described above only due to the well-known degeneracy of the genetic code.

The invention also provides purified and isolated polynucleotides encoding cyclized mimetic peptides to the epitope(s) specific to GDF8, e.g., GE1, GE2, GE3, GE4, and GE5. Preferred DNA sequences of the invention include genomic and cDNA sequences and chemically synthesized DNA sequences. One of skill in the art will recognize that the present invention also includes other cyclized molecules, such as cyclized mimetic peptides based on other binding domains specific to GDF8. Additionally, a cyclized mimetic peptide of the invention may be acetylated and/or amide blocked using well-known methods.

Antibodies Specific to GDF8

The present disclosure provides novel antibodies (e.g., antibody or antigen binding protein fragments) that specifically interact with GDF8. Nonlimiting illustrative embodiments of such antibodies are termed RK22. The antibodies of the invention possess unique and beneficial characteristics. First, these antibodies are capable of binding mature GDF8 with high affinity (Example 2). Second, the disclosed antibodies specifically interact with GDF8, i.e., the antibodies of the invention do not bind with high affinity to other members of the TGF-β subfamily, e.g., BMP11 (Example 2). Third, the antibodies of the invention inhibit GDF8 activity in vitro and in vivo as demonstrated (Example 3). Fourth, the disclosed antibodies may inhibit GDF8 activity associated with negative regulation of skeletal muscle mass and bone density (Example 3).

In one embodiment, the presently disclosed antibodies are capable of specifically interacting with GDF8; i.e., it is contemplated that the antibodies will not extensively react with other proteins, for example, those belonging to the TGF-β superfamily such as BMP11, activin, mullerian-inhibiting substance, glial-derived neurotrophic factor, or growth and differentiation factors other than GDF8. In one non-limiting embodiment of the invention, a specific GDF8 antibody or antigen binding protein of the invention binds GDF8 with 5-10 fold greater preference than it binds BMP11. In a nonlimiting embodiment of the invention, a specific anti-GDF8 antibody or antigen binding protein of the invention binds GDF8 with 10-100 fold greater preference than it binds BMP11. In one nonlimiting embodiment of the invention, a specific anti-GDF8 antibody or antigen binding protein of interest binds GDF8 with 100-1000 fold greater preference than it binds BMP11. In another embodiment, a specific anti-GDF8 antibody or antigen binding protein of the invention binds to epitope(s) specific to GDF8, including those disclosed herein (e.g., epitope(s) specific to GDF8 having and/or consisting essentially of an amino acid sequence set forth as SEQ ID NOs.: 4, 6, 8, and 12, or active fragments thereof). In one embodiment of the invention, the contemplated antibodies specifically interact with the predicted ALK4/ALK5 binding site of mature GDF8, e.g., GDF8 epitopes with an amino acid sequence set forth as SEQ ID NOs:4, 6 or 8.

One of ordinary skill in the art will recognize that the antibodies of the invention may be used to detect, measure, and inhibit GDF8 proteins derived from various species, e.g., those described in the present specification. The percent identity is determined by standard alignment algorithms such as, for example, Basic Local Alignment Tool (BLAST) described in Altschul et al. ((1990) *J. Mol. Biol.* 215:403-10), the algorithm of Needleman et al. ((1970) *J. Mol. Biol.* 48:444-53), or the algorithm of Meyers et al. ((1988) *Comput. Appl. Biosci.* 4:11-17). In general, the antibodies and antibody or antigen binding protein fragments of the invention can be used with any protein that retains substantial GDF8 biological activity and comprises an amino acid sequence that is at least about 70%, 80%, 90%, 95%, or more identical to any sequence of at least 100, 80, 60, 40, 20, or 15 contiguous amino acids of the mature form of GDF8 set forth as SEQ ID NO:1.

Intact antibodies, also known as immunoglobulins, are typically tetrameric glycosylated proteins composed of two light (L) chains of approximately 25 kDa each, and two heavy (H) chains of approximately 50 kDa each. Two types of light chain, termed lambda and kappa, exist in antibodies. Depending on the amino acid sequence of the constant domain of heavy chains, immunoglobulins are assigned to five major classes: A, D, E, G, and M, and several of these may be further divided into subclasses (isotypes), e.g., IgG1, IgG2, IgG3, IgG4, IgA1, and IgA2. Each light chain is composed of an N-terminal variable (V) domain (VL) and a constant (C) domain (CL). Each heavy chain is composed of an N-terminal V domain (VH), three or four C domains (CHs), and a hinge region. The CH domain most proximal to VH is designated CH1. The VH and VL domains consist of four regions of relatively conserved sequences named framework regions (FR1, FR2, FR3, and FR4), which form a scaffold for three regions of hypervariable sequences (complementarity determining regions, CDRs). The CDRs contain most of the residues responsible for specific interactions of the antibody or antigen binding protein with the antigen. CDRs are referred to as CDR1, CDR2, and CDR3. Accordingly, CDR constituents on the heavy chain are referred to as H1, H2, and H3, while CDR constituents on the light chain are referred to as L1, L2, and L3. CDR3 is the greatest source of molecular diversity within the antibody or antigen binding protein-binding site. H3, for example, can be as short as two amino acid residues or greater than 26 amino acids. The subunit structures and three-dimensional configurations of different classes of immunoglobulins are well known in the art. For a review of the antibody structure, see Antibodies: A Laboratory Manual, Cold Spring Harbor Laboratory, Eds. Harlow et al., 1988. One of skill in the art will recognize that each subunit structure, e.g., a CH, VH, CL, VL, CDR, and/or FR structure, comprises active fragments. For example, active fragments may consist of the portion of the VH, VL, or CDR subunit that binds the antigen, i.e., the antigen-binding fragment, or the portion of the CH subunit that binds to and/or activates an Fc receptor and/or complement.

Nonlimiting examples of binding fragments encompassed within the term "antibody or antigen binding protein fragment" used herein include: (i) an Fab fragment, a monovalent fragment consisting of the VL, VH, CL and CH1 domains; (ii) an F(ab')2 fragment, a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment, which consists of a VH domain; and (vi) an isolated CDR. Furthermore, although the two domains of the Fv fragment, VL and VH, are coded for by separate genes, they may be recombinantly joined by a synthetic linker, creating a single protein chain in which the VL and VH domains pair to form monovalent molecules (known as single chain Fv (scFv)). The most commonly used linker is a 15-residue (Gly4Ser)$_3$ peptide, but other linkers are also known in the art. Single chain antibodies are also intended to be encompassed within the terms "antibody or antigen binding protein," or "antigen-binding fragment" of an antibody.

These antibodies are obtained using conventional techniques known to those skilled in the art, and the fragments are screened for utility in the same manner as intact antibodies. Antibody diversity is created by multiple germline genes encoding variable domains and a variety of somatic events. The somatic events include recombination of variable gene segments with diversity (D) and joining (J) gene segments to make a complete VH domain, and the recombination of variable and joining gene segments to make a complete VL domain. The recombination process itself is imprecise, resulting in the loss or addition of amino acids at the V(D)J junctions. These mechanisms of diversity occur in the developing B cell prior to antigen exposure. After antigenic stimulation, the expressed antibody genes in B cells undergo somatic mutation. Based on the estimated number of germline gene segments, the random recombination of these segments, and random VH-VL pairing, up to $1.6 \times 10^7$ different antibodies may be produced (Fundamental Immunology, 3rd ed. (1993), ed. Paul, Raven Press, New York, N.Y.). When other processes that contribute to antibody diversity (such as somatic mutation) are taken into account, it is thought that upwards of $1 \times 10^{10}$ different antibodies may be generated (Immunoglobulin Genes, 2nd ed. (1995), eds. Jonio et al., Academic Press, San Diego, Calif.). Because of the many processes involved in generating antibody diversity, it is unlikely that independently derived monoclonal antibodies with the same antigen specificity will have identical amino acid sequences.

Thus, the present invention provides novel antibodies that specifically interact with GDF8 i.e., specific GDF8 antibodies. The antibody or antigen binding protein fragments of the invention, e.g., structures containing a CDR, will generally be an antibody or antigen binding protein heavy or light chain sequence, or an active fragment thereof, in which the CDR is placed at a location corresponding to the CDR of naturally occurring VH and VL. The structures and locations of immunoglobulin variable domains, e.g., CDRs, may be defined using well-known numbering schemes, e.g., the Kabat numbering scheme, the Chothia numbering scheme, a combination of Kabat and Chothia (AbM), etc. (see, e.g., Sequences of Proteins of Immunological Interest, U.S. Department of Health and Human Services (1991), eds. Kabat et al.; Al-Lazikani et al. (1997) *J. Mol. Bio.* 273:927-948).

Thus, the present invention further provides novel CDRs. The structure for carrying a CDR of the invention will generally be a polypeptide, e.g., an antibody or antigen binding protein heavy or light chain sequence or a substantial portion thereof, in which the CDR is located at a position corresponding to the CDR of naturally occurring VH and VL domains. The structures and locations of immunoglobulin variable domains may be determined as described in, e.g., Kabat et al., supra and Al-Lazikani et al., supra.

Antibody or antigen binding protein molecules capable of specifically interacting with the polypeptides of the present invention may be produced by methods well known to those skilled in the art. For example, monoclonal antibodies can be produced by generation of hybridomas in accordance with known methods. Hybridomas formed in this manner are then screened using standard methods, such as enzyme-linked immunosorbent assay (ELISA) and Biacore analysis, to identify one or more hybridomas that produce an antibody that specifically interacts with GDF8 (e.g., binds GDF8) and/or antagonizes (e.g., inhibits, reduces, and/or neutralizes) at least one GDF8 activity, (e.g., GDF8 binding to its receptor or other downstream GDF8 signaling events)).

Recombinant GDF8, naturally occurring GDF8, and antigenic peptide fragments of GDF8 may be used as the immunogen. An antigenic peptide fragment comprises at least six contiguous amino acids and encompasses an epitope such that an antibody raised against it forms a specific immune complex with GDF8. Preferably, the antigenic peptide comprises at least four amino acids residues. Additionally, it is preferable that the antigenic peptide fragment of GDF8 comprises an epitope specific to GDF8 (e.g., a peptide having and/or consisting essentially of an amino acid sequence set forth as SEQ ID NOs: 4,6,8,10, 12, or active fragments transfer).

In one embodiment of the invention, a full-length GDF8 polypeptide may be used as the immunogen, or, alternatively, antigenic peptide fragments of the polypeptide may be used. For example, the immunogen may be a GDF8 specific epitope (e.g., an epitope specific to GDF8, and/or an epitope of which specific anti-GDF8 antibodies and/or mimetic peptides directed thereto are specific antagonists of GDF8 signaling (e.g., one or more of the amino acid sequences of SEQ ID NOs: 4,6,8,10, 12, and active fragments thereof)) and/or a related peptide or cyclized peptide. An antigenic peptide of a polypeptide of the present invention comprises at least four continuous amino acid residues and encompasses an epitope such that an antibody raised against the peptide forms a specific immune complex with the polypeptide. Preferably, the antigenic peptide comprises at least four amino acid residues, more preferably at least six amino acid residues, and even more preferably at least nine amino acid residues.

As an alternative to preparing monoclonal antibody-secreting hybridomas, a monoclonal antibody to a polypeptide of the present invention may be identified and isolated by screening a recombinant combinatorial immunoglobulin library (e.g., an antibody phage display library) with a polypeptide of the present invention to thereby isolate immunoglobulin library members that bind to the polypeptide. Techniques and commercially available kits for generating and screening phage display libraries are well known to those skilled in the art. Additionally, examples of methods and reagents particularly amenable for use in generating and screening antibody or antigen binding protein display libraries can be found in the literature.

Polyclonal sera and antibodies may be produced by immunizing a suitable subject with GDF8, its variants, and/or portion thereof, e.g., with a specific GDF8 epitope of the present invention. The antibody titer in the immunized subject may be monitored over time by standard techniques, such as with ELISA, or by using immobilized GDF8 or other marker protein (e.g., FLAG). If desired, the antibody molecules directed against a polypeptide of the present invention may be isolated from the subject or culture media and further purified by well known techniques, such as protein A chromatography, to obtain an IgG fraction.

Additionally, chimeric, humanized, and single-chain antibodies to the polypeptides of the present invention, comprising both human and nonhuman portions, may be produced using standard recombinant DNA techniques. Humanized antibodies may also be produced using transgenic mice that are incapable of expressing endogenous immunoglobulin heavy and light chain genes, but that can express human heavy and light chain genes.

Antibody or antigen binding protein molecules (which includes fragments) of the present invention (e.g., antibody or antigen binding protein molecules that specifically interact with GDF8) include, but are not limited to, monoclonal RK22 antibody, variants thereof (e.g., humanized variants) and fragments thereof. Antibody or antigen binding protein molecules of the invention that specifically interact with GDF8 may also be specific GDF8 antagonists, and thus, these antibody or antigen binding protein molecules may be useful in preventing or treating GDF8 associated disorders, e.g., bone, muscle, adipose and glucose metabolism-related pathologies.

Thus, the invention also provides purified and isolated polynucleotides encoding the regions of specific GDF8 antibodies that may antagonize at least one GDF8 activity e.g., RK22 and variants thereof. Preferred DNA sequences of the invention include genomic, cDNA, and chemically synthesized DNA sequences. As discussed above, the polynucleotides encoding regions of an antibody or antigen binding protein of the invention may comprise DNA or RNA and may be wholly or partially synthetic. Reference to a nucleotide sequence as set out herein encompass DNA molecules with the specified sequences or genomic equivalents (e.g., complementary sequences), as well as RNA molecules with the specified sequence where T is substituted with U, unless context requires otherwise.

The nucleotide sequences of the invention include those that encode the light chain variable domain of murine RK22, e.g., the nucleotide sequence set forth as SEQ ID NO:15. The nucleotide sequences of the invention also include those that encode the heavy chain variable domain of murine RK22, e.g., the nucleotide sequence set forth as SEQ ID NO:13. Polynucleotides of the present invention also include polynucleotides that hybridize under stringent conditions to polynucleotides having and/or consisting essentially of the nucleic acid sequence(s) substantially set forth as SEQ ID NOs: 13 and 15, and complements thereof, and/or that encode polypeptides that retain substantial biological activity (i.e., active fragments) of the variable domains of RK22. Polynucleotides of the present invention also include continuous portions of the sequence set forth as SEQ ID NOs: 13 and 15, comprising at least 15 consecutive nucleotides.

The amino acid sequence of the light chain variable domains of murine RK22 is set forth as SEQ ID NO: 16. The amino acid sequences of the heavy chain variable domains of murine RK22 is set forth as SEQ ID NO: 14. The amino acid sequence of humanized variable heavy and light chain domains are set out in SEQ ID NOs: 17 and 18, respectively. The amino acid sequences of the CDRs contained within the heavy chains of murine RK22 are set forth as SEQ ID NOs: 19-21 and 25-27. The amino acid sequences of the CDRs contained within the light chains of murine RK22 are set forth as SEQ ID NOs: 22-24 and 28-30. Polypeptides of the present invention also include continuous portions of any of the sequences substantially set forth as SEQ ID NOs: 14, 16, 17, 18, and 19-30 comprising at least 5 consecutive amino acids. A preferred polypeptide of the present invention includes active fragments as SEQ ID NOs: 14, 16, 17, 18, and 19-30, i.e., any continuous portion of any sequence set forth as SEQ ID NOs: 14, 16, 17, 18, and 19-30 retaining substantial biological activity of an antibody or antigen binding protein of the invention. In addition to those polynucleotides described above, the present invention also includes polynucleotides that encode an amino acid sequence substantially set forth as SEQ ID NOs: 14, 16, 17, 18, and 19-30, or a continuous portion thereof, and that differ from the antibody or antigen binding protein polynucleotides described above only due to the well-known degeneracy of the genetic code.

As described above, the CDRs contain most of the residues responsible for specific interactions with an antigen, and are contained within the VH and VL domains, i.e., the heavy chain variable domain and the light chain variable domain, respectively. Consequently, provided that an antibody comprises at least one CDR of an antibody or antigen binding protein of the invention, e.g., a CDR comprising an amino acid sequence selected from the amino acid sequences set forth as SEQ ID NOs: 19-30, or active antibody or antigen binding protein fragments thereof, it is an antibody of the invention, i.e., one that specifically interacts with GDF8 (e.g., binds to GDF8) and/or specifically antagonizes GDF8 activity. Therefore, an embodiment of the invention includes antibodies that contain one or more CDRs that comprise(s) an amino acid sequence selected from an amino acid sequence set forth as SEQ ID NOs: 19-30, or an amino acid sequence of active fragments thereof. Consequently, one of skill in the art will recognize that the antibodies of the invention includes an antibody or antigen binding protein in which the CDRs of the VL chain are one or more CDRs of those set forth as SEQ ID NOs:22-24 and 28-30, and/or the CDRs of the VH chain are one or more CDRs of those set forth as SEQ ID NOs:1921 and 25-27.

An antigen-binding fragment may be an Fv fragment, which consists of VH and VL domains. Thus, an Fv fragment of RK22 may constitute an antibody of the invention, provided that the fragment specifically interacts with GDF8. One of skill in the art will recognize that any antibody or antigen binding protein fragment containing the Fv fragment of RK22 may also be an antibody of the invention. Additionally, any Fv fragment, scFv fragment, Fab fragment, or F(ab')2 fragment, which contains one or more CDRs having an amino acid sequence selected from the group consisting of the amino acid sequences set forth as SEQ ID NOs:19-30 may also be an antibody or antigen binding protein of the invention.

Certain embodiments of the invention comprise the VH and/or VL domain of the Fv fragment of RK22. Fragments of antibodies of the present invention, e.g., Fab, F(ab')2, Fd, and dAb fragments, may be produced by cleavage of the antibodies e.g., RK22 in accordance with methods well known in the art. For example, immunologically active Fab and F(ab')2 fragments may be generated by treating the antibodies with an enzyme, e.g., papain and pepsin respectively.

Further embodiments comprise one or more CDRs (e.g., one or more CDRs set forth as SEQ ID NOs: 19-21 and 25-27) of any of the VH domains of an antibody disclosed herein (e.g., the VH domains of RK22 (set forth as SEQ ID NOs:14 and 17) and VL domains of an antibody disclosed herein (e.g., the VL domains of RK22 (set forth as SEQ ID NOs:16 and 18. One embodiment comprises an H3 fragment of the VH domain of RK22 (set forth as SEQ ID NO:21.

For convenience, the approximate positions of each CDR within the VH and VL domains are listed in Table 2.

TABLE 2

Approximate CDR position according to Kabat (not ital) or AbM (*ital*) definitions within variable domains of RK22 mouse and humanized antibodies

| CDR | RK22 SEQ ID NO: 14 | RK22 SEQ ID NO: 17 |
|---|---|---|
| H1 | 50-54 or *45-54* | 26-35 |
| H2 | 69-85 or *69-77* | 50-66 |
| H3 | 116-128 or *116-128* | 99-109 |

| | RK22 SEQ ID NO: 16 | RK22 SEQ ID NO: 18 |
|---|---|---|
| L1 | 44-60 or *44-60* | 24-40 |
| L2 | 76-82 or *76-82* | 56-62 |
| L3 | 115-123 or *115-123* | 95-101 |

Presently disclosed antibodies may further comprise antibody or antigen binding protein constant domains or parts thereof. For example, a VL domain of the invention may be attached at its C-terminal end to an antibody or antigen binding protein light chain constant domain, e.g., a human Cκ or Cλ chain, preferably a Cλ chain. Similarly, a specific antigen-binding fragment based on a VH domain may be attached at its C-terminal end to all or part of an immunoglobulin heavy chain derived from any antibody isotype, e.g., IgG, IgA, IgE, and IgM, and any of the isotype subclasses, particularly IgG1 and IgG4. In exemplary embodiments, antibodies comprise C-terminal fragments of heavy and light chains of human IgG1λ. It is understood that, due to the degeneracy of the genetic code, DNA sequences listed in the Brief Description of the Sequences 1 are merely representative of nucleic acids that encode the amino acid sequences, peptides, and antibodies of interest, and are not to be construed as limiting.

Certain embodiments of the invention comprise the VH and/or VL domain of the Fv fragment of RK22. Further embodiments comprise one or more complementarity determining regions (CDRs) of any of these VH and VL domains. One embodiment comprises an H3 fragment of the VH domain of RK22. The VH and VL domains of the invention, in certain embodiments, are germlined, i.e., the framework regions (FRs) of these domains are changed using conventional molecular biology techniques to match the consensus amino acid sequences of human germline gene products. This is also known as a humanized or germlined antibody. In other embodiments, the framework sequences remain diverged from the germline. Humanized antibodies may be produced using transgenic mice that are incapable of expressing endogenous immunoglobulin heavy and light chain genes, but are capable of expressing human heavy and light chain genes.

A further aspect of the invention provides methods for obtaining an antibody antigen-binding domain specific for GDF8. The skilled artisan will appreciate that the antibodies of the invention are not limited to the specific sequences of VH and VL domains as stated in Table 2, but also include variants of these sequences that retain antigen binding ability. Such variants may be derived from the provided sequences using techniques known in the art. Amino acid substitution, deletions, or additions, can be made in either the FRs or in the CDRs. While changes in the framework regions are usually designed to improve stability and reduce immunogenicity of the antibody, changes in the CDRs are usually designed to increase affinity of the antibody for its target. Such affinity-increasing changes are typically determined empirically by altering the CDR and testing the antibody. Such alterations can be made according to the methods described in, e.g., Antibody Engineering, 2nd ed., ed. Borrebaeck, Oxford University Press, 1995.

Thus, the antibodies or antigen binding protein (or fragments thereof) of the invention also include those that specifically interact with GDF8, and have mutations in the constant domains of the heavy and light chains. It is sometimes desirable to mutate and inactivate certain fragments of the constant domain. For example, mutations in the heavy constant domain are sometimes desirable to produce antibodies with reduced binding to the Fc receptor (FcR) and/or complement; such mutations are well known in the art. One of skill in the art will also recognize that the determination of which active fragments of the CL and CH subunits are necessary will depend on the application to which an antibody of the invention is applied. For example, the active fragments of the CL and CH subunits that are involved with their covalent link to each other will be important in the generation of an intact antibody.

The method for making a VH domain that is an amino acid sequence variant of a VH domain set out herein comprises a step of adding, deleting, substituting or inserting one or more amino acids in the amino acid sequence of the presently disclosed VH domain, optionally combining the VH domain thus provided with one or more VL domains, and testing the VH domain or VH/VL combination or combinations for specific interaction with GDF8, and (preferably) testing the ability of such antigen-binding domain to modulate one or more GDF8-associated activities. The VL domain may have an amino acid sequence that is substantially as set out herein. An analogous method may be employed in which one or more sequence variants of a VL domain disclosed herein are combined with one or more VH domains.

A further aspect of the invention provides a method of preparing an antigen-binding fragment that specifically interacts with GDF8. The method comprises: providing a starting repertoire of nucleic acids encoding a VH domain which either include a CDR, e.g., CDR3, to be replaced or a VH domain that lacks a CDR, e.g., CDR3, encoding region; combining the repertoire with a donor nucleic acid encoding a donor CDR of the invention (e.g., a donor nucleic acid encoding a CDR comprising an active fragment of SEQ ID NO:14, 16, 17, 18 such that the donor nucleic acid is inserted into the CDR, e.g., CDR3, region in the repertoire so as to provide a product repertoire of nucleic acids encoding a VH domain; expressing the nucleic acids of the product repertoire; selecting an antigen-binding fragment specific for GDF8; and recovering the specific antigen-binding fragment or nucleic acid encoding it. Again, an analogous method may be employed in which a VL CDR (e.g., L3) of the invention is combined with a repertoire of nucleic acids encoding a VL domain, which either include a CDR to be replaced or lack a CDR encoding region.

A coding sequence of a CDR of the invention (e.g., CDR3) may be introduced into a repertoire of variable domains lacking a CDR (e.g., CDR3), using recombinant DNA technology. For example, Marks et al. ((1992) *Bio/Technology* 10:779-83) describes methods of producing repertoires of antibody or antigen binding protein variable domains in which consensus primers directed at or adjacent to the 5' end of the variable domain area are used in conjunction with consensus primers to the third framework region of human VH genes to provide a repertoire of VH variable domains lacking a CDR3. The repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide specific antigen-binding fragments of the invention. The repertoire may then be displayed in a suitable host system, such as the phage display system of WO 92/01047, so that suitable antigen-binding fragments can be selected.

Analogous shuffling or combinatorial techniques are also disclosed by Stemmer ((1994) *Nature* 370:389-91), who describes a technique in relation to a β-lactamase gene but observes that the approach may be used for the generation of antibodies. A further alternative is to generate novel VH or VL domains carrying a CDR-derived sequence of the invention using random mutagenesis of one or more selected VH and/or VL genes to generate mutations within the entire variable domain. Such a technique is described in Gram et al. ((1992) *Proc. Natl. Acad. Sci. U.S.A.* 89:3576-80) by using error-prone PCR. Another method that may be used to generate novel antibodies or fragments thereof is to direct mutagenesis to CDRs of VH or VL genes. Such techniques are disclosed in Barbas et al. ((1994) *Proc. Natl. Acad. Sci. U.S.A.* 91:3809-13) and Schier et al. ((1996) *J. Mol. Biol.* 263:551-67).

Similarly, one, two, or all three CDRs may be grafted into a repertoire of VH or VL domains, which are then screened for a specific binding partner or binding fragments specific for GDF8. A substantial portion of an immunoglobulin variable domain will comprise at least the CDRs and, optionally, their intervening framework regions from the antibody fragments as set out herein. The portion will also include at least about 50% of either or both of FR1 and FR4, the 50% being the C-terminal 50% of FR1 and the N-terminal 50% of FR4. Additional residues at the N-terminal or C-terminal end of the substantial part of the variable domain may be those not normally associated with naturally occurring variable domains. For example, construction of specific antibody or antigen binding protein fragments of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including immunoglobulin heavy chains, other variable domains (for example, in the production of diabodies) or protein labels as discussed in more details below.

Although the embodiments illustrated in the Examples comprise a "matching" pair of VH and VL domains, the invention also encompasses binding fragments containing a single variable domain, e.g., a dAb fragment, derived from either VH or VL domain sequences, especially VH domains. In the case of either of the single chain specific binding domains, these domains may be used to screen for complementary domains capable of forming a two-domain specific antigen-binding domain capable of binding GDF8. This may be achieved by phage display screening methods using the so-called hierarchical dual combinatorial approach as disclosed in, e.g., WO 92/01047. In this technique, an individual colony containing either an H or L chain clone is used to infect a complete library of clones encoding the other chain (L or H) and the resulting two-chain specific antigen-binding domain is selected in accordance with phage display techniques, such as those described in that reference. This technique is also disclosed in Marks et al., supra.

Antibodies can be conjugated by chemical methods with radionuclides, drugs, macromolecules, or other agents, and may be made as fusion proteins comprising one or more CDRs of the invention.

An antibody or antigen binding protein fusion protein contains a VH-VL pair in which one of these chains (usually VH) and another protein are synthesized as a single polypeptide chain. These types of products differ from antibodies in that they generally have an additional functional element, (e.g., the active moiety of a small molecule or the principal molecular structural feature of the conjugated or fused macromolecule).

In addition to the changes to the amino acid sequence outlined above, the antibodies can be glycosylated, pegylated, or linked to albumin or a nonproteinaceous polymer. For instance, the presently disclosed antibodies may be linked to one of a variety of non-proteinaceous polymers, e.g., polyethylene glycol, polypropylene glycol, or polyoxyalkylenes. The antibodies may be chemically modified, e.g., to increase their circulating half-life by covalent conjugation to a polymer. Exemplary polymers, and methods to attach them to peptides are known in the art.

In other embodiments, the antibody or antigen binding protein may be modified to have an altered glycosylation pattern (i.e., relative to the original or native glycosylation pattern). As used herein, "altered" means having one or more carbohydrate moieties deleted, and/or having one or more glycosylation sites added to the original antibody. Addition of glycosylation sites to the presently disclosed antibodies is accomplished by well-known methods of altering the amino acid sequence to contain glycosylation site consensus sequences. Another means of increasing the number of carbohydrate moieties on the antibodies is by chemical or enzymatic coupling of glycosides to the amino acid residues of the antibody. Removal of any carbohydrate moieties present on the antibodies may be accomplished chemically or enzymatically as known in the art.

Antibodies of the invention may also be tagged with a detectable or functional label such as 131I or 99Tc, which may be attached to antibodies of the invention using conventional chemistry known in the art. Labels also include enzyme labels such as horseradish peroxidase or alkaline phosphatase. Labels further include chemical moieties such as biotin, which may be detected via binding to a specific cognate detectable moiety, e.g., labeled avidin.

Antibodies in which CDR sequences differ only insubstantially from CDR sequences of the antibodies disclosed herein are encompassed within the scope of this invention. Insubstantial differences include minor amino acid changes, e.g., substitutions of one or two out of any five amino acids in the sequence of a CDR. Typically, an amino acid is substituted by a related amino acid having similar charge, hydrophobicity, or stereochemical characteristics. Such substitutions would be within the ordinary skills of an artisan. The structure framework regions (FRs) can be modified more substantially than CDRs without adversely affecting the binding properties of an antibody. Changes to FRs include, but are not limited to, humanizing a nonhuman derived framework or engineering certain framework residues that are important for antigen contact or for stabilizing the binding site, e.g., changing the class or subclass of the constant domain, changing specific amino acid residues which might alter an effector function such as Fc receptor binding (e.g., Lund et al. (1991) *J. Immunol.* 147:2657-62; Morgan et al. (1995) *Immunology* 86:319-24), or changing the species from which the constant domain is derived. Antibodies may have mutations in the CH2 domain of the heavy chain that reduce or alter effector function, e.g., Fc receptor binding and complement activation. For example, antibodies may have mutations such as those described in U.S. Pat. Nos. 5,624,821 and 5,648,260. Antibodies may also have mutations that stabilize the disulfide bond between the two heavy chains of an immunoglobulin, such as mutations in the hinge region of IgG4, as disclosed in, e.g., Angal et al. (1993) *Mol. Immunol.* 30:105-08.

The polypeptides and antibodies of the present invention also encompass proteins that are structurally different from the disclosed polypeptides and antibodies, e.g., which have an altered sequence but substantially the same biochemical properties as the disclosed polypeptides and antibodies, e.g., have changes only in functionally nonessential amino acids. Such molecules include naturally occurring allelic variants and deliberately engineered variants containing alterations, substitutions, replacements, insertions, or deletions. Techniques for such alterations, substitutions, replacements, insertions, or deletions are well known to those skilled in the art.

Antibodies of the invention may additionally be produced using transgenic nonhuman animals that are modified so as to produce fully human antibodies rather than the animal's endogenous antibodies in response to challenge by an antigen. See, e.g., PCT publication WO 94/02602. The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. One embodiment of such a nonhuman animal is a mouse, and is termed the XENOMOUSE™ as disclosed in PCT publications WO 96/33735 and WO 96/34096. This animal produces B cells that secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable domains can be recovered and expressed to obtain the antibodies directly, or can be further modified to obtain analogs of antibodies such as, for example, single chain Fv molecules.

Consequently, the term antibody or antigen binding protein as used herein includes intact antibodies, fragments of antibodies, e.g., Fab, F(ab')2 Fd, dAb and scFv fragments, and intact antibodies and fragments that have been mutated either in their constant and/or variable domains (e.g., mutations to produce chimeric, partially humanized, or fully humanized antibodies, as well as to produce antibodies with a desired trait, e.g., enhanced GDF8 binding and/or reduced FcR binding). As such these antibodies or antigen binding protein are included in the scope of the invention, provided that the antibody or antigen binding protein specifically interacts with GDF8.

Other protein-binding molecules may also be employed to modulate the activity of GDF8. Such antigen binding molecules include small modular immunopharmaceutical (SMIP™) drugs (Trubion Pharmaceuticals, Seattle, Wash.). SMIPs are single-chain polypeptides composed of a binding domain for a cognate structure such as an antigen, a counter-receptor or the like, a hinge-region polypeptide having either one or no cysteine residues, and immunoglobulin CH2 and CH3 domains. SMIPs and their uses and applications are disclosed in, e.g., U.S. Published Patent Appln. Nos. 2003/0118592, 2003/0133939, 2004/0058445, 2005/0136049, 2005/0175614, 2005/0180970, 2005/0186216, 2005/0202012, 2005/0202023, 2005/0202028, 2005/0202534, and 2005/0238646, and related patent family members thereof, all of which are hereby incorporated by reference herein in their entireties.

The binding capacity of an antibody or antigen binding protein of the invention may be measured by the following methods: Biacore analysis, enzyme linked immunosorbent assay (ELISA), X-ray crystallography, sequence analysis and scanning mutagenesis as described in the Examples below, and other methods that are well known in the art. The ability of an antibody or antigen binding protein of the invention to inhibit, reduce, and/or neutralize one or more GDF8-associated activities may be measured by the following nonlimiting list of methods: assays for measuring the proliferation of a GDF8-dependent cell line; assays for measuring the expression of GDF8-mediated polypeptides; assays measuring the activity of downstream signaling molecules; assays testing the efficiency of an antibody or antigen binding protein of the invention to prevent muscle disorders in a relevant animal model; assays as described in the Examples below; and other assays that are well known in the art.

A further aspect of the invention provides a method of selecting antibodies capable of specifically interacting with GDF8, and/or specifically antagonizing one or more GDF8 activities. The method comprises: contracting a plurality of antibodies with GDF8; choosing a second plurality of antibodies that bind to GDF8; testing the ability of the second plurality of antibodies to bind other members of the TGF-$\beta$ superfamily; and selecting a third plurality of antibodies from the second plurality of antibodies wherein the third plurality of antibodies binds with less affinity to other members of the TGF-$\beta$ super family.

In another embodiment, the method further comprises the steps of: testing the ability of the third plurality of antibodies to antagonize at least one GDF8 activity (e.g., prevent GDF8 from binding to the GDF8 receptor); and selecting antibodies capable of antagonizing one or more GDF8 activity (e.g., preventing GDF8 from binding to its receptor).

The anti-GDF8 antibodies of the invention are also useful for isolating, purifying, and/or detecting GDF8 in supernatant(s), cellular lysates, or on a cell surface. Antibodies disclosed in this invention can be used diagnostically to monitor GDF8 protein levels as part of a clinical testing procedure. Additionally, antibodies of the invention can be used in treatments requiring the neutralization and/or inhibition of one or more GDF8-associated disorders, e.g., treatments for muscle-related pathologies. The present invention also provides novel isolated and purified polynucleotides and polypeptides related to novel antibodies directed against human GDF8.

The genes, polynucleotides, proteins, and polypeptides of the present invention include, but are not limited to, murine and humanized antibodies to GDF8, e.g., RK22, and variants thereof.

Antagonist Recombinant Polynucleotides and Polypeptides

The present invention further provides as specific GDF8 antagonists the isolated and purified nucleic acids that encode epitopes specific to GDF8, or the peptide mimetics or antibodies thereto, as described above. Nucleic acids according to the present invention may comprise DNA or RNA and may be wholly or partially synthetic. Reference to a nucleotide sequence as set out herein encompass DNA molecules with the specified sequences or genomic equivalents, as well as RNA molecules with the specified sequences in which T is substituted with U, unless context requires otherwise.

The isolated polynucleotides of the present invention, for example, SEQ ID NOs: 3, 5, 7, 9 11, 13 and 15 may be used as hybridization probes and primers to identify and isolate nucleic acids having sequences identical to or similar to those encoding the disclosed polynucleotides. As a nonlimiting example, the polynucleotides isolated using antibody or antigen binding protein polynucleotides in this fashion may be used, for example, to produce specific antibodies against GDF8 or to identify cells expressing such antibodies. Hybridization methods for identifying and isolating nucleic acids include polymerase chain reaction (PCR), Southern hybridizations, in situ hybridization and Northern hybridization, and are well known to those skilled in the art.

Hybridization reactions can be performed under conditions of different stringencies. The stringency of a hybridization reaction includes the difficulty with which any two nucleic acid molecules will hybridize to one another. Preferably, each hybridizing polynucleotide hybridizes to its corresponding polynucleotide under reduced stringency conditions, more preferably stringent conditions, and most preferably highly stringent conditions. Examples of stringency conditions are shown in Table 3 below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE 3

| Condition | Hybrid | Hybrid Length (bp)1 | Hybridization Temperature and Buffer2 | Wash Temperature and Buffer2 |
|---|---|---|---|---|
| A | DNA:DNA | >50 | 65° C.; 1X SSC -or- 42° C.; 1X SSC, 50% formamide | 65° C.; 0.3X SSC |
| B | DNA:DNA | <50 | TB*; 1X SSC | TB*; 1X SSC |
| C | DNA:RNA | >50 | 67° C.; 1X SSC -or- 45° C.; 1X SSC, 50% formamide | 67° C.; 0.3X SSC |
| D | DNA:RNA | <50 | TD*; 1X SSC | TD*; 1X SSC |
| E | RNA:RNA | >50 | 70° C.; 1X SSC -or- 50° C.; 1X SSC, 50% formamide | 70° C.; 0.3X SSC |
| F | RNA:RNA | <50 | TF*; 1X SSC | TF*; 1X SSC |
| G | DNA:DNA | >50 | 65° C.; 4X SSC -or- 42° C.; 4X SSC, 50% formamide | 65° C.; 1X SSC |
| H | DNA:DNA | <50 | TH*; 4X SSC | TH*; 4X SSC |
| I | DNA:RNA | >50 | 67° C.; 4X SSC -or- 45° C.; 4X SSC, 50% formamide | 67° C.; 1X SSC |
| J | DNA:RNA | <50 | TJ*; 4X SSC | TJ*; 4X SSC |
| K | RNA:RNA | >50 | 70° C.; 4X SSC -or- 50° C.; 4X SSC, 50% formamide | 67° C.; 1X SSC |
| L | RNA:RNA | <50 | TL*; 2X SSC | TL*; 2X SSC |
| M | DNA:DNA | >50 | 50° C.; 4X SSC -or- 40° C.; 6X SSC, 50% formamide | 50° C.; 2X SSC |
| N | DNA:DNA | <50 | TN*; 6X SSC | TN*; 6X SSC |
| O | DNA:RNA | >50 | 55° C.; 4X SSC -or- 42° C.; 6X SSC, 50% formamide | 55° C.; 2X SSC |
| P | DNA:RNA | <50 | TP*; 6X SSC | TP*; 6X SSC |
| Q | RNA:RNA | >50 | 60° C.; 4X SSC -or- 45° C.; 6X SSC, 50% formamide | 60° C.; 2X SSC |
| R | RNA:RNA | <50 | TR*; 4X SSC | TR*; 4X SSC |

1The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
2SSPE (1xSSPE is 0.15M NaCl, 10 mM NaH2PO4, and 1.25 mM EDTA, pH 7.4) can be substituted for SSC (1xSSC is 0.15M NaCl and 15 mM sodium citrate) in the hybridization and wash buffers; washes are performed for 15 minutes after hybridization is complete.
TB*-TR*: The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm (° C.) = 2(# of A + T bases) + 4(# of G + C bases). For hybrids between 18 and 49 base pairs in length, Tm (° C.) = 81.5 + 16.6(log10Na+) + 0.41(% G + C) − (600/N), where N is the number of bases in the hybrid, and Na+ is the concentration of sodium ions in the hybridization buffer (Na+ for 1X SSC = 0.165M).

Additional examples of stringency conditions for polynucleotide hybridization are provided in Sambrook et al., *Molecular Cloning: A Laboratory Manual*, Chs. 9 & 11, Cold Spring Harbor Laboratory Press, Cold Spring Harbor, N.Y. (1989), and Ausubel et al., eds., *Current Protocols in Molecular Biology*, Sects. 2.10 & 6.3-6.4, John Wiley & Sons, Inc. (1995), herein incorporated by reference.

The isolated polynucleotides of the present invention may be used as hybridization probes and primers to identify and isolate DNAs having sequences encoding allelic variants of the disclosed polynucleotides. Allelic variants are naturally occurring alternative forms of the disclosed polynucleotides that encode polypeptides that are identical to or have significant similarity to the polypeptides encoded by the disclosed polynucleotides. Preferably, allelic variants have at least 90% sequence identity (more preferably, at least 95% identity; most preferably, at least 99% identity) with the disclosed polynucleotides.

The isolated polynucleotides of the present invention may also be used as hybridization probes and primers to identify and isolate DNAs having sequences encoding polypeptides homologous to the disclosed polynucleotides. These homologs are polynucleotides and polypeptides isolated from a different species than that of the disclosed polypeptides and polynucleotides, or within the same species, but with significant sequence similarity to the disclosed polynucleotides and polypeptides. Preferably, polynucleotide homologs have at least 50% sequence identity (more preferably, at least 75% identity; most preferably, at least 90% identity) with the disclosed polynucleotides, whereas polypeptide homologs have at least 30% sequence identity (more preferably, at least 45% identity; most preferably, at least 60% identity) with the disclosed antibodies/polypeptides. Preferably, homologs of the disclosed polynucleotides and polypeptides are those isolated from mammalian species.

The isolated polynucleotides of the present invention may also be used as hybridization probes and primers to identify cells and tissues that express the epitope(s) specific to GDF8 or antibodies of the present invention and the conditions under which they are expressed.

Additionally, the isolated polynucleotides of the present invention may be used to alter (i.e., enhance, reduce, or modify) the expression of the genes corresponding to the polynucleotides of the present invention in a cell or organism. These "corresponding genes" are the genomic DNA sequences of the present invention that are transcribed to produce the mRNAs from which the polynucleotides of the present invention are derived.

Altered expression of sequences related to the invention in a cell or organism may be achieved through the use of various inhibitory polynucleotides, such as antisense polynucleotides, ribozymes that bind and/or cleave the mRNA transcribed from the genes of the invention, triplex-forming oligonucleotides that target regulatory regions of the genes, and short interfering RNA that causes sequence-specific degradation of target mRNA (e.g., Galderisi et al. (1999) *J. Cell. Physiol.* 181:251-57; Sioud (2001) *Curr. Mol. Med.* 1:575-88; Knauert and Glazer (2001) *Hum. Mol. Genet.* 10:2243-51; Bass (2001) *Nature* 411:428-29). Such inhibitory polynucleotides are considered antagonists of the invention. A skilled artisan will recognize that inhibitory polynucleotides of the invention should be directed against the epitope(s) specific to GDF8 as provided above (and not antagonist antibodies of the invention).

The inhibitory triplex-forming oligonucleotides (TFOs) encompassed by the present invention bind in the major groove of duplex DNA with high specificity and affinity (Knauert and Glazer, supra). Expression of the genes of the present invention can be inhibited by targeting TFOs complementary to the regulatory regions of the genes (i.e., the promoter and/or enhancer sequences) to form triple helical structures that prevent transcription of the genes.

In one embodiment of the invention, the inhibitory polynucleotides of the present invention are short interfering RNA (siRNA) molecules (see, e.g., Galderisi et al. (1999) *J. Cell Physiol.* 181:251-57; Sioud (2001) *Curr. Mol. Med.* 1:575-88). These siRNA molecules are short duplex RNA molecules that cause sequence-specific degradation of the targeted mRNA. This degradation is known as RNA interference (RNAi) (e.g., Bass (2001) *Nature* 411:428-29). Originally identified in lower organisms, RNAi has been effectively applied to mammalian cells and has recently been shown to prevent fulminant hepatitis in mice treated with siRNA molecules targeted to Fas mRNA (Song et al. (2003) *Nature Med.* 9:347-51). In addition, intrathecally delivered siRNA has recently been reported to block pain responses in two models (agonist-induced pain model and neuropathic pain model) in the rat (Dorn et al. (2004) *Nucleic Acids Res.* 32(5):e49).

The duplex structure of siRNA molecules of the invention may comprise one or more strands of polymerized RNA, i.e., the duplex structure may be formed by a single-self complementary RNA strand comprising a hairpin loop or two complementary strands. siRNA sequences with insertions, deletions, and single point mutations relative to the targeted sequence have also been found to be effective in inhibiting the expression of the targeted sequence (Fire et al., U.S. Pat. No. 6,506,559). Accordingly, it is preferred that siRNA molecules of the invention comprise a nucleotide sequence with substantial sequence identity to at least a portion of the mRNA corresponding to a targeted epitope specific to GDF8 of the invention. For example, the duplex region of an siRNA molecule of the invention may have greater than 90%, sequence identity, and preferably 100% sequence identity, to at least of portion of the mRNA corresponding to the targeted epitope specific to GDF8. Alternatively, substantial sequence identity may be defined as the ability of at least one strand of the duplex region of the siRNA molecule to hybridize to at least a portion of the targeted epitope specific to GDF8 under at least, e.g., stringent conditions as defined as conditions G-L in Table 3, above. In a preferred, but nonlimiting, embodiment of the invention, the siRNA molecule hybridizes to at least of a portion of the targeted epitope specific to GDF8 under highly stringent conditions, e.g., those that are at least as stringent as, for example, conditions A-F in Table 3, above. The length of the substantially identical nucleotide sequences may be at least 10, 15, 19, 21, 23, 25, 50, 100, 200, 300, 400, or 500 nucleotides, is preferably 19-27 nucleotides, and is most preferably 19 or 21 nucleotides (see Fire, et al., supra).

The inhibitory polynucleotides of the invention may be designed based on criteria well known in the art (e.g., Elbashir et al. (2001) *EMBO J.* 20:6877-88) and/or by using well-known algorithms (e.g., publicly available algorithms). For example, the targeting portion of an inhibitory polynucleotide of the invention (e.g., the duplex region of an siRNA molecule) preferably should begin with AA (most preferred), TA, GA, or CA; an siRNA molecule of the invention preferably should comprise a sequence whereby the GC ratio is 45-55%; an siRNA molecule of the invention preferably should not contain three of the same nucleotides in a row; and an siRNA molecule of the invention preferably should not contain seven mixed G/Cs in a row. Based on these criteria, or on other known criteria (e.g., Reynolds et al. (2004) *Nat. Biotechnol.* 22:326-30), siRNA molecules of the present invention that target an epitope specific to GDF8 may be designed by one of ordinary skill in the art. For example, in one embodiment, an siRNA molecule of the invention may have and/or consist essentially of a nucleotide sequence selected from the group consisting of the nucleotide sequence of SEQ ID NO:3, the nucleotide sequence of SEQ ID NO:5, the nucleotide sequence of SEQ ID NO:7, the nucleotide sequence of SEQ ID NO:9, the nucleotide sequence of SEQ ID NO:11, and fragments thereof. In this embodiment, an siRNA molecule of the invention further comprises the complement of the nucleotide sequence of SEQ ID NO:3, the complement of the nucleotide sequence of SEQ ID NO:5, the complement of the nucleotide sequence of SEQ ID NO:7, the complement of the nucleotide sequence of SEQ ID NO:9, the complement of the nucleotide sequence of SEQ ID NO:11, and the complements of fragments thereof.

For example, the siRNA molecules of the present invention may be generated by annealing two complementary single-stranded RNA molecules together (Fire et al., supra) or through the use of a single hairpin RNA molecule that folds back on itself to produce the requisite double-stranded portion (Yu et al. (2002) *Proc. Natl. Acad. Sci. USA* 99:6047-52). The siRNA molecules may be chemically synthesized (Elbashir et al. (2001) *Nature* 411:494-98) or produced by in vitro transcription using single-stranded DNA templates (Yu et al., supra). Alternatively, the siRNA molecules can be produced biologically, either transiently (Yu et al., supra; Sui et al. (2002) *Proc. Natl. Acad. Sci. USA* 99:5515-20) or stably (Paddison et al. (2002) *Proc. Natl. Acad. Sci. USA* 99:1443-48), using an expression vector(s), described below, comprising polynucleotides related to the present invention in sense and/or antisense orientation relative to their promoter. Recombinant RNA polymerase may be used for transcription in vivo or in vitro, or endogenous RNA polymerase of a modified cell may mediate transcription in vivo. Recently, reduction of levels of target mRNA in primary human cells, in an efficient and sequence-specific manner, was demonstrated using adenoviral vectors that express hairpin RNAs, which are further processed into siRNA molecules (Arts et al. (2003) *Genome Res.* 13:2325-32).

The inhibitory polynucleotides of the invention may be constructed using chemical synthesis and enzymatic ligation reactions including procedures well known in the art. The nucleoside linkages of chemically synthesized polynucleotides may be modified to enhance their ability to resist nuclease-mediated degradation, avoid a general panic response in some organisms that is generated by duplex RNA, and/or to increase their sequence specificity. Such linkage modifications include, but are not limited to, phosphorothioate, methylphosphonate, phosphoroamidate, boranophosphate, morpholino, and peptide nucleic acid (PNA) linkages (Galderisi et al., supra; Heasman (2002) *Dev. Biol.* 243:209-14; Micklefield (2001) *Curr. Med. Chem.* 8:1157-79).

As described above, the isolated polynucleotides, or continuous portions thereof, related to the present invention may be operably linked in sense or antisense orientation to an expression control sequence and/or ligated into an expression vector for recombinant expression of the inhibitory polynucleotides (e.g., siRNA molecules) of the invention.

The present invention also provides constructs in the form of plasmids, vectors, transcription or expression cassettes which comprise at least one nucleic acid of the invention as above.

The isolated polynucleotides of the present invention may be operably linked to an expression control sequence for recombinant production of the specific epitopes (e.g., as peptide mimetics) or antibodies of the present invention. Additionally one of skill in the art will recognize that the antibody or antigen binding protein encoding polynucleotides of the invention may be operably linked to well-known nucleotide sequences encoding the constant domain for various antibody isotypes. For example, a polynucleotide of the invention that encodes a light chain variable domain of the invention (e.g., polynucleotides with a nucleotide sequence set forth as SEQ ID NO: 15 may be operably linked to a nucleotide sequence that encodes the constant domain (or derivatives thereof) of either a K light chain or A light chain, such that the expression of the linked nucleotides will result in a full kappa or lambda light chain with a variable domain that specifically interacts with and/or specifically antagonizes GDF8. Similarly, a polynucleotide of the invention that encodes a heavy chain variable domain of the invention (e.g., a polynucleotide with a nucleotide sequence set forth as SEQ ID NOs: 13 may be operably linked to a nucleotide sequence that encodes the constant domain of a heavy chain isotype (or derivatives thereof), e.g., IgM, IgD, IgE, IgG and IgA. General methods of expressing recombinant proteins are well known in the art. Such recombinant proteins may be expressed in soluble form for use in treatment of disorders related to GDF8 The recombinant expression vectors of the invention may carry additional sequences, such as sequences that regulate replication of the vector in host cells (e.g., origins of replication), tag sequences such as histidine, and selectable marker genes. The selectable marker gene facilitates selection of host cells into which the vector has been introduced. For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr host cells with methotrexate selection/amplification) and the neo gene (for G418 selection).

Suitable vectors, containing appropriate regulatory sequences, including promoter sequences, terminator sequences, polyadenylation sequences, enhancer sequences, marker genes and other sequences as appropriate, may be either chosen or constructed. Vectors may be plasmids or viral, e.g., phage, or phagemid, as appropriate. For further details see, for example, Molecular Cloning: a Laboratory Manual: 2nd ed., Sambrook et al., Cold Spring Harbor Laboratory Press, 1989. Many known techniques and protocols for manipulation of nucleic acid, for example, in preparation of nucleic acid constructs, mutagenesis, sequencing, introduction of DNA into cells and gene expression, and analysis of proteins, are described in detail in Current Protocols in Molecular Biology, 2nd ed., Ausubel et al. eds., John Wiley & Sons, 1992.

The present invention also provides a host cell that comprises one or more constructs as above, e.g., a recombinant nucleic acid encoding any epitope specific to GDF8, CDR (H1, H2, H3, L1, L2, or L3), VH domain, VL domain, or specific antigen-binding fragment as provided herein, forms an aspect of the present invention.

The present invention also includes a method of producing a peptide by expressing the protein from the encoding nucleic acid in a host cell. Expression may be achieved by culturing recombinant host cells containing the nucleic acid under appropriate conditions.

A number of cell lines are suitable host cells for recombinant expression of the polypeptides and antibodies of the present invention. Mammalian host cell lines include but are not limited to: COS cells, CHO cells, 293T cells, A431 cells, 3T3 cells, CV-1 cells, HeLa cells, L cells, BHK21 cells, HL-60 cells, U937 cells, HaK cells, Jurkat cells as well as cell strains derived from in vitro culture of primary tissue and primary explants. Such host cells also allow splicing of the polynucleotides of the invention that consist of genomic DNA.

Alternatively, it may be possible to recombinantly produce the polypeptides and antibodies of the present invention in lower eukaryotes such as yeast or in prokaryotes. Potentially suitable yeast strains include but are not limited to *Saccharomyces cerevisiae, Schizosaccharomyces pombe, Kluyveromyces* strains, and *Candida* strains. Potentially suitable bacterial strains include *Escherichia coli, Bacillus subtilis*, and *Salmonella typhimurium*. If the polypeptides of the present invention are made in yeast or bacteria, it may be necessary to modify them by, for example, phosphorylation or glycosylation of appropriate sites, in order to obtain functional proteins. Such covalent attachments may be accomplished using well-known chemical or enzymatic methods.

The polypeptides and antibodies of the present invention may also be recombinantly produced by operably linking the isolated polynucleotides of the present invention to suitable control sequences in one or more insect expression vectors, such as baculovirus vectors, and employing an insect cell expression system. Materials and methods for baculovirus/Sf9 expression systems are commercially available in kit form (e.g., the MAXBAC® kit, Invitrogen, Carlsbad, Calif.).

Following recombinant expression in the appropriate host cells, the polypeptides and antibodies of the present invention may be purified from culture medium or cell extracts using known purification processes, such as gel filtration and ion exchange chromatography. Purification may also include affinity chromatography with agents known to bind the polypeptides and antibodies of the present invention. These purification processes may also be used to purify the polypeptides and antibodies of the present invention from natural sources.

Alternatively, the polypeptides and antibodies of the present invention may be recombinantly expressed in a form that facilitates purification. For example, the polypeptides may be expressed as fusions with proteins such as maltose-binding protein (MBP), glutathione-S-transferase (GST), or thioredoxin (TRX). Kits for expression and purification of such fusion proteins are commercially available from New England BioLabs (Beverly, Mass.), Pharmacia (Piscataway, N.J.), and Invitrogen, respectively. The polypeptides and antibodies of the present invention can also be tagged with a small epitope and subsequently identified or purified using a specific antibody or antigen binding protein to the epitope. A preferred epitope is the FLAG epitope, which is commercially available from Eastman Kodak (New Haven, Conn.).

The polypeptides and antibodies of the present invention may also be produced by known conventional chemical synthesis. Methods for chemically synthesizing the polypeptides and antibodies of the present invention are well known to those skilled in the art. Such chemically synthetic polypeptides and antibodies may possess biological properties in common with the natural purified polypeptides and antibodies, and thus may be employed as biologically active or immunological substitutes for the natural polypeptides and antibodies.

A further aspect of the present invention provides a host cell comprising nucleic acids, polypeptides, vectors, or antibodies and fragments thereof as disclosed herein. A still further aspect provides a method comprising introducing a nucleic acid of the invention into a host cell. The introduction may employ any available technique. For eukaryotic cells, suitable techniques may include calcium phosphate transfection, DEAE Dextran, electroporation, liposome-mediated transfection and transduction using a retrovirus or another virus, e.g., vaccinia or, for insect cells, baculovirus. For bacterial cells, suitable techniques may include calcium chloride transformation, electroporation and infection using bacteriophage.

The introduction of nucleic acids may be followed by causing or allowing protein production from the nucleic acid, e.g., by culturing the host cells under conditions suitable for gene expression. Such conditions are well-known in the art.

Inhibitory polynucleotides, epitope(s) specific to GDF8 (e.g., as peptide mimetics and/or immunogens), specific antibody or antigen binding protein fragments, VH domains, and/or VL domains, and encoding nucleic acid molecules and vectors according to the present invention may be provided isolated and purified, e.g., from their natural environment, in substantially pure or homogeneous form, or, in the case of nucleic acids, free or substantially free of nucleic acids or genes of origin other than the sequence encoding a polypeptide with the required function.

Methods to Detect and Quantify GDF8 in Biological Samples

The present invention relates to methods to detect and quantify GDF-8 in biological samples. In some embodiments, the methods comprise immunoassays to detect and quantify both free and total GDF-8 in serum, blood, and plasma. In one instance, the immunoassays provide data that are useful as biomarkers of anti-GDF-8 therapies. Specifically, the disclosed immunoassays may be useful as predictive/prognostic markers of clinical outcome at baseline prior to anti-GDF-8 therapy, as a marker of exposure to anti-GDF-8 therapies, as a marker of anti-GDF-8 drug efficacy or response, and as a diagnostic marker of GDF-8 involvement in a particular disease state or biological process.

In particular, the methods provide diagnostic and/or prognostic methods for detecting, diagnosing, and predicting a GDF-8 associated disease or disorder in mammals with or at risk for developing a GDF-8 associated disease or disorder. The methods are especially suitable for use in evaluating the suitability of human patients to receive GDF-8 modulating agents, for example, those that bind to GDF-8, or inhibit a biological activity of GDF-8.

In certain embodiments, the invention provides methods to monitor the progress of individuals who are receiving GDF-8 modulating agents or anti-GDF-8 therapies. For example, methods are provided to assess an individual's response to therapy with a GDF-8 modulating agent. In order to assess an individual's response to therapy, the immunoassay methods may be provided prior to, during, and post administration of the GDF-8 modulating agent. Methods to detect the presence of GDF-8 in mammals that are receiving the therapeutic antibody MYO-029 are also encompassed by the invention.

In one embodiment, the immunoassay methods of the invention detect free GDF-8. For example, free GDF-8 is GDF-8 that is not bound to GDF-8 binding proteins or GDF-8 modulating agents, such as, GDF-8 binding or neutralizing antibodies. In another embodiment, methods to detect total GDF-8, for example, free GDF-8 plus any bound GDF-8, are encompassed.

An individual having, or at risk for developing, a muscle-related disorder is a candidate for the methods provided herein. Inhibition of GDF-8 activity increases muscle mass in individuals, including those suffering from muscle-related disorders. A number of disorders are associated with functionally impaired muscle tissue, e.g., muscular dystrophies, amyotrophic lateral sclerosis (ALS), muscle atrophy, organ atrophy, frailty, congestive obstructive pulmonary disease, heart failure, sarcopenia, cachexia, and muscle wasting syndromes caused by other diseases and conditions. Further, an individual or mammal desiring to increase muscle mass or muscle strength, to increase growth or muscle tissue mass in feedstock animals, is a candidate for a method provided herein.

An individual having, or at risk for developing, an adipose tissue, metabolic, or bone-related disorder or condition is also a candidate for a method as described and claimed herein. Such disorders or conditions include those associated with glucose homeostasis such as, e.g., development of type 2 diabetes, impaired glucose tolerance, metabolic syndromes (e.g., syndrome X), insulin resistance induced by trauma, such as burns or nitrogen imbalance, and adipose tissue disorders (e.g., obesity) (Kim et al., Biochem. Biophys. Res. Comm. 281:902-906 (2001)). For example, GDF-8 modulates preadipocyte differentiation to adipocytes (Id.) and inhibits adipocyte formation from mesenchymal precursor cells and preadipocytes (Rebbapragada et al., Mol. Cell. Bio. 23:7230-7242 (2003)). Fat accumulation is reduced both in GDF-8 knockout mice and in wild-type adult mice in which GDF-8 protein has been systematically administered (McPherron et al., J. Clinical Invest. 109:595-601 (2002); Zimmers et al., Science 296:1486-1488 (2002)).

Other uses for the methods of the present invention will be apparent to those of skill in the art, and are further exemplified below.

Immunoassays

The immunoassays described herein are sandwich-type ELISA's that utilize at least two anti-GDF-8 antibodies; one present as a GDF-8 capture reagent specific for GDF8 and one present as a GDF-8 detection reagent specific for GDF8. Both antibodies are capable of binding GDF-8 antigens present in biological samples. One of the antibodies preferentially recognizes GDF-8 over BMP-11. Both antibodies are capable of recognizing and binding GDF-8. Furthermore, in certain embodiments, the antibodies are capable of binding to GDF-8 that is present in any of its biological forms (e.g., active GDF-8, latent GDF-8, GDF-8 bound to serum proteins, GDF-8 bound to neutralizing anti-GDF-8 antibodies MYO-029).

In certain embodiments, the antibody used in the subject assay is RK35 (see SEQ ID NO:s 31-35 and US Application US2007/0087000 hereby incorporated by reference), which is an isolated murine monoclonal antibody that binds to GDF-8. In some embodiments, RK35 is utilized as a capture antibody. Fragments of RK35 that bind to GDF-8 may also be used in the methods of the invention.

In certain embodiments, a second antibody used in the subject assay is RK22, an isolated murine monoclonal antibody that binds to GDF-8. RK22 does not bind to BMP-11, as exemplified below. In some embodiments, RK22 is utilized as a detection reagent, in some embodiments it is used as a capture reagent. Fragments of RK22 that bind to GDF-8 may also be used in the assays of the invention.

In another embodiment, the immunoassays of the present invention utilize the antibody MYO-029, which is a human IgG1 anti-GDF-8 antibody. MYO-029 (see SEQ ID NO:s 33 and 34, US Published Applications 2006/0240488 and 2006/0240487, hereby incorporated by reference) may be used to block the detection of GDF-8 in the immunoassays so as to obtain a background level that can be subtracted from the signal generated in the absence of MYO-029. This embodiment can be employed to increase the sensitivity and accuracy of the quantitative assay.

The antibodies useful in the methods of the invention also encompass antigen-binding fragments, such as, for example, Fv fragments, which consist of the VH and VL domains, Fab fragments (Fragment antigen binding), which consist of the VH—CH1 and VL-CL domains covalently linked by a disulfide bond between the constant regions. For other possible antigen binding fragments, and a review of the antibody structure, see Antibodies: A Laboratory Manual, Cold Spring Harbor Laboratory, eds. Harlow et al., 1988.

E. coli cultures individually transformed with the phagemid vector pCANTAB6 encoding nongermlined scFv's MYO-029 was deposited on Oct. 2, 2002, at American Tissue Culture Collection (ATCC) under respective Deposit Designation Numbers PTA-4741. The address of the depository is 10801 University Blvd, Manassas, Va. 20110, U.S.A.

After combining the sample containing GDF8 with the capture reagent any non-bound components are removed by washing, and components are then contacted with a sample suspected of containing GDF-8 under suitable binding conditions. After washing to remove any non-bound molecules, a second anti-GDF-8 antibody is added under suitable binding conditions. This second antibody is termed the detection antibody or reagent. The detection antibody may include a detectable label, and bind molecules that have reacted with the capture antibody. Thus, any GDF-8 present will bind both the capture reagent bound to GDF8 in the sample, as well as the detection antibody reagent. Unbound molecules and components are removed by washing. The presence of a label therefore indicates the presence of GDF-8 in the biological sample.

More particularly, a sandwich ELISA method can be used. A biological sample containing or suspected of containing GDF-8 is a capture reagent specific for GDF8. After a period of incubation sufficient to allow GDF-8 binding to the capture reagent, the plate(s) can be washed to remove unbound components and a detection component is added. These molecules are allowed to react with any captured sample GDF-8, the plate washed and the presence of the label detected using methods well known in the art.

The above-described assay reagents, including the immunoassay with antigens, as well as antibodies to be reacted with the captured sample, may be provided in kits, with suitable instructions and other necessary reagents, in order to conduct immunoassays as described above. The kit may also contain, depending on the particular immunoassay used, suitable labels and other packaged reagents and materials (i.e. wash buffers and the like). Immunoassays, such as those described above, can be conducted using these kits.

Specific Embodiments of The Immunoassays
Analysis of Free GDF-8

Figure 21:
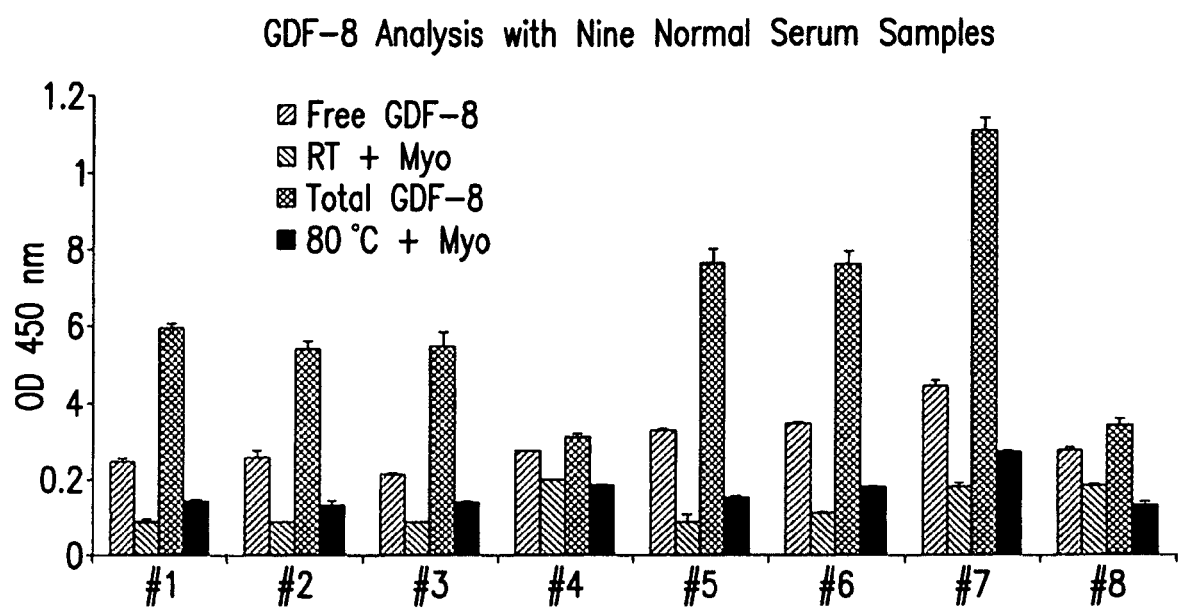
FIG. 21 shows the results of an assay to measure free and total GDF-8 in nine normal serum samples. Results are displayed as +/−MYO-029. Values are given in pg/ml of GDF-8 and correspond to the endogenous level of GDF-8 in 100% serum.

In one embodiment, the present invention comprises a method for detecting the presence of free GDF-8 in a biological sample. A representative example of this embodiment is depicted in FIG. 21.

As used herein, the term free GDF-8 includes GDF-8 that is present in its active, mature state. Mature GDF-8 may be a monomer, dimer, or homodimer. Free GDF-8 does not encompass latent GDF-8 (i.e., mature GDF-8 associated with GDF-8 propeptide), GDF-8 associated with GDF-8 binding proteins, or GDF-8 that is associated with anti-GDF-8 modulating agents, such as, for example, GDF-8 binding and neutralizing antibodies.

In one embodiment, methods to detect and quantify free GDF-8 comprise the following steps: (a) combining a GDF-8 capture antibody and a sample under conditions which allow GDF-8, when present in the biological sample, to bind to the one or more capture antibodies forming a capture antibody-GDF-8 complex; adding a detection antibody under complex-forming conditions, wherein the detection antibody binds the capture antibody-GDF-8 complex; and (b) detecting complexes formed between the capture antibody-GDF-8 complex and the detection antibody, if any, as an indication of GDF-8 in the biological sample.

The detection antibody or antigen binding protein may further comprise a detectable label. In some instances, the detection antibody is not labeled and a detection agent that specifically recognizes the detection antibody is utilized.

Analysis of Total GDF-8

In one embodiment, the present invention comprises a method for detecting the presence of total GDF-8 in a biological sample.

As used herein, the term total GDF-8 includes GDF-8 that is present in its active, mature state, and any GDF-8 that is present in its latent form (i.e., mature GDF-8 associated with GDF-8 propeptide), GDF-8 associated with GDF-8 binding proteins, or GDF-8 that is associated with anti-GDF-8 modulating agents, such as, for example, GDF-8 binding and neutralizing antibodies. A measurement of total GDF-8 includes a measurement of GDF-8 that is bound by therapeutic antibody MYO-029.

Acid Dissociation

In one embodiment, methods to detect and quantify total GDF-8 utilize an acid dissociation method, and comprise the following steps: (a) combining a GDF-8 capture antibody with a biological sample under acidic conditions (between about pH1.0 to about pH 6.0, preferable about pH 2.5) which allow GDF-8, when present in the biological sample, to bind to one or more capture antibodies forming a capture antibody-GDF-8 complex; adding a GDF-8 detection antibody) under complex-forming conditions, wherein the detection antibody binds the capture antibody-GDF-8 complex; and (b) detecting complexes formed between the capture antibody-GDF-8 complex and the detection antibody, if any, as an indication of GDF-8 in the biological sample.

The detection antibody or antigen binding protein may further comprise a detectable label. In some instances, the detection antibody is not labeled and a detection agent that specifically recognizes the detection antibody is utilized.

Heat Dissociation

In another embodiment, methods to detect and quantify total GDF-8 utilize a heat dissociation method, and comprise the following steps: (a) contacting a GDF-8 capture antibody or antigen binding protein with a surface of a solid support; (b) heating a biological sample to at least 63° C., such as, e.g., 65° C., 70° C., 75° C., 80° C., 85° C., or 90° C., for at least 3 minutes, such as, e.g., 5, 7, 9, 10, 12, 14, or 15 minutes and combining a biological sample with the solid support under conditions which allow GDF-8, when present in the biological sample, to bind to one or more capture antibodies forming a capture antibody-GDF-8 complex; (c) adding a detection antibody to the solid support from step (b) under complex-forming acidic conditions, wherein the detection antibody binds the capture antibody-GDF-8 complex; and (d) detecting complexes formed between the capture antibody-GDF-8 complex and the detection antibody, if any, as an indication of GDF-8 in the biological sample.

The detection antibody or antigen binding protein may further comprise a detectable label. In some instances, the detection antibody is not labeled and a detection agent that specifically recognizes the detection antibody is utilized.

Figure 12:
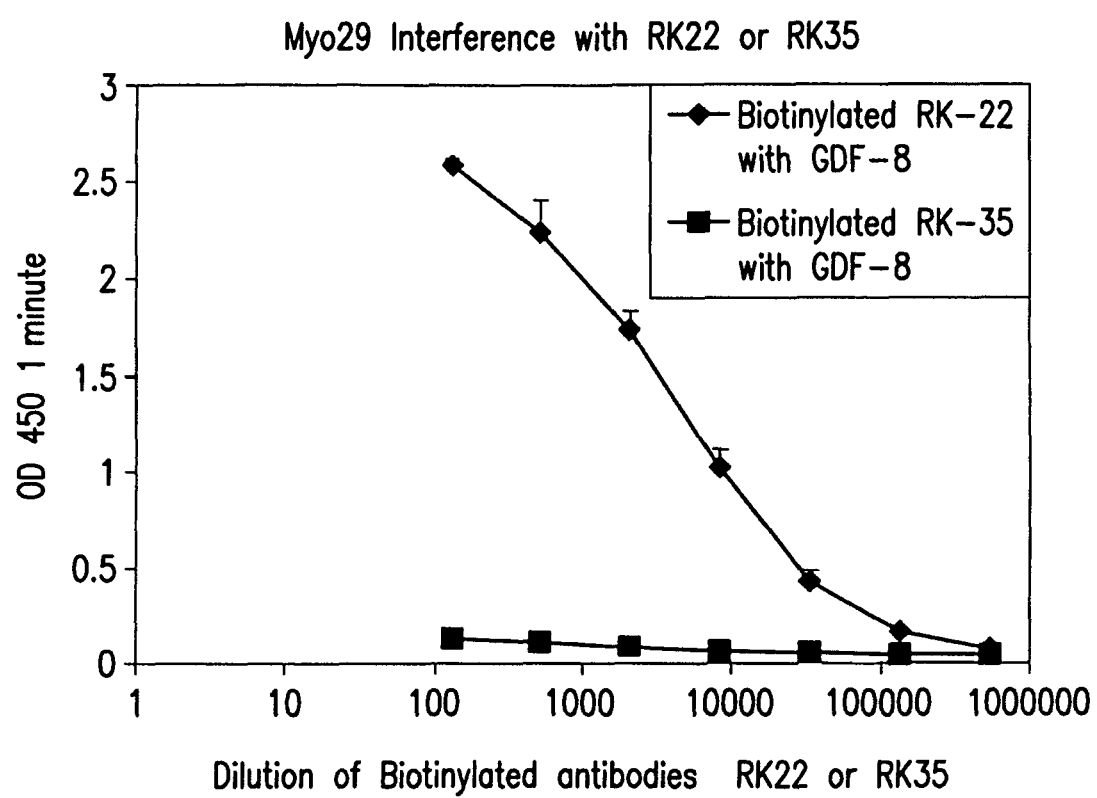
FIG. 12 shows that the antibody RK35 does not bind to GDF-8 in the presence of MYO-029. MYO-029 antibody was coated onto HBX assay plates and GDF-8 was added at 1200 pg/ml with increasing concentrations of biotinylated detection antibodies (RK22 or RK35). No signal is produced with biotinylated RK35. The results indicate crossreactivity between RK35 and MYO-029 for binding to GDF-8.

One embodiments of this method are depicted in FIG. 12, where it is shown that the antibody MYO-029 inhibits signal produced by the detection antibody (e.g., biotinylated-RK22). In this manner, the assay background can be calculated and subtracted from the value obtained in step (d).

Alternative Embodiments for The Analysis of Free and Total GDF-8

In certain embodiments, the capture antibody is contacted with the surface of a solid support, or a reaction vessel, for example by being either covalently or non-covalently bound to the surface. The contact may be direct or indirect. The surface may be modified, for example by chemical or radiation treatment to affect the binding characteristics of the surface.

In certain embodiments, after contacting the capture antibody with the biological sample and washed to remove unbound components. Non-specific interactions may be minimized with a blocking step, wherein a buffer comprising at least one blocking agent, such as a protein that does not specifically bind to the target is added to the reaction vessel. Blocking buffers may comprise commercially available blocking buffers, serum, bovine serum albumin, milk, casein, gelatin, and/or non-ionic detergents, for example. In some embodiments the reaction vessel is washed with a buffer with a pH between about 5 and about 9, such as citrate buffer, phosphate buffer, Tris buffer or acetate buffer. Alternatively, the buffer is between about pH 3.0 and pH 5.0, for example, in the acid dissociation methods to detect and quantify total GDF-8.

The biological sample to be tested in the methods of the invention may be chosen from serum, blood, plasma, biopsy sample, tissue sample, cell suspension, saliva, oral fluid, cerebrospinal fluid, amniotic fluid, milk, colostrum, mammary gland secretion, lymph, urine, sweat, synovial fluid, and lacrimal fluid. In certain embodiments, the biological sample is a fluid. In some embodiments, the biological sample is chosen from blood, serum, and plasma. In specific embodiments, the biological sample is serum from, e.g., such as human, monkey, rat, mouse, bovine, ovine, or chicken serum.

In other embodiments, the biological sample is isolated from an individual or individuals and optionally treated prior to testing. For example, the sample may be diluted. The dilution buffer may optionally comprise a constant amount of a control biological sample, chosen to correspond to the test biological sample, for example to control for background effects or interference of the sample matrix. In one embodiment, a test sample of human plasma is diluted in THST (50 mM Tris-HCl, pH 8.0, containing 1.0 mM glycine, 0.5 M NaCl, and 0.05% (v/v) Tween 20®) buffer 1:8 fold, and dilutions of the biological sample beyond 8-fold are prepared in THST plus 12.5% human serum that has been depleted of GDF-8. A biological sample may be diluted approximately 2, 4, 5, 8, 10, 12, 14, 15, 16, 32, 64, or 128-fold. In other embodiments, a biological sample is serially diluted 1:1.5 or 1:1.6 to obtain a range of data points that allow verification of dilutional linearity and matrix effects. For some biological sample matrices, a dilution may be selected at which matrix interference and assay sensitivity are optimized.

The diluent is not particularly restricted but may comprise serum, including e.g., human serum, human serum that has been depleted of GDF-8, mouse serum, mouse serum that has been depleted of GDF-8, deionized water or various buffers having a buffer action within the range of pH about 3.0 to pH about 9.0, depending on whether the assay is to be performed at acidic conditions or not. For analysis of free GDF-8, performed at neutral pH, the pH is about 6.5 to about 8.5, about 6.5 to about 7.0, about 7.0 to about 7.5, about 7.5 to about 8.0, or about 8.0 to about 8.5 (e.g. citrate buffer, phosphate buffer, Tris buffer, acetate buffer, or borate buffer). For analysis of total GDF-8, performed at an acidic pH, the pH is, for example, about 1.0 to about 2.5, about 2.5 to about 5.5, about 2.5 to about 3.0, about 3.0 to about 3.5, about 3.5 to about 4.0, about 4.0 to about 4.5, or about 4.5 to about 5.5, about 5.5 to about 6.5.

In some embodiments, the biological sample may be optionally fractionated or concentrated using well known methods and then added to an assay as described herein to detect GDF-8. Fractionation (including purification) or concentration may be used, for example, if matrix interference limits detection of a GDF-8 modulating agent in the assay. Fractionation and concentration techniques, include, but are not limited to, centrifugation, ammonium sulfate precipitation, polyethylene glycol precipitation, trichloroacetic acid (TCA) precipitation, affinity techniques (such as immunoprecipitation with a resin conjugated to a specific binding partner such as an antibody, e.g., an anti-GDF-8 antibody), chromatographic techniques, and other separation techniques.

A biological sample may be collected from a naïve individual, or a biological sample may be taken before, during or after administration of a GDF-8 modulating agent. For example, a sample may be obtained from an individual 1, 2, 4, 6, 7, 8, 10, 12, 14, 15, 20, 25, 30, or more days after administration of a GDF-8 modulating agent. A biological sample may also be obtained 1, 2, 3, 4, 6, 7, 8, 10, 12, 14, 16, or more weeks after administration of a GDF-8 modulating agent. In some cases, timepoints of up to a year or beyond are appropriate. Biological samples may be tested for both free and total GDF-8. An analysis of total GDF-8 is particularly important in individuals being treated with GDF-8 modulating agents, as these agents may interfere with the ability of either the detection or the capture agent to bind GDF-8 in a biological sample. Thus, the acid or heat dissociation method utilized in the analysis of total GDF-8 becomes particularly important.

In certain embodiments, an aliquot of the biological sample to be tested is contacted with the capture antibody or antigen binding protein and incubated for a period of time sufficient (e.g., 2-120 minutes, or 1-4 hours) and under suitable conditions (e.g., 23° C.) to allow binding the capture antibody to the GDF-8, if any, present in the biological sample and to allow antibody/GDF-8 complexes to form. In other embodiments, the GDF-8/antibody reaction is conducted under the conditions in routine use for conventional immunoassays. A typical procedure comprises incubating or allowing to stand a reaction system comprising the capture antibody and biological sample at a temperature of not over 45° C., such as, e.g., between about 4° C. and about 40° C., or between about 23° C. and about 40° C. for between about 0.5 and 40 hours, such as, e.g., between about 1 and about 20 hours.

Following an incubation period, the antibody/GDF-8 complex is, in some embodiments, washed with buffer to remove unbound solutes. In other embodiments a simultaneous assay is performed, whereby the biological sample and detection antibody are added to the reaction vessel concurrently.

In particular embodiments, in which the detection antibody is added after the biological sample, a procedure may comprise incubating or allowing to stand a reaction system comprising the antibody/GDF-8 complex and detection antibody at a temperature of not over 45° C., such as, e.g., between about 4° C. and about 40° C., or between about 25° C. and about 40° C. for between about 0.5 and 40 hours, or between about 1 and about 20 hours.

In some embodiments, the detection antibody, antigen binding protein or fragment thereof comprises a detectable label. In further embodiments, the detection antibody is indirectly detected, for example by a detection agent. In some embodiments, the detection agent is in excess, so that essentially all detection antibodies that are present in the reaction vessel are bound.

In some embodiments, a "direct" label may be any molecule bound or conjugated to a specific binding member that is capable of spontaneously producing a detectible signal without the addition of ancillary reagents. Some examples include a radioisotope (e.g., 125I, 3H, 14C), a fluorophore (e.g., luciferase, green fluorescent protein, fluorescein isothiocyanate, tetramethylrhodamine isothiocyanate, 1-N-(2,2,6,6-tetramethyl-1-oxyl-4-piperidyl)-5-N-(aspartate)-2, 4-dinitrobenzene), a dye (e.g., phycocyanin, phycoerythrin, Texas Red, o-phthalaldehyde), luminescent molecules, including chemiluminescent and bioluminescent molecules, colloidal gold particles, colloidal silver particles, other colloidal metal particles, polystyrene dye particles, minute colored particles such as dye sols, and colored latex particles. Many other suitable label molecules are well known to those skilled in the art and may be utilized in the methods of the invention.

In certain instances, the label may be an enzyme such as, e.g., alkaline phosphatase, horseradish peroxidase, glucose oxidase, or β-galactosidase. In various embodiments, the substrates to be used with the specific enzymes are chosen for the production, in the presence of the corresponding enzyme, of a detectable change in color, fluorescence, or luminescence. The enzyme may be conjugated to the antibody or antigen binding protein by glutaraldehyde or reductive amination cross-linking. As will be readily recognized, however, wide varieties of different conjugation techniques exist, and are readily available to the skilled artisan.

In a preferred embodiment, the detection antibody or antigen binding protein is biotinylated. Anti-GDF-8 antibodies useful as detection antibodies may be biotinylated as set forth in Example 1 (see, e.g., Example 1: section 1, subsection 5). Various biotinylation reagents are capable of efficiently labeling proteins, including antibodies. Molar ratios of biotin derivative to antibody may be about 10, 15, 20, 40, or 80 to 1, and reaction times, reactant concentrations, and temperatures may be varied to adjust the amount of biotin incorporated in the reaction. Biotin derivatives are well known and available in the art, including variable spacer arms, modifications to affect solubility, and/or reactive groups to allow cleavage of the biotin moiety. Succinimidyl esters of biotin and its derivatives, including water-soluble sulfosuccinimidyl esters may be used for biotinylation of GDF-8, for example. To quantitate the amount of biotin incorporated, well-known analytical and sizing techniques are used including, for example, reverse phase high pressure liquid chromatography, mass spectroscopy, etc. Additionally, commercial kits for quantitating biotin by colorimetric or fluorimetric assays, for example, are available (see, e.g., EZ™ Biotin Quantitation Kit, Pierce, utilizing HABA (2-(4'-hydroxyazo benzene)-benzoic acid)).

In one embodiment, biotinylated RK-22 is a detection agent for detecting GDF-8 binding to RK35.

In a particular embodiment, the biotinylated and/or enzyme-labeled detection agent such as an antibody or antigen binding protein is added to the GDF-8/antibody complex, and allowed to bind. The excess reagent is washed away, and a solution containing an appropriate substrate is then added to reaction vessel. The substrate undergoes an enzyme-catalyzed reaction resulting in a spectrophotometrically-measurable change that is indicative of the amount of GDF-8 present in the sample.

For example, a biotinylated detection antibody or antigen binding protein can be detected through its interaction with an avidin-enzyme conjugate, e.g., avidin-horseradish peroxidase, after sequential incubation with the avidin-enzyme conjugate and a suitable chromogenic or fluorogenic substrate. A biotinylated detection antibody may also be detected with Europium labeled streptavidin.

In certain embodiments, an antibody/GDF-8/antibody complex associated with the surface of the reaction vessel is detected by qualitative or quantitative assessment of the signal of the label. In some instances, the label is measured directly, e.g., by fluorescence or luminescence, or indirectly, via addition of a substrate. In others, the label is measured following incubation with an additional reagent. In embodiments in which the label is biotin, an avidin conjugate (such as horseradish peroxidase) may be added in a subsequent step. In one particular embodiment, the avidin conjugate may bind to the immobilized detection antibody or antigen binding protein. Excess avidin conjugate is washed away. A substrate of the enzyme is then added, resulting in a measurable change in, e.g., color, fluorescence, or luminescence. In some embodiments the substrate for horseradish peroxidase is 3,3', 5,5'-tetramethylbenzidine.

Quantitation of Free and Total GDF-8

GDF-8 levels may be quantified using methods well known to those of skill in the art. In certain embodiments, the GDF-8 levels in a biological sample are compared to a known level, such as is obtained, for example, by using a standard curve. The generation of GDF-8 standard curves is demonstrated in Example 15. The standard curve may comprise GDF-8 of known concentrations diluted in a buffer. In certain embodiments the buffer is serum, such as, e.g., human serum, mouse serum, primate serum, bovine serum, or ovine serum. The serum is optionally depleted of endogenous GDF-8 prior to the addition of known concentrations of GDF-8. The serum may be obtained from Belgian Blue cattle, which is naturally devoid of GDF-8.

In one embodiment, a method for quantifying free GDF-8 in a biological sample comprises combining a GDF-8 capture antibody or antigen binding protein and a biological sample under conditions which allow GDF-8, when present in the biological sample, to bind to the one or more capture antibodies forming a capture antibody or antigen binding protein-GDF-8 complex; adding a labeled GDF-8 detection antibody or antigen binding protein to the solid support from step (b); (d) detecting complexes formed between the capture antibody-GDF-8 complex and the detection antibody by detecting a signal generated by the label on the GDF-8 detection antibody; and (e) quantifying the level of GDF-8 in the biological sample by comparing the signal generated by complexes containing the labeled GDF-8 detection antibody to a standard curve generated by determining the corresponding signal intensities for known amounts of GDF-8.

Methods to quantify total GDF-8 are similar, except that the biological sample is diluted in acidic buffer.

Methods of Treating, Ameliorating, Preventing, and Inhibiting the Progress of GDF8-Associated Disorders The involvement of GDF8 in development and/or regulation of GDF8-associated disorders, e.g., skeletal muscle, bone, glucose homeostasis, etc., and the discovery of the novel specific GDF8 antagonists of the invention enable methods for treating, ameliorating or preventing GDF8-associated disorders, e.g., muscle disorders, neuromuscular disorders, bone-degenerative disorders, metabolic or induced bone disorders, glucose metabolism disorders, adipose disorders, and insulin-related disorders. In addition, the antagonists allow for diagnosing, prognosing and monitoring the progress of such disorders by measuring the level of GDF8 in a biological sample. In particular, antagonists epitope(s) specific to GDF8 (e.g., peptide mimetics thereto, inhibitory polynucleotides thereto, antibodies thereto, small molecules, etc.) of the invention can be used to treat an individual with a GDF8 associated disorder, or in a method of distinguishing whether a patient is suffering from a GDF8-associated disorder.

The antagonists of the present invention are useful to prevent, diagnose, or treat various medical GDF8 associated disorders in humans or animals. The antagonists can be used to inhibit, reduce and/or neutralize one or more activities associated with GDF8. Most preferably, the antagonists inhibit or reduce one or more of the activities of GDF8 relative to GDF8 that is not in the presence of an antagonist of the invention. In certain embodiments, an antagonist of the invention inhibits the activity of GDF8 by at least 50%, preferably at least 60, 62, 64, 66, 68, 70, 72, 72, 76, 78, 80, 82, 84, 86, or 88%, more preferably at least 90, 91, 92, 93, or 94%, and even more preferably at least 95% to 100% relative to a mature GDF8 protein that is not bound by one or more anti-GDF8 antibodies. Inhibition or neutralization of GDF8 activity can be measured, e.g., in pGL3(CAGA)12 reporter gene assays (RGA) as described in Thies et al., supra, and in ActRIIB receptor assays as illustrated in the Examples.

The medical disorders diagnosed, prognosed, monitored, treated, ameliorated or prevented by the presently disclosed antagonists are GDF8 associated disorders, e.g., muscle or neuromuscular disorders including, e.g., muscular dystrophy (MD; including Duchenne's muscular dystrophy), amyotrophic lateral sclerosis (ALS), muscle atrophy, organ atrophy, frailty, carpal tunnel syndrome, congestive obstructive pulmonary disease, sarcopenia, cachexia, and muscle wasting syndromes (e.g., caused by other diseases and conditions). In addition, other medical disorders that may be diagnosed, prognosed, monitored, treated, ameliorated or prevented by the GDF8 antibodies are adipose tissue disorders such as obesity, type 2 diabetes, impaired glucose tolerance, metabolic syndromes (e.g., syndrome X), insulin resistance, induced by trauma (such as burns or nitrogen imbalance), or bone-degenerative diseases (e.g., osteoarthritis and osteoporosis). In preferred, but nonlimiting, embodiments of the invention, the medical disorders that are diagnosed, prognosed, monitored, treated, ameliorated or prevented by the presently disclosed antagonists are muscular or neuromuscular disorders. In a more preferred, but nonlimiting, embodiment of the invention, the muscular or neuromuscular disorder that is diagnosed, prognosed, monitored, treated, ameliorated or prevented by the presently disclosed antagonists is either MD or ALS.

Other medical disorders that may be diagnosed, treated, ameliorated or prevented by the presently disclosed antagonists are those associated with a loss of bone, which include osteoporosis, especially in the elderly and/or postmenopausal women, glucocorticoid-induced osteoporosis, osteopenia, osteoarthritis, and osteoporosis-related fractures. Other target metabolic bone diseases and disorders include low bone mass due to chronic glucocorticoid therapy, premature gonadal failure, androgen suppression, vitamin D deficiency, secondary hyperparathyroidism, nutritional deficiencies, and anorexia nervosa. The antagonists of the invention are preferably used to prevent, diagnose, ameliorate or treat such medical disorders in mammals, particularly in humans, e.g., women who will be or are pregnant.

The antagonists of the present invention are administered in therapeutically effective amounts. Generally, a therapeutically effective amount may vary with the subject's age, condition, and sex, as well as the severity of the medical condition in the subject. The dosage may be determined by a physician and adjusted, as necessary, to suit observed effects of the treatment. Toxicity and therapeutic efficacy of such compounds can be determined by standard pharmaceutical procedures in cell cultures or experimental animals, e.g., for determining the LD50 (the dose lethal to 50% of a population) and the ED50 (the dose therapeutically effective in 50% of a population). The dose ratio between toxic and therapeutic effects, i.e., the LD50/ED50, is the therapeutic index, and antagonists exhibiting large therapeutic indices are preferred.

The data obtained from cell culture assays and animal studies can be used in formulating a range of dosage for use in humans. The dosage of such compounds lies preferably within a range of circulating concentrations that includes the ED50 with little or no toxicity. The dosage may vary within this range depending upon the form of dosage and the route of administration. For any antagonist used in the present invention, the therapeutically effective dose can be estimated initially from cell culture assays. A dose may be formulated in animal models to achieve a circulating plasma concentration range that includes the IC50 (e.g., the concentration of the test antagonist which achieves a half-maximal inhibition of symptoms or biological activity) as determined in cell culture. Levels in plasma may be measured, for example, by high performance liquid chromatography. The effects of any particular dosage can be monitored by a suitable bioassay. Examples of suitable bioassays include, but are not limited to, DNA replication assays, transcription-based assays, GDF8 protein/receptor binding assays, creatine kinase assays, assays based on the differentiation of preadipocytes, assays based on glucose uptake in adipocytes, and immunological assays.

Generally, the compositions are administered so that antagonists or their binding fragments are given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 10 µg/kg to 1 mg/kg, 10 µg/kg to 100 µg/kg, 100 µg to 1 mg/kg, and 500 µg/kg to 1 mg/kg. Preferably, the antagonists are given as a bolus dose to maximize the circulating levels of antagonists for the greatest length of time after the dose. Continuous infusion may also be used before, after or in place of the bolus dose.

Methods of Identifying Therapeutic Agents for GDF8-Associated Disorders

Yet another aspect of the invention provides a method of identifying therapeutic agents useful in treatment of, e.g., muscle, glucose metabolism, adipose, and bone disorders.

Appropriate screening assays, e.g., ELISA-based assays, are known in the art. In such a screening assay, a first binding mixture is formed by combining an antagonist, particularly a peptide mimetic of an epitope specific to GDF8 or an antibody or antigen binding protein of the invention and its ligand, GDF8, and the amount of binding between the ligand and the antibody in the first binding mixture (M0) is measured. A second binding mixture is also formed by combining the antagonist, the ligand, and a compound or agent to be screened, and the amount of binding between the ligand and the antibody in the second binding mixture (M1) is measured. The amounts of binding in the first and second binding mixtures are then compared, for example, by calculating the M1/M0 ratio. The compound or agent is considered to be capable of specifically interacting with GDF8 if a decrease in binding in the second binding mixture as compared to the first binding mixture is observed (i.e., M1/M0<1). The formulation and optimization of binding mixtures is within the level of skill in the art; such binding mixtures may also contain buffers and salts necessary to enhance or to optimize binding, and additional control assays may be included in the screening assay of the invention.

Compounds found to reduce the antagonist-ligand binding by at least about 10% (i.e., M1/M0<0.9), preferably greater than about 30%, may thus be identified and then, if desired, secondarily screened for the capacity to inhibit GDF8 activity in other assays such as the ActRIIB binding assay, or other cell-based and in vivo assays as described in the Examples or well known in the art.

Small Molecules

Inhibiting GDF8 activity in an organism (or subject) afflicted with (or at risk for) a GDF8-associated disorder, or in a cell from such an organism involved in such disorders, may also be achieved through the use of antagonist small molecules (usually organic small molecules) that antagonize, i.e., inhibit the activity of, GDF8. Novel antagonistic small molecules may be identified by the screening methods described above and may be used in the treatment methods of the present invention described herein.

Conversely, increasing GDF8 activity in an organism (or subject) afflicted with (or at risk for) a disorder related to decreased GDF8 expression and/or activity or a disorder related to decreased GDF8 levels may also be achieved through the use of small molecules (usually organic small molecules) that agonize, i.e., enhance the activity of, GDF8. Novel agonistic small molecules may be identified by screening methods and may be used in the treatment methods of the present invention described herein.

Methods of Diagnosing, Prognosing, and Monitoring the Progress of GDF8-Associated Disorders In addition to treating e.g., muscle, bone, glucose metabolism, and adipose disorders, the present invention provides methods for diagnosing such disorders by detecting the decrease or increase of GDF8 in a biological sample, e.g., serum, plasma, bronchoalveolar lavage fluid, sputum, biopsies (e.g., of muscle tissue) etc. "Diagnostic" or "diagnosing" means identifying the presence or absence of a pathologic condition. Diagnostic methods involve detecting the presence of GDF8 by, e.g., determining a test amount of GDF8 polypeptide in a biological sample from a subject (human or nonhuman mammal), and comparing the test amount with a normal amount or range (e.g., an amount or range from an individual(s) known not to suffer from such a disorder) for the GDF8 polypeptide. While a particular diagnostic method may not provide a definitive diagnosis of GDF8-associated disorders, it suffices if the method provides a positive indication that aids in diagnosis.

The present invention also provides methods for prognosing GDF8-associated disorders, e.g., muscle, bone, glucose metabolism, and adipose disorders, by detecting upregulation of GDF8. "Prognostic" or "prognosing" means predicting the probable development and/or severity of a pathologic condition. Prognostic methods involve determining the test amount of GDF8 in a biological sample from a subject, and comparing the test amount to a prognostic amount or range (e.g., an amount or range from individuals with varying severities of, e.g., ALS) for GDF8. Various amounts of the GDF8 in a test sample are consistent with certain prognoses for GDF8-associated disorders. The detection of an amount of GDF8 at a particular prognostic level provides a prognosis for the subject.

The present invention also provides methods for monitoring the course of GDF8-associated muscle, bone, glucose metabolism, and adipose disorders by detecting the upregulation or downregulation of GDF8. Monitoring methods involve determining the test amounts of GDF8 in biological samples taken from a subject at a first and second time, and comparing the amounts. A change in amount of GDF8 between the first and second time indicates a change in the course of, e.g., severity of, GDF8-associated disorders. A skilled artisan will recognize that in GDF8-associated disorders where an increase in muscle mass is desirable, a decrease in amount of GDF8 protein and/or activity between the first and second time indicates remission of the disorder, and an increase in amount indicates progression of the disorder. Conversely, for GDF8-associated disorders where a decrease in muscle mass is desirable, a decrease in amount in GDF8 protein and/or activity between the first and second time indicates progression of the disorder, and an increase in amount indicates remission of the disorder. Such monitoring assays are also useful for evaluating the efficacy of a particular therapeutic intervention (e.g., disease attenuation and/or reversal) in patients being treated for GDF8-associated disorders.

The antagonists of the present invention may be used for diagnosis, prognosis or monitoring by detecting the presence of GDF8 in vivo or in vitro. Such detection methods are well known in the art and include ELISA, radioimmunoassay, immunoblot, Western blot, immunofluorescence, immunoprecipitation, and other comparable techniques. The antagonists may further be provided in a diagnostic kit that incorporates one or more of these techniques to detect GDF8. Such a kit may contain other components, packaging, instructions, or other material to aid the detection of the protein and use of the kit.

Where the antagonists are intended for diagnostic, prognostic, or monitoring purposes, it may be desirable to modify them, for example, with a ligand group (such as biotin) or a detectable marker group (such as a fluorescent group, a radioisotope or an enzyme). If desired, the antagonists (whether polyclonal or monoclonal) may be labeled using conventional techniques. Suitable labels include fluorophores, chromophores, radioactive atoms, electron-dense reagents, enzymes, and ligands having specific binding partners. Enzymes are typically detected by their activity. For example, horseradish peroxidase can be detected by its ability to convert tetramethylbenzidine (TMB) to a blue pigment, quantifiable with a spectrophotometer. Other suitable labels may include biotin and avidin or streptavidin, IgG and protein A, and the numerous receptor-ligand couples known in the art. Other permutations and possibilities will be readily apparent to those of ordinary skill in the art, and are considered as equivalents within the scope of the instant invention.

Pharmaceutical Compositions and Methods of Administration

The present invention provides compositions comprising the presently disclosed antagonists of the invention, i.e., polypeptides, polynucleotides, vectors, antibodies, antibody or antigen binding protein fragments, and small molecules. Such compositions may be suitable for pharmaceutical use and administration to patients. The compositions typically comprise one or more molecules of the present invention, preferably an antibody or antigen binding protein, and a pharmaceutically acceptable excipient. The antagonists of the present invention can be used in vitro, ex vivo, or incorporated into a pharmaceutical composition when combined with a pharmaceutically acceptable carrier. As used herein, the phrase "pharmaceutically acceptable excipient" includes any and all solvents, solutions, buffers, dispersion medias, coatings, antibacterial and antifungal agents, isotonic and absorption delaying agents, and the like, that are compatible with pharmaceutical administration. Such a composition may contain, in addition to the antagonists of the invention and carrier, various diluents, fillers, salts, buffers, stabilizers, solubilizers, and other materials well known in the art. The term "pharmaceutically acceptable" means a nontoxic material that does not interfere with the effectiveness of the biological activity of the active ingredient(s). The characteristics of the carrier will depend on the route of administration. The use of such media and agents for pharmaceutically active substances is well known in the art. The compositions may also contain other active compounds providing supplemental, additional, or enhanced therapeutic functions. The pharmaceutical compositions may also be included in a container, pack, or dispenser together with instructions for administration.

The pharmaceutical composition of the invention may be in the form of a liposome in which an antagonist of the invention is combined, in addition to other pharmaceutically acceptable carriers, with amphipathic agents such as lipids that exist in aggregated form as micelles, insoluble monolayers, liquid crystals, or lamellar layers while in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art.

As used herein, the term "therapeutically effective amount" means the total amount of each active component of the pharmaceutical composition or method that is sufficient to show a meaningful patient benefit, e.g., amelioration of symptoms of, healing of, or increase in rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of, e.g., an antagonist specific for GDF8 is administered to a subject, e.g., mammal (e.g., a human). An antagonist of the invention may be administered in accordance with the method of the invention either alone or in combination with other therapies such as anti-inflammatory agents. When coadministered with one or more agents, an antagonist of the invention may be administered either simultaneously with the second agent, or sequentially. If administered sequentially, the attending physician will decide on the appropriate sequence of administering an antagonist of the invention in combination with other agents.

In one embodiment, the antagonists of the invention, e.g., pharmaceutical compositions thereof, are administered in combination therapy, i.e., combined with other agents, e.g., therapeutic agents, that are useful for treating pathological conditions or disorders, such as muscle disorders, neuromuscular disorders, bone degenerative disorders, metabolic or induced bone disorders, adipose disorders, glucose metabolism disorders or insulin-related disorders, e.g., as well as allergic and inflammatory disorders. The term "in combination" in this context means that the agents are given substantially contemporaneously, either simultaneously or sequentially. If given sequentially, at the onset of administration of the second compound, the first of the two compounds is preferably still detectable at effective concentrations at the site of treatment or in the subject.

A pharmaceutical composition of the invention is formulated to be compatible with its intended route of administration. Methods to accomplish the administration are known to those of ordinary skill in the art. It may also be possible to obtain compositions which may be topically or orally administered, or which may be capable of transmission across mucous membranes. Administration of an antagonist of the invention used in a pharmaceutical composition to practice the method of the present invention can be carried out in a variety of conventional ways, such as oral ingestion, inhalation, cutaneous, subcutaneous, or intravenous injection.

Solutions or suspensions used for intradermal or subcutaneous application typically include one or more of the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. The pH can be adjusted with acids or bases, such as hydrochloric acid or sodium hydroxide. Such preparations may be enclosed in ampoules, disposable syringes or multiple dose vials made of glass or plastic.

Pharmaceutical compositions suitable for injection include sterile aqueous solutions or dispersions and sterile powders for the extemporaneous preparation of sterile injectable solutions or dispersion. For intravenous administration, suitable pharmaceutically acceptable carriers include physiological saline, bacteriostatic water, Cremophor™ EL (BASF, Parsippany, N.J.) or phosphate buffered saline (PBS). In all cases, the composition must be sterile and should be fluid to the extent that easy syringability exists. A pharmaceutically acceptable carrier must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

When a therapeutically effective amount of an antibody or antigen binding protein of the invention is administered by, e.g., intravenous, cutaneous or subcutaneous injection, the binding agent will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to binding agents, an isotonic vehicle such as sodium chloride injection, Ringer's injection, dextrose injection, dextrose and sodium chloride injection, lactated Ringer's injection, or other vehicle as known in the art. The pharmaceutical composition(s) of the present invention may also contain stabilizers, preservatives, buffers, antioxidants, or other additive known to those of skill in the art.

The amount of an antagonist of the invention in the pharmaceutical composition of the present invention will depend upon the nature and severity of the condition being treated, and on the nature of prior treatments undergone by the patient. Ultimately, the attending physician will decide the amount of antagonist with which to treat each individual patient. Initially, an attending physician administers low doses of the antagonist and observes the patient's response. Larger doses of antagonist may be administered until the optimal therapeutic effect is obtained for the patient, and at that point the dosage is generally not increased further. It is contemplated that the various pharmaceutical compositions used to practice the method of the present invention should contain about 0.1 mg to 50 µg antagonist per kg body weight.

The duration of therapy using the pharmaceutical composition of the present invention will vary, depending on the severity of the disease being treated and the condition and potential idiosyncratic response of each individual patient. It is contemplated that the duration of each application of antagonist will be via, e.g., the subcutaneous route and, e.g., in the range of once a week. Ultimately the attending physician will decide on the appropriate duration of therapy using the pharmaceutical composition of the present invention.

Oral compositions generally include an inert diluent or an edible carrier. They can be enclosed in gelatin capsules or compressed into tablets. For the purpose of oral therapeutic administration, the antagonist (e.g., antibody or antigen binding protein, small molecule, etc.) of the invention can be incorporated with excipients and used in the form of tablets or capsules. Pharmaceutically compatible binding agents, and/or adjuvant materials can be included as part of the composition. The tablets, pills, capsules, and the like can contain any of the following ingredients, or compounds of a similar nature; a binder such as microcrystalline cellulose, gum tragacanth or gelatin; an excipient such as starch or lactose; a disintegrating agent such as alginic acid, Primogel™, or corn starch; a lubricant such as magnesium stearate or Sterotes™; a glidant such as colloidal silicon dioxide; a sweetening agent such as sucrose or saccharin; or a flavoring agent such as peppermint, methyl salicylate, or orange flavoring.

When a therapeutically effective amount of a pharmaceutical composition of the invention, e.g., an antagonist specific for GDF8, is administered orally, the binding agent will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% binding agent, and preferably from about 25 to 90% binding agent. When administered in liquid form, a liquid carrier such as water, petroleum, oils of animal or plant origin such as peanut oil, mineral oil, soybean oil, or sesame oil, or synthetic oils may be added (after taking into account the allergies of the individual patient and/or a large population of individuals to such liquid carriers). The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of the binding agent, and preferably from about 1 to 50% the binding agent.

For administration by inhalation, an antagonist of the invention is delivered in the form of an aerosol spray from a pressured container or dispenser, which contains a suitable propellant, e.g., a gas such as carbon dioxide, or a nebulizer. Accordingly, the compounds described herein can be administered by inhalation to pulmonary tissue. The term "pulmonary tissue" as used herein refers to any tissue of the respiratory tract and includes both the upper and lower respiratory tract, except where otherwise indicated. A specific GDF8 antagonist can be administered in combination with one or more of the existing modalities for treating pulmonary diseases.

In one example of administration, the compound is formulated for a nebulizer. In one embodiment, the compound can be stored in a lyophilized form (e.g., at room temperature) and reconstituted in solution prior to inhalation.

It is also possible to formulate the compound for inhalation using a medical device, e.g., an inhaler (see, e.g., U.S. Pat. Nos. 6,102,035 (a powder inhaler) and 6,012,454 (a dry powder inhaler)). The inhaler can include separate compartments for the active compound at a pH suitable for storage and another compartment for a neutralizing buffer, and a mechanism for combining the compound with a neutralizing buffer immediately prior to atomization. In one embodiment, the inhaler is a metered dose inhaler.

Although not necessary, delivery enhancers such as surfactants can be used to further enhance pulmonary delivery. A "surfactant" as used herein refers to a compound having hydrophilic and lipophilic moieties that promote absorption of a drug by interacting with an interface between two immiscible phases. Surfactants are useful with dry particles for several reasons, e.g., reduction of particle agglomeration, reduction of macrophage phagocytosis, etc. When coupled with lung surfactant, a more efficient absorption of the compound can be achieved because surfactants, such as DPPC, will greatly facilitate diffusion of the compound. Surfactants are well known in the art and include, but are not limited to, phosphoglycerides, e.g., phosphatidylcholines, L-alpha-phosphatidylcholine dipalmitoyl (DPPC) and diphosphatidyl glycerol (DPPG); hexadecanol; fatty acids; polyethylene glycol (PEG); polyoxyethylene-9-; auryl ether; palmitic acid; oleic acid; sorbitan trioleate (Span 85); glycocholate; surfactin; poloxomer; sorbitan fatty acid ester; sorbitan trioleate; tyloxapol; and phospholipids.

Systemic administration can also be by transmucosal or transdermal means. For example, in the case of antibodies that comprise the Fc portion, compositions may be capable of transmission across mucous membranes (e.g., intestine, mouth, or lungs) via the FcRn receptor-mediated pathway (e.g., U.S. Pat. No. 6,030,613). In general, transmucosal administration can be accomplished, for example, through the use of lozenges, nasal sprays, inhalers, or suppositories. For transdermal administration, the active compounds are formulated into ointments, salves, gels, patches or creams as generally known in the art. For transmucosal or transdermal administration, penetrants appropriate to the barrier to be permeated are used in the formulation. Such penetrants are generally known in the art, and include, for example, detergents, bile salts, and fusidic acid derivatives.

Pharmaceutical compositions may also consist of compositions suitable for gene therapy, i.e., compositions comprised of the polynucleotides disclosed herein. In the case of gene therapy, the pharmaceutically acceptable carrier may include, e.g., lipids, collagen spheres, cationic emulsion systems, water, saline buffers, viral vectors, chylomicron remnants, polymer nanoparticles (e.g., gelatin-DNA or chitosan-DNA), gold particles, polymer complexes, lipoplexes, polyplexes, etc. (see, e.g., Gardlik et al. (2005) *Med. Sci. Monit.* 11(4): RA110-21).

Stabilization and Retention

In one embodiment, a specific GDF8 antagonist is physically associated with a moiety that improves its stabilization and/or retention in circulation, e.g., in blood, serum, lymph, bronchopulmonary or bronchoalveolar lavage, or other tissues, e.g., by at least 1.5, 2, 5, 10, or 50 fold.

The presently disclosed antagonists of the invention may be prepared with carriers that will protect against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions containing the presently disclosed antagonists can also be used as pharmaceutically acceptable carriers. These can be prepared according to methods known to those skilled in the art.

For example, a specific GDF8 antagonist can be associated with a polymer, e.g., a substantially nonantigenic polymer, such as polyalkylene oxides or polyethylene oxides. Suitable polymers will vary substantially by weight. Polymers having molecular number average weights ranging from about 200 to about 35,000 (or about 1,000 to about 15,000, or about 2,000 to about 12,500) can be used.

For example, a specific GDF8 antagonist can be conjugated to a water-soluble polymer, e.g., hydrophilic polyvinyl polymers, e.g., polyvinylalcohol and polyvinylpyrrolidone. A nonlimiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; branched or unbranched polysaccharides, which comprise the saccharide monomers D-mannose, D- and L-galactose, fucose, fructose, D-xylose, L-arabinose, D-glucuronic acid, sialic acid, D-galacturonic acid, D-mannuronic acid (e.g., polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g., hyaluronic acid; polymers of sugar alcohols such as polysorbitol and polymannitol; heparin; etc.

Other compounds can also be attached to the same polymer, e.g., a cytotoxin, a label, or another targeting agent, e.g., another GDF8 antagonist or an unrelated ligand. Mono-activated, alkoxy-terminated polyalkylene oxides (PAOs), e.g., monomethoxy-terminated polyethylene glycols (mPEGs), C1-4 alkyl-terminated polymers, and bis-activated polyethylene oxides (glycols) can be used for cross-linking (see, e.g., U.S. Pat. No. 5,951,974).

In one embodiment, the polymer prior to cross-linking to the ligand need not be, but preferably is, water-soluble. Generally, after cross-linking, the product is water-soluble, e.g., exhibits a water solubility of at least about 0.01 mg/ml, and more preferably at least about 0.1 mg/ml, and still more preferably at least about 1 mg/ml. In addition, the polymer should not be highly immunogenic in the conjugate form, nor should it possess viscosity that is incompatible with intravenous infusion, aerosolization, or injection, if the conjugate is intended to be administered by such routes.

In one embodiment, the polymer contains only a single group that is reactive. This helps to avoid cross-linking of ligand molecules to one another. However, it is within the scope herein to maximize reaction conditions to reduce cross-linking between ligand molecules, or to purify the reaction products through gel filtration or ion exchange chromatography to recover substantially homogenous derivatives. In other embodiments, the polymer contains two or more reactive groups for the purpose of linking multiple ligands to the polymer backbone. Again, gel filtration or ion exchange chromatography can be used to recover the desired derivative in substantially homogeneous form.

The molecular weight of the polymer can range up to about 500,000 D, and preferably is at least about 20,000 D, or at least about 30,000 D, or at least about 40,000 D. The molecular weight chosen can depend upon the effective size of the conjugate to be achieved, the nature (e.g., structure, such as linear or branched) of the polymer, and the degree of derivatization.

A covalent bond can be used to attach a specific GDF8 antagonist to a polymer, for example, cross-linking to the N-terminal amino group of the ligand and epsilon amino groups found on lysine residues of the ligand, as well as other amino, imino, carboxyl, sulfhydryl, hydroxyl or other hydrophilic groups. The polymer may be covalently bonded directly to the GDF8 antagonist without the use of a multifunctional (ordinarily bifunctional) cross-linking agent. Covalent binding to amino groups is accomplished by known chemistries based upon cyanuric chloride, carbonyl diimidazole, and aldehyde-reactive groups (PEG alkoxide plus diethyl acetyl of bromoacetaldehyde, PEG plus DMSO and acetic anhydride, or PEG chloride plus the phenoxide of 4-hydroxybenzaldehyde, activated succinimidyl esters, activated dithiocarbonate PEG, 2,4,5-trichlorophenylcloroformate or P-nitrophenylchloroformate activated PEG). Carboxyl groups can be derivatized by coupling PEG-amine using carbodiimide. Sulfhydryl groups can be derivatized by coupling to maleimido-substituted PEG (e.g., alkoxy-PEG amine plus sulfosuccinimidyl 4-(N-maleimidomethyl)cyclohexane-1-carboxylate) (see WO 97/10847) or PEG-maleimide). Alternatively, free amino groups on the ligand (e.g., epsilon amino groups on lysine residues) can be thiolated with 2-imino-thiolane (Traut's reagent) and then coupled to maleimide-containing derivatives of PEG, e.g., as described in Pedley et al. (1994) *Br. J. Cancer* 70:1126-30.

Functionalized PEG polymers that can be attached to a GDF8 antagonist are available, e.g., from Shearwater Polymers, Inc. (Huntsville, Ala.). Such commercially available PEG derivatives include, e.g., amino-PEG, PEG amino acid esters, PEG-hydrazide, PEG-thiol, PEG-succinate, carboxymethylated PEG, PEG-propionic acid, PEG amino acids, PEG succinimidyl succinate, PEG succinimidyl propionate, succinimidyl ester of carboxymethylated PEG, succinimidyl carbonate of PEG, succinimidyl esters of amino acid PEGs, PEG-oxycarbonylimidazole, PEG-nitrophenyl carbonate, PEG tresylate, PEG-glycidyl ether, PEG-aldehyde, PEG vinylsulfone, PEG-maleimide, PEG-orthopyridyl-disulfide, heterofunctional PEGs, PEG vinyl derivatives, PEG silanes, and PEG phospholides. The reaction conditions for coupling these PEG derivatives may vary depending on the specific GDF8 antagonist, the desired degree of PEGylation, and the PEG derivative utilized. Some factors involved in the choice of PEG derivatives include: the desired point of attachment (such as lysine or cysteine R-groups), hydrolytic stability and reactivity of the derivatives, stability, toxicity and antigenicity of the linkage, suitability for analysis, etc. Specific instructions for the use of any particular derivative are available from the manufacturer.

The conjugates of a GDF8 antagonist and a polymer can be separated from the unreacted starting materials, e.g., by gel filtration or ion exchange chromatography, or other forms of chromatography, e.g., HPLC. Heterologous species of the conjugates are purified from one another in the same fashion. Resolution of different species (e.g., containing one or two PEG residues) is also possible due to the difference in the ionic properties of the unreacted amino acids (see, e.g., WO 96/34015).

The polynucleotides and proteins of the present invention are expected to exhibit one or more of the uses or biological activities (including those associated with assays cited below) identified herein. Uses or activities described for proteins of the present invention may be provided by administration or use of such proteins, or by administration or use of polynucleotides encoding such proteins (such as, e.g., in gene therapies or vectors suitable for introduction of DNA).

It may be advantageous to formulate oral or parenteral compositions in dosage unit form for ease of administration and uniformity of dosage. Dosage unit form as used herein refers to physically discrete units suited as unitary dosages for the subject to be treated, each unit containing a predetermined quantity of active compound calculated to produce the desired therapeutic effect in association with the required pharmaceutical carrier. The specification for the dosage unit forms of the invention are dictated by and directly dependent on the unique characteristics of the active compound, the particular therapeutic effect to be achieved, and the limitations inherent in the art of formulating such an active compound for the treatment of individuals.

Another aspect of the present invention accordingly relates to kits for carrying out the administration of the GDF8 antagonists of the invention, e.g., with or without other therapeutic compounds, or for using the GDF8 antagonists as a research or therapeutic tool to determine the presence and/or level of GDF8 in a biological sample, such as an ELISA kit. In one embodiment, the kit comprises one or more anti-GDF8 antagonists formulated in a pharmaceutical carrier, and at least one agent, e.g., a therapeutic agent, formulated as appropriate, in one or more separate pharmaceutical preparations.

The Examples which follow are set forth to aid in the understanding of the invention but are not intended to, and should not be construed to, limit the scope of the invention in any way. The Examples do not include detailed descriptions of conventional methods, such as hybridoma formation, ELISA, proliferation assays, flow cytometric analysis and recombinant DNA techniques. Such methods are well known to those of ordinary skill in the art.

The entire contents of all references, patents, published patent applications, and other patent documents cited throughout this application are herein incorporated by reference.

The present invention is further illustrated and supported by the following examples. However, these examples should in no way be considered to further limit the scope of the invention. To the contrary, one having ordinary skill in the art would readily understand that there are other embodiments, modifications, and equivalents of the present invention without departing from the spirit of the present invention and/or the scope of the appended claims.

EXAMPLES

Example 1

Creation of Hybridoma Cells and Isolation of RK22 Anti-GDF8 Antibody

GDF8 (myostatin) knockout mice (McPherron et al. (1997) *Proc. Natl. Acad. Sci. U.S.A.* 94:12457-61) were immunized by subcutaneous injection with Freund's complete adjuvant and 20 µg recombinant GDF8 dimer that was purified from CHO cell conditioned media as described in Lee and McPherron (1999) *Curr. Opin. Genet. Dev.* 9:604-07. Several booster injections of the same amount of GDF8 and Freund's incomplete adjuvant were given at 2-week intervals. A final intravenous injection in the tail vein of 2 µg PBS was given prior to isolation of splenocytes from mice demonstrating the high titers of anti-GDF8 antibodies. Isolated splenocytes were fused with mouse myeloma cells (ATCC Accession No. P3×63.Ag8.653). After 10-14 days the supernatants from hybridomas were harvested and tested by ELISA for anti-GDF8 antibody levels, see Example 2. To ensure monoclonality, hybridomas chosen for further studies were cloned by repeated limiting dilution.

Supernatants from anti-GDF8-expressing hybridomas and/or antibodies purified from the supernatants using standard affinity chromatography methods well known in the art, were tested for specificity in assays described in Example 2. Of thirteen clones initially tested for binding to GDF8, RK22 was among those selected for further analysis.

Example 2

RK22 Antibody Specifically Interact with GDF8

Example 2.1

RK22 has a Higher Affinity for GDF8 than for BMP11 in ELISA Assays

Standard ELISA techniques using either GDF8 or BMP11 were used to determine the specificity of RK22 binding to GDF8, i.e., to determine whether the antibodies demonstrated a higher affinity for GDF8 than for BMP11. Recombinant human GDF8 (mature GDF8 and GDF8 propeptide) and BMP11 protein were purified and characterized as previously disclosed in U.S. Patent Published Application No. 2004/0142382. The GDF8 latent complex and the BMP11 latent complex were each individually biotinylated at a ratio of 20 moles of EZ-link Sulfo-NHS-Biotin (Pierce, Rockford, Ill., Cat. No. 21217) to 1 mole of complex for 2 hrs on ice. The reaction was terminated by decreasing the pH using 0.5% TFA, and biotinylated complex was subjected to chromatography on a C4 Jupiter 250×4.6 mm column (Phenomenex, Torrance, Calif.) to separate mature protein (e.g., mature GDF8 from GDF8 propeptide or mature BMP11 from BMP11 propeptide). Fractions of mature biotinylated GDF8 or mature biotinylated BMP11 eluted with a TFA/CH3CN gradient were pooled, concentrated, and quantified by MicroBCA™ protein assay reagent kit (Pierce, Rockford, Ill., Cat. No. 23235).

A 96-well microtiter plate (precoated overnight at 4° C. with 5 µg/ml streptavidin in PBS) was coated with 0.5 µg/ml biotinylated GDF8 or biotinylated BMP11 for 1 hr at room temperature. Excess GDF8 or BMP11 was removed by washing with PBS containing 0.1% (v/v) Tween 20 (PBST buffer). The plates were blocked for 1 hr at room temperature in SuperBlock™ solution (Pierce) and then rinsed with PBS. GDF8 or BMP11 coated plates were incubated at room temperature for 1 hr with 100 µl of pre-blocked supernatant collected from RK22 hybridomas, or with purified RK22 antibody at various concentrations. To control for non-specific binding the RK35 antibody (see U.S. Patent Application No. 60/709,704, hereby incorporated by reference in its entirety) that has been shown to bind and inhibit both GDF8 and BMP11 was used along with an irrelevant antibody (Irr. Ab) that has demonstrated no binding to either GDF8 or BMP11, and control media were also individually tested. Unbound antibody was removed by 3 washes of PBST followed by 3 washes with PBS. Fifty µl of a 1:5000 dilution of goat anti-mouse IgG HRP conjugate was added to each well. The plates were incubated at room temperature for 1 hr. Each plate was washed three times with PBST, and subsequently, 3 times with PBS and developed for a color reaction by the addition of the TMB (tetramethylbenzidine) reagent. The color reaction was stopped by the addition of 100 µl of 0.18 M $H_2SO_4$. The signal generated was measured by reading the optical density at 450 nm of each well using a microtiter plate reader.

Figure 1B:
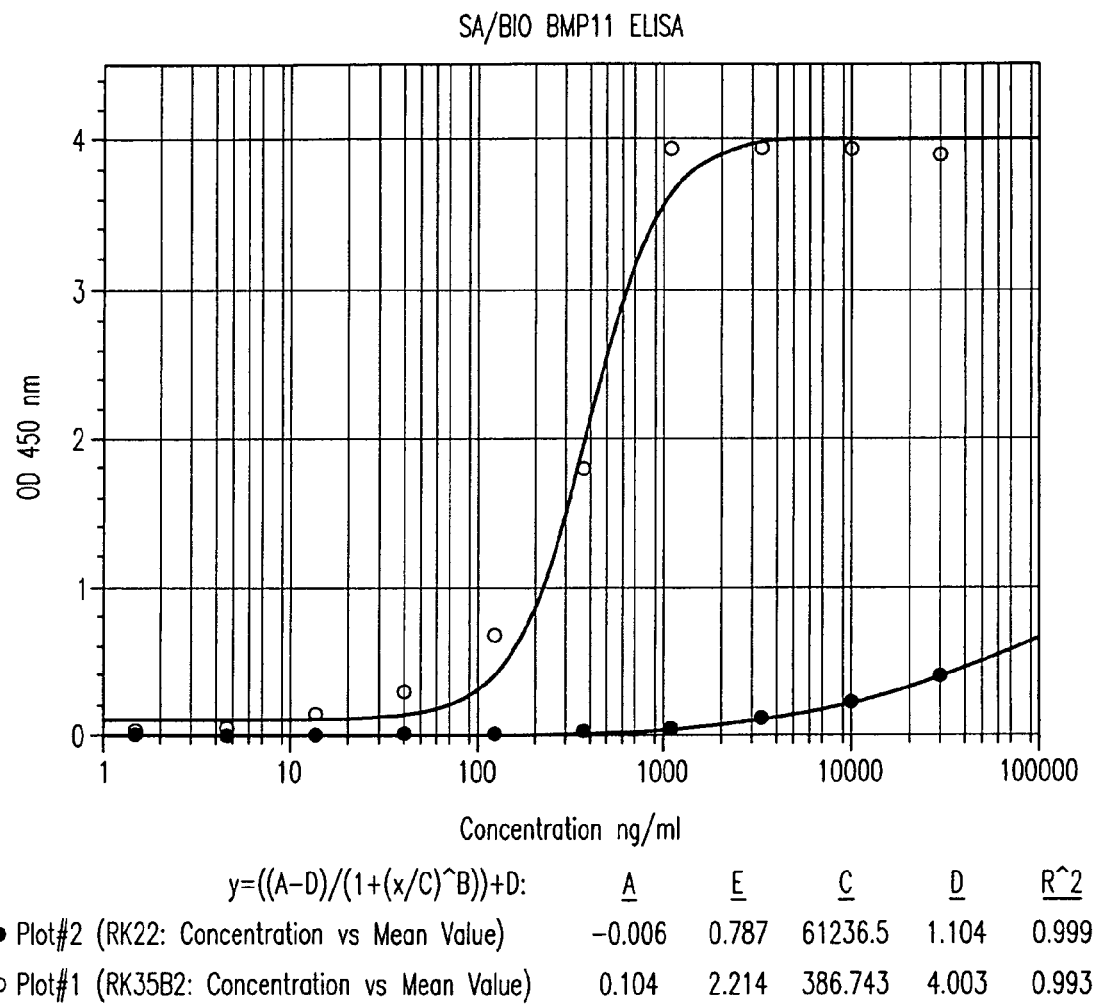

As shown in FIGS. 1A and 1B, the supernatants from RK22 hybridomas had greater binding to GDF8 than BMP11 compared to supernatant isolated from the control antibody, RK35. The uniformity of higher affinity for GDF8 by RK22 was confirmed by demonstrating that the higher affinity for GDF8 of these antibodies was not dose dependent. As can be seen in FIGS. 1A and B, at every concentration tested RK22 antibodies demonstrated greater binding to GDF8 than to BMP11. RK22 showed very little binding to BMP11 while in contrast, the RK35 control antibody bound to both GDF8 and BMP11.

Example 2.2

Binding Affinities of RK22 for GDF8

Molecular kinetic interactions of RK22 antibody with GDF-8 were quantitatively analyzed using BIAcore plasmon resonance technology, and apparent kinetic rate constants were derived. In these studies we measured the binding of soluble antibody to solid phase bound GDF-8. The surface orientation of the immobilized GDF-8 onto the biosensor surface was controlled using biotinylated GDF-8 (bio-GDF-8), the bio GDF-8 was immobilized onto streptavidin biosensor chips then, various concentrations of antibody were applied in triplicates and the binding was measured as function of time. From these measurements the apparent dissociation ($K_d$) and association ($K_a$) rate constants were derived and used to calculate a binding affinity constant ($K_d$) for the interaction. The active concentration of RK22, defined as the fraction of antibody that are biologically functional, was determined by measuring the fraction of antibody able to bind to the bio GDF-8 immobilized on the chip using the BIAcore under partial mass transport limitations by coating a high surface density and injecting the antibody at different flow rates. The association and dissociation rate for each concentration of antibody were calculated simultaneously using global fit with the biaevaluation software version 3.0.2.

The BIAcore 2000 system, Sensor Chip SA (BR-1000-32), HBS/EP buffer (0.01 M HEPES pH.7.4, 0.15 M NaCl, 3.0 mM EDTA and 0.005% polysorbate 20 (v/v), N-hydroxysuccinimide (NHS-EP) were obtained from BIAcore AB, Uppsala, Sweden. The human bio-GDF8 (Lot 25251-15) was purified. 0.1% TFA (v/v) (Sigma) was made in water. Experimental data from kinetic determinations of the antibody-antigen interaction was analyzed using the BIAevaluation software version 3.0.2.

To prepare the bio-GDF8 surface, a continuous flow of HBS/EP buffer was maintained over the sensor surface. The streptavidin on the sensor surface was conditioned with 3 injections (1 minute each) of a solution containing 1 M NaCl and 25 mM NaOH. For high-density coating (>2000RU) bio-GDF8 was diluted to 1 ug/ml in HBS/EP buffer and immobilized on the streptavidin chip by flowing over it. For low-density coating (20-60 RU) the GDF-8 was further diluted to 0.1 ug/ml and the volume of injected bio-GDF-8 varied according to the density required. The streptavidin surface on flow cell one was used as reference surface. As control the first flow cell was used as reference surface to correct for bulk refractive index, matrix effects and non-specific binding, the second, third and four flow cells were coated with the capturing molecule.

The fraction of RK22 antibody able to bind to the bio GDF-8 immobilized on the chip was analyzed using the BIAcore under partial mass transport limitations. In this experiments anti-GDF-8 antibody at 200 nM and 100 nM (concentrations measured based on OD 280) were injected at flow rates of 2, 10, 30, 50 and 100 ul/min. Mass transport limitations could be detected by visual inspection of the sensor grams, since the slopes increased with increasing flow rates. Biosensor surfaces were regenerated using 5 ul of 0.1% TFA.

Both RK22 anti-GDF-8 antibody were diluted in HBS-EP buffer (Biacore AB), aliquots were injected over the immobilized bio-GDF-8 at a flow rate of 30 ul/min, following injection for three minutes, dissociation was monitored in BIAcore buffer for ten minutes at the same flow rate. The concentrations of antibody injected were 300, 150, 75, 37.5, 18.7, 9.3, 4.6, 2.3 and 0 nM; each injection was done in triplicate. Blank and buffer effects were subtracted for each sensorgram using double referencing. Biosensor surfaces were regenerated using 5 ul of 0.1% TFA, before the injection of the next sample HBS-EP alone flowed through each cell. The response was measured in resonance units (RU) representing the mass of bound of RK22.

The kinetic data was analyzed using BIAevaluation software 3.0.2. Assuming both a bivalent analyte (A) binding to monovalent ligand (B). A+B=AB $K_a1*K_d1$; AB+B=AB2 $K_a2*K_d2$; and a monovalent analyte (A) binding to monovalent ligand (B) A+B=AB $K_a1*K_d1$. The apparent dissociation ($k_d$) and association ($k_a$) rate constants were calculated from the appropriate regions of the sensorgrams. The binding affinity constant of the interaction between antibody and GDF8 was calculated from the kinetic rate constants by the following formula: $K_d$=kd/ka. As can be seen in FIG. 2, RK22 demonstrated a $K_d$ value of 7 nM in the average of three experiments.

Example 3

RK22 Inhibit GDF8 Signaling In Vitro and In Vivo

Example 3.1

Inhibition of the Biological Activity of Purified Recombinant Human GDF-8 in the Cell Based Reporter Gene Assay Using RK22

To demonstrate the activity of GDF-8 in the in vitro cell based assay, a reporter gene assay (RGA) was developed using a reporter vector pGL3 (CAGA)12 expressing luciferase under control of TGF-β induced promoter. The CAGA sequence was previously reported to be a TGF-β responsive sequence within the promoter of the TGF-β induced gene PAI-1 (Thies S et al 2001). A reporter vector containing 12 CAGA boxes was made using the basic luciferase reporter plasmid pGL3 (Promega, Madison, Wis.). The TATA box and transcription initiation site from the adenovirus major later promoter (−35/+10) was inserted between the BgIII and HindIII sites. Oligonucleotides containing 12 repeats of the CAGA boxes AGCCAGACA were annealed and cloned into the XhoI site. The human rhabdomyosarcoma cell line A204 (ATCC HTB-82) was transiently transfected with pGL3 (CAGA)12 using FuGENE 6 transfection reagent (Boehringer Manheim, Germany). Following transfection, cells were cultured on 96 well plates in McCoy's 5A medium supplemented with 2 mM glutamine, 100 U/ml streptomycin, 100 µg/ml penicillin and 10% fetal calf serum for 16 hrs. Cells were then treated with or without 10 ng/ml GDF-8 in McCoy's 5A media with glutamine, streptomycin, penicillin, and 1 mg/ml bovine serum albumin for 6 hrs at 37° C. Luciferase was quantified in the treated cells using the Luciferase Assay System (Promega). The assay was repeated using 10 ng/ml BMP-11.

To test the inhibitory activity of RK22, GDF-8 was preincubated with RK22 antibody for 1 hour at room temperature. This mixture was then added to the transfected cells and were incubated for 6 hrs at 37° C. Luciferase was quantified using the Luciferase Assay System (Promega). The ability of RK22 to block BMP-11 activity was measured using the same protocol.

Figure 3:
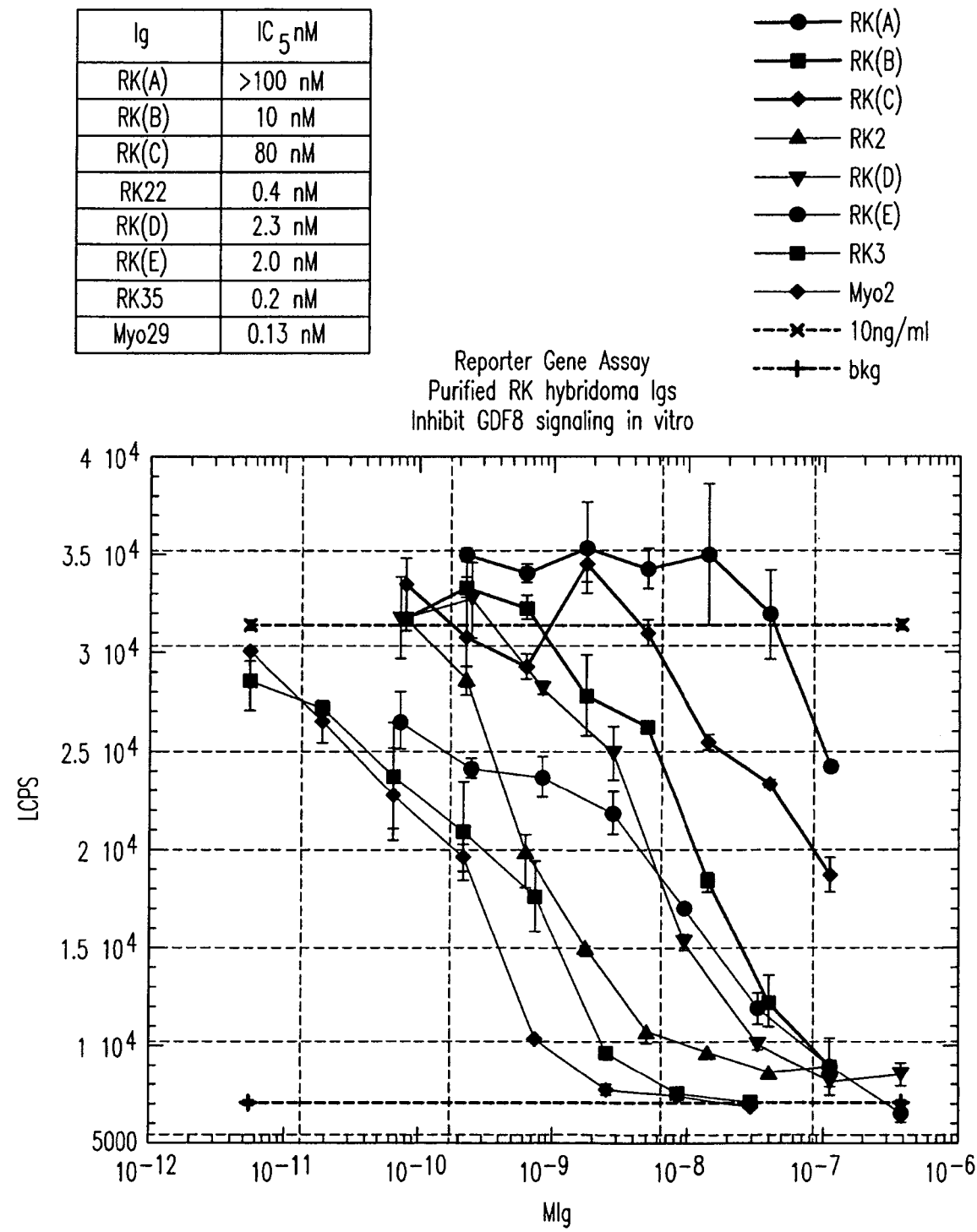
FIG. 3 shows the induction of pGL3 (CAGA)12-TGF-β promoter reporter gene activity as measured by luciferase activity (LCPS; y-axis) in A204 rhabdosarcoma cells treated with 10 ng/ml of GDF8 in the absence (10 mg/ml) or presence of various concentrations (M Ig; x-axis) of the RK22 and RK35 antibody and other RK antibodies (A through E) that bind to either GDF8 and/or BMP11.

As seen in FIG. 3, induction of pGL3(CAGA)12 reporter activity as LCPS when cells were untreated (bkgd) or treated with 10 ng/ml GDF-8 in the absence or presence of RK22. Each of these antibodies reduced at least one GDF8 activity, i.e., GDF8-mediated luciferase induction, in a dose-responsive manner, with an IC50 of 0.4 nM for RK22. The control antibody RK35 had an IC50 of 0.2 nm, and an irrelevant antibody had an IC50 of >100 nM. Although RK22 inhibited GDF8-mediated signaling, these antibodies did not significantly inhibit the biological activity of BMP11; the IC50 for inhibition of BMP11 activity by RK22 was not detectable, 30 nM, and >100 nM, respectively. These data demonstrate that RK22 inhibit specifically GDF8 signaling in vitro to a similar degree as the nonspecific antibody RK35.

Example 3.2

RK22 Inhibits GDF8 Activity In Vivo

In order to determine whether RK22 antibodies antagonize GDF8 activity in vivo, RK22 was selected as a representative antibody for further testing in adult SCID mice. SCID mice suffer from a severe combined immune deficiency, and therefore do not generate an immunological reaction following injections of antibodies such as RK22. RK22 was injected into SCID mice over a period of four weeks. Three dosages of RK22 were administered: 1 mg/kg/week, 10 mg/kg/week and 40 mg/kg/week. Myo-29 administered at a dose of 10 mg/kg/week was used as a positive control and compared to the different concentrations of RK22 administered.

Figure 4A:
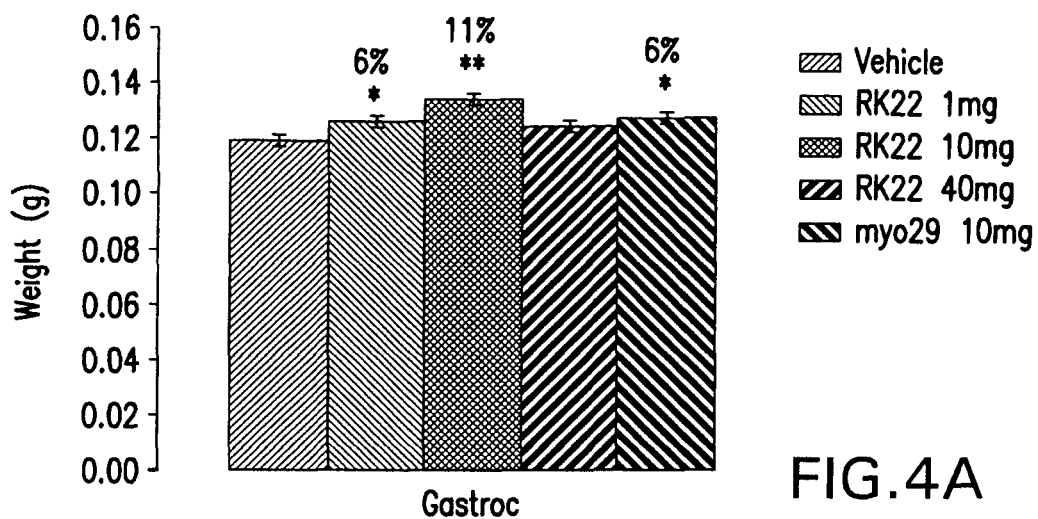
FIG. 4 shows the weight (g; y-axes) of gastrocnemius (Gastroc), quadricep (Quad), and anterior tibialis (Tibialis anterior) muscles dissected from SCID mice after four weeks of treatment with vehicle in the absence (vehicle), or presence of 1, 10 or 40 mg/kg/week of RK22 or Myo-29.
Figure 4B:
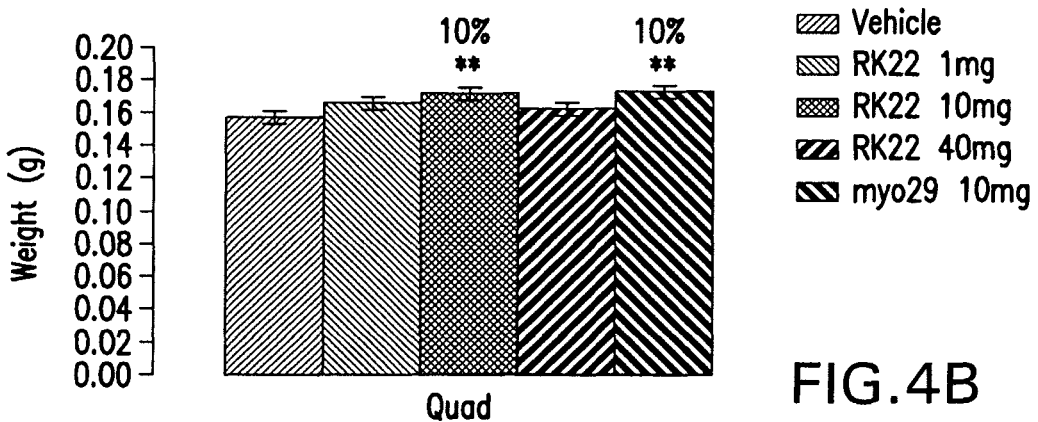
Figure 4C:
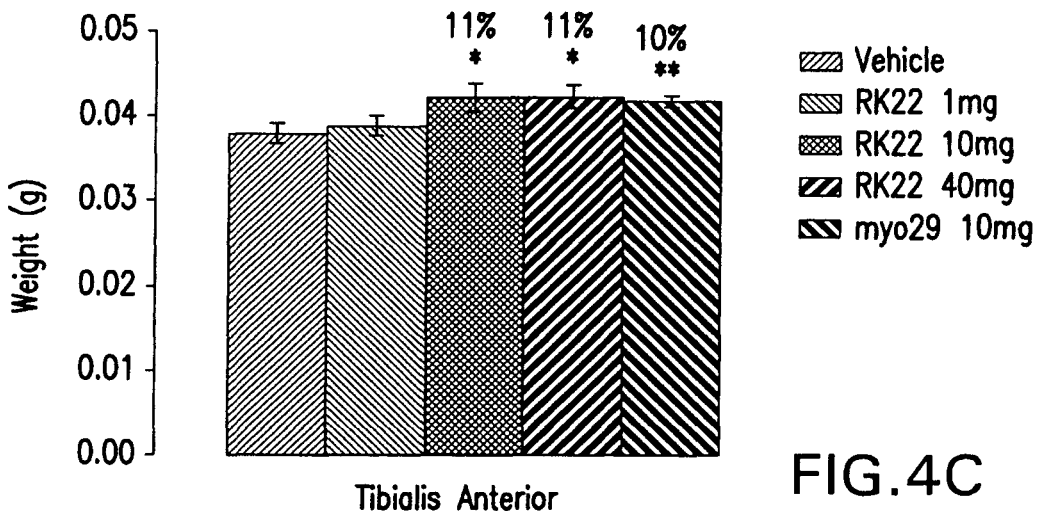

Muscle mass was used as an indicator for GDF8 activity in mice treated with RK22. Three different muscle groups, gastroc, tibialis anterior and quad, were removed and muscle weight was determined. As shown in FIG. 4, RK22 significantly increased muscle mass at a dose of 10 mg/kg/week. In comparison to the positive control, Myo29, the muscle mass increased approximately 10% in both 10 mg/kg/week of for both RK22 and Myo29.

Example 4

Characterization of RK22 Binding Sites

Example 4.1

Assessment of RK22 Inhibition of GDF8 Binding to ActRIIB

To determine whether RK22 antibodies are capable of antagonizing GDF8 activity by preventing GDF8 from binding its ActRIIB receptor, the antibodies were tested in an ActIIRB binding assay (e.g., a neutralization assay). Purified RK22 antibodies were screened for the ability to inhibit the binding of biotinylated GDF8 to ActRIIB fusion protein immobilized on plastic in a 96-well microtiter plate assay. Recombinant ActRIIB-Fc chimera (R&D Systems, Minneapolis, Minn., Cat. No. 339-RB/CF) was coated onto 96-well flat-bottom assay plates (Costar, N.Y., Cat. No. 3590) at 1 µg/ml in 0.2 M sodium carbonate buffer overnight at 4° C. Plates were then blocked with 1 mg/ml bovine serum albumin and washed following a standard ELISA protocol. Twenty ng/ml of biotinylated GDF8 alone or preincubated for one hour at room temperature with various concentrations of RK22 was added to the blocked ELISA plate. To establish clone potency as measured by $IC_{50}$ values, a titration of antibodies was added. Biotinylated GDF8 preincubated with irrelevant antibody or a control antibody that blocks GDF8 binding to ActIIRB were included as controls. After one hour at room temperature, the antibody-blocked protein complexes were washed away, and the amount of GDF8 bound to plate-bound ActIIRB was detected with Europeium-labeled streptavidin using the DELFIA™ reagent kit (PerkinElmer LifeSciences, Boston, Mass.) in a time-resolved fluorometric (TRF) assay.

Figure 5:
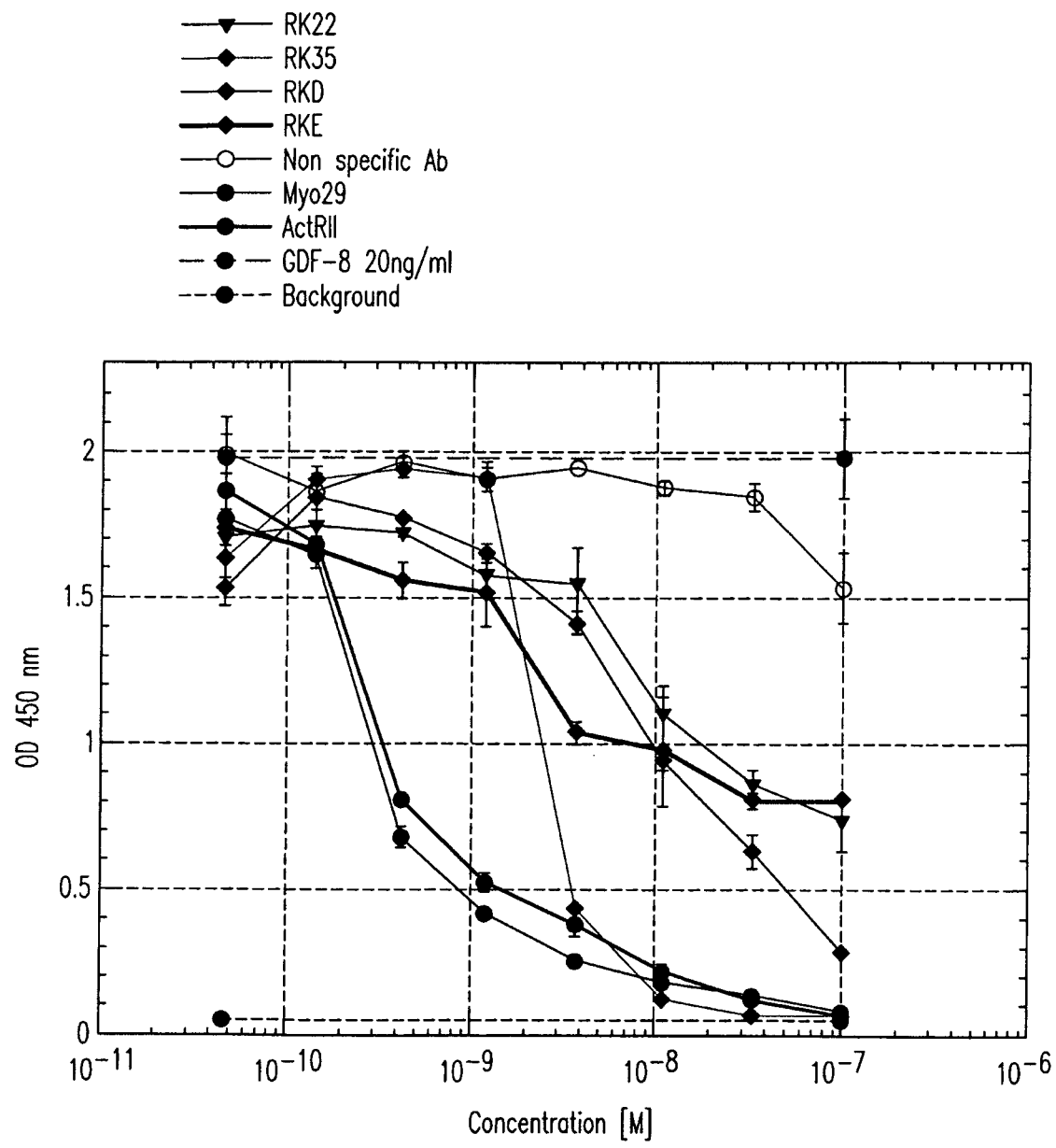
FIG. 5 shows binding to ActRIIB (OD450; y-axis) by GDF8 alone or GDF8 preincubated with various concentrations ([M]; x-axis) of RK22, non-specific antibody, other RK antibodies (D and E), a control antibody that blocks GDF8 binding to ActRIIB (RK35), control IgG antibody, or soluble ActRIIB.

The results of the ActRIIB neutralization assay are shown in FIG. 5. Therefore, although it is possible that RK22 antibodies inhibit GDF8 signaling by inhibiting the ability of GDF8 to bind to ActRIIB, it is more likely that another mechanism is involved.

Example 4.2

RK22 Binds to GDF8-Specific Epitopes

Although GDF8 and BMP11 are closely related, RK22 is specific for GDF8. Consequently, it is hypothesized that the epitopes recognized by these antibodies are also specific to GDF8, and thus, the epitopes specific to GDF8 may be used as antagonists (e.g., as peptide mimetics) to specifically inhibit GDF8 signaling and/or to screen for or make GDF8-specific antagonists.

To determine the GDF8 epitopes recognized by antibodies RK22, 48 overlapping 13-residue peptides presenting the entire sequence of mature GDF8 set forth as SEQ ID NO:1 were synthesized directly on cellulose paper using the spot synthesis technique (Molina et al. (1996) *Peptide Res.* 9:151-55; Frank et al. (1992) *Tetrahedron* 48:9217-32). The overlap of the peptides was 11 amino acids. In this array, cysteine residues were replaced with serine in order to reduce the chemical complications that are caused by the presence of cysteines. Cellulose membranes modified with polyethylene glycol and Fmoc-protected amino acids were purchased from Abimed (Lagenfeld, Germany). The array was defined on the membrane by coupling a β-alanine spacer, and peptides were synthesized using standard DIC (diisopropylcarbodiimide)/HOBt (hydroxybenzotriazole) coupling chemistry as described previously (Molina et al., supra; Frank et al., supra).

Figure 6:
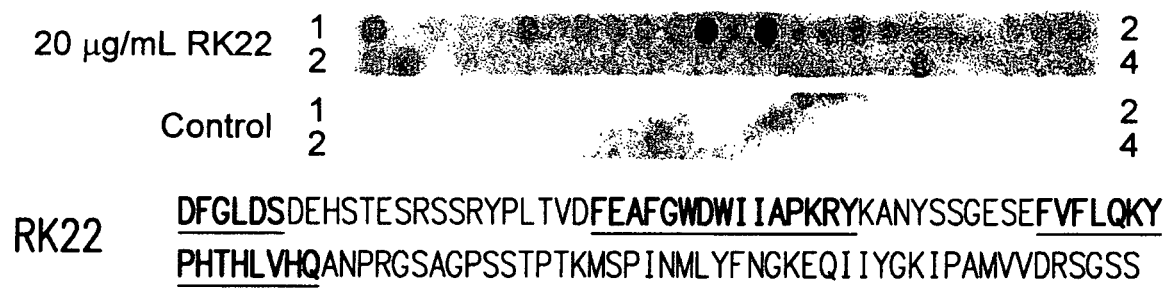
FIG. 6 shows the resulting of epitope mapping dot blots of 20 ng/ml of a control antibody, RK22 antibody, incubated with 48 individual and overlapping 13-residue peptides representing the entire mature GDF8 peptide. Under each dot blot is the sequence of GDF8 with the GDF8 epitopes for the antibodies underlined (as indicated in the respective dot blots).

Activated amino acids were spotted using an Abimed ASP 222 robot. Washing and deprotection steps were done manually and the peptides were N-terminally acetylated after the final synthesis cycle. Following peptide synthesis, the membrane was washed in methanol for 10 min and in blocker (TBST (Tris-buffered saline with 0.1% (v/v) Tween™ 20) and 1% (w/v) casein) for 10 min. The membrane was then incubated with 2.5 µg/ml of RK22 anti-GDF8 antibody in blocker for one hour with gentle shaking. After washing with blocker 3 times for 10 min, the membrane was incubated with HRP-labeled secondary antibody (0.25 µg/ml in blocker) for 30 min. The membrane was then washed three times for 10 min each with blocker and 2 times for 10 min each with TBST. Bound antibody was visualized using SUPERSIGNAL™ West reagent (Pierce) and a digital camera (Alphananotech Fluoromager). The dot blots are shown in FIG. 6 and the results summarized in Table 4. The dot blots demonstrate that RK22 binds to a GDF8 epitope(s) having and/or consisting essentially of an amino acid sequence selected from the group consisting of: DFGLDS (SEQ ID NO:4), FEAFGWDWI-IAPKRY (SEQ ID NO:6), FVFLQKYPHTLVHQ (SEQ ID NO:8), SSGESEFVF (SEQ ID NO:10), WIIAPKRY-KANYSSGESEFVFLQKY (SEQ ID NO:11), and potentially subsequences thereof. In particular, the epitope(s) for RK22 maps to a GDF8 region that putatively interacts with the GDF8 Type I receptor (ALK4/ALK5).

TABLE 4

Approximate regions of human GDF8 bound by Mouse Monoclonal Antibodies

| | RK22 |
|---|---|
| Epitope Area | N-terminal and Type I receptor recognition regions |
| Interaction with Amino Acids of SEQ ID NO: 1 (approximate) | 1-6; 24-38; 49-63 |

Example 5

Humanization of RK22

Example 5.1

Antibody Sequencing

The variable heavy (VH) and variable light (VL) genes encoding RK22 were cloned from the hybridoma cells producing the RK22 antibody and then the amino acid sequences determined. These sequences are listed in Table 1 as SEQ ID NOs: 14 and 16.

Example 5.2

Germlining RK22 Antibody

Sequence data for the antibodies was used to identify the nearest germline sequence for the heavy and light chain of RK22, e.g., DP-5 and DP-7 displayed about 65% and 71% identity to RK22 VH, respectively (FIG. 7); while DPK 24 displayed about 78% identity to RK22 VL (FIG. 8). Appropriate mutations were made using standard site directed mutagenesis techniques with the appropriate mutagenic primers. Mutation of sequences and antibodies was confirmed by sequence analysis. The specification is most thoroughly understood in light of the teachings of the references cited within the specification, all of which are hereby incorporated by reference in their entirety. The embodiments within the specification provide an illustration of embodiments of the invention and should not be construed to limit the scope of the invention. The skilled artisan recognizes that many other embodiments are encompassed by the claimed invention.

Example 6

Sandwich Immunoassay Formats for Quantifying and Detecting GDF8

Each of the antibodies described in the Examples below were biotinylated using an EZ Link Sulfo-LC biotinylation kit from Pierce. From previous studies, it was determined that a 40-fold excess of NHS-biotin was optimal for biotinylation of both of these antibodies. 400 ug of each antibody was biotinylated using a 40 fold molar excess biotin. This resulted in an incorporation of approximately 3 to 5 mmoles of biotin per mmole of antibody. After biotinylation, all antibodies were dialyzed into PBS overnight at 4° C. and total protein concentration determined by BCA. To determine the molar ratio of biotin incorporation, a solution of the biotinylated antibody was added to a mixture of 2-(4'-Hydroxyazobenzene) benzoic acid (HABA) and avidin. Because of its higher affinity for avidin, biotin displaced the HABA from its interaction with avidin and the absorbance at 500 nm decreased proportionately. The amount of biotin conjugated to an antibody can be quantitated by measuring the absorbance of the HABA-avidin solution before and after the addition of the biotinylated sample. The change in absorbance relates to the amount of biotin incorporated into the antibody.

Additionally, the serum used in the studies described below is devoid of endogenous GDF8. An affinity column for GDF-8 serum depletion was prepared using 1 mg of MYO-029 monoclonal antibody immobilized onto cyanogen bromide activated Sepharose beads. The column was pre-washed with 0.1 M acetic acid and neutralized with PBS containing 250 mM NaCl pH 7.2 before the addition of human serum. Due to the apparent activation of latent GDF-8 by heating to 65° C., serum was preheated to 65° C. for ten minutes and then passed three times over the 1 mg MYO-029 anti-GDF8 affinity column and checked for activity in the free and total GDF-8 assays. Initially 2.5 ml volumes of serum were passed over the column. After initial testing, larger volumes of serum (13 ml aliquots) were heated and depleted of GDF-8 by multiple passes over the affinity column with intermediate column washes in 0.1 M acetic acid. This depleted serum was used as the matrix for generation of standard curves with known concentrations of mature GDF-8.

Example 6.1

Antibody Pairing Experiments: Comparison of Immunoassay Formats: RK35 Capture with RK22 Detector or RK22 Capture with RK35 Detector Each anti-GDF-8 monoclonal antibody was individually coated in 0.1 M sodium borate on a high binding, 96-well plate (Immulon 4 HBX) overnight at 4° C. or for 1 hour at 37° C. at a concentration of 1 µg/ml. The plate was washed and then blocked for ten minutes with Pierce Superblock reagent. Stock GDF-8 (1.77 mg/ml in 0.1% trifluoroacetic acid-TFA) was diluted to 10 µg/ml in 0.1% trifluoroacetic acid (TFA) in siliconized plastic tubes and further diluted into GDF8 depleted human serum at concentrations ranging from 12.5 ng/ml to 0.2 ng/ml as calibrators for generation of standard curves. The standard curve was run in triplicate using columns 1-3 of the assay plate. In a separate pre-blocked, 96-well plate, 30 µl aliquots of test serum was added to each of 6 wells (for triplicate determinations) containing 120 µl of THST buffer (final concentration, 20% serum; total volume, 150 µl). For the total GDF-8 assay, 80 µl of this solution was transferred to a 96-well PCR plate and heated to 80° C. for 5 minutes. The heated samples were cooled on ice before addition to the assay plate.

Figure 9A:
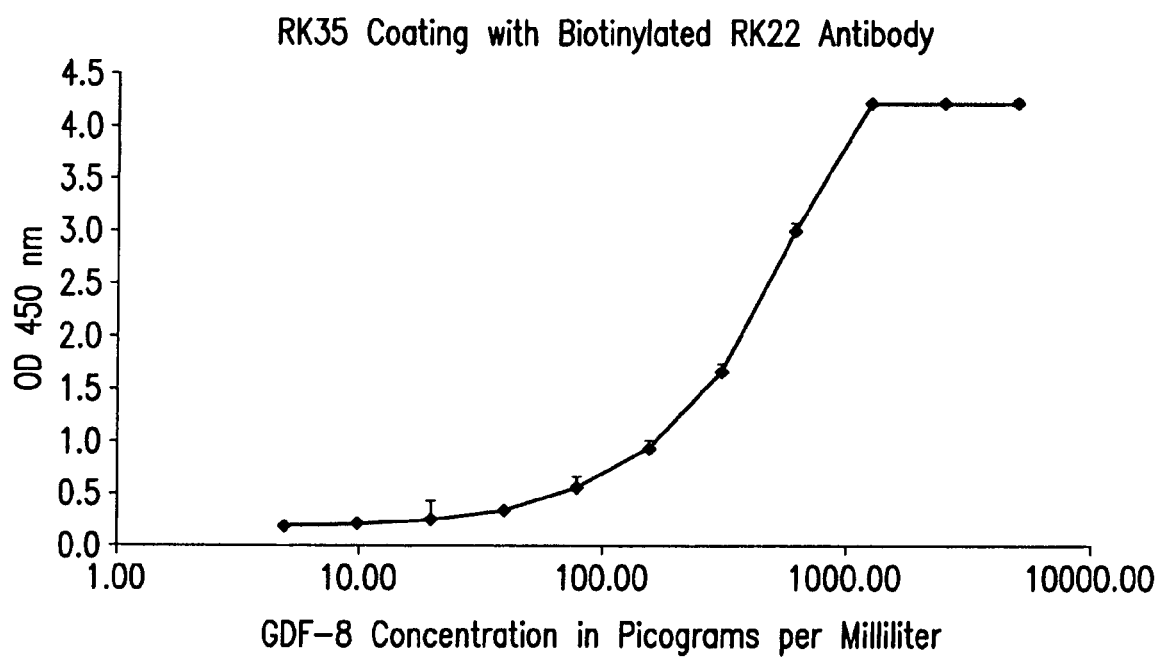
FIG. 9A shows a comparison of immunoassay formats: RK35, the capture reagent and biotinylated RK22 as the detection reagent.
Figure 9B:
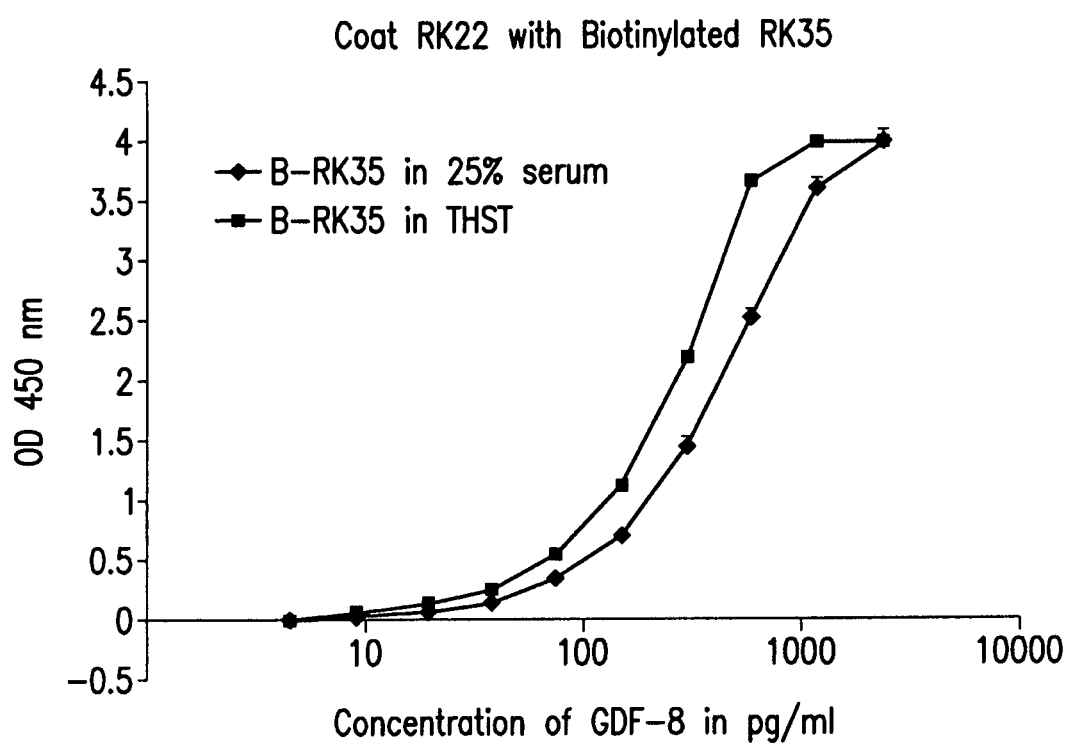
FIG. 9B shows RK22 as the capture with biotinylated RK35 as the detection antibody.

To the wells used for the standard curve, 65 µl of THST buffer was added to all wells followed by 10 µl of the calibrator serum, to bring the final volume to 100 µl. From the preparation plate, 50 µl of unheated 20% serum sample was removed and added to the assay plate for a final serum concentration of 10% serum in a total volume of 100 µl. From the heated plate, 50 µl of 20% serum was added to a second assay plate. These second assay plates were incubated at room temperature with shaking. After 1.5 hours, the plates were washed and Superblock reagent was added for 5 minutes. Biotinylated RK22 or biotinylated RK35 was added to the wells at 150 ng/ml for 1.5 hours with shaking. The plates were washed and re-blocked again before the addition of 100 ul of ultrasensitive strepavidin-HRP (1:20,000) dilution for 1 hour at room temperature with shaking. Plates were washed and re-blocked before the addition of TMB substrate for 15 minutes at room temperature with shaking. The reaction was stopped by the addition of 0-5 M H2S04 and read on a Molecular Devices Spectramax plate reader at 450 nm. A comparison of the immunoassay formats: RK35 capture/RK22 detector or RK22 capture/RK35 detector can be seen in FIGS. 9A and 9B. As shown, either format was capable of detecting between 100 and 10 pg/ml of GDF8 in THST assay buffer or in 10% serum.

Example 6.2

Effects of Serum on the GDF-8 Assay

Figure 10:
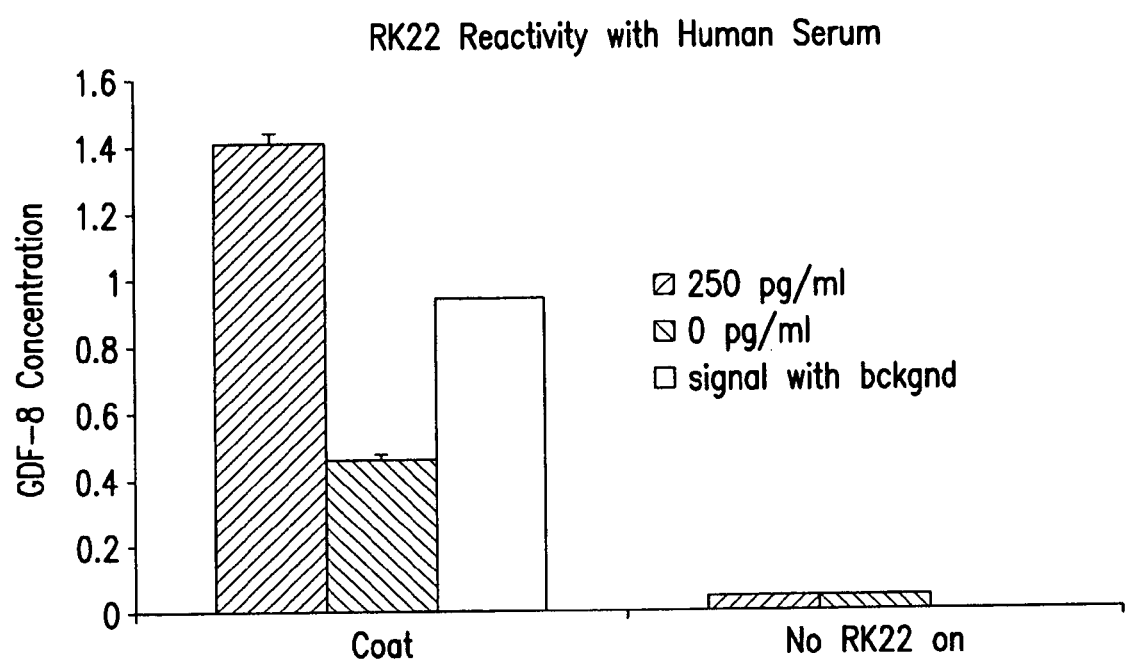
FIG. 10. demonstrates that the ELISA assays previously described exhibit background, and that this background is likely a human anti-mouse antibody (HAMA) effect. Assay background was due to serum cross reactivity with monoclonal antibody RK22 that was used as a capture antibody in the ELISA. The same effect is observed when RK35 is used as the capture antibody (data not shown).

Previous results suggested that serum background effects increased absorbance values in the range of 0.3 OD units to approximately 0.5 OD units depending on the serum sample being analyzed (data not shown). It was determined that the cause of the signal increase was HAMA effect (i.e. a reaction of human serum IgG with the mouse monoclonal antibodies used in the assay) by testing human serum against RK22 coated or uncoated (control) HBX assay plates (FIG. 10). Plates without monoclonal antibody show no increase in signal suggesting the background increase was not due to serum nonspecifically binding to the plate but was dependent on the presence of monoclonal antibody.

Figure 11:
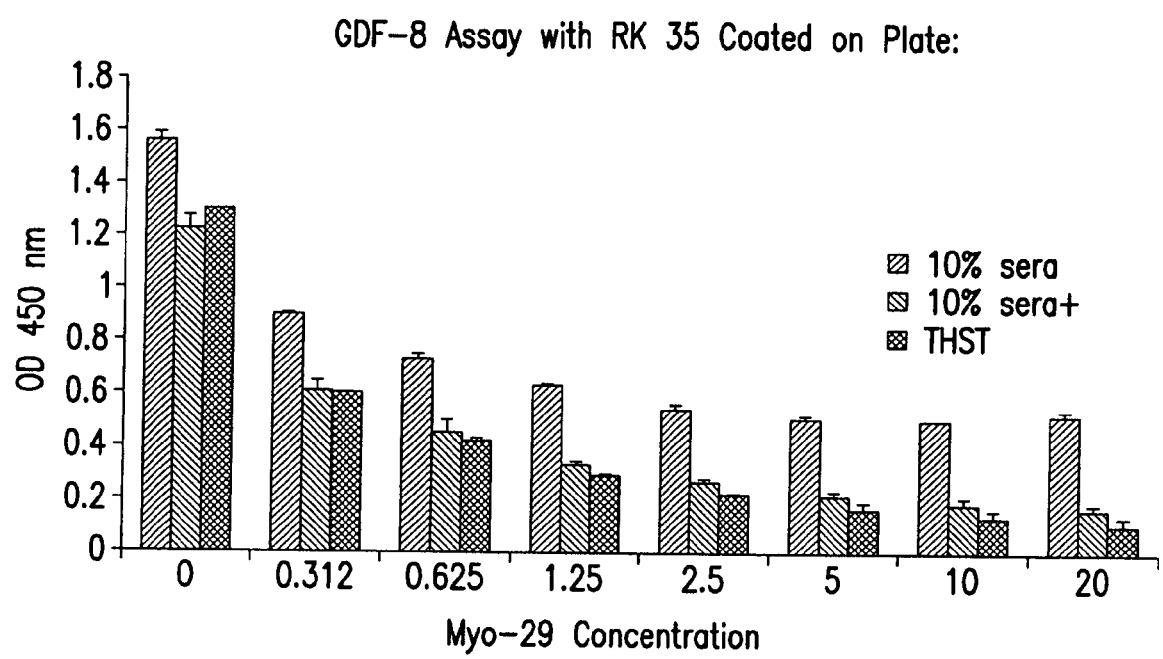
FIG. 11 shows the results of a GDF-8 ELISA where the RK35 antibody was coated on the plate, and the background of the ELISA was reduced using the commercially available reagent IIR (Immunoglobulin Inhibiting Reagent-Bioreclamation, NY). The results using IIR compare favorably with background with buffer only.

Several attempts made to reduce background were unsuccessful, including acid dissociation and the addition of excess IgG from various species to block the binding of the human IgG to the murine IgGs (data not shown). The addition of a commercially available reagent, specifically designed to reduce HAMA assay interference Immunoglobulin Inhibiting Reagent (II R) was successful when added to the following immunoassay. 1 ug/ml of RK35 diluted in 0.1M Na Borate pH 8.5 was used as the capture reagent. Myo-029 was titrated onto the plate+/−serum+/−IIR and also 250 pg/ml GDF8 and incubated for 1.5 hours. Biotinylated RK22 was added at a 1:10,000 dilution in THST assay buffer and incubated for 1.5 hours. 100 µl of strepavidin-HRP diluted 1:20, 000 in THST followed by developing the reaction in TMB. As can be seen in FIG. 11, the HAMA background is reduced using the IIR reagent.

Example 6.3

Inhibition of GDF8 Binding with MyO-029 Antibody

MyO-029 (deposited on Oct. 2, 2002, at American Tissue Culture Collection (ATCC) under respective Deposit Designation Numbers PTA-4741) is a therapeutic antibody that has been used in clinical trials in an effort to increase muscle strength in patients with muscular disorders. In the immunoassay to detect GDF8 in patients who have been administered Myo-029, as described herein there has been shown to be cross-reactivity of assay antibody RK35 with the MYO-029 for binding to GDF-8. To verify this cross-reactivity MYO-029 was coated onto assay plates. 1200 pg/ml GDF-8 was added to each well. Increasing concentrations of either biotinylated RK22 or biotinylated RK35 were then added. As seen in FIG. 12, unlabeled GDF-8 competes with biotinylated RK35 for binding to MYO-029 as no signal was generated in this configuration. No signal was produced with biotinylated RK35, which indicates cross reactivity between RK35 and Myo-029 for binding to GDF8.

Example 6.4

The Use of MyO-029 as a Competitor for GDF8

Figure 13A:
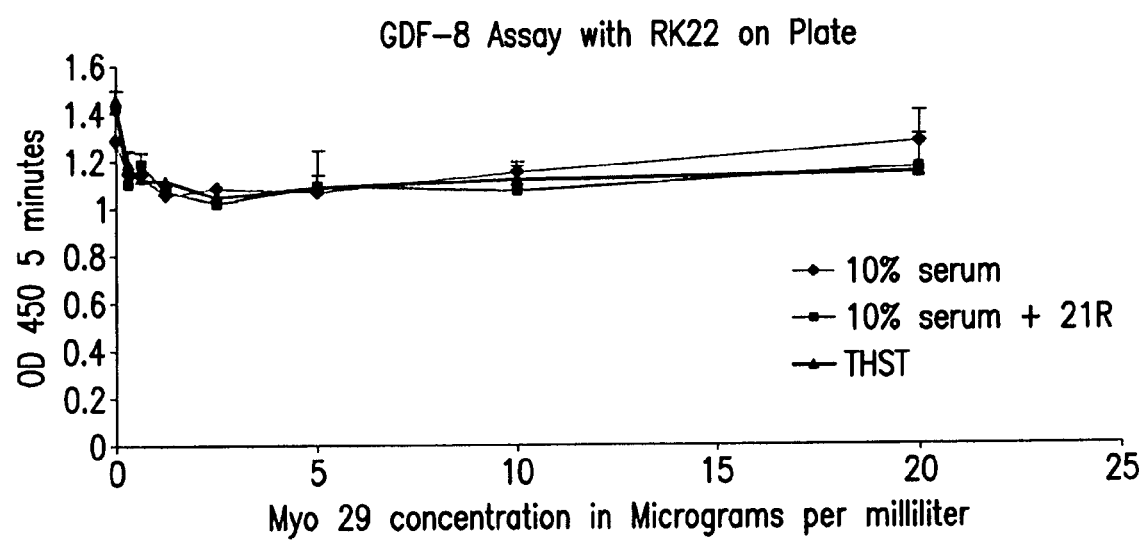
FIGS. 13A and 13B show that MYO-029 can be used as an inhibitor of GDF-8 in an ELISA assay. Increasing concentrations of MYO-029 with a constant concentration of GDF-8 (250 pg/ml) spiked into assay buffer or into 10% human serum were assayed for GDF-8 via ELISA.
Figure 13B:
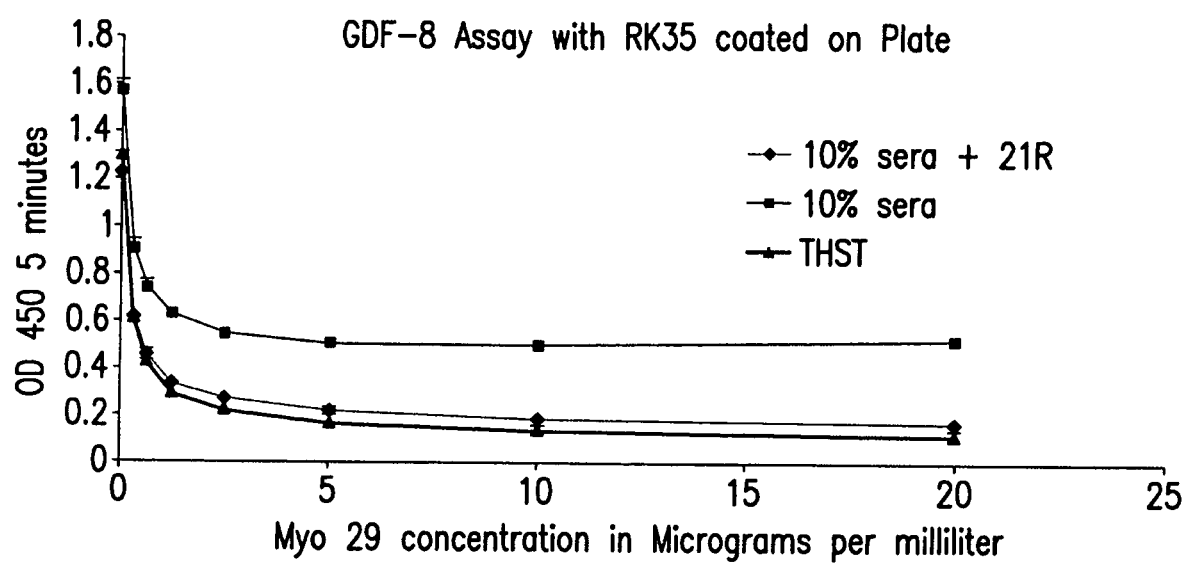

Assays were performed using both assay configurations (RK35/RK22 or RK22/RK35) and increasing amounts of MYO-029 therapeutic antibody with a constant concentration of GDF-8 (250 pg/ml) spiked into assay buffer or into 10% human serum. As seen in FIGS. 13A, RK22 was used as the capture antibody. GDF-8 at 250 pg/ml was incubated for 1.5 hours at room temperature with biotinylated RK35 at 150 ng/ml and increasing concentrations of MYO-029 (0 to 20 ug/ml). Even at the highest concentration of MYO-029 only approximately 30% inhibition was seen. As shown in FIG. 13B, RK35 is used as the capture antibody. GDF-8 at 250 pg/ml was incubated for 1.5 hours at room temperature with biotinylated RK22 and increasing concentrations of MYO-029. Nearly 100% inhibition of signal was observed at concentrations of MYO-029≧5 ug/ml.

Example 6.5

Spike Recovery in Human Serum Using the RK35 Capture/RK22 Detection Format

Figure 14A:
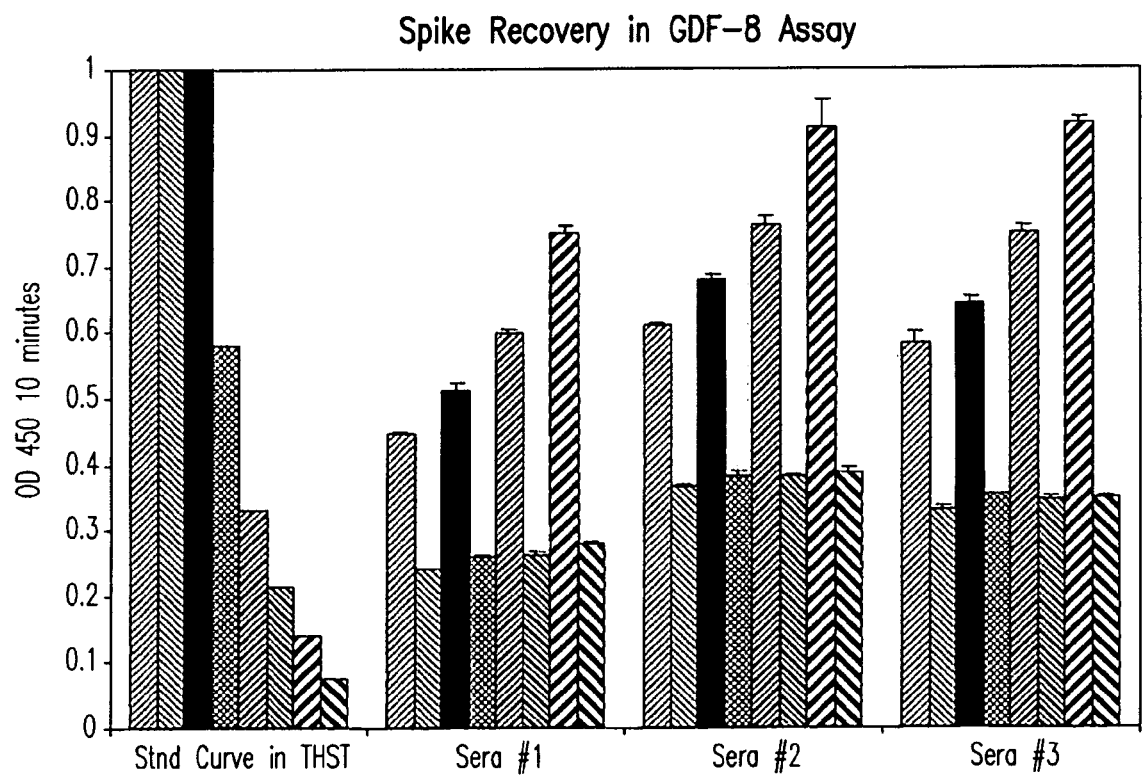
FIGS. 14A and 14B show the results from a "spike recovery experiment," where GDF-8 was added to 100% serum in three separate serum samples (Sera #1, #2, and #3). Each sample was analyzed +/−20 pg/ml MYO-029. The addition of 20 pg/ml MYO-029 blocks assay signal at all concentrations of GDF-8 tested (FIG. 13A).
Figure 14B:
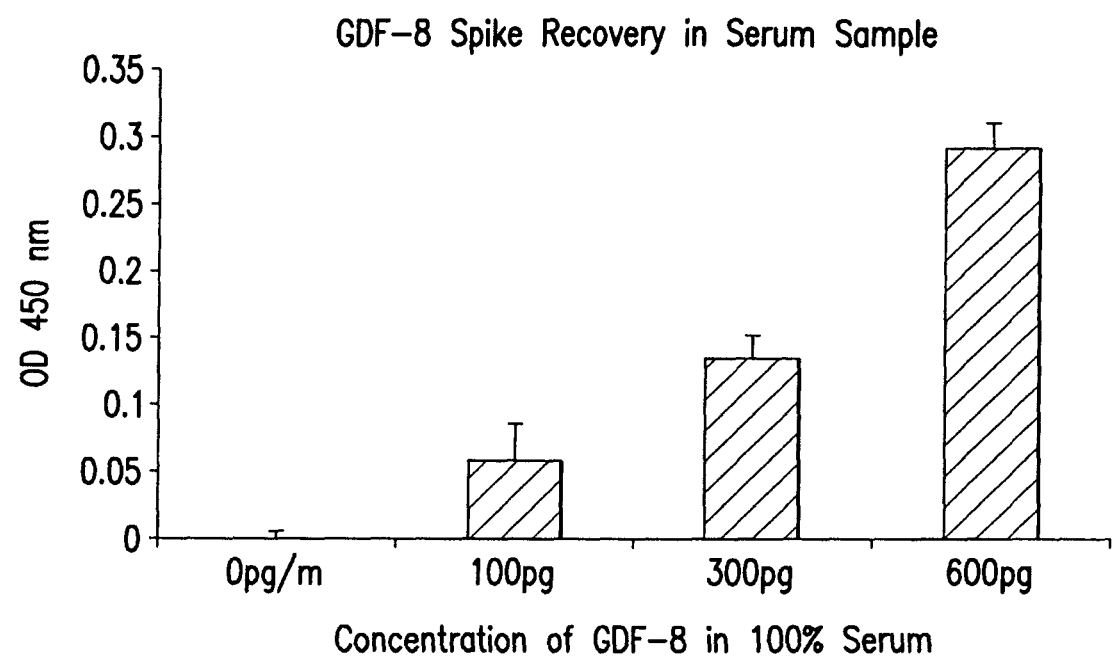
Figure 15:
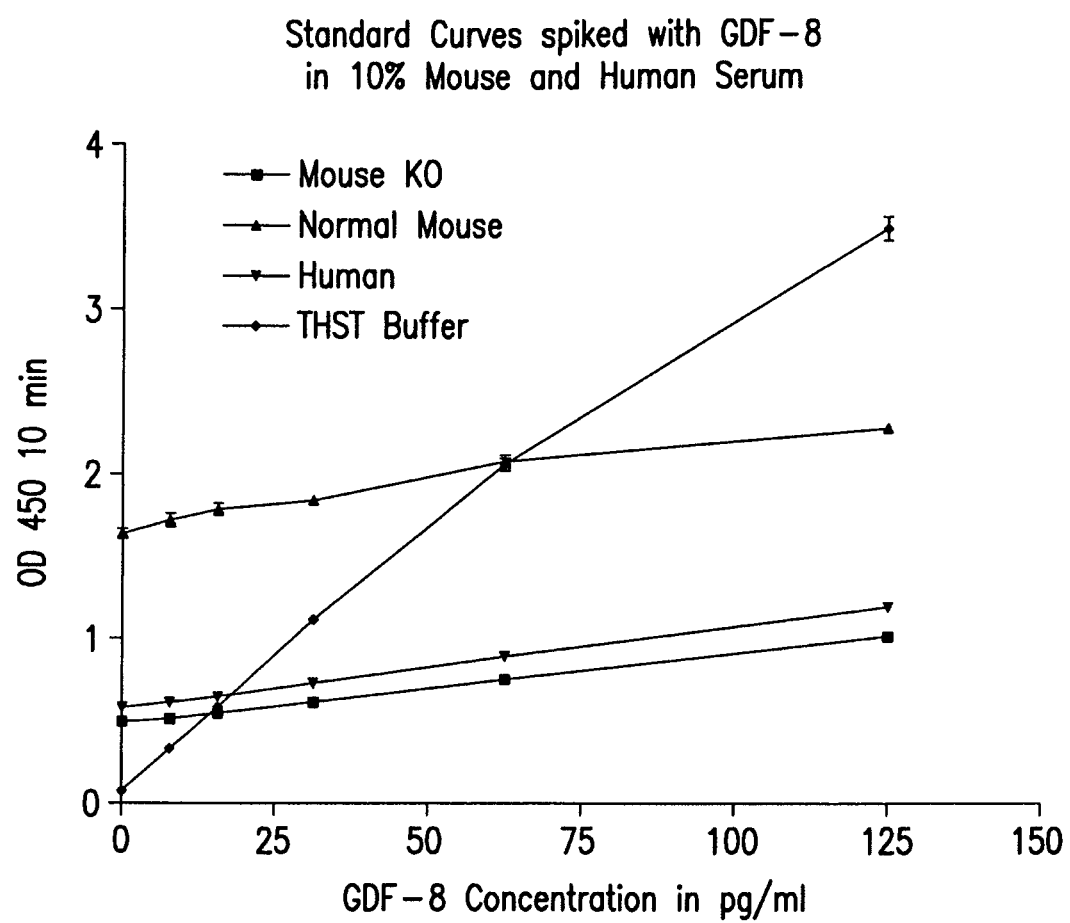
FIG. 15 shows a comparison of standard curves generated in normal mouse, knockout (KO) mouse and human serum. The slope of the curve with THST buffer alone is much steeper than those generated in serum and cannot be used to quantitate values in serum.

Three human serum samples were analyzed for GDF-8 recovery in spike recovery experiments. Each sample was diluted to 600 pg/ml in 100% serum of mature GDF-8 and, serially diluted two fold to produce samples of 600, 300, and 150 pg/ml of GDF-8. Each of these samples was analyzed in the RK35 capture/RK22 detection format with or without the addition of 20 μg/ml of MYO-029 see FIG. 14A. The reduction in signal due to the addition of MYO-029 is calculated, see FIG. 14B. These values were compared to a GDF-8 standard curve generated in THST assay buffer and observed vs. expected values for GDF-8 are plotted in FIG. 15. The observed values are well below the expected values indicating that standard curves in buffer alone do not accurately quantitate GDF-8 values found in serum samples.

Example 6.6

The Use of Serum Versus Assay Buffer for the Generation of Standard Curves

Figure 16:
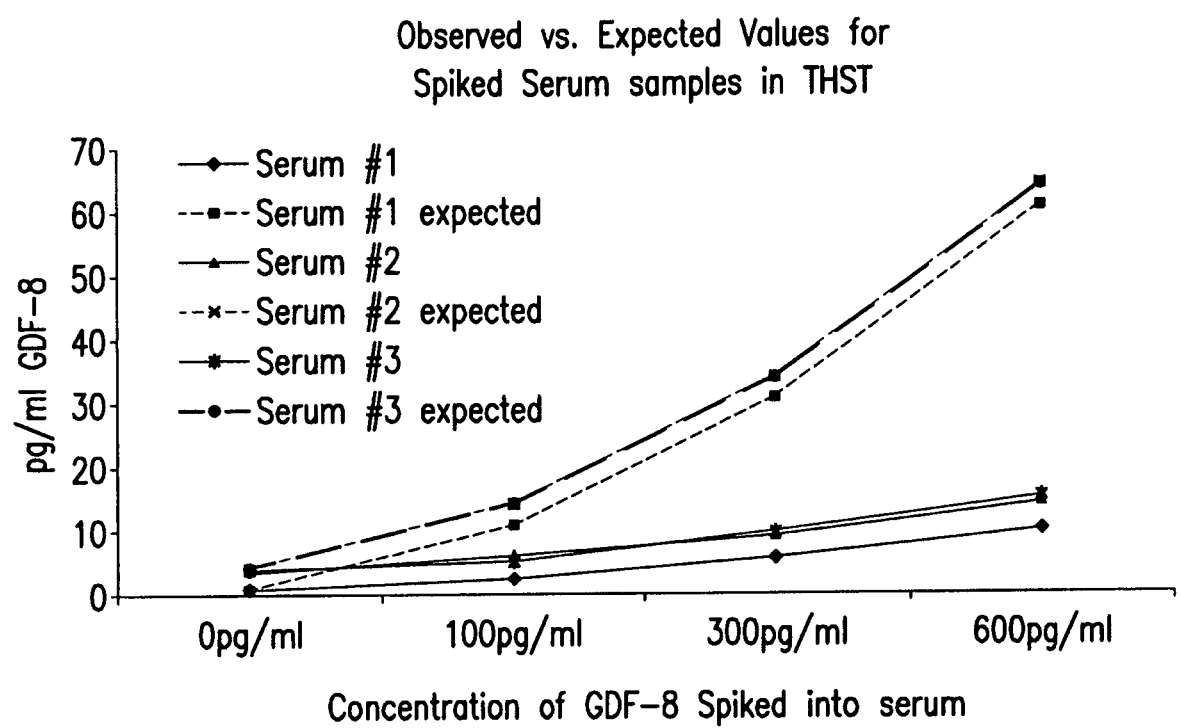
FIG. 16 demonstrates observed versus expected GDF8 values as generated in THST buffer.

Normal mouse serum and GDF-8 KO mouse serum was used in this study. These sera, along with normal human serum and THST buffer, were utilized to generate standard curves using mature GDF-8 protein, see FIG. 15. The difference in slope between standard curves generated in serum vs. buffer explains why the observed vs. predicted values in spike/recovery experiments differ so drastically (FIG. 16) when buffer is the medium used for generation of standard curves. The reduced slope of the standard curve in serum compared to standard curve in buffer highlights the matrix effects of serum on the signal produced and suggests that standard curves should be generated in serum. KO mouse serum is not available in quantities necessary for assay development and normal mouse serum has high endogenous levels of GDF-8 that would interfere with prediction of GDF-8 in unknown serum samples. Normal human serum also has endogenous levels of GDF-8, albeit lower than normal mouse, that also adds an unwanted interference factor. A possible alternative would be to deplete a pool of normal human serum of GDF-8 for use as an assay calibration matrix.

Example 6.7

Inactivation/Dissociation of Myo-029 Antibody in Serum

Figure 17:
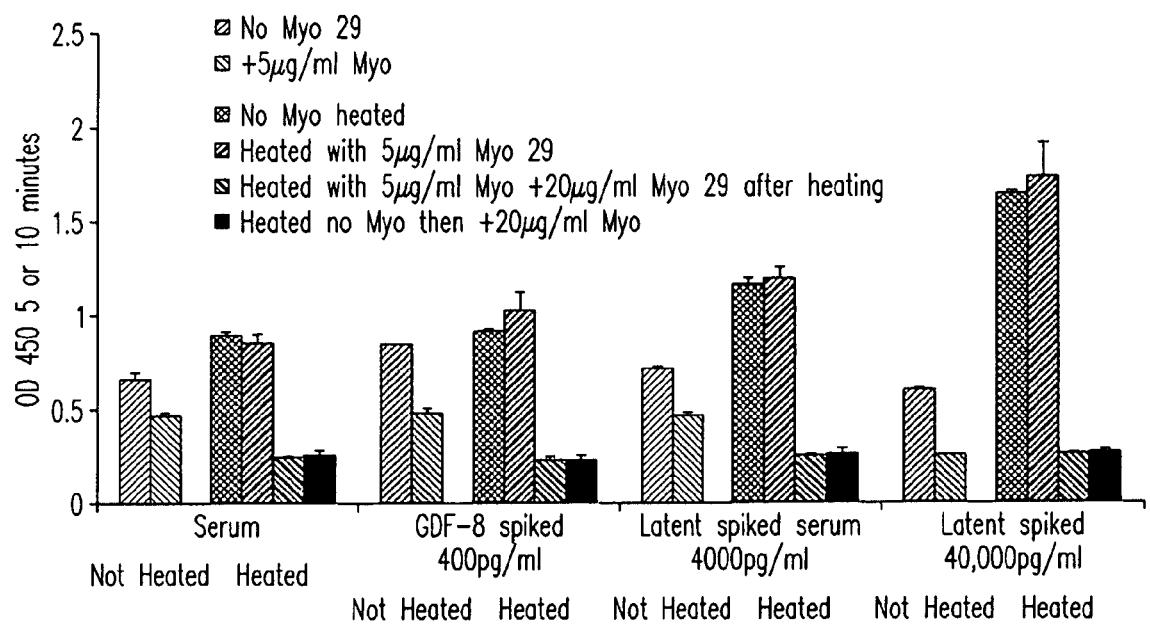
FIG. 17 presents the results from an experiment where it is shown that MYO-029 can be inactivated/dissociated from GDF-8 when heated to approximately 80° C. Serum samples were spiked with GDF-8 or latent GDF-8 +/−5 pg/ml MYO-029 and heated to 80° C. The results show that heating the MYO-029 samples restores the ability to detect GDF-8, indicating that MYO-029 is dissociated from GDF-8, and activated upon heating to 80° C. The results also show that when MYO-029 is added back to the heated sample, the GDF-8 signal is once again reduced. Also shown is an increase in endogenous GDF-8 signal upon heating that is even more pronounced in samples spiked with latent GDF-8 as compared to mature GDF-8 samples.

Previous studies demonstrated that the presence of MYO-029 interfered with the accurate quantitation of GDF-8 in the RK35/RK22 format by cross-reactivity with the epitope for the RK35 antibody. It was hypothesized that if one could dissociate GDF-8/MYO-029 complexes in a sample, it might be possible to develop an immunoassay that accurately measures GDF-8 in the presence of MYO-029. A few possibilities exist for dissociation of antibodies from their antigens, including acid dissociation and heat denaturation. Based upon a report (Brown et al., 1990, Growth Factors 3, 35-43) that latent TGF-β could be irreversibly activated by heat treatment. A temperature gradient from 65° C. to 80° C. in THST assay buffer had no effect on the inhibition demonstrated by MYO-029 antibody in the GDF-8 assay. However, a pilot experiment with normal unspiked serum, serum spiked with 400 pg/ml mature GDF-8, or serum spiked with latent GDF-8 was performed. In this experiment, MYO-029 antibody was spiked into 20% serum and heated to 80° C. for seven minutes (see FIG. 17). The results indicated that GDF-8 activity in the assay was retained at this temperature and that the MYO-029 antibody was inactivated in serum heated to 80° C. This inactivation was demonstrated in two ways: 1) serum samples heated in the presence of Myo-029 had the same signal output as control heated samples with no MYO-029 addition, and 2) assay signal could again be reduced to background levels by the addition of fresh MYO-029 post sample heating. These results were observed in normal serum, serum spiked with mature GDF.8, and in serum spiked with latent GDF.8. Serum samples spiked with latent GDF-8 demonstrate an increase in signal that seems dependent on latent GDF-8 material and not on mature GDF.8. To determine a more precise duration for effective inactivation, a time course experiment was conducted using normal serum spiked with 5 μg/ml MYO-029. The results indicated that the MYO-029 antibody is fully inactivated in as early as three minutes at 80° C.

Example 6.8

GDF8 Depletion in Human Serum

Figure 18:
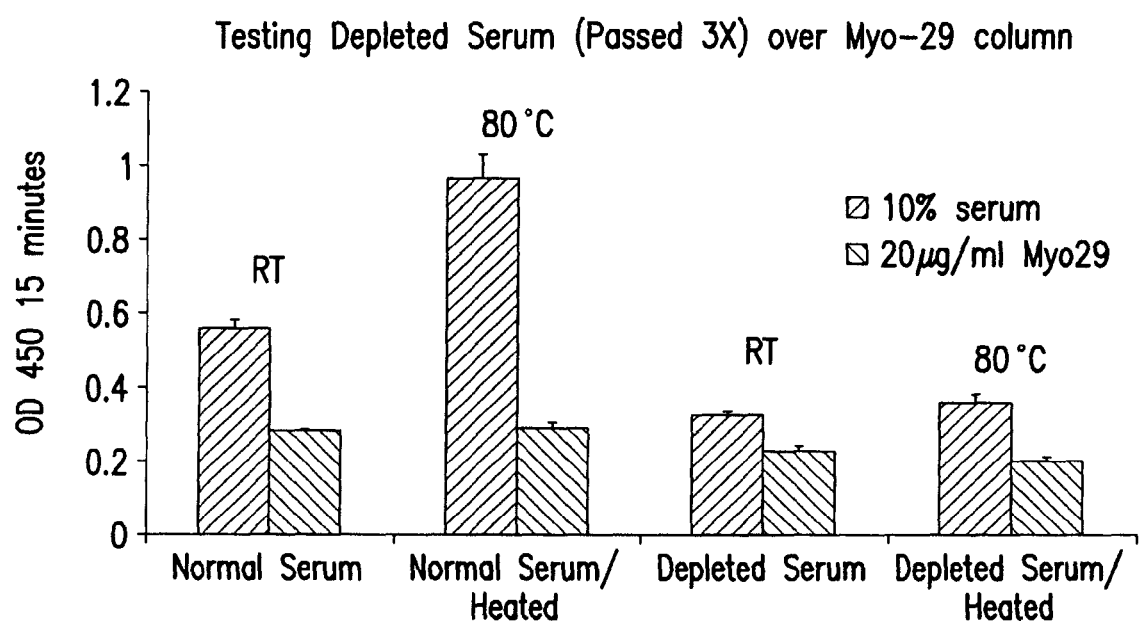
FIG. 18 shows the results of an ELISA assay for GDF-8 before and after depleting GDF-8 from the human serum. Normal human serum +/−20 pg/ml MYO-029 was analyzed for GDF-8 at room temperature ("RT"), and after heating to 80° C. These values were compared to the same samples that were first depleted of GDF-8 by pre-heating to 65° C. for 10 minutes, and passing three times over a 1 mg MYO-029 affinity column. The results indicate that depleting GDF-8 from human serum is effective at reducing the background level of GDF-8 in this ELISA. The results also show that heating the depleted serum does not show the original increase in signal that is observed with normal serum upon heating. This heated/GDF-8 depleted (H/D) serum can be used for generation of GDF-8 standard curves.

In order to deplete human serum of endogenous GDF-8, an affinity column was made with 1 mg of MYO-029 antibody covalently immobilized to Sepharose beads via cyanogen bromide activation. The column was pre-washed and small aliquots of human serum were passed over the column and tested for GDF-8 activity in the GDF-8 ELISA assay. Additionally, serum was pre-heated to 65° C. and then cooled before being passed over the column. Heated serum, when run in the GDF-8 assay, displays an increased signal that may be due to immunological activation of latent GDF-8 in serum. FIG. 18 shows the signal increase in the GDF-8 assay upon heating and also the depletion of signal in the heated/depleted H/D serum. Notably, there was no observed increase in signal in the H/D serum when it was reheated to 80° C.

Example 6.9

Standard Curves in HID Serum

Figure 19:
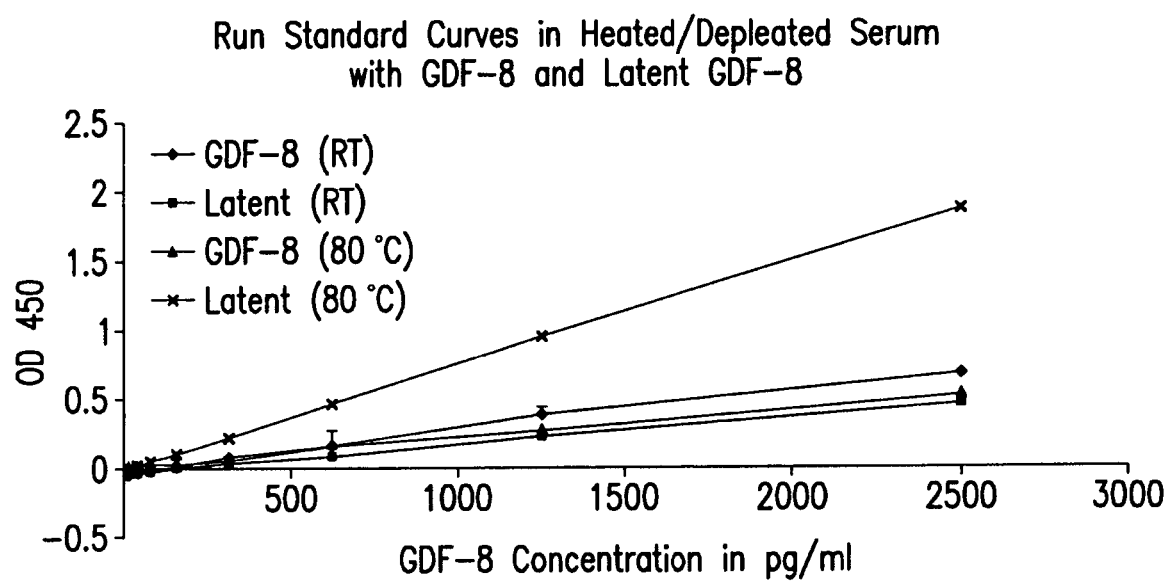
FIG. 19 shows a graph of standard curves that were generated in heated, GDF-8 depleted serum, and then spiked with increasing concentrations of mature GDF-8 or latent GDF-8. The standard curves were assayed at room temperature (RT) or with heating to 80° C. Serum samples spiked with latent GDF-8 show a large signal increase after heating that was not observed in samples spiked with mature GDF-8.

Using serum devoid of endogenous GDF-8 immunoreactivity standard curves were generated under heated and unheated conditions using both mature GDF-8 and latent GDF-8. Mature GDF-8 was spiked into 100% serum and serially diluted from 2500 pg/ml to 40 pg/ml. Latent GDF-8 was used at a protein concentration 20 times that of mature GDF8 ranging from 50,000 pg/ml to 800 pg/ml (FIG. 19). The results of this experiment show a significant increase in assay signal when latent GDF-8 is heated in 100% H/D serum to 80° C. Note that in FIG. 18 H/D serum heated to 80° C. did not show the characteristic signal increase that is observed in normal serum. This lends credence to the hypothesis that the increase seen in normal serum is due to endogenous latent GDF-8. In contrast, the signal generated with mature GDF-8 does not increase upon heating and in repeated experiments has a tendency to decrease with heating at 80° C.

Example 6.10

Analysis of Free and Total GDF8 in Eight Normal Serum Samples

Figure 20:
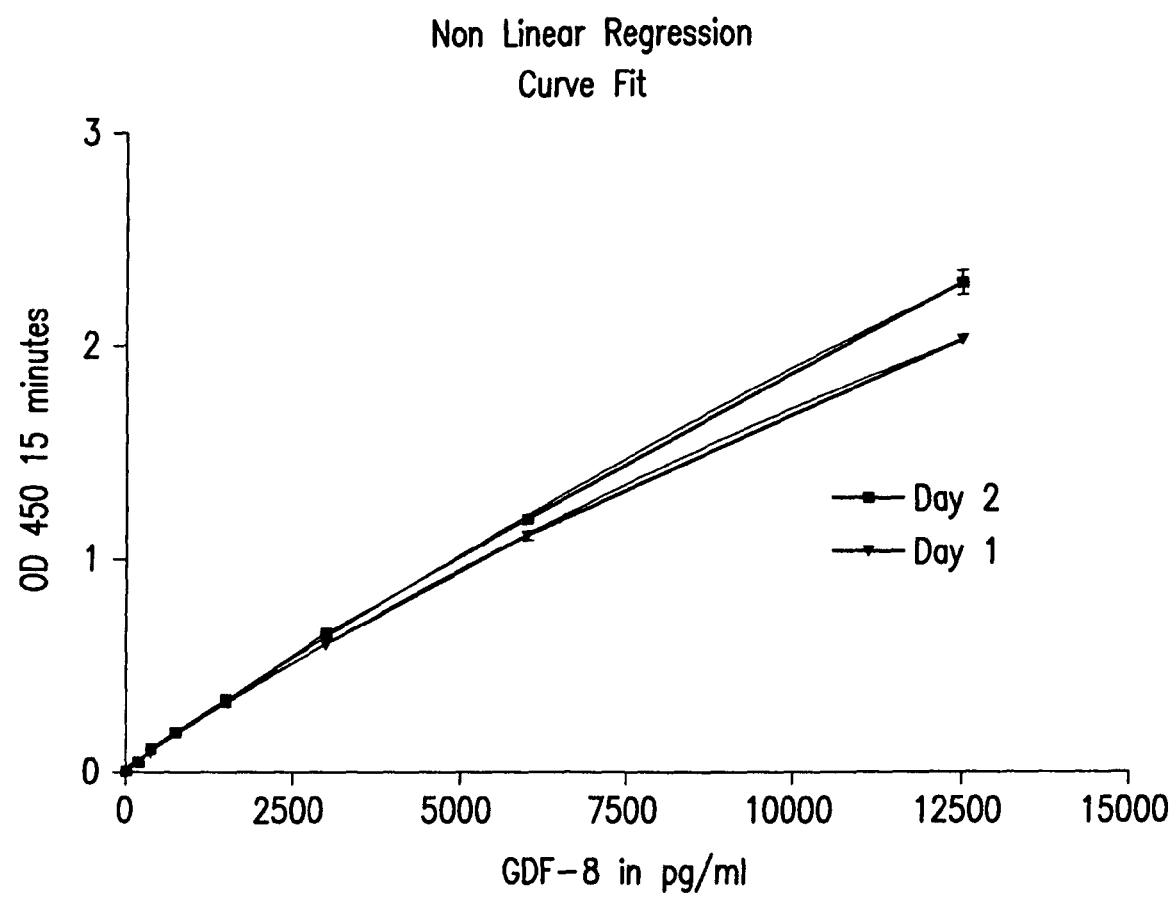
FIG. 20 shows the analysis of two standard curves run on different plates on two successive days. Heated/GDF-8 depleted serum with known concentrations of mature GDF-8 is used to generate the standard curves. OD values from each curve are plotted versus mature GDF-8 concentration. Non-linear regression curve fit is a more accurate correlation for GDF-8 values generated in heated/GDF-8 depleted serum. The curve fit has a better correlation co-efficient and has more range for accuracy than linear regression curves. Software from Prism Graph was used to calculate GDF-8 concentration from the OD values generated in the GDF-8 ELISA assay.
Figure 22:
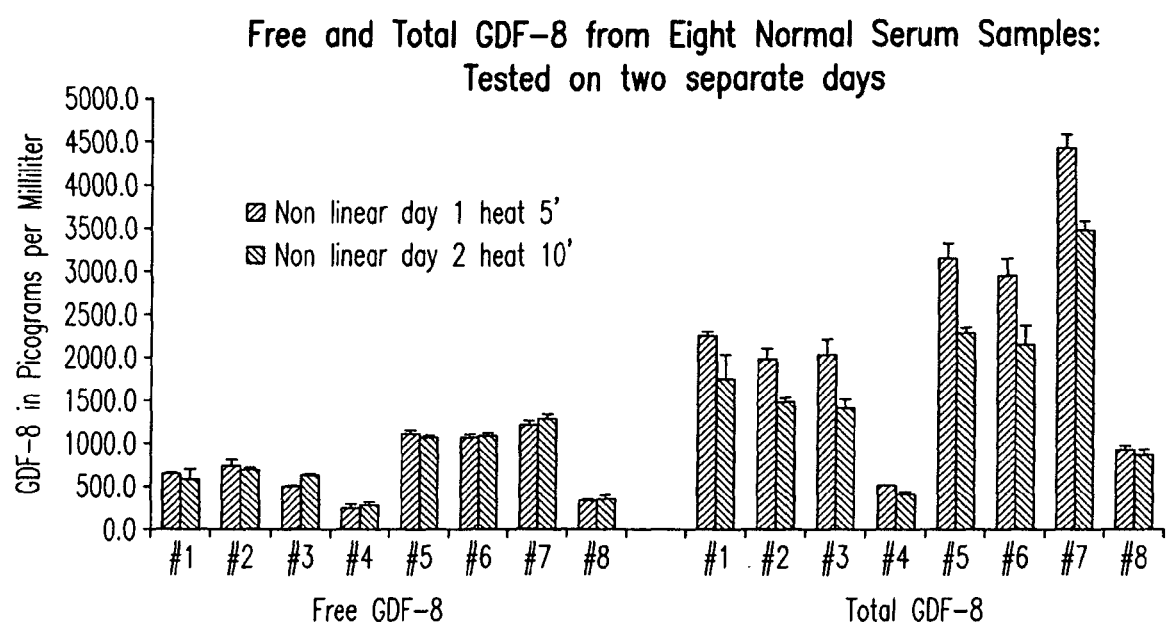
FIG. 22 shows the results of an assay to measure free and total GDF-8 in eight normal serum samples. The graph represents two separate experiments conducted on two separate days. On the second day of the experiment, total GDF-8 was analyzed by heating the samples for ten minutes (as compared to the five minute heating conducted on the first day of the experiment). Values ranged from 227 to 1241 pg/ml for free GDF-8 and from 514 to 4329 pg/ml for total GDF-8.

Eight normal serum samples, previously frozen, thawed and assayed for free and total GDF-8 using the room temperature assay (free) and the 80° C. heating step (total) to activate latent GDF-8. The standard curve for this analysis was generated using H/D serum with known concentrations of mature GDF-8 protein spiked in as the GDF-8 calibrator. The standard curve ranged from 12,500 pg/ml to 188 pg/ml and a non-linear regression curve fit analysis with a correlation coefficient 0.999 (see FIG. 20) was used to calculate GDF-8 values in the eight unknown serum samples. As previously described, the change in optical density induced by the addition of Myo-029 is directly proportional to endogenous amount of GDF-8 in the sample. FIG. 21 is a presentation of the raw data that is used to determine the concentration of GDF-8. This figure illustrates the free GDF-8 signal and its corresponding reduced signal by the addition of MYO-029 antibody, as well as the total GDF-8 and its corresponding reduced signal by the addition of MYO-029. FIG. 22 presents the results of an assay reproducibility experiment. The free and total GDF8 assay exhibits a high degree of reproducibility. This is especially true for the free GDF-8 (room temperature) assay. The increased assay signal in the total (heated to 80° C.), assay from day to day is due to an increase in heating time from five to ten minutes. The reduction in assay signal with increased time duration of sample heating was observed repeatedly and may reflect denaturation of the antigen and loss of immunoreactivity.

Example 6.11

Heat Activated Endogenous GDF8 is Under Detected in the Presence of MYO-029

Figure 23:
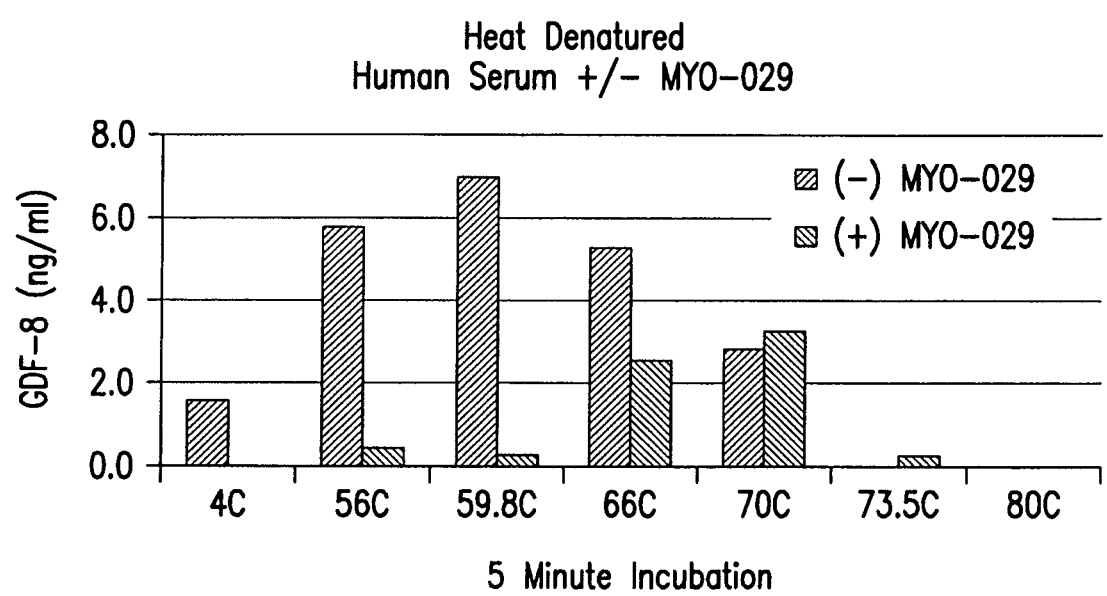
FIG. 23 shows the results of an assay to measure GDF-8 via ELISA after heat denaturation. Aliquots of human serum were incubated at room temperature for one hour +/−10 μg/ml of MYO-029. The samples were next heat denatured in a gradient thermocycler at various temperatures prior to ELISA analysis. Quantitation of GDF-8 levels in test samples was performed by interpolation from the assay results of a standard curve consisting of a dilution series of purified recombinant GDF-8 dimer of known concentration spiked into pooled human serum depleted of GDF-8 by affinity chromatography. Maximum detection of GDF-8 in the absence of MYO-029 occurs at approximately 60° C. The presence of MYO-029 masks detection of GDF-8 in serum at low temperature, but at temperatures greater than 65° C., GDF-8 detection was partially restored.

In the experiment shown in FIG. 23 human serum was incubated in the presence or absence of MYO-029, then heat denatured at various temperatures prior to analysis by ELISA. Quantitation of GDF-8 levels in test samples was performed by interpolation from the assay results of a standard curve consisting of a dilution series of purified recombinant GDF-8 dimer of known concentration spiked into pooled human serum depleted of GDF-8 by affinity chromatography. Maximum detection of GDF-8 in the absence of MYO-029 occurred at approximately 60° C. The presence of MYO-029 masked detection of GDF-8 in serum at low temperatures. Incubation at temperatures greater than 65° C. partially restored detection of GDF-8 in the presence of MYO-029. However, calculated concentrations of GDF-8 at temperatures greater than 65° C. showed that the assay substantially underestimated the total amount of GDF8 present in the serum.

Example 6.12

GDF8 is Detected in the Presence of Myo-029 at Low pH

Figure 24A:
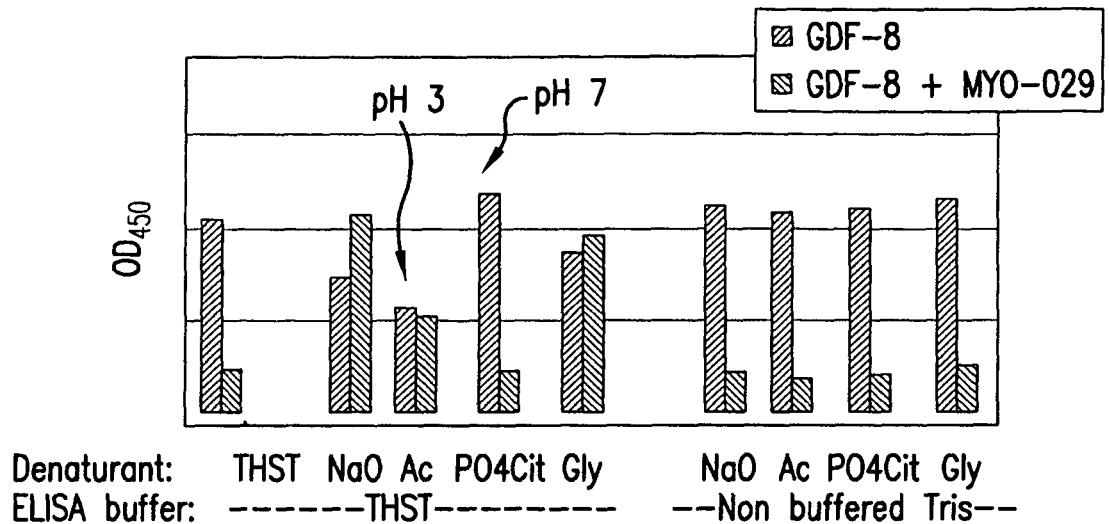
FIGS. 24A and 24B show that GDF-8 can be detected in the presence of MYO-029 at low pH.
Figure 24B:
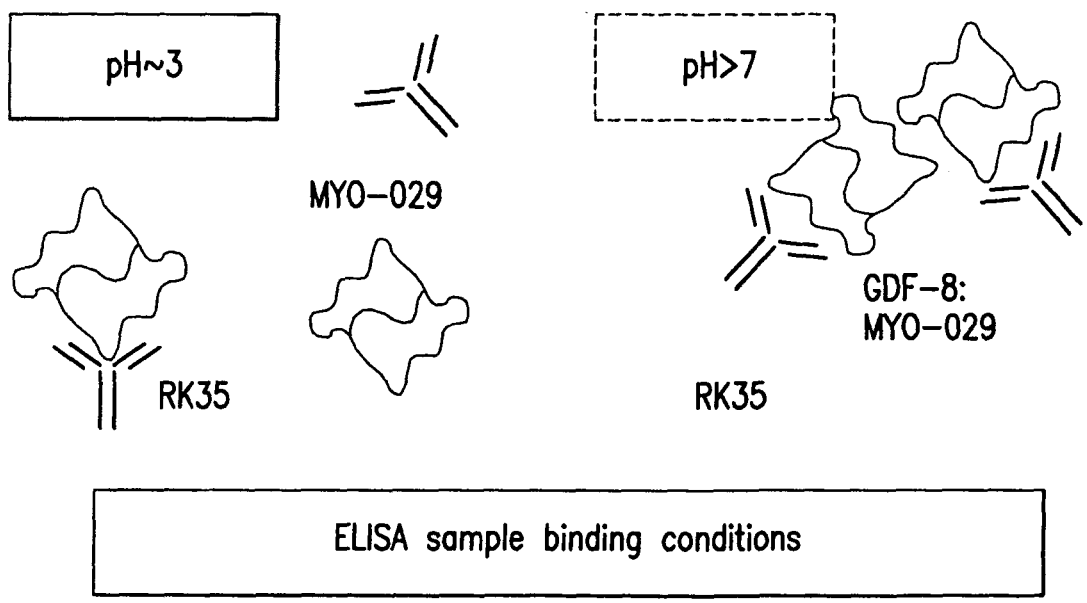

The suboptimal detection of GDF-8 when heated to temperatures necessary for dissociation of MYO-029 prompted evaluation of alternative methods. FIG. 24 demonstrates the ability of the acid dissociation ELISA to detect similar levels of GDF-8 in the absence and presence of MYO-029. In previous experiments the GDF-8/MYO-029 mixture was neutralized prior to binding to capture antibody. Under those conditions MYO-029 was able to compete for binding with the capture antibody, RK35, upon neutralization. In FIG. 24 it is demonstrated that when the capture conditions are maintained at low acidic pH, RK35 is still capable of binding GDF-8 while MYO-029 is not, and therefore full recovery of GDF-8 detection can be achieved in the presence or absence of therapeutic antibody.

Example 6.13

RK35 Binds GDF8 Under Acidic Conditions

Figure 25:
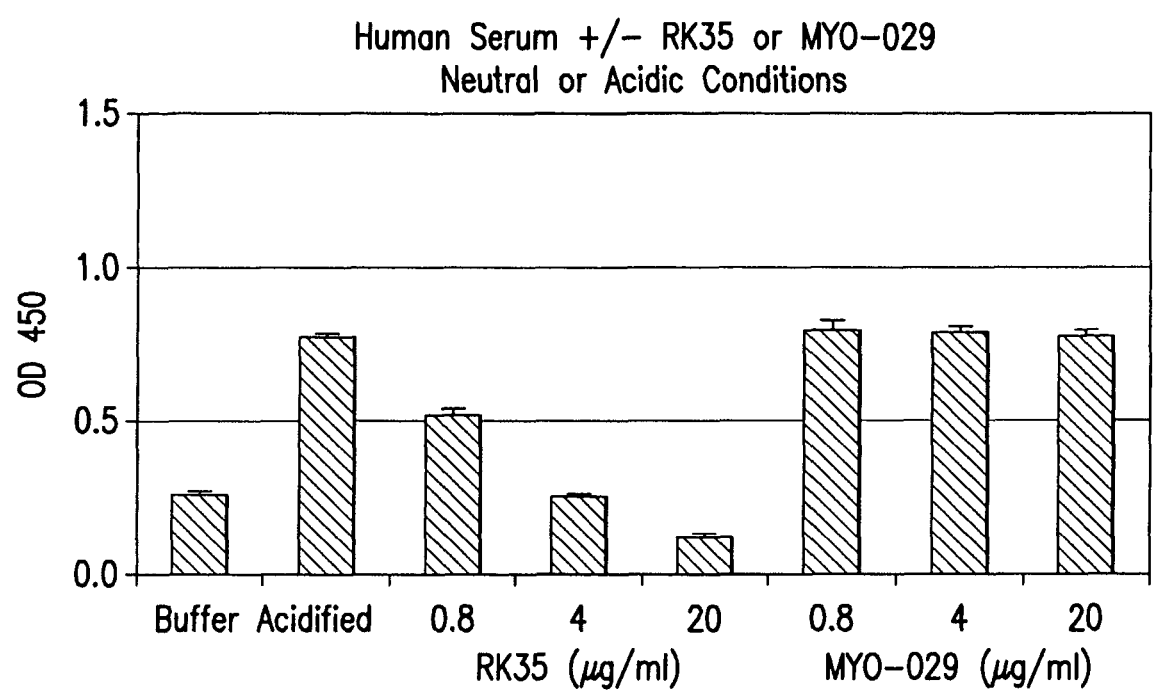
FIG. 25 provides the results of an experiment that shows that the murine antibody RK35 binds to GDF-8 under acidic conditions, while MYO-029 does not. Human serum was pre-incubated +/−various concentrations of RK35 or MYO-029, and was diluted five-fold with THST buffer (neutral pH) or glycine-HCl (acidic pH). The serum was then added to ELISA wells that contained plate-bound RK35 and either THST or glycine-HCl buffer. In the absence of RK35 or MYO-029, more endogenous GDF-8 is detected in acidic conditions than in neutral conditions due to complex dissociation and the release of free GDF-8 proteins (see first two bars). The last six bars represent data obtained at acidic pH. Increasing amounts of RK35 in solution was able to bind and compete for GDF-8 binding to the plate-bound RK35, resulting in decreased detection of GDF-8 under acidic conditions. MYO-029 was incapable of binding GDF-8 in solution approaching pH3, leaving the GDF-8 in solution available to bind to the RK35 antibody coated on the ELISA plate.
Figure 26:
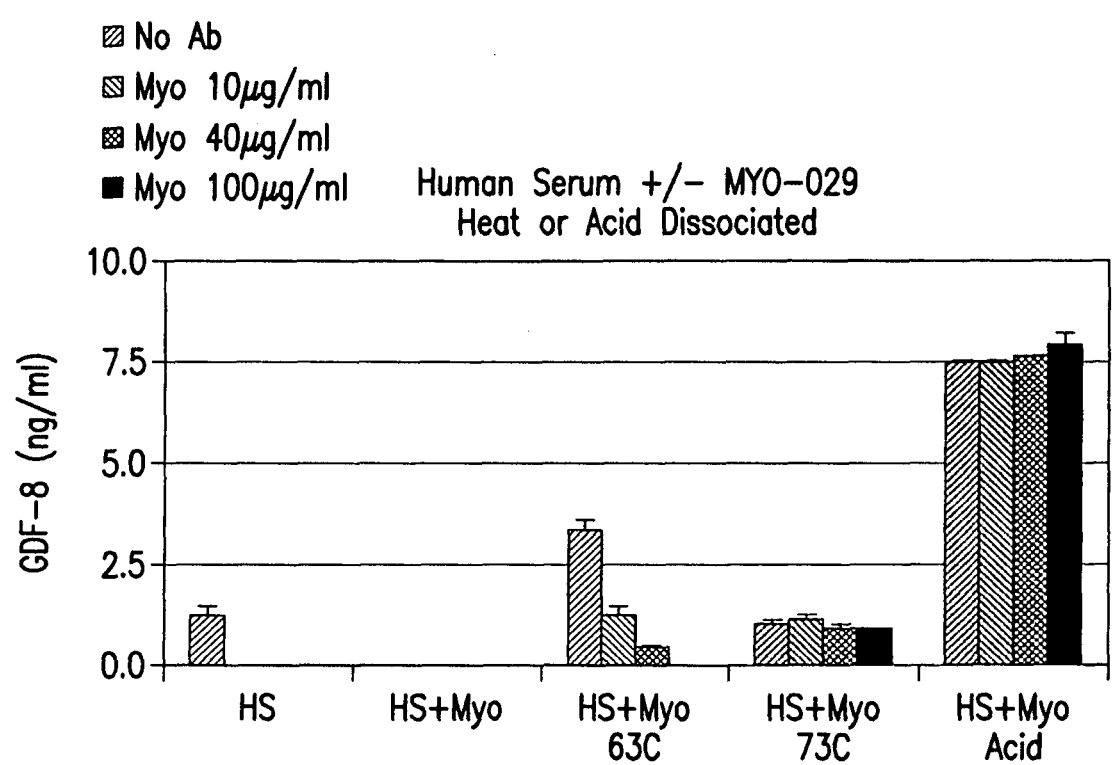
FIG. 26 shows that increasing the MYO-029 concentration to 100 μg/ml did not diminish detection of GDF-8 using the acid dissociation ELISA protocol. Human serum +/−10, 40, or 100 μg/ml of MYO-029 was assayed following heat or acid dissociation. The concentration of GDF-8 was estimated by interpolation from a standard curve of recombinant GDF-8 mature dimer spiked into pooled human serum depleted of GDF-8. In the absence of MYO-029, the concentration of GDF-8 in serum was determined to be ~1 ng/ml when analyte capture was performed at near neutral pH (HS). Detection of GDF-8 following the release of serum binding proteins via heat dissociation was ~3 ng/ml in the absence of MYO-029 (HS+Myo, 63° C.; no Ab). In the presence of MYO-029, even at the lowest concentration tested, heat dissociation failed to permit the same level of detection as in the absence of MYO-029 (HS+MYO, 73° C.). Acid treatment of serum samples detected very similar amounts of GDF-8 independent of the amount of MYO-029 present (HS+MYO, Acid).

To verify that RK35 (but not MYO-029) is capable of binding GDF-8 under acidic conditions, RK35 and MYO-029 were individually titrated into human serum and the analyte capture step was performed in acidic conditions. Increasing amounts of RK35 in solution was able to bind and compete for GDF-8 binding to the plate-bound RK35, resulting in decreased detection of GDF-8 under acidic conditions. MYO-029 was incapable of binding GDF-8 in solution approaching pH 3.0, regardless of the concentration of MYO-029 added, leaving the GDF-8 in solution available to bind to the RK35 antibody coated in the ELISA well (see FIG. 25). Thus, the ability of RK35 to bind GDF-8 under conditions in which MYO-029 cannot serves as a useful attribute that can be exploited to measure GDF-8 levels in the presence of MYO-029. Acid dissociation of MYO-029 from GDF-8 is effective even with escalating concentrations of MYO-029. Data in FIG. 25 show that increasing the MYO-029 concentration to 100 pg/ml did not diminish detection of GDF-8 using the acid dissociation protocol. This figure also shows the significant reduction in the detection of GDF-8 using the heat dissociation protocol, FIG. 26.

Figure 27:
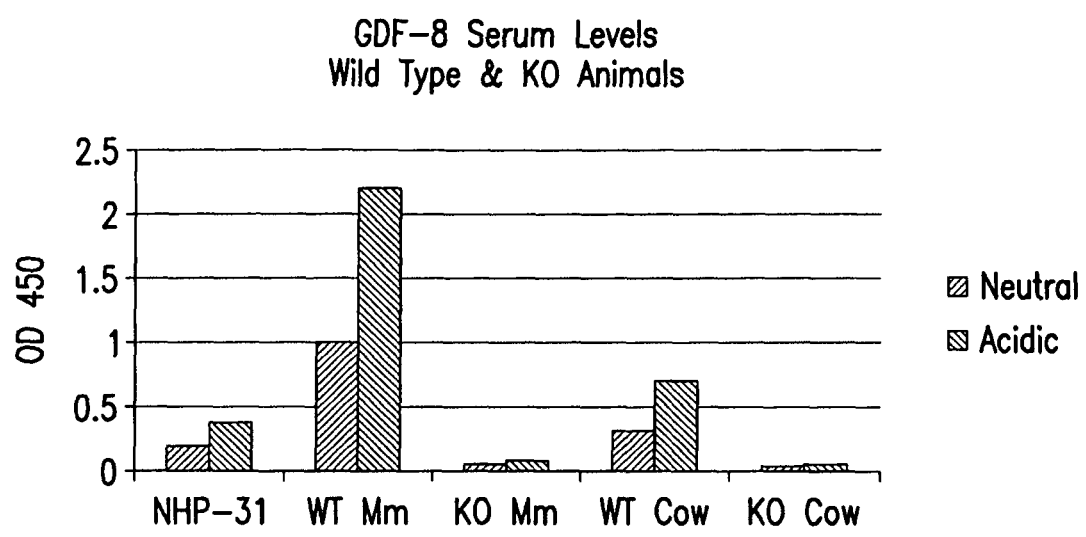
FIG. 27 demonstrates that acidic conditions during analyte capture do not reduce assay specificity. Acidification of serum resulted in greater signal detection (white bars vs. black bars) in all wild type (WT) animals tested, Cynomolgus monkey (NHP-31), mouse (WT Mm), and dairy cow (WT cow). Serum measured at neutral or acidic pH from either a genetically engineered GDF-8 knockout (KO Mm) mouse or the naturally occurring GDF-8 KO Belgian Blue cow (KO Cow) failed to produce a signal over the plate background.

Acidification of human serum results in much greater estimates of GDF-8 serum levels than previously reported. To demonstrate that the increased serum estimates are the result of greater detection of GDF-8 and not due to an acid induced artifact, serum from both a genetically engineered knockout mouse and a naturally occurring GDF-8 knockout animal, the Belgian Blue cow, was analyzed. FIG. 27 shows that serum from both the knockout mouse and the Belgian Blue cow failed to produce a signal over plate background when measured at either neutral or acidic pH. Values reported here are in units of optical density and allow for comparative evaluation however the lack of a calibrator curve results in the inability to determine the absolute quantity of GDF-8.

Example 6.14

Calibration Curve Fitting

To evaluate the inter-assay and intra-assay variability of the acid-dissociate method, aliquots of Belgian Blue serum spiked with recombinant GDF-8 dimer were analyzed. Four stock solutions were prepared independent of the calibration curve and were assayed in triplicate in five different locations of a 96 well plate.

A 4 or 5-parameter logistic model can be used to fit a calibration curve for this assay. The arithmetic mean of the triplicates can be used as the raw data for model fitting. Typically, variances at different concentration levels tend to be different. To obtain a calibration curve that is accurate at both low and high concentrations, a weighted nonlinear least squares method, or a variance-stabilizing transformation of the optical density data followed by a non-weighted nonlinear least squares method, should be employed.

Figure 28A:
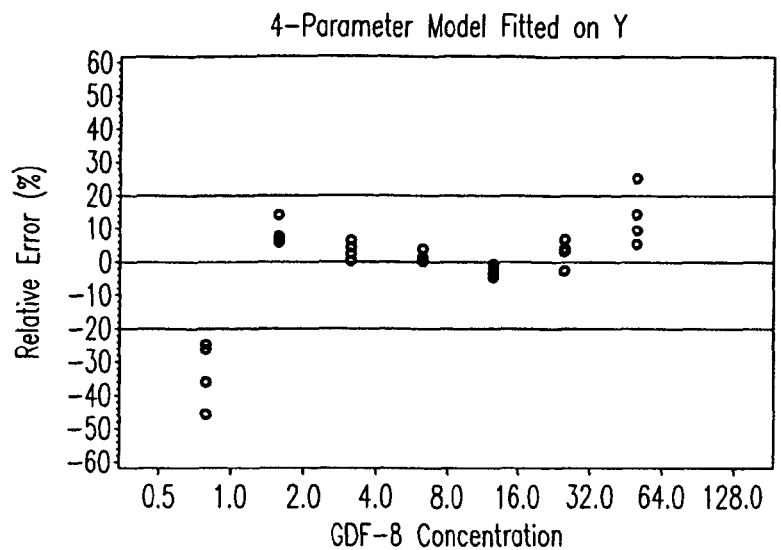
FIG. 28A-C contrast three different methods of calibration curve fitting for five GDF-8 ELISA plates in terms of their relative errors of the back-calculated concentrations for calibrating standards. Results from five GDF-8 ELISA plates are plotted. Relative error is defined as $(B-N)/N \times 100$, where B is the back-calculated concentration for a standard using the calibration curve, and N is the nominal concentration of the standard. Three curve fitting methods were: 1) FIG. 36A—4-parameter logistic model on optical density by least squares (LS); 2) FIG. 36B—4-parameter logistic model on square root of optical density by LS; and 3) FIG. 36C—5-parameter logistic model on square root of optical density by LS. Reference lines are at −20 and 20.
Figure 28B:
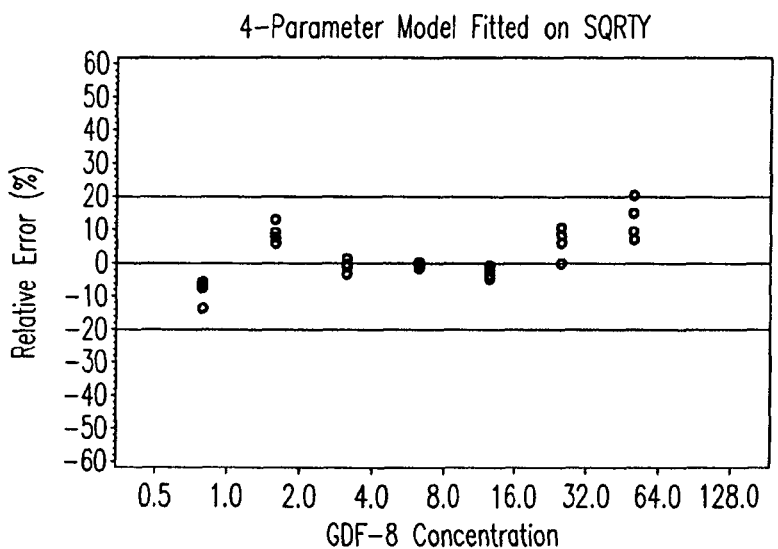
Figure 28C:
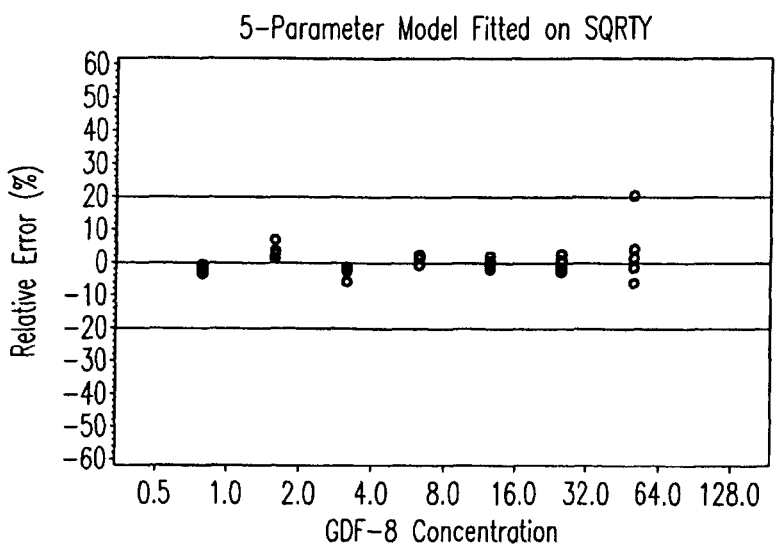

FIGS. 28 A-C contrasts three different methods of calibration curve fitting for five GDF-8 ELISA plates in terms of their relative errors of the back-calculated concentrations for calibrating standards. If we take 20% relative errors as acceptable, then both 4- and 5-parameter logistic model fitted on square root of optical density can be used.

Example 6.15

Precision and Accuracy of the Assay

Figure 29A:
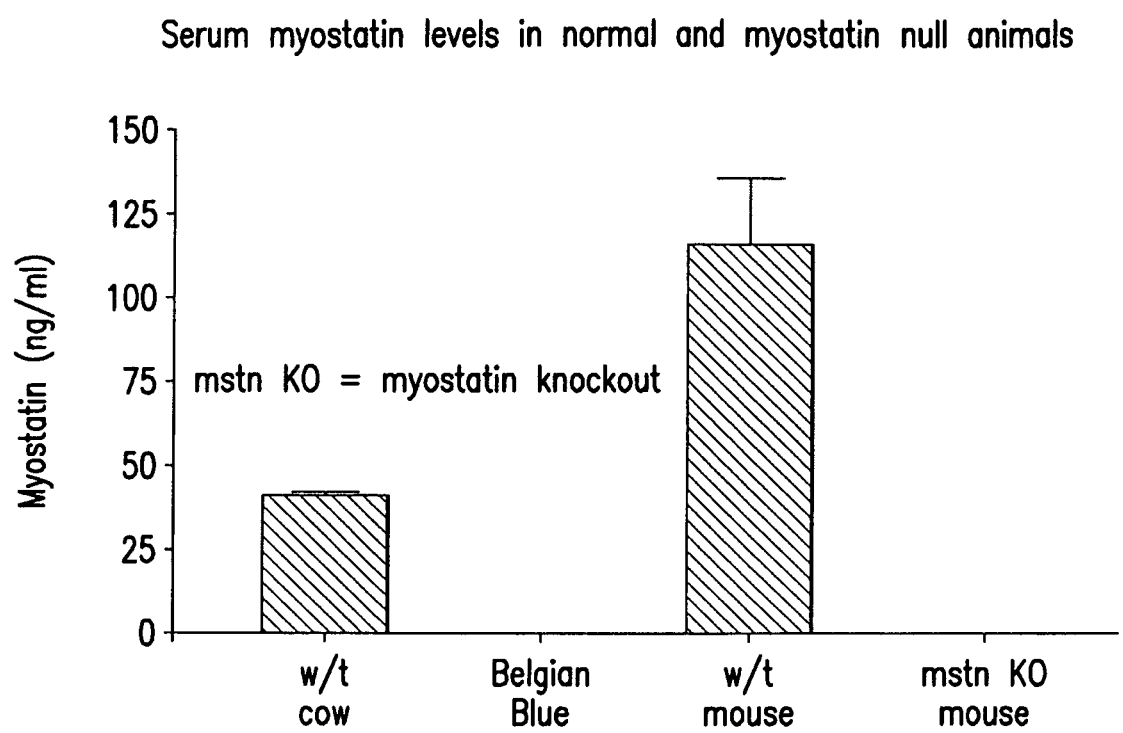
FIG. 29A. Serum myostatin levels in normal and myostatin-null animals. Serum from Belgian Blue cattle, normal cattle (wt cow), myostatin null mice (mstn KO mouse) and wild-type littermates (wt mouse) were measured under dissociative, acidic conditions (pH2.5), and values were extrapolated from a standard curve of recombinant human myostatin in myostatin-deficient serum matrix. Bars represent mean in +/−SD of replicate samples (n=3). Myostatin concentrations in myostatin-null animals fell below the concentration of the lowest calibrator sample (147 pg/mL).
Figure 29B:
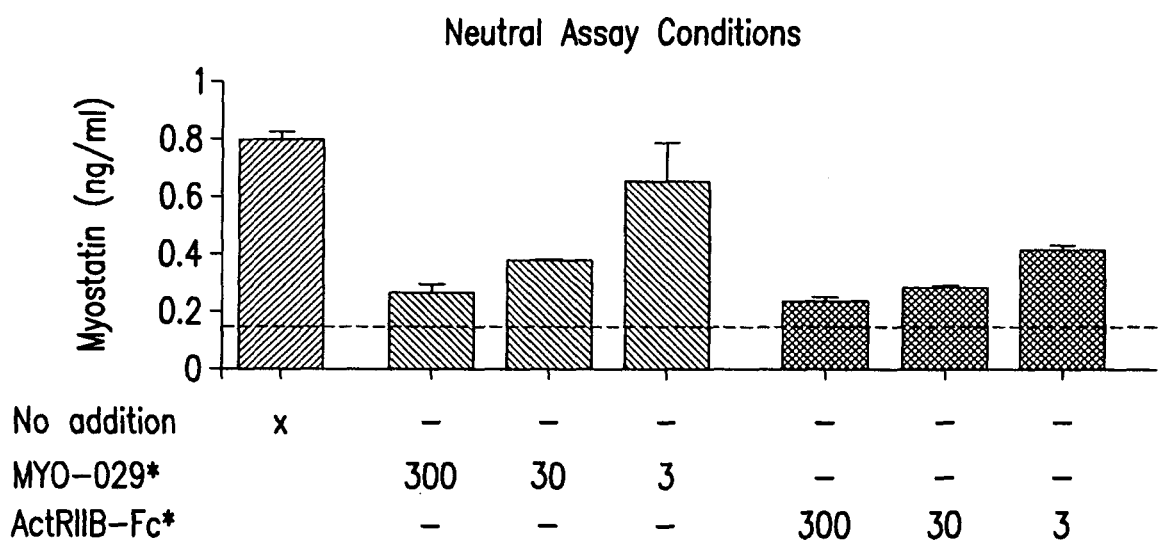

To evaluate the -inter and -intra assay variability of the acid-dissociate method aliquots of Belgian Blue serum spiked with recombinant GDF-8 dimer were analyzed. Four stock solutions were prepared independent of the calibration curve and were assayed in triplicate in five different locations of a 96 well plate. FIG. 29 shows the plate design of five plates that were processed on three different days. Concentrations of the spiked samples were calculated from a calibration curve fitted to each plate by a 5-parameter logistic model. Intra-plate and inter-plate coefficients of variation (CV) and relative errors (RE) are summarized in Tables 1 and 2. Both intra-plate and inter-plate precisions were well within 20% based on either method of CV calculations.

TABLE 5

Intra-Plate Variability of Spiked Samples

| Sample | Nominal (ne/ml) | Number of Plates | Average CV#I (%) | Average CV (%) | Average Relative (%) |
|---|---|---|---|---|---|
| LLOQ | 0.5 | 5 | 2.9 | 4.5 | 55.0 |
| L-QC | 2.0 | 5 | 2.4 | 3.2 | 37.1 |
| M-QC | 10.0 | 5 | 2.6 | 3.2 | 23.3 |
| H-QC | 40.0 | 5 | 10.2 | 11.5 | 11.7 |

CV#1 = SD/Sample Mean
CV#2 = SD/Nominal Concentration

TABLE 6

Inter-Plate Variability of Spiked Samples

| Sample | Nominal Concentration | CV#I (%) | CV#2 (%) | Relative Error |
|---|---|---|---|---|
| LLOQ | 0.5 | 7.0 | 10.8 | 55.0 |
| L-QC | 2.0 | 6.0 | 8.3 | 37.1 |
| M-QC | 10.0 | 7.2 | 8.9 | 23.3 |
| H-QC | 40.0 | 12.1 | 13.5 | 11.7 |

CV#I = Inter-Plate SD/Sample Mean
CV#2 = Inter-Plate SD/Nominal Concentration

Example 7

Measurement of Myostatin Concentrations in Human Serum

Using the assay as described above, circulating concentrations of myostatin were measured and compared in healthy human sera. In one study the sera of young and older men were evaluated for myostatin levels. The effects of testosterone treatment on circulating myostatin levels using stored samples from a testosterone dose response study were also examined. In that study, the details of which have been published previously (Bhasin S et al. J Clin Endocrinol Metab 2005; 90:678-88, Bhasin S et al. Am J Physiol Endocrinol Metab 2001; 281 :EI 172-81, and Storer T V V et al. J Clin Endocrinol Metab 2003; 88: 1478-85) the administration of graded doses of testosterone to healthy young and older men was associated with dose-dependent increases in skeletal muscle mass and strength. In another study the sera of healthy and surgically menopausal women were evaluated.

In the first study serum samples were derived from healthy young men, aged 18-35 years, and older men, aged 60-75 years, with normal testosterone levels, who were participants in a testosterone dose response study as cited above. The study protocols were approved by the institutional review boards of Charles R. Drew University and Harbor-UCLA Research and Education Institute. Exclusion criteria included a history of prostate cancer, PSA>4 ng/ml, a score of >7 on the AUA lower urinary tract symptoms questionnaire, a hematocrit >48%, severe sleep apnea, diabetes mellitus, congestive heart failure, myocardial infarct in the preceding six months, use of androgens in the preceding year, or participation in moderate to intense exercise training regimens. After a four-week control period, participants were randomly assigned to one of five treatment groups to receive monthly injections of a GnRH agonist (leuprolide depot, 7.5 mg; TAP, North Chicago, Ill.) to suppress endogenous gonadotropin production. The participants also received weekly intramuscular injections of testosterone enanthate (TE, Delatestryl, 200 mg/ml; Savient Pharmaceuticals, Inc., Iselin, N.J.) in one of five doses: 25 mg, 50 mg, 125 mg, or 300 mg weekly.

Serum samples (or calibrator samples in Belgian Blue serum) were mixed with acid dissociation buffer (0.2M Glycine-HCl pH 2.5) at a ratio of 1:13.3. For non-dissociative assays, samples were mixed with THST buffer (50 mM Tris-HCl pH 8.0, 500 mM NaCl, 1 mM Glycine, 0.05% Tween-20; pH 8.0) instead of the Glycine-HCl buffer. Assay plates (Immulon 4 HBX #3855) were incubated with 2.0 mg/ml RK35 in coating buffer (100 mM Sodium Borate, pH 9.1) overnight at 4° C., washed, and blocked with 200 µl/well of Super-Block-TBS (Pierce #37535). Diluted serum samples (100 µL) were transferred to the assay plate, incubated at room temperature for 90 min, washed 4 times with THST and 100 µl biotinlylated RK-22 secondary antibody (0.1 µg/ml) added to each well for 90 minutes at room temperature. Plates were washed four times with THST, and 100 µL Streptavidin-HRP (SouthernBiotech #7100-05) diluted 1:40,000 in THST buffer added for one hour at room temperature. Plates were washed again four times with THST, and developed by addition of 100 µL of TMB substrate for 12 minutes at room temperature. 100 µl of 0.5M $H_2SO_4$ added per well, and ELISA plates were read at OD 450 nm with wavelength correction set at 540 nm.

Calibration curve range: A calibration curve was generated by plotting the OD and corresponding concentration of each calibrator. A 5-parameter logistic fit was used to fit the calibration curve. A calibration curve consisting of two-fold dilutions of recombinant human mature myostatin in Belgian Blue serum extending from 73 pg/ml to 75,000 pg/mL was prepared prior to each assay. The intra- and inter-assay imprecision of the read-back values for the eleven calibrators were determined from six analytical runs. The mean, SD, % CV, and % Bias of the extrapolated concentrations were calculated for each analytical run (to assess intra-assay imprecision) and for all analytical runs (to assess inter-assay imprecision). The lower and upper limits of quantitation were defined as the lowest (LLQ) and highest (ULQ) calibrator concentrations (respectively) that could be measured with an intraassay % CV and % Bias≦30%.

Preparation of Validation Samples: Three Sets of Validation Samples Corresponding to low, mid-range, and high serum concentrations of myostatin were prepared using serum samples from healthy subjects with endogenous myostatin concentrations in the lower end and mid-range of the calibration curve, respectively. The high validation sample was a serum sample from a healthy subject spiked with recombinant myostatin protein.

Intra- and Inter-Assay Imprecision: Intra- and inter-assay CVs were measured in six separate aliquots of each of the three validation samples (low, mid, high) in five independent analytical runs. The QC analytical run acceptance range (total assay variation mean+/−2SD) was determined from myostatin concentrations measured in 23 separate aliquots of each of the three QC samples in 25 independent analytical runs. One aliquot of each of the three QC samples (QC-low, QC-mid, and QC-high) was analyzed in each analytical run of samples. An analytical run was accepted if the measured concentrations of myostatin in two out of the three QC samples were within the established acceptance range.

Other assays: Serum total testosterone levels were measured by a specific radioimmunoassay that has been validated previously against liquid chromatography tandem massspectrometry (LC-MSI/MS). The intra- and inter-assay coefficients of variation for the total T assay were 8.2% and 13.2%, respectively. Free T, separated from serum by an equilibrium dialysis procedure, was measured by a sensitive radioimmunoassay that has a sensitivity of 0.22 pg/ml, and intra- and inter-assay coefficients of variation 4.2% and 12.3%, respectively (Sinha-Hikim et al. J Clin Endocrinol Metab 1998; 83:1312-8). The radioimmunoassay and LC-MS/MS methods were compared by analyzing samples prepared in charcoal stripped serum to which known amounts of T had been added. These measurements demonstrated a correlation of 0.99 between the radioimmunoassay and LC-MS/MS measurement. Serum sex hormone binding globulin (SHBG) levels were measured by an immunofluorometric assay that has a sensitivity of 6.25 nmol/L. Body composition was assessed at baseline and during week 20 by dual-energy X-ray absorptiometry (DEW, Hologic 4500, Waltham, Mass.). A body composition phantom was used to calibrate the machine before each measurement.

Statistical Analyses: All outcome variables were evaluated for distribution and homogeneity of variance; variables that did not meet the assumptions of homogeneity of variance or normal distribution were log-transformed. ANOVA was used to evaluate differences across dose groups stratified by age, younger vs. older, at a single time point with Sheffe's test to determine which groups differed significantly if a difference was identified by ANOVA. Changes within groups from baseline to treatment were evaluated with paired t-tests. Alpha was set at 0.05 for determining statistical significance. Data are presented as mean+/−SEM or mean % change from baseline+/−SEM, unless otherwise indicated in the figure legends.

Myostatin Assay Characteristics: Linear Range: The mean intra- and inter-assay imprecision was determined from six analytical runs for each of the eleven calibrators (73-75,000 pg/mL) in the standard curve (Table 7, below). The inter-assay CV for the 73 pg/mL calibrator was 36.4%, which exceeded the acceptable limit (<30%). Therefore, the LLQ of the assay was determined by the next calibrator point (147 pg/mL) at which the inter-assay CV and % Bias were 19.7% and 3.4%, respectively. The inter-assay CV of 32.4% for the 75,000 pg/mL calibrator was also not within the acceptable limit (<30%) thereby defining the ULQ to the next lowest calibrator point (37,500 pg/mL) at which the CV and % Bias were 3.6% and 0.8%, respectively. The linear quantitative range of the assay extended from 143 pg/mL to 37,500 pg/mL in a biologically relevant matrix.

TABLE 7

Intra and Inter-Assay Imprecision of the Myostatin Calibration Curve

| | Concentration (pg/mL) | | | | | | | | | | |
|---|---|---|---|---|---|---|---|---|---|---|---|
| | 75,000 | 37,500 | 18,750 | 9,375 | 4,688 | 2,344 | 1,172 | 586 | 293 | 147 | 73 |

Intra-Assay CV

| | | | | | | | | | | | |
|---|---|---|---|---|---|---|---|---|---|---|---|
| Mean intra-assay % CV | 36.2 | 13.2 | 5 | 4.4 | 2.9 | 3.9 | 8.6 | 11.3 | 12.1 | 7.9 | 14.1 |
| # Analytical Runs | 2 | 6 | 6 | 6 | 6 | 6 | 6 | 6 | 6 | 6 | 6 |

Inter-Assay CV

| Analytical Run # | Mean back-calculated concentrations from individual analytical runs | | | | | | | | | | |
|---|---|---|---|---|---|---|---|---|---|---|---|
| 1 | 77,628 | 38,353 | 18,715 | 9,398 | 4,786 | 2,274 | 1,168 | 541 | 271 | 122 | 154 |
| 2 | 48,648 | 39,596 | 18,532 | 9,393 | 4,906 | 2,284 | 1,012 | 608 | 273 | 168 | 107 |
| 3 | 93,777 | 37,040 | 18,865 | 9,386 | 4,706 | 2,254 | 1,239 | 629 | 266 | 159 | 55 |
| 4 | 47.567 | 35,705 | 18,875 | 9,354 | 4,674 | 2,407 | 1,123 | 605 | 280 | 117 | 106 |
| 5 | 53,495 | 37,477 | 18,862 | 9,224 | 4,889 | 2,316 | 1,070 | 611 | 261 | 149 | 109 |
| 6 | 45,918 | 38,503 | 18,926 | 9,264 | 4,736 | 2,420 | 1,135 | 524 | 286 | 198 | 64 |
| Mean (pg/mL) | 61,172 | 37,789 | 18,796 | 9,336 | 4,782 | 2,326 | 1,124 | 586 | 273 | 152 | 99 |
| SD | 19,837 | 1,348 | 147 | 75 | 96 | 71 | 79 | 43 | 9 | 30 | 36 |
| % CV | 32.4 | 3.6 | 0.8 | 0.8 | 2 | 3.1 | 7 | 7.3 | 3.3 | 19.7 | 36.4 |
| % Bias | −18.4 | 0.8 | 0.2 | −0.4 | 2.0 | −0.8 | −4.1 | 0.0 | −6.8 | 3.4 | 35.6 |
| N | 6 | 6 | 6 | 6 | 6 | 6 | 6 | 6 | 6 | 6 | 6 |

Intra- and Inter-Assay Imprecision: The mean myostatin concentrations (pg/mL, +/−SD) in the low, mid, and high validation samples in five analytical runs were 3739+/−146, 7615+/−125, and 18268+/−948, respectively. The measured intra-assay CV for the low, mid, and high validation samples (n=5 for each validation sample) was 4.1%, 4.7%, and 7.2%, respectively, and the inter-assay CV was 3.9%, 1.6%, and 5.2%, respectively.

Assay Specificity: The mature myostatin protein has a high degree of sequence conservation between mammalian species (4), allowing use of the myostatin assay on many non-human samples, including mouse, rat, dog, cow, and monkey. Serum samples from myostatin-deficient cattle (Belgian Blue) and from mice with an inactivating mutation in the myostatin gene (mstn KO) were assayed under dissociative acidic conditions, and compared to normal animals of the same species (FIG. 29A). Serum myostatin was abundant in normal mice (~120 ng/ml), while normal cow serum averaged approximately 40 ng/mL. In contrast, myostatin protein was undetectable in sera from both the Belgian Blue cattle and the myostatin KO mice, confirming the specificity of the assay for myostatin since the mutations in these myostatin-null animals abolish the synthesis of the protein.

Baseline Characteristics of Human Subjects: Fifty-two of the 61 randomized young men and 51 of 60 randomized older men completed the treatment phase. Sufficient serum for myostatin assays and body composition data were available through week 20 for 50 young men and 48 older men; these subjects were included in this secondary analysis and their baseline characteristics are shown in Table 8, below. Overall drug compliance rate was greater than 99%.

The baseline total testosterone, free testosterone, percent free testosterone, SHBG concentration, did not differ among the five dose groups at baseline in either the young or older groups. However, older men had lower serum total and free testosterone, and higher SHBG than younger men. Body weight, body mass index, and percent fat mass were greater in the older men than the younger men, while height was similar in both.

TABLE 8

Baseline Characterics of Evaluated Subjects

|  | Young Men (n = 50) | Older Men (n = 48) |
| --- | --- | --- |
| Age (years) | 26.5 ± 4.6 | 66.4 ± 4.7 |
| Height (cm) | 176.3 ± 6.4 | 175.9 ± 5.7 |
| Weight (kg) | 75.1 ± 10.9 | 83.2 ± 11.7 |
| BMI (kg/m2) | 24.1 ± 3.0 | 26.9 ± 3.5 |
| Lean body mass (kg) | 57.6 ± 7.2 | 57.9 ± 6.3 |
| Percent fat mass | 18.0 ± 6.4 | 26.6 ± 5.4 |
| Total testosterone level | 578.4 ± 165.2 | 330.6 ± 96.1 |

Figure 30A:
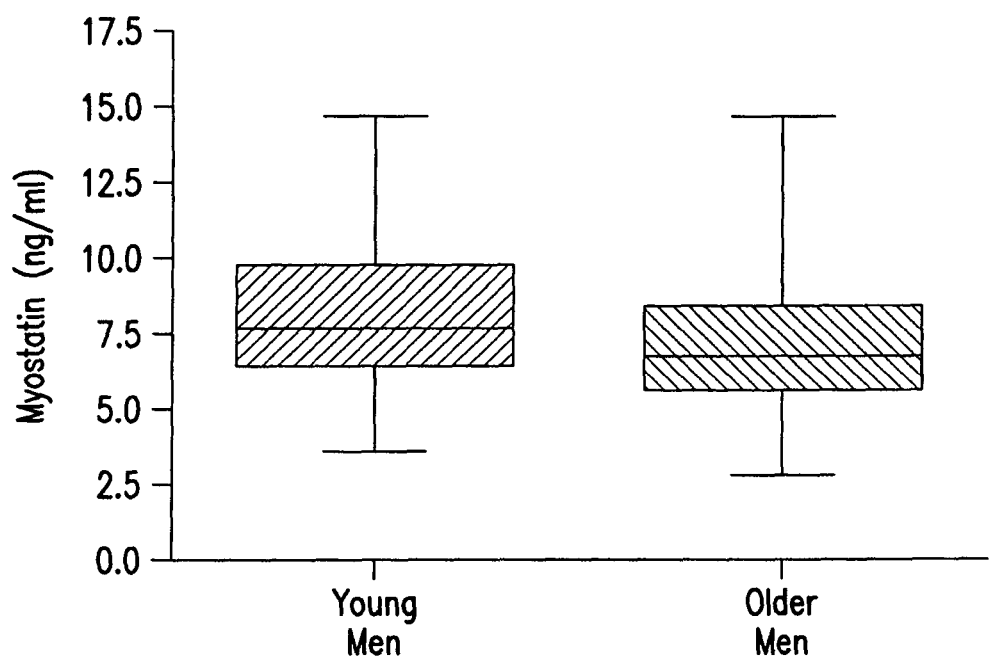
FIG. 30A. Box and whisker plots of serum myostatin levels (mean, SD, median and first and third quartile values) in young and older men. The horizontal line in the box represents the mean, the lower and upper boundaries of the box represent the first and third quartiles, and the vertical bars represent the SDs. *, P=0.03.
Figure 30B:
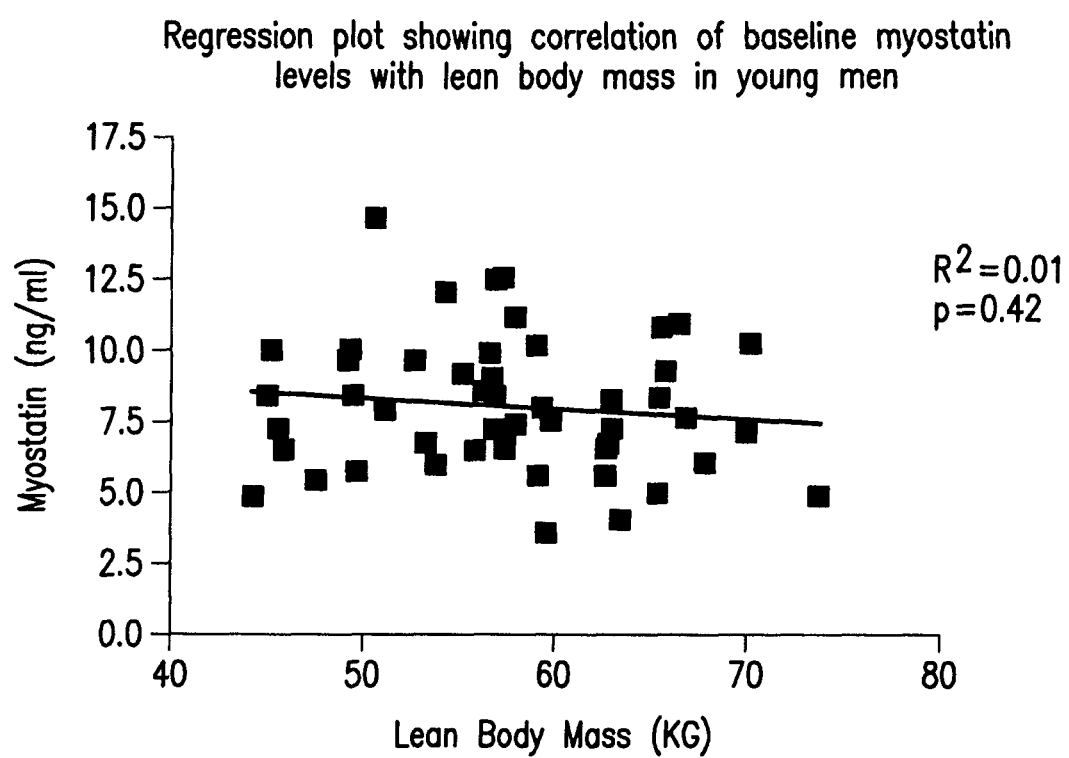
FIG. 30B. Regression plot showing correlation of baseline myostatin levels with lean body mass in young men.
Figure 30C:
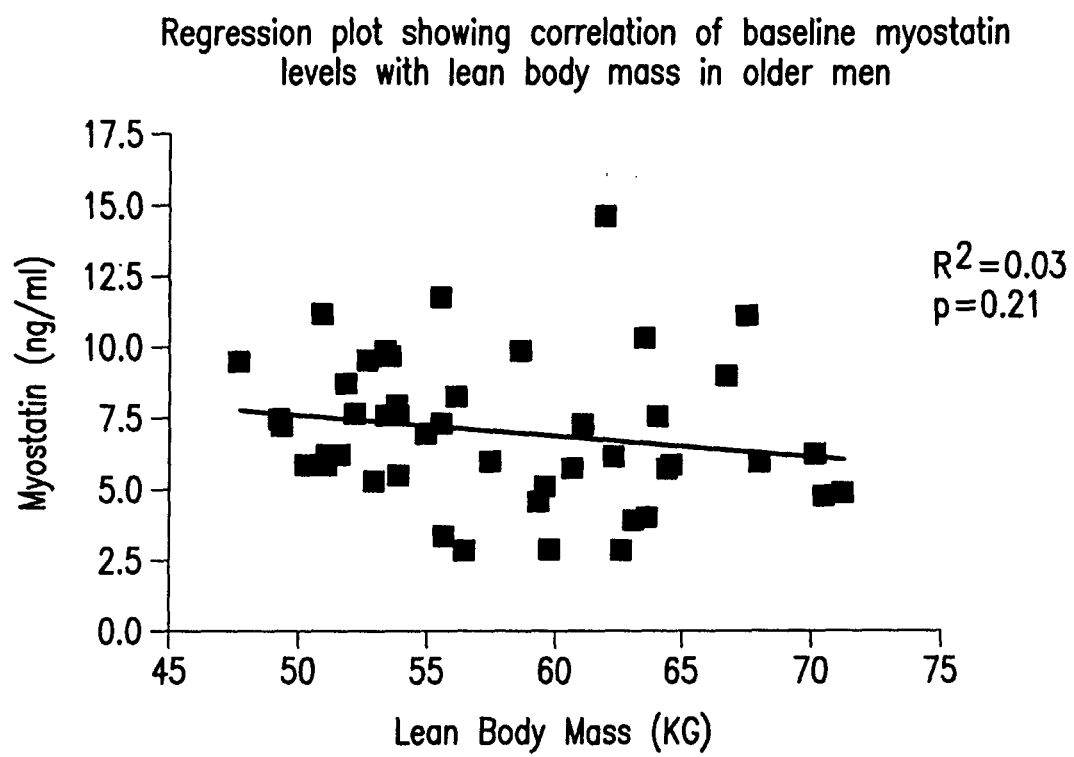
FIG. 30C. Regression plot showing correlation of baseline myostatin levels with lean body mass in older men.

Myostatin Levels in Young and Older Men: Serum myostatin levels were normally distributed in both young and older men. Young men had significantly higher myostatin levels than older men (8.0+/−0.3 vs. 7.0+/−0.4 ng/mL, P=0.03) (FIG. 30A). Serum myostatin levels were not significantly correlated with lean body mass measured by DEXA in either young or older men (FIGS. 30B and 30C). Similarly, there was no significant correlation between myostatin levels and body weight, body mass index, or serum testosterone levels at baseline (not shown).

Figure 31A:
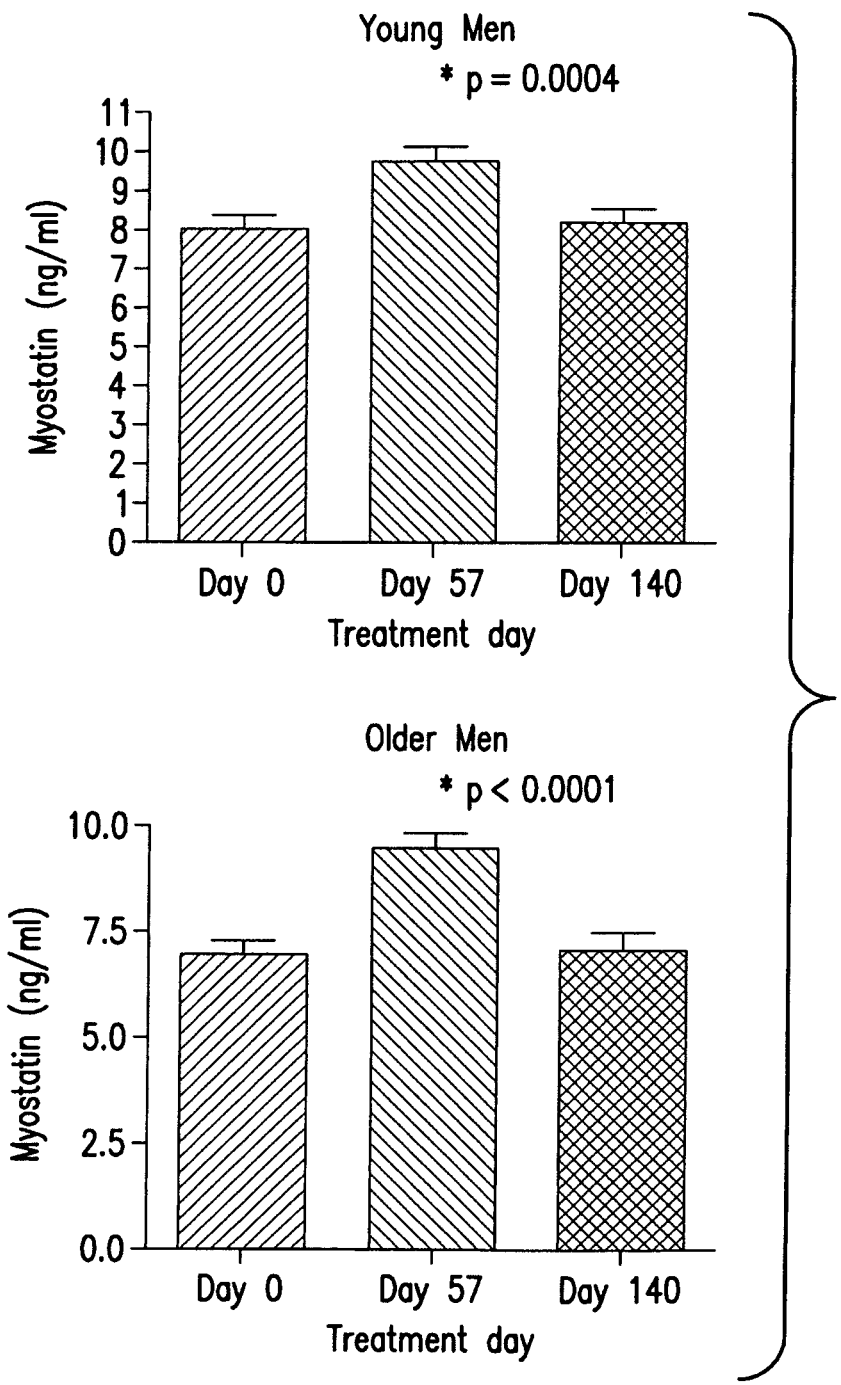
FIG. 31A shows the myostatin levels at baseline, treatment day 56, and 140 in young (left panel) and older men (right panel). The data are mean+/−SEM. *, P value as in comparison to baseline levels. Myostatin levels on day 140 were not significantly different from baseline levels.
Figure 31B:
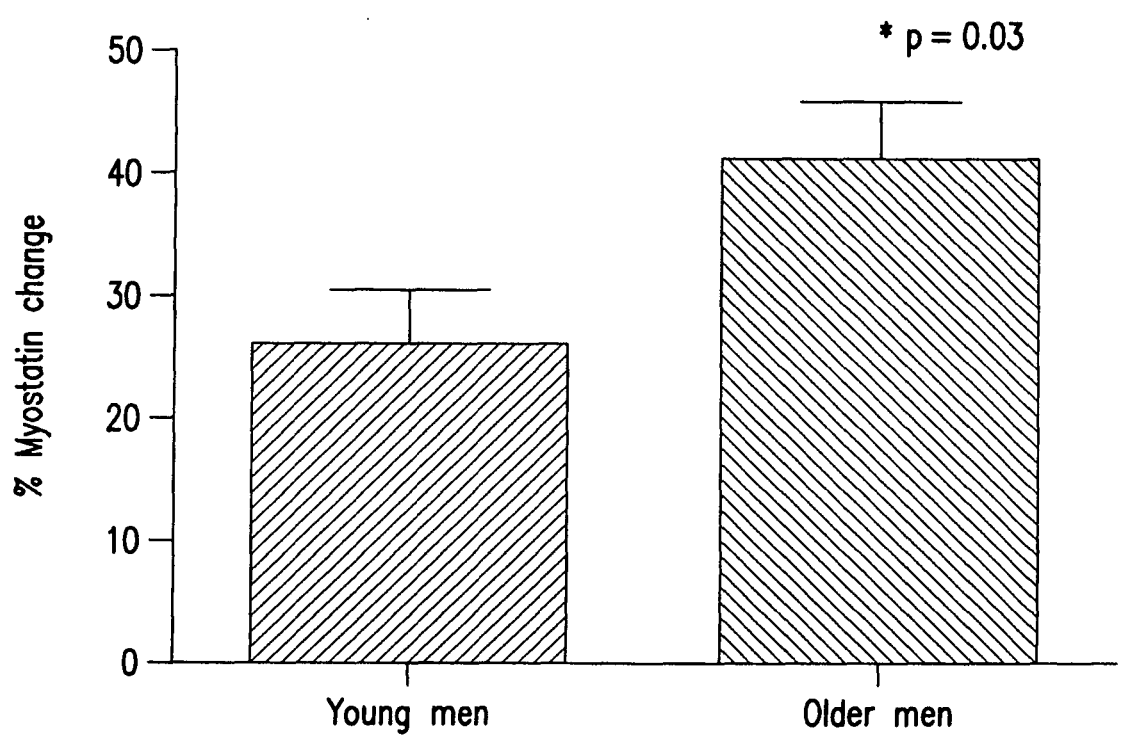
FIG. 31B shows the percent change from baseline in serum myostatin levels from baseline to day 56 in young and older men. *, P=0.03
Figure 32A:
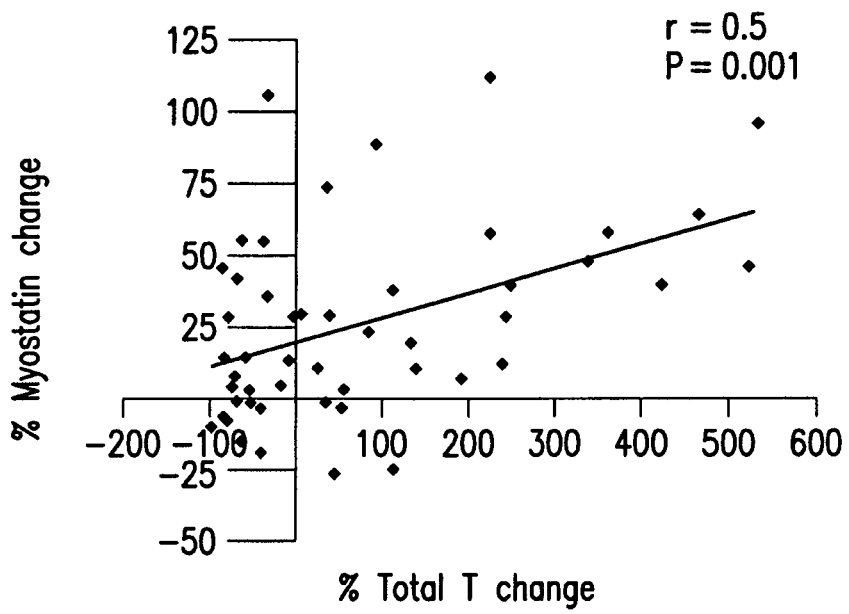
FIG. 32A shows the linear regression plot of percent change in myostatin levels from baseline to day 56 and percent change in serum total testosterone concentrations in young men.
Figure 32B:
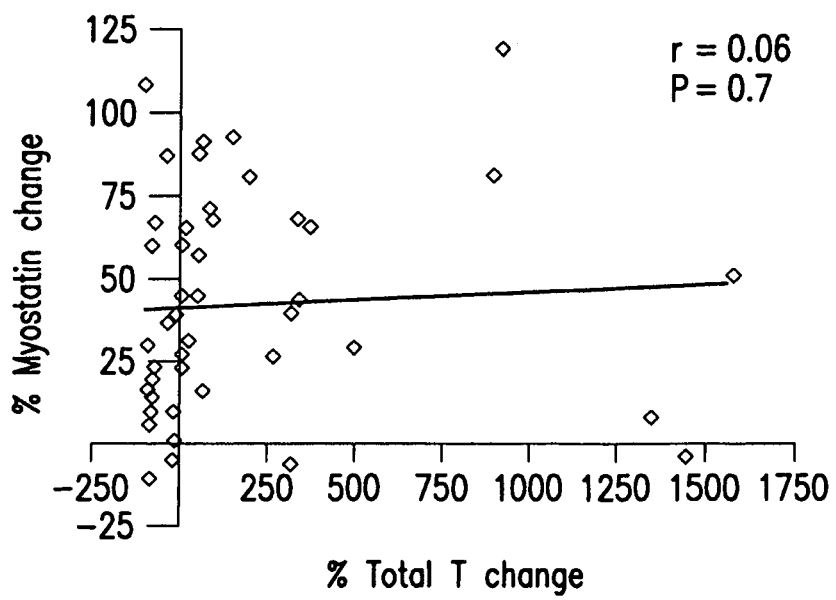
FIG. 32B shows the linear regression plot of percent change in myostatin levels from baseline to day 56 and percent change in serum total testosterone concentrations in older men.
Figure 32C:
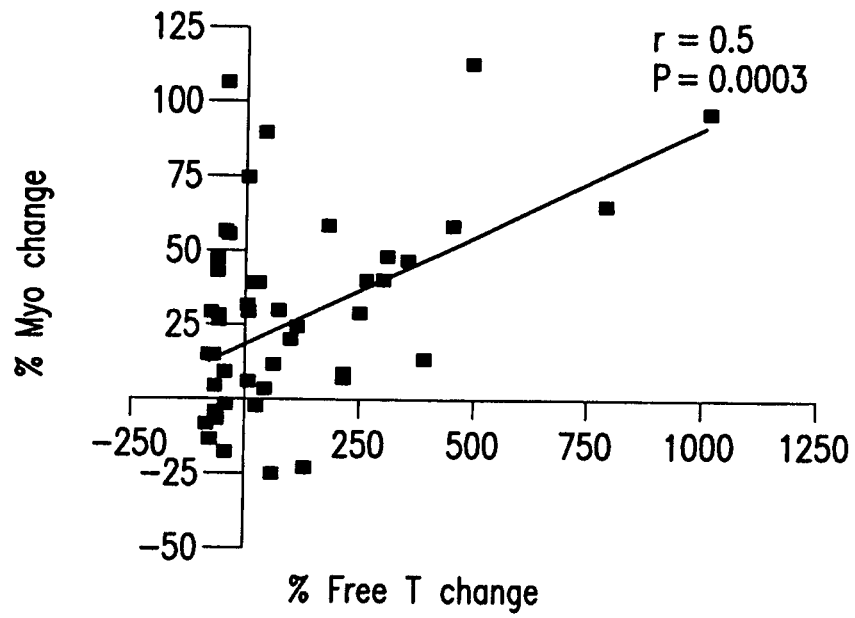
FIG. 32C shows the linear regression of percent change in myostatin levels from baseline to day 56 and percent change in serum free testosterone concentrations in young men.
Figure 32D:
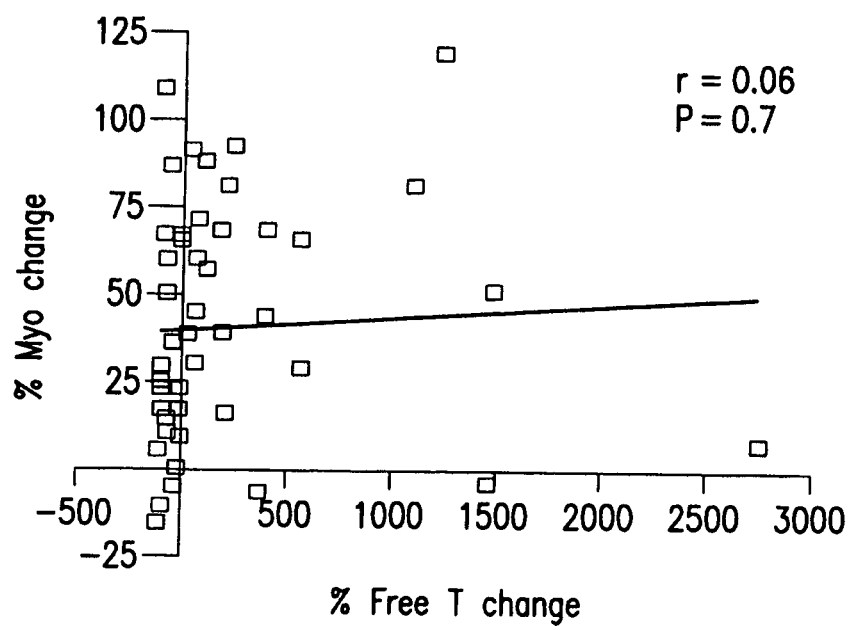
FIG. 32D shows the linear regression of percent change in myostatin levels from baseline to day 56 and percent change in serum free testosterone concentrations in older men.
Figure 32E:
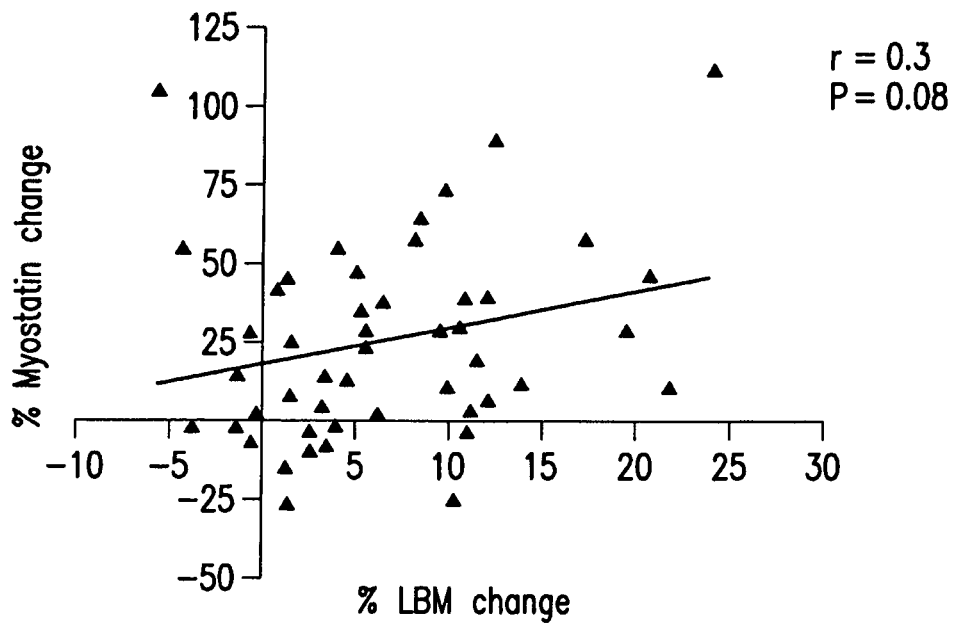
FIG. 32E shows the linear regression of percent change in myostatin levels from baseline to day 56 and percent change in lean body mass from baseline to day 140 in young men.
Figure 32F:
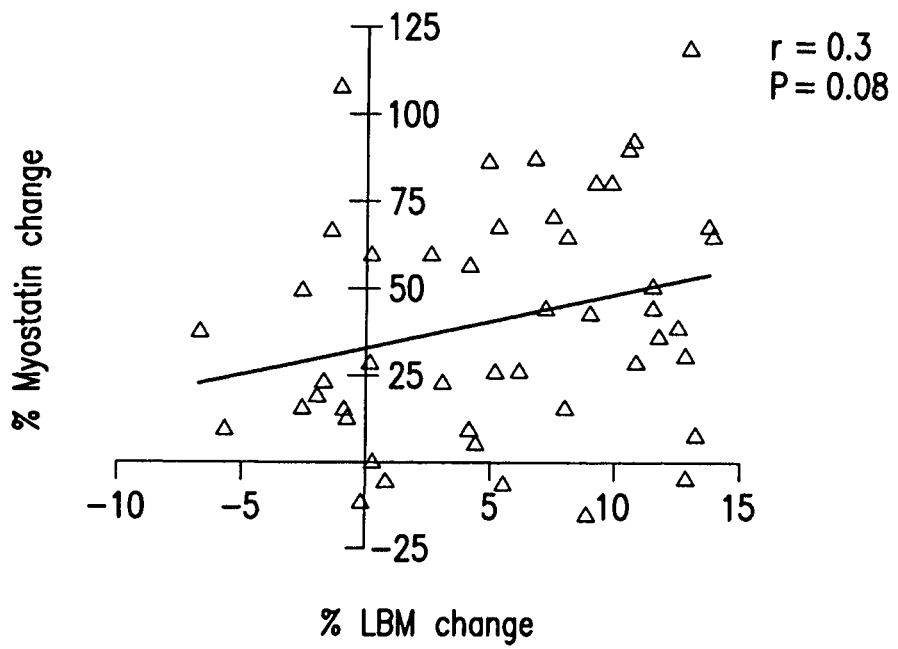
FIG. 32F shows the linear regression of percent change in myostatin levels from baseline to day 56 and percent change in serum lean body mass from baseline to day 140 in older men.

Effects of Testosterone Administration on Myostatin Levels in Men: Serum myostatin levels at baseline did not differ significantly across the five dose groups within either young or older men. Serum myostatin levels were significantly higher on day 56 compared to baseline in both young and older men (FIG. 31A). The changes in serum myostatin concentrations did not differ significantly among the five dose groups either within young or older men. Older men experienced a significantly greater percent increase in myostatin levels than young men (FIG. 31B). The increases in myostatin levels during testosterone therapy were not sustained; thus, serum myostatin levels on day 140 were not significantly different from those at baseline.

The increments in myostatin levels above baseline were related to changes in testosterone concentrations. Changes in myostatin levels from baseline to day 56 were significantly positively correlated with changes in total (FIG. 32A) and free (FIG. 32C) testosterone concentrations in young men, but not in older men (FIGS. 32 B and 32D). As previously reported, testosterone treatment was associated with significant gains in lean body mass; the changes in lean body mass were significantly correlated with testosterone dose and testosterone concentration, as previously described. However, changes in lean body mass were not significantly correlated with either absolute or percent change (FIGS. 32E and 32F) in myostatin concentrations.

Myostatin Levels in Females: In another study, serum samples of healthy, young menstruating women, 19-21 years of age, and postmenopausal women, 67-87 years of age, were purchased from BioServe, Beltsville, Md. These participants had consented to participate in an IRB-approved Bioserve study. Surgically menopausal women were 18-55 years of age, who had ovarian surgery at least 6 months before enrollment and serum FSH>30 U/L, BMI<35 kg/m$^2$, a normal PAP smear and mammogram in the preceding 12 months, and who had provided a written informed consent approved by the Boston University IRB.

Figure 33:
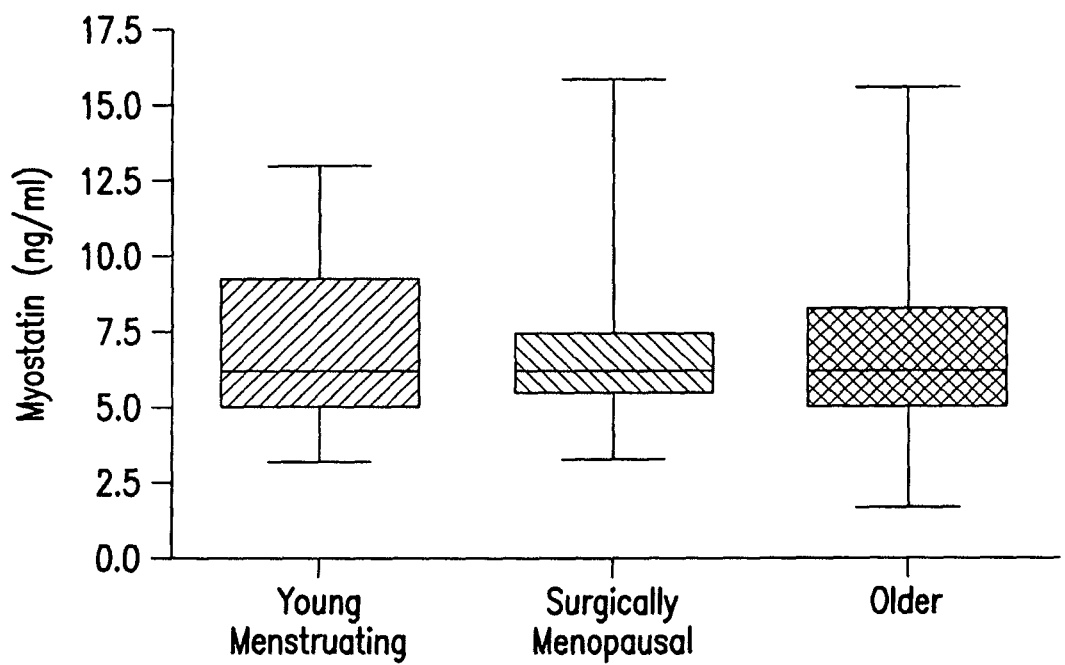
FIG. 33. Box and whisker plots of myostatin levels (mean, SD, median and first and third quartile values) in young menstruating, surgically menopausal, and older women. The horizontal line in the box represents the mean, the lower and upper boundaries of the box represent the first and third quartiles, and the vertical bars represent the SDs. Myostatin levels in the three groups were not statistically significant.

Serum myostatin levels in young women were not significantly different from those in young men (FIG. 33). Myostatin levels in young menstruating women, surgically menopausal and naturally menopausal women did not differ significantly.

What is claimed is:

1. An anti-GDF8 antibody or antigen binding fragment thereof that specifically binds to GDF8 comprising:
   an antibody variable heavy (VH) region comprising the first, second and third complementarity determining regions (CDRs) from the VH region defined by the amino acid sequence of SEQ ID NO:14 or SEQ ID NO:17; and
   an antibody variable light (VL) region comprising the first, second and third CDRs from the VL region defined by the amino acid sequence or SEQ ID NO:16 or SEQ ID NO:18.

2. The anti-GDF8 antibody or antigen binding fragment of claim 1,
   wherein VH CDR1 comprises SEQ NO:19 or SEQ ID NO:25, wherein VH CDR2 comprises SEQ ID NO:20 or SEQ ID NO:26, and wherein VH CDR3 comprises SEQ ID NO:21 or SEQ ID NO:27; and
   wherein VL CDR1 comprises SEQ ID NO:22 or SEQ ID NO:28, wherein VL CDR2 comprises SEQ ID NO:23 or SEQ ID NO:29, and wherein VL, CDR3 comprises SEQ ID NO:24 or SEQ ID NO:30.

3. The anti-GDF8 antibody or antigen binding fragment of claim 1, wherein said VH region comprises the amino acid sequence of SEQ ID NO:14 or SEQ ID NO:17.

4. The anti-GDF8 antibody or antigen binding fragment of claim 1, wherein said VL region comprises the amino acid sequence of SEQ ID NO:16 or SEQ ID NO:18.

5. The anti-GDF8 antibody or antigen binding fragment of claim 1, wherein said VL region comprises the amino acid sequence of SEQ ID NO:16 and said VH region comprises the amino acid sequence of SEQ ID NO:14.

6. The anti-GDF8 antibody or antigen binding fragment of claim 1, wherein said VL region comprises the amino acid sequence of SEQ ID NO:18 and said VH region comprises the amino acid sequence of SEQ ID NO:17.

7. The anti-GDF8 antibody or antigen binding fragment of claim 1, wherein said VL, region is joined to a human kappa or lambda constant light region.

8. The anti-GDF8 antibody or antigen binding fragment Of claim 1, wherein said VH region is joined to the constant heavy region of a human antibody subtype selected from the group consisting of IgA1, IgA2, IgD, IgE, IgG1, IgG2, IgG3, IgG4 and IgM.

9. The anti-GDF8 antibody or fragment of claim 8, wherein said VH region is joined to the constant heavy region of the IgG1 human antibody subtype.

10. The anti-GDF8 antibody or fragment of claim 8, wherein the constant heavy region comprises one or more mutations altering a constant heavy region effector function.

11. The anti-GDF8 antibody or fragment of claim 10, wherein said one or more mutations reduces Fc receptor binding.

12. The anti-GDF8 antibody or antigen binding fragment of claim 1, wherein said anti-GDF8 antibody or fragment is partially or fully humanized.

13. The anti-GDF8 antibody or antigen binding fragment of claim 1, wherein said antibody or fragment binds GDF8 with an affinity at least about 10-fold higher than BMP11.

14. The anti-GDF8 antibody or antigen binding fragment of claim 1, wherein said anti-GDF8 antibody or fragment binds GDF8 with an affinity at least about 100-fold higher than BMP11.

15. The anti-GDF8 antibody or antigen binding fragment of claim 1, wherein said anti-GDF8 antibody or fragment binds GDF8 with an affinity of about $10^{-9}$ M or greater affinity.

16. The anti-GDF8 antibody or antigen binding fragment of claim 1, wherein said antibody or fragment binds GDF8 with an affinity of about $10^{-10}$ M or greater affinity.

17. An anti-GDF8 antibody or antigen binding fragment thereof that specifically binds to GDF8 comprising a VL region at least 95% identical to the amino acid sequence of SEQ ID NO:16 or SEQ ID NO:18 and a VH region at least 95% identical to the amino acid sequence of SEQ ID NO:14 or SEQ ID NO:17.

18. An intact anti-GDF8 antibody, comprising:
   two antibody heavy chains, each comprising a VH region comprising the first, second and third CDRs from the VH region defined by the amino acid sequence of SEQ ED NO:17 and a human IgG1 constant heavy region: and
   two antibody light chains, each comprising a VL region comprising the first, second and third CDRs from the VL region defined by the amino acid sequence of SEQ ID NO:18 and to human lambda constant light region.

19. The antibody of claim 18 wherein said VH region comprises the amino acid sequence of SEQ ID NO:17 and said VL region comprises the amino acid sequence of SEQ ID NO: 18.

20. The antibody of claim 19, wherein said heavy chains comprise one or more mutations reducing Fc receptor binding.

* * * * *

SEQUENCE LISTING

<160> NUMBER OF SEQ ID NOS: 39

<210> SEQ ID NO 1
<211> LENGTH: 109
<212> TYPE: PRT
<213> ORGANISM: Homo sapiens

<400> SEQUENCE: 1

```
Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95
```

```
Lys Ile Pro Ala Met Val Val Asp Arg Cys Gly Cys Ser
                100                 105

<210> SEQ ID NO 2
<211> LENGTH: 375
<212> TYPE: PRT
<213> ORGANISM: Homo sapiens

<400> SEQUENCE: 2

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Asp Tyr His
            100                 105                 110

Ala Thr Thr Glu Thr Ile Ile Thr Met Pro Thr Glu Ser Asp Phe Leu
        115                 120                 125

Met Gln Val Asp Gly Lys Pro Lys Cys Cys Phe Phe Lys Phe Ser Ser
130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Phe Gly Trp Asp Trp Ile Ile Ala Pro Lys Arg Tyr
    290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
        355                 360                 365
```

Val Asp Arg Cys Gly Cys Ser
    370                 375

<210> SEQ ID NO 3
<211> LENGTH: 18
<212> TYPE: DNA
<213> ORGANISM: Homo sapiens

<400> SEQUENCE: 3
gattttggtc ttgactgt                                           18

<210> SEQ ID NO 4
<211> LENGTH: 6
<212> TYPE: PRT
<213> ORGANISM: Homo sapiens

<400> SEQUENCE: 4

Asp Phe Gly Leu Asp Cys
1               5

<210> SEQ ID NO 5
<211> LENGTH: 45
<212> TYPE: DNA
<213> ORGANISM: Homo sapiens

<400> SEQUENCE: 5
tttgaagctt ttggatggga ttggattatc gctcctaaaa gatat             45

<210> SEQ ID NO 6
<211> LENGTH: 15
<212> TYPE: PRT
<213> ORGANISM: Homo sapiens

<400> SEQUENCE: 6

Phe Glu Ala Phe Gly Trp Asp Trp Ile Ile Ala Pro Lys Arg Tyr
1               5                   10                  15

<210> SEQ ID NO 7
<211> LENGTH: 45
<212> TYPE: DNA
<213> ORGANISM: Homo sapiens

<400> SEQUENCE: 7
tttgtatttt tacaaaaata tcctcatact catctggtac accaa             45

<210> SEQ ID NO 8
<211> LENGTH: 15
<212> TYPE: PRT
<213> ORGANISM: Homo sapiens

<400> SEQUENCE: 8

Phe Val Phe Leu Gln Lys Tyr Pro His Thr His Leu Val His Gln
1               5                   10                  15

<210> SEQ ID NO 9
<211> LENGTH: 27
<212> TYPE: DNA
<213> ORGANISM: Homo sapiens

<400> SEQUENCE: 9
tgctctggag agtgtgaatt tgtattt                                 27

<210> SEQ ID NO 10
<211> LENGTH: 9
<212> TYPE: PRT

<213> ORGANISM: Homo sapiens

<400> SEQUENCE: 10

Cys Ser Gly Glu Cys Glu Phe Val Phe
1               5

<210> SEQ ID NO 11
<211> LENGTH: 75
<212> TYPE: DNA
<213> ORGANISM: Homo sapiens

<400> SEQUENCE: 11
tggattatcg ctcctaaaag atataaggcc aattactgct ctggagagtg tgaatttgta    60
tttttacaaa aatat                                                    75

<210> SEQ ID NO 12
<211> LENGTH: 25
<212> TYPE: PRT
<213> ORGANISM: Homo sapiens

<400> SEQUENCE: 12

Trp Ile Ile Ala Pro Lys Arg Tyr Lys Ala Asn Tyr Cys Ser Gly Glu
1               5                   10                  15

Cys Glu Phe Val Phe Leu Gln Lys Tyr
            20                  25

<210> SEQ ID NO 13
<211> LENGTH: 360
<212> TYPE: DNA
<213> ORGANISM: Mus musculus

<400> SEQUENCE: 13
caggttcagc tccagcagtc tggggctgag ctggcaagac ctggggcttc agtgaagttg    60
tcctgcaagg cttctggcta cacctttact agctactgga tgcagtgggt aaaacagagg   120
cctggacagg gtctggaatg gattggggct atttatcctg agatggtga tactaggtac    180 actcagaagt tcaagggcaa ggccacattg actgcagata atcctccag cacagcctac    240 atgcaactca gcagcttggc atctgaggac tctgcggtct attactgtgc aagaatgggt   300
ggttacgacc ggtactactt tgactactgg ggccaaggca ccactctcac agtctcctca   360

<210> SEQ ID NO 14
<211> LENGTH: 120
<212> TYPE: PRT
<213> ORGANISM: Mus musculus

<400> SEQUENCE: 14

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Ala Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Met Gly Gly Tyr Asp Arg Tyr Tyr Phe Asp Tyr Trp Gly Gln

Gly Thr Thr Leu Thr Val Ser Ser
        115                 120

<210> SEQ ID NO 15
<211> LENGTH: 339
<212> TYPE: DNA
<213> ORGANISM: Mus musculus

<400> SEQUENCE: 15
gacattgtga tgacacagtc tccatcctcc ctggctatgt cagtaggaca gaaggtcact    60
atgagctgca agtccagtca gagccttttta aatagtgcca atcaaaagaa ctatttggcc   120
tggtaccagc agaaaccagg acagtctcct aaacttctgg tatactttgc atccactagg   180
gaatctgggg tccctgatcg cttcataggc agtggatctg ggacagattt cactcttacc   240
atcagcagtg tgcaggctga agacctggca gattacttct gtcagcaaca ttataacact   300
ccgctcacgt tcggtgctgg gaccaagctg gagctgaaa                          339

<210> SEQ ID NO 16
<211> LENGTH: 113
<212> TYPE: PRT
<213> ORGANISM: Mus musculus

<400> SEQUENCE: 16

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ala Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Asn Thr Pro Leu Thr Phe Gly Ala Gly Thr Lys Leu Glu Leu
            100                 105                 110

Lys

<210> SEQ ID NO 17
<211> LENGTH: 120
<212> TYPE: PRT
<213> ORGANISM: Homo sapiens

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Gln Trp Val Arg Gln Ala Pro Gly Gln Gly Leu Glu Trp Met
        35                  40                  45

Gly Ala Ile Tyr Pro Gly Asp Gly Asp Thr Arg Tyr Thr Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys

```
                85                  90                  95

Ala Arg Met Gly Gly Tyr Asp Arg Tyr Tyr Phe Asp Tyr Trp Gly Gln
            100                 105                 110

Gly Thr Leu Val Thr Val Ser Ser
        115                 120

<210> SEQ ID NO 18
<211> LENGTH: 113
<212> TYPE: PRT
<213> ORGANISM: Homo sapiens

<400> SEQUENCE: 18

Asp Ile Val Met Thr Gln Ser Pro Asp Ser Leu Ala Val Ser Leu Gly
1               5                  10                  15

Glu Arg Ala Thr Ile Asn Cys Lys Ser Ser Gln Ser Leu Leu Asn Ser
            20                  25                  30

Ala Asn Gln Lys Asn Tyr Leu Ala Trp Tyr Gln Gln Lys Pro Gly Gln
        35                  40                  45

Pro Pro Lys Leu Leu Ile Tyr Phe Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Asn Thr Pro Leu Thr Phe Gly Gly Gly Thr Lys Val Glu Ile
            100                 105                 110

Lys

<210> SEQ ID NO 19
<211> LENGTH: 5
<212> TYPE: PRT
<213> ORGANISM: Mus musculus

<400> SEQUENCE: 19

Ser Tyr Trp Met Gln
1               5

<210> SEQ ID NO 20
<211> LENGTH: 17
<212> TYPE: PRT
<213> ORGANISM: Mus musculus

<400> SEQUENCE: 20

Ala Ile Tyr Pro Gly Asp Gly Asp Thr Arg Tyr Thr Gln Lys Phe Lys
1               5                  10                  15

Gly

<210> SEQ ID NO 21
<211> LENGTH: 13
<212> TYPE: PRT
<213> ORGANISM: Mus musculus

<400> SEQUENCE: 21

Ala Arg Met Gly Gly Tyr Asp Arg Tyr Tyr Phe Asp Tyr
1               5                  10

<210> SEQ ID NO 22
<211> LENGTH: 17
<212> TYPE: PRT
<213> ORGANISM: Mus musculus
```

```
<400> SEQUENCE: 22

Lys Ser Ser Gln Ser Leu Leu Asn Ser Ala Asn Gln Lys Asn Tyr Leu
1               5                   10                  15

Ala

<210> SEQ ID NO 23
<211> LENGTH: 7
<212> TYPE: PRT
<213> ORGANISM: Mus musculus

<400> SEQUENCE: 23

Phe Ala Ser Thr Arg Glu Ser
1               5

<210> SEQ ID NO 24
<211> LENGTH: 9
<212> TYPE: PRT
<213> ORGANISM: Mus musculus

<400> SEQUENCE: 24

Gln Gln His Tyr Asn Thr Pro Leu Thr
1               5

<210> SEQ ID NO 25
<211> LENGTH: 10
<212> TYPE: PRT
<213> ORGANISM: Mus musculus

<400> SEQUENCE: 25

Gly Tyr Thr Phe Thr Ser Tyr Trp Met Gln
1               5                   10

<210> SEQ ID NO 26
<211> LENGTH: 9
<212> TYPE: PRT
<213> ORGANISM: Mus musculus

<400> SEQUENCE: 26

Ala Ile Tyr Pro Gly Asp Gly Asp Thr
1               5

<210> SEQ ID NO 27
<211> LENGTH: 13
<212> TYPE: PRT
<213> ORGANISM: Mus musculus

<400> SEQUENCE: 27

Ala Arg Met Gly Gly Tyr Asp Arg Tyr Tyr Phe Asp Tyr
1               5                   10

<210> SEQ ID NO 28
<211> LENGTH: 17
<212> TYPE: PRT
<213> ORGANISM: Mus musculus

<400> SEQUENCE: 28

Lys Ser Ser Gln Ser Leu Leu Asn Ser Ala Asn Gln Lys Asn Tyr Leu
1               5                   10                  15

Ala

<210> SEQ ID NO 29
<211> LENGTH: 7
<212> TYPE: PRT
<213> ORGANISM: Mus musculus
```

-continued

<400> SEQUENCE: 29

Phe Ala Ser Thr Arg Glu Ser
1               5

<210> SEQ ID NO 30
<211> LENGTH: 9
<212> TYPE: PRT
<213> ORGANISM: Mus musculus

<400> SEQUENCE: 30

Gln Gln His Tyr Asn Thr Pro Leu Thr
1               5

<210> SEQ ID NO 31
<211> LENGTH: 348
<212> TYPE: DNA
<213> ORGANISM: Mus musculus

<400> SEQUENCE: 31
gaagtgcagc tggtggagtc tgggggaggc ttagtgaagc ctggagggtc cctgaaactc      60
tcctgtgcag cctctggatt cactttcagt agctatgcca tgtcttgggt tcgccagact     120
ccggagaaga ggctggagtg ggtcgcaacc attagtagtg gtggtagtta cacctcctat     180
ccagacagtg tgaagggtcg attcaccatc tccagagaca tgccaagaa cacctgtac       240 ctgcaaatga gcagtctgag gtctgaggac acggccatgt attactgtgc aagacaagac     300
tatgctatga actactgggg tcaaggaacc tcagtcaccg tctcctca                 348

<210> SEQ ID NO 32
<211> LENGTH: 300
<212> TYPE: DNA
<213> ORGANISM: Mus musculus

<400> SEQUENCE: 32
gacattgaga tgacccagtc tcacaaattc atgtccacat cagtaggaga cagggtcagc      60
atcacctgca aggccagtca ggatgtgagt actgctgtag cctggtatca acagaaacca     120
ggacaatctc ctaaactact gctttactcg gcatcctacc ggtacactgg agtccctgat     180
cggttcactg gcagtggatc tgggacggat ttcactttca ccatcagcag tgtgcaggct     240
gaagacctgg cagtttatta ctgtcagcaa cattatagta ctccgtggac gttcggtgga     300

<210> SEQ ID NO 33
<211> LENGTH: 351
<212> TYPE: DNA
<213> ORGANISM: Homo sapiens

<400> SEQUENCE: 33
caggtgcagc tggtgcaatc tggggctgag gtgaagaagc ctggggcctc agtgaaggtt      60
tcctgcaagg catctggata caccttcacc agctactata tgcactgggt gcgacaggcc     120
cctggacaag gcttgagtg gatgggaata atcaaccta gtggtggtag cacaagctac       180
gcacagaagt tccagggcag agtcaccatg accagggaca cgtccacgag cacagtctac     240
atggagctga gcagcctgag atctgaggac acggccgtgt attactgtgc gagagacgag     300
aactgggggt cgaccccctg ggccagggga accctggtca ccgtctcgag t             351

<210> SEQ ID NO 34
<211> LENGTH: 315
<212> TYPE: DNA
<213> ORGANISM: Homo sapiens

<400> SEQUENCE: 34

```
tcctatgagc tgactcagcc accctcagtg tccgtgtctc caggacagac agccaccatt      60
acctgctctg gacatgcact gggggacaaa tttgtttcct ggtatcagca gggatcaggc     120
cagtcccctg tattggtcat ctatgacgat acccagcggc cctcagggat ccctgggcga     180
ttctctggct ccaactctgg gaacacagcc actctgacca tcagcgggac ccaggctatg     240
gatgaggctg actattttg tcaggcgtgg gacagcagct tcgtattcgg cggagggacc     300
aaggtcaccg tccta                                                      315
```

<210> SEQ ID NO 35
<211> LENGTH: 1543
<212> TYPE: DNA
<213> ORGANISM: Homo sapiens

<400> SEQUENCE: 35

```
gaacatgacg gcgccctggg tggccctcgc cctcctctgg ggatcgctgt gcgccggctc      60
tgggcgtggg gaggctgaga cacgggagtg catctactac aacgccaact gggagctgga     120
gcgcaccaac cagagcggcc tggagcgctg cgaaggcgag caggacaagc ggctgcactg     180
ctacgcctcc tggcgcaaca gctctggcac catcgagctc gtgaagaagg gctgctggct     240
agatgacttc aactgctacg ataggcagga gtgtgtggcc actgaggaga ccccccaggt     300
gtacttctgc tgctgtgaag gcaacttctg caacgaacgc ttcactcatt tgccagaggc     360
tggggggccg gaagtcacgt acgagccacc cccgacagcc cccaccctgc tcacggtgct     420
ggcctactca ctgctgccca tcgggggcct ttccctcatc gtcctgctgg ccttttggat     480
gtaccggcat cgcaagcccc cctacggtca tgtggacatc catgaggacc ctgggcctcc     540
accaccatcc cctctggtgg gcctgaagcc actgcagctg ctggagatca aggctcgggg     600
gcgctttggc tgtgtctgga aggcccagct catgaatgac tttgtagctg tcaagatctt     660
cccactccag gacaagcagt cgtggcagag tgaacgggag atcttcagca cacctggcat     720
gaagcacgag aacctgctac agttcattgc tgccgagaag cgaggctcca acctcgaagt     780
agagctgtgg ctcatcacgg cctttcatga aagggctcc ctcacggatt acctcaaggg     840
gaacatcatc acatggaacg aactgtgtca tgtagcagag acgatgtcac gaggcctctc     900
ataccctgcat gaggatgtgc cctggtgccg tggcgagggc cacaagccgt ctattgccca     960
cagggacttt aaaagtaaga atgtattgct gaagagcgac ctcacagccg tgctggctga    1020
ctttggcttg gctgttcgat ttgagccagg gaaacctcca ggggacaccc acggacaggt    1080
aggcacgaga cggtacatgg ctcctgaggt gctcgaggga gccatcaact tccagagaga    1140
tgccttcctg cgcattgaca tgtatgccat ggggttggtg ctgtgggagc ttgtgtctcg    1200
ctgcaaggct gcagacggac ccgtggatga gtacatgctg ccctttgagg aagagattgg    1260
ccagcaccct tcgttggagg agctgcagga ggtggtggtg cacaagaaga tgaggcccac    1320
cattaaagat cactggttga aacacccggg cctggcccag ctttgtgtga ccatcgagga    1380
gtgctgggac catgatgcag aggctcgctt gtccgcgggc tgtgtggagg agcgggtgtc    1440
cctgattcgg aggtcggtca acggcactac ctcggactgt ctcgtttccc tggtgacctc    1500
tgtcaccaat gtggacctgc cccctaaaga gtcaagcatc taa                      1543
```

<210> SEQ ID NO 36
<211> LENGTH: 512
<212> TYPE: PRT
<213> ORGANISM: Homo sapiens

```
<400> SEQUENCE: 36

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
            35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
                100                 105                 110

Phe Thr His Leu Pro Glu Ala Gly Gly Pro Glu Val Thr Tyr Glu Pro
            115                 120                 125

Pro Pro Thr Ala Pro Thr Leu Leu Thr Val Leu Ala Tyr Ser Leu Leu
130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
            195                 200                 205

Leu Met Asn Asp Phe Val Ala Val Lys Ile Phe Pro Leu Gln Asp Lys
210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
            275                 280                 285

His Val Ala Glu Thr Met Ser Arg Gly Leu Ser Tyr Leu His Glu Asp
            290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
            355                 360                 365

Val Leu Glu Gly Ala Ile Asn Phe Gln Arg Asp Ala Phe Leu Arg Ile
370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415
```

```
Glu Ile Gly Gln His Pro Ser Leu Glu Leu Gln Glu Val Val
            420                 425                 430

His Lys Lys Met Arg Pro Thr Ile Lys Asp His Trp Leu Lys His Pro
            435                 440                 445

Gly Leu Ala Gln Leu Cys Val Thr Ile Glu Glu Cys Trp Asp His Asp
450                 455                 460

Ala Glu Ala Arg Leu Ser Ala Gly Cys Val Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
                500                 505                 510
```

<210> SEQ ID NO 37
<211> LENGTH: 99
<212> TYPE: PRT
<213> ORGANISM: Homo sapiens

<400> SEQUENCE: 37

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
                20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Val
```

<210> SEQ ID NO 38
<211> LENGTH: 99
<212> TYPE: PRT
<213> ORGANISM: Homo sapiens

<400> SEQUENCE: 38

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val
```

<210> SEQ ID NO 39
<211> LENGTH: 104
<212> TYPE: PRT
<213> ORGANISM: Homo sapiens -continued

```
<400> SEQUENCE: 39

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Gly Val Ile
            100
```